US012559749B2

(12) United States Patent
Ahern et al.

(10) Patent No.: US 12,559,749 B2
(45) Date of Patent: Feb. 24, 2026

(54) METHODS OF RESCUING STOP CODONS VIA GENETIC REASSIGNMENT WITH ACE-tRNA

(71) Applicant: UNIVERSITY OF IOWA RESEARCH FOUNDATION, Iowa City, IA (US)

(72) Inventors: Christopher Ahern, Iowa City, IA (US); John D. Lueck, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 228 days.

(21) Appl. No.: 18/137,931

(22) Filed: Apr. 21, 2023

(65) Prior Publication Data

US 2024/0182891 A1     Jun. 6, 2024

Related U.S. Application Data

(62) Division of application No. 16/761,205, filed as application No. PCT/US2018/059065 on Nov. 2, 2018, now Pat. No. 11,661,600.

(60) Provisional application No. 62/687,015, filed on Jun. 19, 2018, provisional application No. 62/580,887, filed on Nov. 2, 2017.

(51) Int. Cl.
| | |
|---|---|
| *C12N 15/113* | (2010.01) |
| *A61K 9/127* | (2025.01) |
| *A61K 31/7105* | (2006.01) |
| *A61P 43/00* | (2006.01) |

(52) U.S. Cl.
CPC ............ *C12N 15/113* (2013.01); *A61K 9/127* (2013.01); *A61K 31/7105* (2013.01); *A61P 43/00* (2018.01)

(58) Field of Classification Search
CPC ...... C12N 15/113; C12N 15/11; A61K 9/127; A61K 31/7105; A61K 48/00; A61P 43/00
USPC .................... 435/6.1, 91.1, 91.31, 455, 458; 514/44 A, 44 R; 536/23.1, 24.5
See application file for complete search history.

(56) References Cited

U.S. PATENT DOCUMENTS

| | | | |
|---|---|---|---|
| 4,687,737 | A | 8/1987 | Sharp et al. |
| 5,840,702 | A | 11/1998 | Bedwell |
| 6,309,830 | B1 | 10/2001 | Panchal et al. |
| 6,964,859 | B2 | 11/2005 | Rajbhandary et al. |
| 7,029,665 | B2 | 4/2006 | Panchal et al. |
| 8,338,386 | B2 | 12/2012 | Mclean et al. |
| 10,513,699 | B2 | 12/2019 | Short |
| 10,905,778 | B2 | 2/2021 | Coller et al. |
| 10,982,209 | B2 | 4/2021 | Xia et al. |
| 11,661,600 | B2 | 5/2023 | Ahern et al. |
| 2005/0014835 | A1 | 1/2005 | Arakawa et al. |
| 2009/0298920 | A1 | 12/2009 | Dardel et al. |
| 2012/0077186 | A1 | 3/2012 | Skach et al. |
| 2012/0117673 | A1 | 5/2012 | Ardell |
| 2017/0342422 | A1 | 11/2017 | Holzmann et al. |
| 2017/0354672 | A1 | 12/2017 | Siegwart et al. |
| 2018/0171321 | A1 | 6/2018 | Mureev et al. |
| 2019/0119675 | A1 | 4/2019 | Xia et al. |
| 2020/0263180 | A1 | 8/2020 | Mali et al. |
| 2020/0277607 | A1 | 9/2020 | Mali et al. |
| 2020/0291401 | A1 | 9/2020 | Ahern et al. |
| 2020/0407714 | A1 | 12/2020 | Ignatova et al. |
| 2021/0023120 | A1 | 1/2021 | Siegwart et al. |
| 2021/0163948 | A1 | 6/2021 | Mali et al. |
| 2021/0198673 | A1 | 7/2021 | Mali et al. |
| 2023/0203482 | A1 | 6/2023 | Puchalt et al. |

FOREIGN PATENT DOCUMENTS

| | | |
|---|---|---|
| WO | 1999036519 A1 | 7/1999 |
| WO | 2007070659 A2 | 6/2007 |
| WO | 2017049409 A1 | 3/2017 |
| WO | 2017152809 A1 | 9/2017 |
| WO | 2017201091 A1 | 11/2017 |
| WO | 2018031531 A4 | 4/2018 |
| WO | 2018161032 A1 | 9/2018 |
| WO | 2019090169 A1 | 5/2019 |
| WO | 2020069194 A1 | 4/2020 |
| WO | 2020208169 A1 | 10/2020 |
| WO | 2021072201 A1 | 4/2021 |
| WO | 2021087401 A1 | 5/2021 |
| WO | 2021092064 A1 | 5/2021 |
| WO | 2021113218 A1 | 6/2021 |

OTHER PUBLICATIONS

U.S. Appl. No. 16/760,932, 2023-0203482.
(Continued)

*Primary Examiner* — Jane J Zara
(74) *Attorney, Agent, or Firm* — Viksnins Harris Padys Malen LLP

(57) ABSTRACT

In certain embodiments, the present invention provides a modified transfer RNA (tRNA) comprising a T-arm, a D-arm, an anticodon-arm and an acceptor arm, wherein the T-arm comprises nucleotides that interact with the elongation factor 1 alpha protein, and methods of use thereof. In certain embodiments, the present invention provides a modified transfer RNA (tRNA) comprising a T-arm, a D-arm, an anticodon-arm and an acceptor arm, (a) wherein the anticodon-arm comprises a tri-nucleotide anticodon, wherein the anticodon is 5'-UCA-3' and recognizes TGA stop codons, and wherein the acceptor arm is operably linked to a arginine, tryptophan or glycine; (b) wherein the anticodon-arm comprises a tri-nucleotide anticodon, wherein the anticodon is 5'-UUA-3' and recognizes TAA stop codons, and wherein the acceptor arm is operably linked to a glutamine or, glutamate; or (c) wherein the anticodon-arm comprises a tri-nucleotide anticodon, wherein the anticodon is 5'-CUA-3' and recognizes TAG stop codons, and wherein the acceptor arm is operably linked to a tryptophan, glutamate or glutamine.

5 Claims, 51 Drawing Sheets
Specification includes a Sequence Listing.

(56) References Cited

OTHER PUBLICATIONS

Baudin-Baillieu, A , et al., "Genome-wide Translational Changes Induced by the Prion [PSI+]", Cell Reports 8, 439-448 (2014).

Goodenbour, J , et al., "Diversity of tRNA genes in eukaryotes", Nucleic Acids Research 34 (21), 6137-6146 (2006).

Loughran, G , et al., "Evidence of efficient stop codon readthrough in four mammalian genes", Nucleic Acids Research 42 (14), 8928-8938 (2014).

Pakula, A , et al., "Genetic Analysis of Protein Stability and Function", Annu Rev Genet 23, 289-310 (1989).

Albers, S , et al., "Repurposing tRNAs for nonsense suppression", Nature Communications 12 (3850), 1-10 (2021).

Andersen, G , et al., "Elongation factors in protein biosynthesis", Trends in Biochemical Sciences 28(8), 434-441 (2003).

Atkinson, J , et al., "Mutations to nonsense codons in human genetic disease: implications for gene therapy by nonsense suppressor tRNAs", Nucleic Acids Research 22(8), 1327-1334 (1994).

Bednarova, A , et al., "Lost in Translation: Defects in Transfer RNA Modifications and Neurological Disorders", Front Mol Neurosci 10(135), 1-8 (2017).

Biddle, W , et al., "Modification of orthogonal tRNAs: unexpected consequences for sense codon reassignment", Nucleic Acids Res 44(21), 10042-10050 (2016).

Bordeira-Carrico, R , et al., "Rescue of wild-type E-cadherin expression from nonsense-mutated cancer cells by a suppressor-tRNA", European Journal of Human Genetics 22, 1085-1092 (2014).

Capone, J , et al., "Amber, ochre and opal suppressor tRNA genes derived from a human serine tRNA gene", The EMBO Journal 4(1), 213-221 (1985).

Dreher , et al., "Quantitative Assessment of EF-1α•GTP Binding to Aminoacyl-tRNAs, Aminoacyl-viral RNA, and tRNA Shows Close Correspondence to the RNA Binding Properties of EF-Tu", Journal of Biochemistry 274(2), 666-672 (1999).

Forster, C , et al., "Discrimination between initiation and elongation of protein biosynthesis in yeast: identity assured by a nucleotide modification in the initiator tRNA", Nucleic Acids Research 21(24), 5679-5683 (1993).

Gatti, R , "SMRT compounds correct nonsense mutations in primary immunodeficiency and other genetic models", Am N Y Acad Sci 1250, 33-40 (2012).

Geiduschek, E , et al., "Transcription by RNA Polymerase III", Annu Rev Biochem 57, 873-914 (1988).

Guy, M , et al., "Identification of the determinants of tRNA function and susceptibility to rapid tRNA decay by high-throughput in vivo analysis", Genes & Development 28, 1721-1732 (2014).

Huang, Q , et al., "In vivo identification of essential nucleotides in tRNA Leu to its functions by using a constructed yeast tRNA Leu knockout strain", Nucleic Acids Research 40(20), 10463-10477 (2012).

Katrekar, D , et al., "In vivo RNA targeting of point mutations via suppressor tRNAs and adenosine deaminases", URL:https://www.biorxiv.org/content/biorxiv/early/2017/10/28/210278.full.pdf, doi:http://dx.doi.org/10.1101/210278, 25 pages (2017).

Keeling, K , et al., "Therapeutics based on stop codon readthrough", Annual Review of Genomics and Human Genetics 15(1), 371-394 (2014).

Klassen , et al., "Collaboration of tRNA modifications and elongation factor eEF1A in decoding and nonsense suppression", Scientific Reports 8(12749), pp. 1-12 (2018).

Kleina, L , et al., "Construction of Escherichia coli Amber Suppressor tRNA Genes", J Mol Biol 213, 705-717 (1990).

Koukuntla, R , et al., "U6 promoter-enhanced GlnUAG suppressor tRNA has higher suppression efficacy and can be stably expressed in 293 cells", Journal of Gene Medicine 15, 93-101 (2013).

Lueck, J , et al., "Engineered transfer RNAs for suppression of premature termination codons", Nature Communications 10(822), 1-11 (2019).

Lueck , et al., "Engineered tRNA suppression of a CFTR nonsense mutation", bioRxiv 20, pp. 1-9 (2016).

Muller, S , et al., "Spliceosomal Peptide P140 for Immunotherapy of Systemic Lupus Erythematosus Results of an Early Phase II Clinical Trial", Arthritis & Rheumatism 58 (12), 3873-3883 (2008).

Olejniczak, M , et al., "Idiosyncratic tuning of tRNAs to achieve uniform ribosome binding", Nature Structural & Molecular Biology 12(9), 788-793 (2005).

Panchal, R , et al., "Partial Functional Correction of Xeroderma Pigmentosum Group A Cells by Suppressor tRNA", Human Gene Therapy 10, 2209-2219 (1999).

Patent Cooperation Treaty , International Searching Authority, Search Report and Written Opinion for PCT/US2018/059065, 12 pages, dated Apr. 15, 2019.

Raftery, L , et al., "Systematic alterations in the anticodon arm make tRNA Glu-Suoc a more efficient suppressor", EMBO Journal 6(5), 1499-1506 (1987).

Russian Office Action , for RU Application No. 2020117787, 6 pages, dated Nov. 1, 2022. [English Translation].

Saks, M , et al., "Functional consequences of T-stem mutations in E. coli tRNAThrUGU in vitro and in vivo", RNA 17 (6), 1038-1047 (2011).

Schmid, S , et al., "A Versatile RNA Vector for Delivery of Coding and Noncoding RNAs", J Virol 88(4), 2333-2336 (2014).

Schrader, J , et al., "Tuning the affinity of aminoacyl-tRNA to elongation factor Tu for optimal decoding", PNAS 108 (13), 5215-5220 (2011).

Schrader, J , et al., "Understanding the Sequence Specificity of tRNA Binding to Elongation Factor Tu using tRNA Mutagenesis", J Mol Biol 386, 1255-1264 (2009).

Sharp, S , et al., "Structure and transcription of eukaryotic tRNA genes", Crit Rev Biochem 19(2), 107-144 (1985).

Singer, M , et al., "Genes and genomes", Moscow, "Mir" vol. 1, p. 52, Table 1.5.) (1998). [Non-English].

Sissler, M , et al., "Arginine aminoacylation identity is context-dependent and ensured by alternate recognition sets in the anticodon loop of accepting tRNA transcripts", The EMBO Journal 15(18), 5069-5076 (1996).

Temple, G , et al., "Construction of a functional human suppressor tRNA gene: an approach to gene therapy for beta-thalassaemia", Nature 296, 537-540 (1982).

Tuorto , et al., "Genome recoding by tRNA modifications", Open Biol 6(12), 1-9 (2016).

Vasil'eva, I , et al., "Influence of Nucleotide Changes in tRNAPhe on the Acceptor End Positioning in the Complex With Phenylalanyl tRNA Synthetase", Biochemistry 69, 192-203 (2004). [English Abstract].

Lueck, J , et al., "Engineered transfer RNAs for suppression of premature termination codons", bioRxiv preprint doi: https://doi.org/10.1101/400127, 25 pages, (2018).

Patent Cooperation Treaty , International Search Report and Written Opinion for PCT/US2018/059085, 11 pages, dated Feb. 21, 2019.

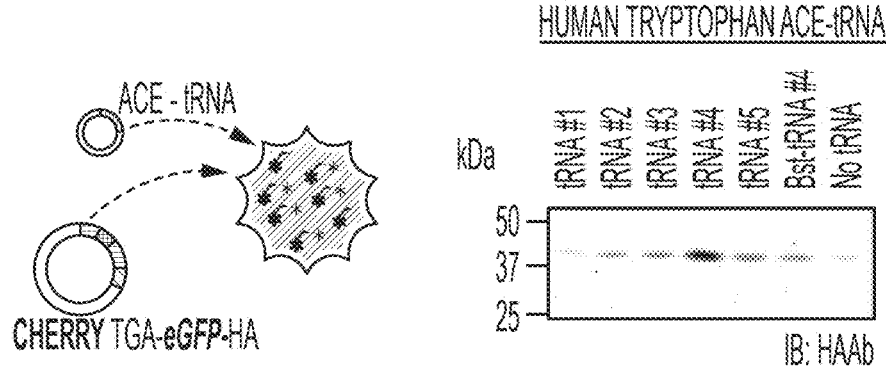
Figure 6A
Figure 6B
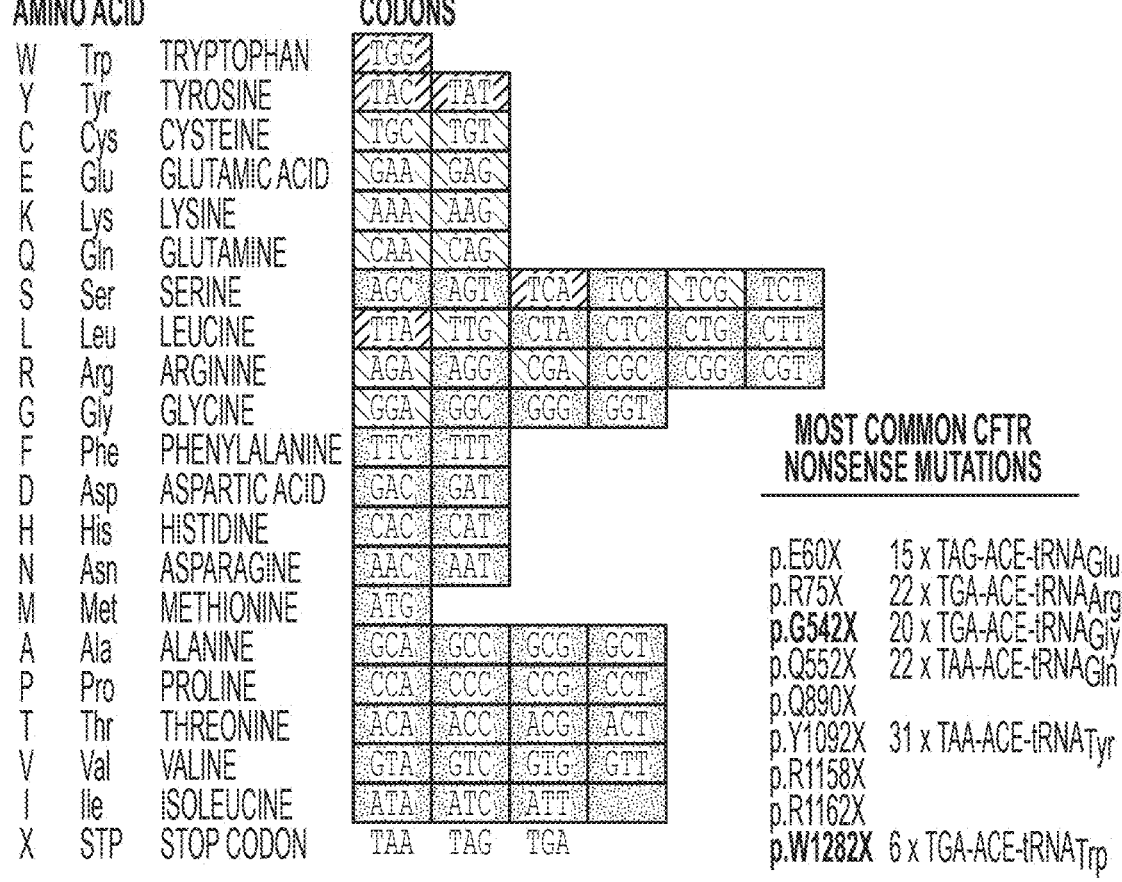
Figure 7

NLuc-PTC + ACE-tRNA/NLuc-PTC

Figure 29A

```
                                                .<<<<<.....>>>>>.......<<<<<<<<<<<,
---------------------------------------------AUCAGAAGGUUGCGUGUUCAAAUCACGUCGGGGUCA
---------------------------------------------AUCAGAAGGUUGCGUGUUCAAAUCACGUCGGGGUCA
---------------------------------------------AUCAGAAGGUUGUAUGUUCAAAUCACGUAGGGGUCA
---------------------------------------------AUCAGAAGGUUGCGUGUUCAAGUCACGUCGGGGUCA
---------------------------------------------AUCAGAAGGUUGCGUGUUCAAAUCACGUCGGGGUCA
---------------------------------------------AUCAGAAGCCUGCGUGUUGAAUCACGUCGGGGUCA

---------------------------------------------AUCAGAAGGUUGCGUGUUCAAAUCACGUCGGGGUCA
---------------------------------------------AUCAGAAGGUUGCGUGUUCAAAUCACGUCGGGGUCA
ucuuggaaauuccacggaauaagauugcaAUCGAAGGGUUGCAGGUUCAAUUCCUGUCCUUUCA
---------------------------------------------AUCGAAGGGUUGCAGGUUCAAUUCCUGUCGUUUCA
---------------------------------------------AUCAGAAGGUUGUAUGUUCAAAUCACAUAGGGGUCA
---------------------------------------------AUCAGGAGGUUGUGUGUUCAAGUCACAUCAGGGUCA
---------------------------------------------AUCAGGAGGUUGUGUGUUCAAGUCACAUCAGGGUCA
---------------------------------------------AUCAGAAGGCUGCGUGUUCGAAUCACCCCGGGGUCA
---------------------------------------------AUCAGGAGGUUGCACGUUCAAAUCAUCCCGGGGUCA
---------------------------------------------AUCAGAAGGUUGCGUGUUCAAAUCACGUCGGGGUCA
---------------------------------------------AUCAGAAGGUUGCGUAUUCAAAUCACGUCGGGGUCA
---------------------------------------------AUUAGAAGGUUGCGUGUUCAAAUCACGUCGGGGUCA
---------------------------------------------AUCAGAAGGUUGCGUGUUCAAAUCACAUCGGGGUCA
---------------------------------------------AUCAGAAGGUUGCGUGUUCAAAUCACGUCGGGGUCA
---------------------------------------------AUCAGAAGGUUGCGUGUUCAAAUCACGUCGGGGUCA
---------------------------------------------AACCGAAGGUUGUAGGUUCGAUUCCUAUUCCCCUGCCA
---------------------------------------------AUCAGAAGGUUGCGUGUUCAAAUCACGUCGGGGUCA
---------------------------------------------AUCAGAAGGUUGCGUGUUCAAAUCACGUCGGGGUCA
---------------------------------------------AACCGGGUGUCGGCAGUUCGAGCCUCUCUCCCGUG
---------------------------------------------AUCAGAAGGUUGCAUGUUCAAAUCACGUCGGGGUCA
---------------------------------------------AUCGGAAGGUUGCGUGUUCAAAUCACGUCGGGGUCA
---------------------------------------------AUCAGAAGGUUGCGUGUUCAAAUCACGUCGGGGUCA ---------------------------------------------AUCAGAAGGUUGCGUGUUCAAAUCACGUCGGGGUCA
---------------------------------------------AUCAGAAGGUUGCGUGUUCAAAUCACGUCGGGGUCA
---------------------------------------------AUCAGAAGGUUGCGUGUUCAAAUCACGUCGGGGUCA
---------------------------------------------AUCAGAAGGUUGCGUGUUCAAAUCACGUCGGGGUCA
---------------------------------------------AUCAGAAGGUUGCGUGUUCAAAUCACGUCGGGGUCA
---------------------------------------------AUCAGAAGGUUGCGUGUUCAAAUCACGUCGGGGUCA
```

Figure 29A
CONTINUED

MSFNTIIDWNSCTAEQQRQLLMRPAISASESITRTVNDILDNV
KARGDEALREYSAKFDKTTVTALKVSAEEIAAASERLSDELKQ
AMAVAVKNIETFHTAQKLPPVDVETQPGVRCQQVTRPVASVGL
YIPGGSAPLFSTVLMLATPASIAGCKKVVLCSPPPIADEILYA
AQLCGVQDVFNVGGAQAIAALAFGTESVPKVDKIFGPGNAFVT
EAKRQVSQRLDGAAIDMPAGPSEVLVIADSGATPDFVASDLLS
QAEHGPDSQVILLTPAADMARRVAEAVERQLAELPRAETARQA
LNASRLIVTKDLAQCVEISNQYGPEHLIIQTRNAREIVDSITS
AGSVFLGDWSPESAGDYASGTNHVLPTYGYTATCSSLGLADFQ
KRMTVQELSKEGFSALASTIETLAAAERLTAHKNAVTLRVNAL
KEQA*HHHHHHHHSGGSAWSHPQFEK*

Figure 30A

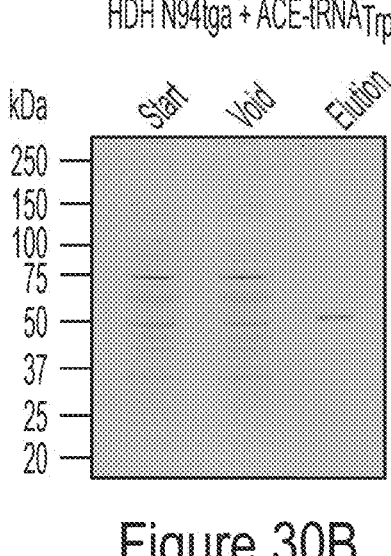

HDH N94tga + ACE-tRNA_Trp

Figure 30B

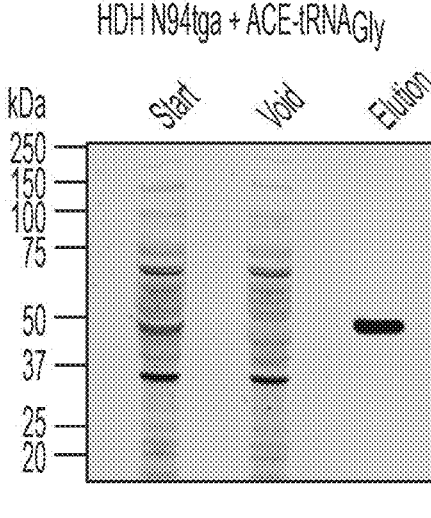

HDH N94tga + ACE-tRNA_Gly

Figure 30C

SEQUENCE LISTING

```
Sequence total quantity: 656
SEQ ID NO: 1              moltype = RNA   length = 72
FEATURE                   Location/Qualifiers
source                    1..72
                          mol_type = other RNA
                          organism = synthetic construct
tRNA                      1..72
                          note = tRNA
SEQUENCE: 1
ggcctcgtgg cgcaacggta gcgcgtctga cttcagatca gaaggttgcg ggttcaaatc   60
ccgtcggggt ca                                                        72

SEQ ID NO: 2              moltype = RNA   length = 72
FEATURE                   Location/Qualifiers
source                    1..72
                          mol_type = other RNA
                          organism = synthetic construct
tRNA                      1..72
                          note = tRNA
SEQUENCE: 2
ggcctcgtgg cgcaacggta gcgcgtctga cttcagatca gaaggttacg ggttcaaatc   60
ccgtcggggt ca                                                        72

SEQ ID NO: 3              moltype = RNA   length = 72
FEATURE                   Location/Qualifiers
source                    1..72
                          mol_type = other RNA
                          organism = synthetic construct
tRNA                      1..72
                          note = tRNA
SEQUENCE: 3
ggcctcgtgg cgcaacggta gcgcgtctga cttcagatca gaaggttccg ggttcaaatc   60
ccggcggggt ca                                                        72

SEQ ID NO: 4              moltype = RNA   length = 77
FEATURE                   Location/Qualifiers
source                    1..77
                          mol_type = other RNA
                          organism = synthetic construct
tRNA                      1..77
                          note = tRNA
SEQUENCE: 4
```

```
cgtcggctct gtggcgcaat ggatagcgca ttggacttca aattcaaagg ttgtgggttc  60
gagtcccacc agagtcg                                                  77

SEQ ID NO: 5            moltype = RNA   length = 77
FEATURE                 Location/Qualifiers
source                  1..77
                        mol_type = other RNA
                        organism = synthetic construct
tRNA                    1..77
                        note = tRNA
SEQUENCE: 5
cgtcgcccca gtggcctaat ggataaggca ctggccttca aagccaggga ttgtgggttc  60
gagtcccacc tggggtg                                                  77

SEQ ID NO: 6            moltype = RNA   length = 77
FEATURE                 Location/Qualifiers
source                  1..77
                        mol_type = other RNA
                        organism = synthetic construct
tRNA                    1..77
                        note = tRNA
SEQUENCE: 6
cgtcggctcc gtggcgcaat ggatagcgca ttggacttca aattcaaagg ttccgggttc  60
gagtcccggc ggagtcg                                                  77

SEQ ID NO: 7            moltype = RNA   length = 77
FEATURE                 Location/Qualifiers
source                  1..77
                        mol_type = other RNA
                        organism = synthetic construct
tRNA                    1..77
                        note = tRNA
SEQUENCE: 7
cgtcgcccca gtggcctaat ggataaggca ttggccttca aagccaggga ttgtgggttc  60
gagtcccatc tggggtg                                                  77

SEQ ID NO: 8            moltype = RNA   length = 77
FEATURE                 Location/Qualifiers
source                  1..77
                        mol_type = other RNA
                        organism = synthetic construct
tRNA                    1..77
                        note = tRNA
SEQUENCE: 8
cgtcggctct gtggcgcaat ggatagcgca ttggacttca aattcaaagg ttgtgggttc  60
gaatcccacc agagtcg                                                  77

SEQ ID NO: 9            moltype = RNA   length = 95
FEATURE                 Location/Qualifiers
source                  1..95
                        mol_type = other RNA
                        organism = synthetic construct
tRNA                    1..95
                        note = tRNA
SEQUENCE: 9
cgtcggctct gtggcgcaat ggatagcgca ttggacttca agctgagcct agtgtggtca  60
ttcaaaggtt gtgggttcga gtcccaccag agtcg                              95

SEQ ID NO: 10           moltype = RNA   length = 77
FEATURE                 Location/Qualifiers
source                  1..77
                        mol_type = other RNA
                        organism = synthetic construct
tRNA                    1..77
                        note = tRNA
SEQUENCE: 10
cgtcgccccg gtggcctaat ggataaggca ttggccttca aagccaggga ttgtgggttc  60
gagtcccacc cggggta                                                  77

SEQ ID NO: 11           moltype = RNA   length = 89
FEATURE                 Location/Qualifiers
source                  1..89
                        mol_type = other RNA
                        organism = synthetic construct
tRNA                    1..89
                        note = tRNA
SEQUENCE: 11
cgtcggctcc gtggcgcaat ggatagcgca ttggacttca agaggctgaa ggcattcaaa  60
ggttccgggt tcgagtcccg gcggagtcg                                     89
```

-continued

```
SEQ ID NO: 12            moltype = RNA   length = 92
FEATURE                  Location/Qualifiers
source                   1..92
                         mol_type = other RNA
                         organism = synthetic construct
tRNA                     1..92
                         note = tRNA
SEQUENCE: 12
cgtcggctct gtggcgcaat ggatagcgca ttggacttca agtgacgaat agagcaattc   60
aaaggttgtg ggttcgaatc ccaccagagt cg                                 92

SEQ ID NO: 13            moltype = RNA   length = 77
FEATURE                  Location/Qualifiers
source                   1..77
                         mol_type = other RNA
                         organism = synthetic construct
tRNA                     1..77
                         note = tRNA
SEQUENCE: 13
cgtcggccgc gtggcctaat ggataaggcg tctgacttca gatcagaaga ttgcaggttc   60
gagtcctgcc gcggtcg                                                  77

SEQ ID NO: 14            moltype = RNA   length = 77
FEATURE                  Location/Qualifiers
source                   1..77
                         mol_type = other RNA
                         organism = synthetic construct
tRNA                     1..77
                         note = tRNA
SEQUENCE: 14
cgtcgaccgc gtggcctaat ggataaggcg tctgacttca gatcagaaga ttgagggttc   60
gagtcccttc gtggtcg                                                  77

SEQ ID NO: 15            moltype = RNA   length = 90
FEATURE                  Location/Qualifiers
source                   1..90
                         mol_type = other RNA
                         organism = synthetic construct
tRNA                     1..90
                         note = tRNA
SEQUENCE: 15
cgtcggctct gtggcgcaat ggatagcgca ttggacttca agatagttag agaaattcaa   60
aggttgtggg ttcgagtccc accagagtcg                                    90

SEQ ID NO: 16            moltype = RNA   length = 76
FEATURE                  Location/Qualifiers
source                   1..76
                         mol_type = other RNA
                         organism = synthetic construct
tRNA                     1..76
                         note = tRNA
SEQUENCE: 16
cgtcggttcc atggtgtaat ggtgagcact ctggactcta aatccagcga tccgagttcg   60
agtctcggtg gaacct                                                   76

SEQ ID NO: 17            moltype = RNA   length = 76
FEATURE                  Location/Qualifiers
source                   1..76
                         mol_type = other RNA
                         organism = synthetic construct
tRNA                     1..76
                         note = tRNA
SEQUENCE: 17
cgtcggcccc atggtgtaat ggttagcact ctggactcta aatccagcga tccgagttca   60
aatctcggtg ggacct                                                   76

SEQ ID NO: 18            moltype = RNA   length = 76
FEATURE                  Location/Qualifiers
source                   1..76
                         mol_type = other RNA
                         organism = synthetic construct
tRNA                     1..76
                         note = tRNA
SEQUENCE: 18
cgtcggtccc atggtgtaat ggttagcact ctggactcta aatccagcaa tccgagttcg   60
aatctcggtg ggacct                                                   76

SEQ ID NO: 19            moltype = RNA   length = 76
```

-continued

```
FEATURE                   Location/Qualifiers
source                    1..76
                          mol_type = other RNA
                          organism = synthetic construct
tRNA                      1..76
                          note = tRNA
SEQUENCE: 19
cgtcggtccc atggtgtaat ggttagcact ctggactcta aatccagcga tccgagttca   60
aatctcggtg ggacct                                                    76

SEQ ID NO: 20             moltype = RNA   length = 76
FEATURE                   Location/Qualifiers
source                    1..76
                          mol_type = other RNA
                          organism = synthetic construct
tRNA                      1..76
                          note = tRNA
SEQUENCE: 20
cgtcggcccc atggtgtaat ggtcagcact ctggactcta aatccagcga tccgagttca   60
aatctcggtg ggaccc                                                    76

SEQ ID NO: 21             moltype = RNA   length = 76
FEATURE                   Location/Qualifiers
source                    1..76
                          mol_type = other RNA
                          organism = synthetic construct
tRNA                      1..76
                          note = tRNA
SEQUENCE: 21
cgtcggttcc atggtgtaat ggtaagcact ctggactcta aatccagcga tccgagttcg   60
agtctcggtg gaacct                                                    76

SEQ ID NO: 22             moltype = RNA   length = 76
FEATURE                   Location/Qualifiers
source                    1..76
                          mol_type = other RNA
                          organism = synthetic construct
tRNA                      1..76
                          note = tRNA
SEQUENCE: 22
cgtcggttcc atggtgtaat ggttagcact ctggactcta aatccggtaa tccgagttca   60
aatctcggtg gaacct                                                    76

SEQ ID NO: 23             moltype = RNA   length = 76
FEATURE                   Location/Qualifiers
source                    1..76
                          mol_type = other RNA
                          organism = synthetic construct
tRNA                      1..76
                          note = tRNA
SEQUENCE: 23
cgtcggttcc atggtgtaat ggttagcact ctggactcta aatccagcga tccgagttca   60
agtctcggtg gaacct                                                    76

SEQ ID NO: 24             moltype = RNA   length = 76
FEATURE                   Location/Qualifiers
source                    1..76
                          mol_type = other RNA
                          organism = synthetic construct
tRNA                      1..76
                          note = tRNA
SEQUENCE: 24
cgtcggttcc atggtgtaat ggtaagcact ctggacttta aatccagcga tccgagttcg   60
agtctcggtg gaacct                                                    76

SEQ ID NO: 25             moltype = RNA   length = 76
FEATURE                   Location/Qualifiers
source                    1..76
                          mol_type = other RNA
                          organism = synthetic construct
tRNA                      1..76
                          note = tRNA
SEQUENCE: 25
cgtcggcccc atggtgtaat ggttagcact ctggacttta aatccagcga tccgagttca   60
aatctcggtg ggacct                                                    76

SEQ ID NO: 26             moltype = RNA   length = 76
FEATURE                   Location/Qualifiers
source                    1..76
```

-continued

```
                              mol_type = other RNA
                              organism = synthetic construct
tRNA                          1..76
                              note = tRNA
SEQUENCE: 26
cgtcggttcc atggtgtaat ggtgagcact ctggacttta aatccagcga tccgagttcg   60
agtctcggtg gaacct                                                     76

SEQ ID NO: 27                 moltype = RNA   length = 76
FEATURE                       Location/Qualifiers
source                        1..76
                              mol_type = other RNA
                              organism = synthetic construct
tRNA                          1..76
                              note = tRNA
SEQUENCE: 27
cgtcggttcc atggtgtaat ggttagcact ctggacttta aatccagcga tccgagttca   60
aatctcggtg gaacct                                                     76

SEQ ID NO: 28                 moltype = RNA   length = 76
FEATURE                       Location/Qualifiers
source                        1..76
                              mol_type = other RNA
                              organism = synthetic construct
tRNA                          1..76
                              note = tRNA
SEQUENCE: 28
cgtcggtccc atggtgtaat ggttagcact ctggacttta aatccagcga tccgagttca   60
aatctcggtg ggacct                                                     76

SEQ ID NO: 29                 moltype = RNA   length = 76
FEATURE                       Location/Qualifiers
source                        1..76
                              mol_type = other RNA
                              organism = synthetic construct
tRNA                          1..76
                              note = tRNA
SEQUENCE: 29
cgtcggtccc atggtgtaat ggttagcact ctggacttta aatccagcaa tccgagttcg   60
aatctcggtg ggacct                                                     76

SEQ ID NO: 30                 moltype = RNA   length = 76
FEATURE                       Location/Qualifiers
source                        1..76
                              mol_type = other RNA
                              organism = synthetic construct
tRNA                          1..76
                              note = tRNA
SEQUENCE: 30
cgtcggttcc atggtgtaat ggttagcact ctggacttta aatccggtaa tccgagttca   60
aatctcggtg gaacct                                                     76

SEQ ID NO: 31                 moltype = RNA   length = 76
FEATURE                       Location/Qualifiers
source                        1..76
                              mol_type = other RNA
                              organism = synthetic construct
tRNA                          1..76
                              note = tRNA
SEQUENCE: 31
cgtcggcccc atggtgtaat ggtcagcact ctggacttta aatccagcga tccgagttca   60
aatctcggtg ggaccc                                                     76

SEQ ID NO: 32                 moltype = RNA   length = 76
FEATURE                       Location/Qualifiers
source                        1..76
                              mol_type = other RNA
                              organism = synthetic construct
tRNA                          1..76
                              note = tRNA
SEQUENCE: 32
cgtcggttcc atggtgtaat ggttagcact ctggacttta aatccagcga tccgagttca   60
agtctcggtg gaacct                                                     76

SEQ ID NO: 33                 moltype = RNA   length = 76
FEATURE                       Location/Qualifiers
source                        1..76
                              mol_type = other RNA
                              organism = synthetic construct
```

-continued

```
tRNA                       1..76
                           note = tRNA
SEQUENCE: 33
cgtcgacctc gtggcgcaat ggtagcgcgt ctgactctag atcagaaggt tgcgtgttca   60
agtcacgtcg gggtca                                                   76

SEQ ID NO: 34              moltype = RNA   length = 76
FEATURE                    Location/Qualifiers
source                     1..76
                           mol_type = other RNA
                           organism = synthetic construct
tRNA                       1..76
                           note = tRNA
SEQUENCE: 34
cgtcgacctc gtggcgcaac ggtagcgcgt ctgactctag atcagaaggt tgcgtgttca   60
aatcacgtcg gggtca                                                   76

SEQ ID NO: 35              moltype = RNA   length = 76
FEATURE                    Location/Qualifiers
source                     1..76
                           mol_type = other RNA
                           organism = synthetic construct
tRNA                       1..76
                           note = tRNA
SEQUENCE: 35
cgtcggcctc gtggcgcaac ggtagcgcgt ctgactctag atcagaaggt tgcgtgttca   60
aatcacgtcg gggtca                                                   76

SEQ ID NO: 36              moltype = RNA   length = 76
FEATURE                    Location/Qualifiers
source                     1..76
                           mol_type = other RNA
                           organism = synthetic construct
tRNA                       1..76
                           note = tRNA
SEQUENCE: 36
cgtcgacctc gtggcgcaac ggtagcgcgt ctgactctag atcagaaggc tgcgtgttcg   60
aatcacgtcg gggtca                                                   76

SEQ ID NO: 37              moltype = RNA   length = 76
FEATURE                    Location/Qualifiers
source                     1..76
                           mol_type = other RNA
                           organism = synthetic construct
tRNA                       1..76
                           note = tRNA
SEQUENCE: 37
cgtcgacctc gtggcgcaac ggcagcgcgt ctgactctag atcagaaggt tgcgtgttca   60
aatcacgtcg gggtca                                                   76

SEQ ID NO: 38              moltype = RNA   length = 76
FEATURE                    Location/Qualifiers
source                     1..76
                           mol_type = other RNA
                           organism = synthetic construct
tRNA                       1..76
                           note = tRNA
SEQUENCE: 38
cgtctcccac atggtctagc ggttaggatt cctggttcta acccaggcgg cccgggttcg   60
actcccggtg tgggaa                                                   76

SEQ ID NO: 39              moltype = RNA   length = 76
FEATURE                    Location/Qualifiers
source                     1..76
                           mol_type = other RNA
                           organism = synthetic construct
tRNA                       1..76
                           note = tRNA
SEQUENCE: 39
cgtctcccat atggtctagc ggttaggatt cctggttcta acccaggtgg cccgggttcg   60
actcccggta tgggaa                                                   76

SEQ ID NO: 40              moltype = RNA   length = 76
FEATURE                    Location/Qualifiers
source                     1..76
                           mol_type = other RNA
                           organism = synthetic construct
tRNA                       1..76
                           note = tRNA
```

-continued

```
SEQUENCE: 40
cgtctccctg gtggtctagt ggctaggatt cggcgctcta accgccgcgg cccgggttcg   60
attcccggtc agggaa                                                    76

SEQ ID NO: 41           moltype = RNA   length = 76
FEATURE                 Location/Qualifiers
source                  1..76
                        mol_type = other RNA
                        organism = synthetic construct
tRNA                    1..76
                        note = tRNA
SEQUENCE: 41
cgtctccctg gtggtctagt ggttaggatt cggcgctcta accgccgcgg cccgggttcg   60
attcccggtc agggaa                                                    76

SEQ ID NO: 42           moltype = RNA   length = 76
FEATURE                 Location/Qualifiers
source                  1..76
                        mol_type = other RNA
                        organism = synthetic construct
tRNA                    1..76
                        note = tRNA
SEQUENCE: 42
cgtctccctg gtggtctagt ggctaggatt cggcgctcta accgccgcgg cccgggttcg   60
attcccggcc agggaa                                                    76

SEQ ID NO: 43           moltype = RNA   length = 76
FEATURE                 Location/Qualifiers
source                  1..76
                        mol_type = other RNA
                        organism = synthetic construct
tRNA                    1..76
                        note = tRNA
SEQUENCE: 43
cgtctcccac atggtctagc ggttaggatt cctggttcta acccaggcgg cccgggttcg   60
actcccggtg tgggaa                                                    76

SEQ ID NO: 44           moltype = RNA   length = 76
FEATURE                 Location/Qualifiers
source                  1..76
                        mol_type = other RNA
                        organism = synthetic construct
tRNA                    1..76
                        note = tRNA
SEQUENCE: 44
cgtctcccat atggtctagc ggttaggatt cctggttcta acccaggtgg cccgggttcg   60
actcccggta tgggaa                                                    76

SEQ ID NO: 45           moltype = RNA   length = 76
FEATURE                 Location/Qualifiers
source                  1..76
                        mol_type = other RNA
                        organism = synthetic construct
tRNA                    1..76
                        note = tRNA
SEQUENCE: 45
cgtctccctg gtggtctagt ggttaggatt cggcgctcta accgccgcgg cccgggttcg   60
attcccggtc agggaa                                                    76

SEQ ID NO: 46           moltype = RNA   length = 76
FEATURE                 Location/Qualifiers
source                  1..76
                        mol_type = other RNA
                        organism = synthetic construct
tRNA                    1..76
                        note = tRNA
SEQUENCE: 46
cgtctccctg gtggtctagt ggttaggatt cggcgctcta accgccgcgg cccgggttcg   60
attcccggtc aggaaa                                                    76

SEQ ID NO: 47           moltype = RNA   length = 76
FEATURE                 Location/Qualifiers
source                  1..76
                        mol_type = other RNA
                        organism = synthetic construct
tRNA                    1..76
                        note = tRNA
SEQUENCE: 47
cgtctccctg gtggtctagt ggctaggatt cggcgctcta accgccgcgg cccgggttcg   60
```

-continued

```
attcccggcc agggaa                                                        76

SEQ ID NO: 48              moltype = RNA   length = 72
FEATURE                    Location/Qualifiers
source                     1..72
                           mol_type = other RNA
                           organism = synthetic construct
tRNA                       1..72
                           note = tRNA
SEQUENCE: 48
ggcctcgtgg cgcaacggta gcgcgtctga cttcagatca gaaggttgcg tgttcaaatc    60
acgtcggggt ca                                                           72

SEQ ID NO: 49              moltype = RNA   length = 72
FEATURE                    Location/Qualifiers
source                     1..72
                           mol_type = other RNA
                           organism = synthetic construct
tRNA                       1..72
                           note = tRNA
SEQUENCE: 49
gacctcgtgg cgcaatggta gcgcgtctga cttcagatca gaaggttgcg tgttcaagtc    60
acgtcggggt ca                                                           72

SEQ ID NO: 50              moltype = RNA   length = 72
FEATURE                    Location/Qualifiers
source                     1..72
                           mol_type = other RNA
                           organism = synthetic construct
tRNA                       1..72
                           note = tRNA
SEQUENCE: 50
gacctcgtgg cgcaacggta gcgcgtctga cttcagatca gaaggttgcg tgttcaaatc    60
acgtcggggt ca                                                           72

SEQ ID NO: 51              moltype = RNA   length = 72
FEATURE                    Location/Qualifiers
source                     1..72
                           mol_type = other RNA
                           organism = synthetic construct
tRNA                       1..72
                           note = tRNA
SEQUENCE: 51
gacctcgtgg cgcaacggta gcgcgtctga cttcagatca gaaggctgcg tgttcgaatc    60
acgtcggggt ca                                                           72

SEQ ID NO: 52              moltype = RNA   length = 72
FEATURE                    Location/Qualifiers
source                     1..72
                           mol_type = other RNA
                           organism = synthetic construct
tRNA                       1..72
                           note = tRNA
SEQUENCE: 52
gacctcgtgg cgcaacggca gcgcgtctga cttcagatca gaaggttgcg tgttcaaatc    60
acgtcggggt ca                                                           72

SEQ ID NO: 53              moltype = RNA   length = 72
FEATURE                    Location/Qualifiers
source                     1..72
                           mol_type = other RNA
                           organism = synthetic construct
tRNA                       1..72
                           note = tRNA
SEQUENCE: 53
gcgttggtgg tatagtggtt agcatagctg ccttcaaagc agttgacccg ggttcgattc    60
ccggccaacg ca                                                           72

SEQ ID NO: 54              moltype = RNA   length = 72
FEATURE                    Location/Qualifiers
source                     1..72
                           mol_type = other RNA
                           organism = synthetic construct
tRNA                       1..72
                           note = tRNA
SEQUENCE: 54
gcgttggtgg tatagtggtg agcatagctg ccttcaaagc agttgacccg ggttcgattc    60
ccggccaacg ca                                                           72
```

-continued

```
SEQ ID NO: 55          moltype = RNA   length = 72
FEATURE                Location/Qualifiers
source                 1..72
                       mol_type = other RNA
                       organism = synthetic construct
tRNA                   1..72
                       note = tRNA
SEQUENCE: 55
gcgttggtgg tatagtggta agcatagctg ccttcaaagc agttgacccg ggttcgattc    60
ccggccaacg ca                                                        72

SEQ ID NO: 56          moltype = RNA   length = 72
FEATURE                Location/Qualifiers
source                 1..72
                       mol_type = other RNA
                       organism = synthetic construct
tRNA                   1..72
                       note = tRNA
SEQUENCE: 56
ggcctcgtgg cgcaacggta gcgcgtctga cttcagatca gaaggttgcg tgttcaaatc    60
acgtcggggt ca                                                        72

SEQ ID NO: 57          moltype = RNA   length = 72
FEATURE                Location/Qualifiers
source                 1..72
                       mol_type = other RNA
                       organism = synthetic construct
tRNA                   1..72
                       note = tRNA
SEQUENCE: 57
gacctcgtgg cgcaatggta gcgcgtctga cttcagatca gaaggttgcg tgttcaagtc    60
acgtcggggt ca                                                        72

SEQ ID NO: 58          moltype = RNA   length = 72
FEATURE                Location/Qualifiers
source                 1..72
                       mol_type = other RNA
                       organism = synthetic construct
tRNA                   1..72
                       note = tRNA
SEQUENCE: 58
gacctcgtgg cgcaacggta gcgcgtctga cttcagatca gaaggttgcg tgttcaaatc    60
acgtcggggt ca                                                        72

SEQ ID NO: 59          moltype = RNA   length = 72
FEATURE                Location/Qualifiers
source                 1..72
                       mol_type = other RNA
                       organism = synthetic construct
tRNA                   1..72
                       note = tRNA
SEQUENCE: 59
gacctcgtgg cgcaacggta gcgcgtctga cttcagatca gaaggctgcg tgttcgaatc    60
acgtcggggt ca                                                        72

SEQ ID NO: 60          moltype = RNA   length = 72
FEATURE                Location/Qualifiers
source                 1..72
                       mol_type = other RNA
                       organism = synthetic construct
tRNA                   1..72
                       note = tRNA
SEQUENCE: 60
gacctcgtgg cgcaacggca gcgcgtctga cttcagatca gaaggttgcg tgttcaaatc    60
acgtcggggt ca                                                        72

SEQ ID NO: 61          moltype = RNA   length = 72
FEATURE                Location/Qualifiers
source                 1..72
                       mol_type = other RNA
                       organism = synthetic construct
tRNA                   1..72
                       note = tRNA
SEQUENCE: 61
ggcctcatgg tgcaacagta gtgtgtctga cttcagatca gaaggttgta tgttcaaatc    60
acgtaggggt ca                                                        72

SEQ ID NO: 62          moltype = RNA   length = 72
FEATURE                Location/Qualifiers
```

-continued

```
source                    1..72
                          mol_type = other RNA
                          organism = synthetic construct
tRNA                      1..72
                          note = tRNA
SEQUENCE: 62
ggcctcgtgg cgcaacggta gcgcgtctga ctctagatca gaaggttgcg tgttcaaatc  60
acgtcggggt ca                                                      72

SEQ ID NO: 63             moltype = RNA   length = 72
FEATURE                   Location/Qualifiers
source                    1..72
                          mol_type = other RNA
                          organism = synthetic construct
tRNA                      1..72
                          note = tRNA
SEQUENCE: 63
gacctcgtgg cgcaatggta gcgcgtctga ctctagatca gaaggttgcg tgttcaagtc  60
acgtcggggt ca                                                      72

SEQ ID NO: 64             moltype = RNA   length = 72
FEATURE                   Location/Qualifiers
source                    1..72
                          mol_type = other RNA
                          organism = synthetic construct
tRNA                      1..72
                          note = tRNA
SEQUENCE: 64
gacctcgtgg cgcaacggta gcgcgtctga ctctagatca gaaggttgcg tgttcaaatc  60
acgtcggggt ca                                                      72

SEQ ID NO: 65             moltype = RNA   length = 72
FEATURE                   Location/Qualifiers
source                    1..72
                          mol_type = other RNA
                          organism = synthetic construct
tRNA                      1..72
                          note = tRNA
SEQUENCE: 65
gacctcgtgg cgcaacggta gcgcgtctga ctctagatca gaaggctgcg tgttcgaatc  60
acgtcggggt ca                                                      72

SEQ ID NO: 66             moltype = RNA   length = 72
FEATURE                   Location/Qualifiers
source                    1..72
                          mol_type = other RNA
                          organism = synthetic construct
tRNA                      1..72
                          note = tRNA
SEQUENCE: 66
gacctcgtgg cgcaacggca gcgcgtctga ctctagatca gaaggttgcg tgttcaaatc  60
acgtcggggt ca                                                      72

SEQ ID NO: 67             moltype = RNA   length = 72
FEATURE                   Location/Qualifiers
source                    1..72
                          mol_type = other RNA
                          organism = synthetic construct
tRNA                      1..72
                          note = tRNA
SEQUENCE: 67
ggcctcatgg tgcaacagta gtgtgtctga ctctagatca gaaggttgta tgttcaaatc  60
acgtaggggt ca                                                      72

SEQ ID NO: 68             moltype = RNA   length = 71
FEATURE                   Location/Qualifiers
source                    1..71
                          mol_type = other RNA
                          organism = synthetic construct
tRNA                      1..71
                          note = tRNA
SEQUENCE: 68
gcattggtgg ttcagtggta gaattctcgc cttcaacgcg ggagacccgg gttcaattcc  60
cggccaatgc a                                                       71

SEQ ID NO: 69             moltype = RNA   length = 72
FEATURE                   Location/Qualifiers
source                    1..72
                          mol_type = other RNA
```

-continued

```
                          organism = synthetic construct
tRNA                      1..72
                          note = tRNA
SEQUENCE: 69
gcgccgctgg tgtagtggta tcatgcaaga tttcaaattc ttgcgacccg ggttcgattc   60
ccgggcggcg ca                                                        72

SEQ ID NO: 70             moltype = RNA   length = 71
FEATURE                   Location/Qualifiers
source                    1..71
                          mol_type = other RNA
                          organism = synthetic construct
tRNA                      1..71
                          note = tRNA
SEQUENCE: 70
gcattggtgg ttcaatggta gaattctcgc cttcaacgca ggagacccag gttcgattcc   60
tggccaatgc a                                                         71

SEQ ID NO: 71             moltype = RNA   length = 71
FEATURE                   Location/Qualifiers
source                    1..71
                          mol_type = other RNA
                          organism = synthetic construct
tRNA                      1..71
                          note = tRNA
SEQUENCE: 71
gcgttggtgg tttagtggta gaattctcgc cttcaatgcg ggagacccgg gttcaattcc   60
cggccactgc a                                                         71

SEQ ID NO: 72             moltype = RNA   length = 71
FEATURE                   Location/Qualifiers
source                    1..71
                          mol_type = other RNA
                          organism = synthetic construct
tRNA                      1..71
                          note = tRNA
SEQUENCE: 72
gccttggtgg tgcagtggta gaattctcgc cttcaacgtg ggagacccgg gttcaattcc   60
cggccaatgc a                                                         71

SEQ ID NO: 73             moltype = RNA   length = 61
FEATURE                   Location/Qualifiers
source                    1..61
                          mol_type = other RNA
                          organism = synthetic construct
tRNA                      1..61
                          note = tRNA
SEQUENCE: 73
ggtggttcag tggtagaatt ctcgccttca acgcgggaga cccgggttta attcccggtc   60
a                                                                    61

SEQ ID NO: 74             moltype = RNA   length = 61
FEATURE                   Location/Qualifiers
source                    1..61
                          mol_type = other RNA
                          organism = synthetic construct
tRNA                      1..61
                          note = tRNA
SEQUENCE: 74
gtggtctagt ggttaggatt cagcgcttca accgccgcag cccgggttcg attcccggtc   60
a                                                                    61

SEQ ID NO: 75             moltype = RNA   length = 71
FEATURE                   Location/Qualifiers
source                    1..71
                          mol_type = other RNA
                          organism = synthetic construct
tRNA                      1..71
                          note = tRNA
SEQUENCE: 75
gcgtcagtgg tttagtggtg gaattcctgc cttcaatgca cgagatccgt gttcaactcc   60
tggttggtgc a                                                         71

SEQ ID NO: 76             moltype = RNA   length = 72
FEATURE                   Location/Qualifiers
source                    1..72
                          mol_type = other RNA
                          organism = synthetic construct
tRNA                      1..72
```

-continued

```
                              note = tRNA
SEQUENCE: 76
gcgtcagtgg ttttagtggt ggaattcctg ccttcaatgc acgagatccg tgttcaactc   60
ctggttggtg ca                                                        72

SEQ ID NO: 77            moltype = RNA   length = 71
FEATURE                  Location/Qualifiers
source                   1..71
                         mol_type = other RNA
                         organism = synthetic construct
tRNA                     1..71
                         note = tRNA
SEQUENCE: 77
gcgttggcag ttcagtggta gaattctcgc cttcaacccg ggagacctgg attccatttc   60
cggcaaatgc a                                                         71

SEQ ID NO: 78            moltype = RNA   length = 71
FEATURE                  Location/Qualifiers
source                   1..71
                         mol_type = other RNA
                         organism = synthetic construct
tRNA                     1..71
                         note = tRNA
SEQUENCE: 78
gcatgggtgg ttcagtggta gaattctcgc cttcaacgcg ggaggcccgg gttcgattcc   60
cggcccatgc a                                                         71

SEQ ID NO: 79            moltype = RNA   length = 71
FEATURE                  Location/Qualifiers
source                   1..71
                         mol_type = other RNA
                         organism = synthetic construct
tRNA                     1..71
                         note = tRNA
SEQUENCE: 79
gcattggtgg ttcagtggta gaattctcgc cttcaacgcg ggaggcccgg gttcgattcc   60
cggccaatgc a                                                         71

SEQ ID NO: 80            moltype = RNA   length = 71
FEATURE                  Location/Qualifiers
source                   1..71
                         mol_type = other RNA
                         organism = synthetic construct
tRNA                     1..71
                         note = tRNA
SEQUENCE: 80
gcattggtgg ttcagtggta gaattctcgc cttcaacgcg ggaggcccgg gtttgattcc   60
cggccagtgc a                                                         71

SEQ ID NO: 81            moltype = RNA   length = 71
FEATURE                  Location/Qualifiers
source                   1..71
                         mol_type = other RNA
                         organism = synthetic construct
tRNA                     1..71
                         note = tRNA
SEQUENCE: 81
gcataggtgg ttcagtggta gaattcttgc cttcaacgca ggaggcccag gtttgattcc   60
tggcccatgc a                                                         71

SEQ ID NO: 82            moltype = RNA   length = 71
FEATURE                  Location/Qualifiers
source                   1..71
                         mol_type = other RNA
                         organism = synthetic construct
tRNA                     1..71
                         note = tRNA
SEQUENCE: 82
gcattggtgg ttcagtggta gaattctcgc cttcaatgcg ggcggccggg cttcgattcc   60
tggccaatgc a                                                         71

SEQ ID NO: 83            moltype = RNA   length = 71
FEATURE                  Location/Qualifiers
source                   1..71
                         mol_type = other RNA
                         organism = synthetic construct
tRNA                     1..71
                         note = tRNA
SEQUENCE: 83
```

-continued

```
gcatgggtga ttcagtggta gaattttcac cttcaatgca ggaggtccag gttcatttcc  60
tggcctatgc a                                                         71

SEQ ID NO: 84          moltype = RNA   length = 72
FEATURE                Location/Qualifiers
source                 1..72
                       mol_type = other RNA
                       organism = synthetic construct
tRNA                   1..72
                       note = tRNA
SEQUENCE: 84
gcgttggtgg tatagtggtt agcatagctg ccttcaaagc agttgacccg ggttcgattc  60
ccggccaacg ca                                                        72

SEQ ID NO: 85          moltype = RNA   length = 72
FEATURE                Location/Qualifiers
source                 1..72
                       mol_type = other RNA
                       organism = synthetic construct
tRNA                   1..72
                       note = tRNA
SEQUENCE: 85
gcgttggtgg tatagtggtg agcatagctg ccttcaaagc agttgacccg ggttcgattc  60
ccggccaacg ca                                                        72

SEQ ID NO: 86          moltype = RNA   length = 72
FEATURE                Location/Qualifiers
source                 1..72
                       mol_type = other RNA
                       organism = synthetic construct
tRNA                   1..72
                       note = tRNA
SEQUENCE: 86
gcgttggtgg tatagtggta agcatagctg ccttcaaagc agttgacccg ggttcgattc  60
ccggccaacg ca                                                        72

SEQ ID NO: 87          moltype = RNA   length = 72
FEATURE                Location/Qualifiers
source                 1..72
                       mol_type = other RNA
                       organism = synthetic construct
tRNA                   1..72
                       note = tRNA
SEQUENCE: 87
gcgttggtgg tatagtggtg agcatagttg ccttcaaagc agttgacccg ggctcgattc  60
ccgcccaacg ca                                                        72

SEQ ID NO: 88          moltype = RNA   length = 72
FEATURE                Location/Qualifiers
source                 1..72
                       mol_type = other RNA
                       organism = synthetic construct
tRNA                   1..72
                       note = tRNA
SEQUENCE: 88
gcgttggtgg tatagtggtg agcatagttg ccttcaaagc agttgacccg ggctcgattc  60
ccggccaacg ca                                                        72

SEQ ID NO: 89          moltype = RNA   length = 73
FEATURE                Location/Qualifiers
source                 1..73
                       mol_type = other RNA
                       organism = synthetic construct
tRNA                   1..73
                       note = tRNA
SEQUENCE: 89
gggccagtgg cgcaatggat aacgcgtctg acttcagatc agaagattcc aggttcgact  60
cctggctggc tcg                                                       73

SEQ ID NO: 90          moltype = RNA   length = 73
FEATURE                Location/Qualifiers
source                 1..73
                       mol_type = other RNA
                       organism = synthetic construct
tRNA                   1..73
                       note = tRNA
SEQUENCE: 90
gggccagtgg cgcaatggat aacgcgtctg acttcagatc agaagattct aggttcgact  60
cctggctggc tcg                                                       73
```

-continued

```
SEQ ID NO: 91              moltype = RNA   length = 73
FEATURE                    Location/Qualifiers
source                     1..73
                           mol_type = other RNA
                           organism = synthetic construct
tRNA                       1..73
                           note = tRNA
SEQUENCE: 91
ggccgcgtgg cctaatggat aaggcgtctg atttcagatc agaagattga gggttcgagt   60
cccttcgtgg tcg                                                      73

SEQ ID NO: 92              moltype = RNA   length = 73
FEATURE                    Location/Qualifiers
source                     1..73
                           mol_type = other RNA
                           organism = synthetic construct
tRNA                       1..73
                           note = tRNA
SEQUENCE: 92
gacccagtgg cctaatggat aaggcatcag ccttcagagc tgggattgt gggttcgagt    60
cccatctggg tcg                                                      73

SEQ ID NO: 93              moltype = RNA   length = 73
FEATURE                    Location/Qualifiers
source                     1..73
                           mol_type = other RNA
                           organism = synthetic construct
tRNA                       1..73
                           note = tRNA
SEQUENCE: 93
gccccagtgg cctaatggat aaggcactgg ccttcaaagc cagggattgt gggttcgagt   60
cccacctggg gta                                                      73

SEQ ID NO: 94              moltype = RNA   length = 73
FEATURE                    Location/Qualifiers
source                     1..73
                           mol_type = other RNA
                           organism = synthetic construct
tRNA                       1..73
                           note = tRNA
SEQUENCE: 94
gccccagtgg cctaatggat aaggcactgg ccttcaaagc cagggattgt gggttcgagt   60
cccacctggg gtg                                                      73

SEQ ID NO: 95              moltype = RNA   length = 73
FEATURE                    Location/Qualifiers
source                     1..73
                           mol_type = other RNA
                           organism = synthetic construct
tRNA                       1..73
                           note = tRNA
SEQUENCE: 95
gccccggtgg cctaatggat aaggcattgg ccttcaaagc cagggattgt gggttcgagt   60
cccacccggg gta                                                      73

SEQ ID NO: 96              moltype = RNA   length = 73
FEATURE                    Location/Qualifiers
source                     1..73
                           mol_type = other RNA
                           organism = synthetic construct
tRNA                       1..73
                           note = tRNA
SEQUENCE: 96
gccccagtgg cctaatggat aaggcattgg ccttcaaagc cagggattgt gggttcgagt   60
cccatctggg gtg                                                      73

SEQ ID NO: 97              moltype = RNA   length = 73
FEATURE                    Location/Qualifiers
source                     1..73
                           mol_type = other RNA
                           organism = synthetic construct
tRNA                       1..73
                           note = tRNA
SEQUENCE: 97
gccccagtgg cctgatggat aaggtactgg ccttcaaagc cagggattgt gggttcgagt   60
tccacctggg gta                                                      73

SEQ ID NO: 98              moltype = RNA   length = 73
```

-continued

```
FEATURE                 Location/Qualifiers
source                  1..73
                        mol_type = other RNA
                        organism = synthetic construct
tRNA                    1..73
                        note = tRNA
SEQUENCE: 98
ggccgcgtgg cctaatggat aaggcgtctg acttcagatc agaagattgc aggttcgagt   60
cctgccgcgg tcg                                                       73

SEQ ID NO: 99          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 99
gaccacgtgg cctaatggat aaggcgtctg acttcagatc agaagattga gggttcgaat   60
ccctccgtgg tta                                                       73

SEQ ID NO: 100         moltype = RNA   length = 73
FEATURE                 Location/Qualifiers
source                  1..73
                        mol_type = other RNA
                        organism = synthetic construct
tRNA                    1..73
                        note = tRNA
SEQUENCE: 100
gaccgcgtgg cctaatggat aaggcgtctg acttcagatc agaagattga gggttcgagt   60
cccttcgtgg tcg                                                       73

SEQ ID NO: 101         moltype = RNA   length = 73
FEATURE                 Location/Qualifiers
source                  1..73
                        mol_type = other RNA
                        organism = synthetic construct
tRNA                    1..73
                        note = tRNA
SEQUENCE: 101
gaccacgtgg cctaatggat aaggcgtctg acttcagatc agaagattga gggttcgaat   60
cccttcgtgg tta                                                       73

SEQ ID NO: 102         moltype = RNA   length = 73
FEATURE                 Location/Qualifiers
source                  1..73
                        mol_type = other RNA
                        organism = synthetic construct
tRNA                    1..73
                        note = tRNA
SEQUENCE: 102
gaccacgtgg cctaatggat aaggcgtctg acttcagatc agaagattga gggttcgaat   60
cccttcgtgg ttg                                                       73

SEQ ID NO: 103         moltype = RNA   length = 73
FEATURE                 Location/Qualifiers
source                  1..73
                        mol_type = other RNA
                        organism = synthetic construct
tRNA                    1..73
                        note = tRNA
SEQUENCE: 103
ggccgtgtgg cctaatggat aaggcgtctg acttcagatc aaaagattgc aggtttgagt   60
tctgccacgg tcg                                                       73

SEQ ID NO: 104         moltype = RNA   length = 85
FEATURE                 Location/Qualifiers
source                  1..85
                        mol_type = other RNA
                        organism = synthetic construct
tRNA                    1..85
                        note = tRNA
SEQUENCE: 104
ggctccgtgg cgcaatggat agcgcattgg acttcaagag gctgaaggca ttcaaaggtt   60
ccgggttcga gtcccggcgg agtcg                                          85

SEQ ID NO: 105         moltype = RNA   length = 73
FEATURE                 Location/Qualifiers
source                  1..73
```

```
                                 mol_type = other RNA
                                 organism = synthetic construct
tRNA                             1..73
                                 note = tRNA
SEQUENCE: 105
ggctccgtgg cgcaatggat agcgcattgg acttcaaatt caaaggttcc gggttcgagt   60
cccggcggag tcg                                                       73

SEQ ID NO: 106          moltype = RNA  length = 88
FEATURE                 Location/Qualifiers
source                  1..88
                        mol_type = other RNA
                        organism = synthetic construct
tRNA                    1..88
                        note = tRNA
SEQUENCE: 106
ggctctgtgg cgcaatggat agcgcattgg acttcaagtg acgaatagag caattcaaag   60
gttgtgggtt cgaatcccac cagagtcg                                       88

SEQ ID NO: 107          moltype = RNA  length = 73
FEATURE                 Location/Qualifiers
source                  1..73
                        mol_type = other RNA
                        organism = synthetic construct
tRNA                    1..73
                        note = tRNA
SEQUENCE: 107
ggctctgtgg cgcaatggat agcgcattgg acttcaaatt caaaggttgt gggttcgaat   60
cccaccagag tcg                                                       73

SEQ ID NO: 108          moltype = RNA  length = 91
FEATURE                 Location/Qualifiers
source                  1..91
                        mol_type = other RNA
                        organism = synthetic construct
tRNA                    1..91
                        note = tRNA
SEQUENCE: 108
ggctctgtgg cgcaatggat agcgcattgg acttcaagct gagcctagtg tggtcattca   60
aaggttgtgg gttcgagtcc caccagagtc g                                   91

SEQ ID NO: 109          moltype = RNA  length = 73
FEATURE                 Location/Qualifiers
source                  1..73
                        mol_type = other RNA
                        organism = synthetic construct
tRNA                    1..73
                        note = tRNA
SEQUENCE: 109
ggctctgtgg cgcaatggat agcgcattgg acttcaaatt caaaggttgt gggttcgagt   60
cccaccagag tcg                                                       73

SEQ ID NO: 110          moltype = RNA  length = 86
FEATURE                 Location/Qualifiers
source                  1..86
                        mol_type = other RNA
                        organism = synthetic construct
tRNA                    1..86
                        note = tRNA
SEQUENCE: 110
ggctctgtgg cgcaatggat agcgcattgg acttcaagat agttagagaa attcaaaggt   60
tgtgggttcg agtcccacca gagtcg                                         86

SEQ ID NO: 111          moltype = RNA  length = 74
FEATURE                 Location/Qualifiers
source                  1..74
                        mol_type = other RNA
                        organism = synthetic construct
tRNA                    1..74
                        note = tRNA
SEQUENCE: 111
gtctctgtgg cgcaatggac gagcgcgctg gacttcaaat ccagaggttc cgggttcgag   60
tcccggcaga gatg                                                      74

SEQ ID NO: 112          moltype = RNA  length = 87
FEATURE                 Location/Qualifiers
source                  1..87
                        mol_type = other RNA
                        organism = synthetic construct
```

-continued

```
tRNA                    1..87
                        note = tRNA
SEQUENCE: 112
ggctctgtgg cgcaatggat agcgcattgg acttcaagcc taaatcaaga gattcaaagg   60
ttgcgggttc gagtccctcc agagtcg                                       87

SEQ ID NO: 113          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 113
ggctctgtgg cgcaatggat agcgcattgg acttcaaatt caaaggttgc gggttcgagt   60
ccctccagag tcg                                                      73

SEQ ID NO: 114          moltype = RNA   length = 69
FEATURE                 Location/Qualifiers
source                  1..69
                        mol_type = other RNA
                        organism = synthetic construct
tRNA                    1..69
                        note = tRNA
SEQUENCE: 114
ggcagcatag cagagtggtt caggttacag gttcaagatg taaactgagt tcaaatccca   60
gttctgcca                                                           69

SEQ ID NO: 115          moltype = RNA   length = 57
FEATURE                 Location/Qualifiers
source                  1..57
                        mol_type = other RNA
                        organism = synthetic construct
tRNA                    1..57
                        note = tRNA
SEQUENCE: 115
tggtgtaata ggtagcacag agaattctag attctcaggg gtaggttcaa ttcctat      57

SEQ ID NO: 116          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 116
taggacatgg tgtgataggt agcatggaga attctagatt ctcaggggta ggttcaattc   60
ctacagttct ag                                                       72

SEQ ID NO: 117          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 117
taggacgtgg tgtgataggt agcatgggga attctagatt ctcaggggtg ggttcaattc   60
ctatagttct ag                                                       72

SEQ ID NO: 118          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 118
taggacgtgg tgtagtaggt agcatggaga atgctaaatt ctcaggggta ggttcaattc   60
ctatagttct ag                                                       72

SEQ ID NO: 119          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 119
```

-continued

```
taggacatgg tgtaataggt agaatggaga attctaaatt ctcaggggta ggttcaattc   60
ctatagttct ag                                                        72

SEQ ID NO: 120        moltype = RNA   length = 72
FEATURE               Location/Qualifiers
source                1..72
                      mol_type = other RNA
                      organism = synthetic construct
tRNA                  1..72
                      note = tRNA
SEQUENCE: 120
taggatgtgg tgtattaggt agcacagaga attctagatt ctcaggggta ggttcgattc   60
ctataattct ac                                                        72

SEQ ID NO: 121        moltype = RNA   length = 72
FEATURE               Location/Qualifiers
source                1..72
                      mol_type = other RNA
                      organism = synthetic construct
tRNA                  1..72
                      note = tRNA
SEQUENCE: 121
taggacttgg tgtaatgggt agcacagaga attctagatt ctcaggggtg ggttcaattc   60
ctttcgtcct ag                                                        72

SEQ ID NO: 122        moltype = RNA   length = 75
FEATURE               Location/Qualifiers
source                1..75
                      mol_type = other RNA
                      organism = synthetic construct
tRNA                  1..75
                      note = tRNA
SEQUENCE: 122
tctaggatgt ggtgtgatag gtagcatgga gaattctaga ttctcagggg taggttcaat   60
tcctatattc tagaa                                                     75

SEQ ID NO: 123        moltype = RNA   length = 72
FEATURE               Location/Qualifiers
source                1..72
                      mol_type = other RNA
                      organism = synthetic construct
tRNA                  1..72
                      note = tRNA
SEQUENCE: 123
taggacgtgg tgtgataggt agcatggaga attctagatt ctcagggatg ggttcaattc   60
ctatagtcct ag                                                        72

SEQ ID NO: 124        moltype = RNA   length = 72
FEATURE               Location/Qualifiers
source                1..72
                      mol_type = other RNA
                      organism = synthetic construct
tRNA                  1..72
                      note = tRNA
SEQUENCE: 124
taggacgtgg tgtgataggt agcacggaga attctagatt ctcagggatg ggttcaattc   60
ctgtagttct ag                                                        72

SEQ ID NO: 125        moltype = RNA   length = 72
FEATURE               Location/Qualifiers
source                1..72
                      mol_type = other RNA
                      organism = synthetic construct
tRNA                  1..72
                      note = tRNA
SEQUENCE: 125
ggttccatgg tgtaatggtt agcactctgg actctaaatc cagcgatccg agttcaaatc   60
tcggtggaac ct                                                        72

SEQ ID NO: 126        moltype = RNA   length = 72
FEATURE               Location/Qualifiers
source                1..72
                      mol_type = other RNA
                      organism = synthetic construct
tRNA                  1..72
                      note = tRNA
SEQUENCE: 126
ggttccatgg tgtaatggtg accactttgg actctaaata cagtgatcag agttcaagtc   60
tcactggaac ct                                                        72
```

-continued

```
SEQ ID NO: 127            moltype = RNA  length = 72
FEATURE                   Location/Qualifiers
source                    1..72
                          mol_type = other RNA
                          organism = synthetic construct
tRNA                      1..72
                          note = tRNA
SEQUENCE: 127
ggttccatgg tgtaatggtg agggctttgg actctaacta cagtgatcag agttcaagtc   60
tcagtgggac ct                                                       72

SEQ ID NO: 128            moltype = RNA  length = 73
FEATURE                   Location/Qualifiers
source                    1..73
                          mol_type = other RNA
                          organism = synthetic construct
tRNA                      1..73
                          note = tRNA
SEQUENCE: 128
ggttccatgg tgtaatggta agcaccctgg actctaaatc cagcaaccag agttccagtc   60
tcagcgtgga cct                                                      73

SEQ ID NO: 129            moltype = RNA  length = 72
FEATURE                   Location/Qualifiers
source                    1..72
                          mol_type = other RNA
                          organism = synthetic construct
tRNA                      1..72
                          note = tRNA
SEQUENCE: 129
ggtagtgtag tctactggtt aaacgcttgg gctctaacat taacgtcctg ggttcaaatc   60
ccagctttgt ca                                                       72

SEQ ID NO: 130            moltype = RNA  length = 72
FEATURE                   Location/Qualifiers
source                    1..72
                          mol_type = other RNA
                          organism = synthetic construct
tRNA                      1..72
                          note = tRNA
SEQUENCE: 130
ggttccatgg tgtaatggtt agcactctgg actctaaatc cagcgatccg agttcaagtc   60
tcggtggaac ct                                                       72

SEQ ID NO: 131            moltype = RNA  length = 72
FEATURE                   Location/Qualifiers
source                    1..72
                          mol_type = other RNA
                          organism = synthetic construct
tRNA                      1..72
                          note = tRNA
SEQUENCE: 131
ggttccatgg tgtaatggtg agcactctgg actctaaatc cagcgatccg agttcgagtc   60
tcggtggaac ct                                                       72

SEQ ID NO: 132            moltype = RNA  length = 72
FEATURE                   Location/Qualifiers
source                    1..72
                          mol_type = other RNA
                          organism = synthetic construct
rRNA                      1..72
                          note = tRNA
SEQUENCE: 132
ggttccatgg tgtaatggta agcactctgg actctaaatc cagcgatccg agttcgagtc   60
tcggtggaac ct                                                       72

SEQ ID NO: 133            moltype = RNA  length = 72
FEATURE                   Location/Qualifiers
source                    1..72
                          mol_type = other RNA
                          organism = synthetic construct
tRNA                      1..72
                          note = tRNA
SEQUENCE: 133
ggttccatgg tgtaatggtt agcactctgg actctaaatc cggtaatccg agttcaaatc   60
tcggtggaac ct                                                       72

SEQ ID NO: 134            moltype = RNA  length = 72
```

-continued

```
FEATURE                 Location/Qualifiers
source                  1..72
                        mol_type = other RNA
                        organism = synthetic construct
tRNA                    1..72
                        note = tRNA
SEQUENCE: 134
ggccccatgg tgtaatggtc agcactctgg actctaaatc cagcgatccg agttcaaatc   60
tcggtgggac cc                                                       72

SEQ ID NO: 135          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 135
ggttccatgg tgtaatggta agcactctgg actctaaatc cagccatctg agttcgagtc   60
tctgtggaac ct                                                       72

SEQ ID NO: 136          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 136
ggttccatgg tgtaatggtg agcactttgg actctaaata cagtgatcag agttcaagtc   60
tcactgggac ct                                                       72

SEQ ID NO: 137          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 137
ggttccatgg gttaatggtg agcaccctgg actctaaatc aagcgatccg agttcaaatc   60
tcggtggtac ct                                                       72

SEQ ID NO: 138          moltype = RNA   length = 68
FEATURE                 Location/Qualifiers
source                  1..68
                        mol_type = other RNA
                        organism = synthetic construct
tRNA                    1..68
                        note = tRNA
SEQUENCE: 138
gtttccatgg tgtaatggtg agcactctgg actctaaatc cagaaataca ttcaaagaat   60
taagaaca                                                            68

SEQ ID NO: 139          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 139
ggtcccatgg tgtaatggtt agcactctgg actctaaatc cagcgatccg agttcaaatc   60
tcggtgggac ct                                                       72

SEQ ID NO: 140          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 140
ggtcccatgg tgtaatggtt agcactctgg actctaaatc cagcaatccg agttcgaatc   60
tcggtgggac ct                                                       72

SEQ ID NO: 141          moltype = RNA   length = 72
FEATURE                 Location/Qualifiers
source                  1..72
```

-continued

```
                              mol_type = other RNA
                              organism = synthetic construct
tRNA                          1..72
                              note = tRNA
SEQUENCE: 141
ggccccatgg tgtaatggtt agcactctgg actctaaatc cagcgatccg agttcaaatc  60
tcggtgggac ct                                                       72

SEQ ID NO: 142           moltype = RNA   length = 72
FEATURE                  Location/Qualifiers
source                   1..72
                         mol_type = other RNA
                         organism = synthetic construct
tRNA                     1..72
                         note = tRNA
SEQUENCE: 142
ggtcccatgg tgtaatggtt agcactctgg gctctaaatc cagcaatccg agttcgaatc  60
ttggtgggac ct                                                       72

SEQ ID NO: 143           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 143
ggctgtgtac ctcagtgggc aagggtatgg actctaaagc cagactattt gggttcaaat  60
cccagcttgg cct                                                      73

SEQ ID NO: 144           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 144
gaccatgtgg cctaagggaa aagacatctc actctaggtc agaagattga gggttcaagt  60
cctttcatgg tca                                                      73

SEQ ID NO: 145           moltype = RNA   length = 74
FEATURE                  Location/Qualifiers
source                   1..74
                         mol_type = other RNA
                         organism = synthetic construct
tRNA                     1..74
                         note = tRNA
SEQUENCE: 145
ggtacagtgt taaaggggag aaaaattgct gactctaaat acagtagacc taggtttgaa  60
tcctggcttt acca                                                     74

SEQ ID NO: 146           moltype = RNA   length = 57
FEATURE                  Location/Qualifiers
source                   1..57
                         mol_type = other RNA
                         organism = synthetic construct
tRNA                     1..57
                         note = tRNA
SEQUENCE: 146
tggtgtaata ggtagcacag agaattttag attctcaggg gtaggttcaa ttcctat      57

SEQ ID NO: 147           moltype = RNA   length = 72
FEATURE                  Location/Qualifiers
source                   1..72
                         mol_type = other RNA
                         organism = synthetic construct
tRNA                     1..72
                         note = tRNA
SEQUENCE: 147
taggacatgg tgtgataggt agcatggaga attttagatt ctcagggta ggttcaattc   60
ctacagttct ag                                                       72

SEQ ID NO: 148           moltype = RNA   length = 72
FEATURE                  Location/Qualifiers
source                   1..72
                         mol_type = other RNA
                         organism = synthetic construct
tRNA                     1..72
```

```
                              note = tRNA
SEQUENCE: 148
taggacgtgg tgtgataggt agcatgggga attttagatt ctcaggggtg ggttcaattc    60
ctatagttct ag                                                        72

SEQ ID NO: 149          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 149
taggacgtgg tgtagtaggt agcatggaga atgttaaatt ctcaggggta ggttcaattc    60
ctatagttct ag                                                        72

SEQ ID NO: 150          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 150
taggacatgg tgtaataggt agaatggaga attttaaatt ctcaggggta ggttcaattc    60
ctatagttct ag                                                        72

SEQ ID NO: 151          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 151
taggatgtgg tgtattaggt agcacagaga attttagatt ctcaggggta ggttcgattc    60
ctataattct ac                                                        72

SEQ ID NO: 152          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 152
taggacttgg tgtaatgggt agcacagaga attttagatt ctcaggggtg ggttcaattc    60
ctttcgtcct ag                                                        72

SEQ ID NO: 153          moltype = RNA   length = 75
FEATURE                 Location/Qualifiers
source                  1..75
                        mol_type = other RNA
                        organism = synthetic construct
tRNA                    1..75
                        note = tRNA
SEQUENCE: 153
tctaggatgt ggtgtgatag gtagcatgga gaattttaga ttctcagggg taggttcaat    60
tcctatattc tagaa                                                     75

SEQ ID NO: 154          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 154
taggacgtgg tgtgataggt agcatggaga attttagatt ctcagggatg ggttcaattc    60
ctatagtcct ag                                                        72

SEQ ID NO: 155          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 155
```

-continued

```
taggacgtgg tgtgataggt agcacggaga attttagatt ctcagggatg ggttcaattc    60
ctgtagttct ag                                                         72

SEQ ID NO: 156          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 156
ggttccatgg tgtaatggtt agcactctgg actttaaatc cagcgatccg agttcaaatc    60
tcggtggaac ct                                                         72

SEQ ID NO: 157          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 157
ggttccatgg tgtaatggtg accactttgg actttaaata cagtgatcag agttcaagtc    60
tcactggaac ct                                                         72

SEQ ID NO: 158          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 158
ggttccatgg tgtaatggtg agggctttgg actttaacta cagtgatcag agttcaagtc    60
tcagtgggac ct                                                         72

SEQ ID NO: 159          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 159
ggttccatgg tgtaatggta agcaccctgg actttaaatc cagcaaccag agttccagtc    60
tcagcgtgga cct                                                        73

SEQ ID NO: 160          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 160
ggtagtgtag tctactggtt aaacgcttgg gctttaacat taacgtcctg ggttcaaatc    60
ccagctttgt ca                                                         72

SEQ ID NO: 161          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 161
ggttccatgg tgtaatggtt agcactctgg actttaaatc cagcgatccg agttcaagtc    60
tcggtggaac ct                                                         72

SEQ ID NO: 162          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 162
ggttccatgg tgtaatggtg agcactctgg actttaaatc cagcgatccg agttcgagtc    60
tcggtggaac ct                                                         72
```

-continued

```
SEQ ID NO: 163          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 163
ggttccatgg tgtaatggta agcactctgg actttaaatc cagcgatccg agttcgagtc   60
tcggtggaac ct                                                       72

SEQ ID NO: 164          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 164
ggttccatgg tgtaatggtt agcactctgg actttaaatc cggtaatccg agttcaaatc   60
tcggtggaac ct                                                       72

SEQ ID NO: 165          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 165
ggccccatgg tgtaatggtc agcactctgg actttaaatc cagcgatccg agttcaaatc   60
tcggtgggac cc                                                       72

SEQ ID NO: 166          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 166
ggttccatgg tgtaatggta agcactctgg actttaaatc cagccatctg agttcgagtc   60
tctgtggaac ct                                                       72

SEQ ID NO: 167          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 167
ggttccatgg tgtaatggtg agcactttgg actttaaata cagtgatcag agttcaagtc   60
tcactgggac ct                                                       72

SEQ ID NO: 168          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 168
ggttccatgg gttaatggtg agcaccctgg actttaaatc aagcgatccg agttcaaatc   60
tcggtggtac ct                                                       72

SEQ ID NO: 169          moltype = RNA   length = 68
FEATURE                 Location/Qualifiers
source                  1..68
                        mol_type = other RNA
                        organism = synthetic construct
tRNA                    1..68
                        note = tRNA
SEQUENCE: 169
gtttccatgg tgtaatggtg agcactctgg actttaaatc cagaaataca ttcaaagaat   60
taagaaca                                                            68

SEQ ID NO: 170          moltype = RNA   length = 72
```

```
FEATURE               Location/Qualifiers
source                1..72
                      mol_type = other RNA
                      organism = synthetic construct
tRNA                  1..72
                      note = tRNA
SEQUENCE: 170
ggtcccatgg tgtaatggtt agcactctgg actttaaatc cagcgatccg agttcaaatc   60
tcggtgggac ct                                                      72

SEQ ID NO: 171        moltype = RNA   length = 72
FEATURE               Location/Qualifiers
source                1..72
                      mol_type = other RNA
                      organism = synthetic construct
tRNA                  1..72
                      note = tRNA
SEQUENCE: 171
ggtcccatgg tgtaatggtt agcactctgg actttaaatc cagcaatccg agttcgaatc   60
tcggtgggac ct                                                      72

SEQ ID NO: 172        moltype = RNA   length = 72
FEATURE               Location/Qualifiers
source                1..72
                      mol_type = other RNA
                      organism = synthetic construct
tRNA                  1..72
                      note = tRNA
SEQUENCE: 172
ggccccatgg tgtaatggtt agcactctgg actttaaatc cagcgatccg agttcaaatc   60
tcggtgggac ct                                                      72

SEQ ID NO: 173        moltype = RNA   length = 72
FEATURE               Location/Qualifiers
source                1..72
                      mol_type = other RNA
                      organism = synthetic construct
tRNA                  1..72
                      note = tRNA
SEQUENCE: 173
ggtcccatgg tgtaatggtt agcactctgg gctttaaatc cagcaatccg agttcgaatc   60
ttggtgggac ct                                                      72

SEQ ID NO: 174        moltype = RNA   length = 73
FEATURE               Location/Qualifiers
source                1..73
                      mol_type = other RNA
                      organism = synthetic construct
tRNA                  1..73
                      note = tRNA
SEQUENCE: 174
ggctgtgtac ctcagtgggc aagggtatgg actttaaagc cagactattt gggttcaaat   60
cccagcttgg cct                                                     73

SEQ ID NO: 175        moltype = RNA   length = 73
FEATURE               Location/Qualifiers
source                1..73
                      mol_type = other RNA
                      organism = synthetic construct
tRNA                  1..73
                      note = tRNA
SEQUENCE: 175
gaccatgtgg cctaagggaa aagacatctc actttaggtc agaagattga gggttcaagt   60
cctttcatgg tca                                                     73

SEQ ID NO: 176        moltype = RNA   length = 74
FEATURE               Location/Qualifiers
source                1..74
                      mol_type = other RNA
                      organism = synthetic construct
tRNA                  1..74
                      note = tRNA
SEQUENCE: 176
ggtacagtgt taaaggggag aaaaattgct gactttaaat acagtagacc taggtttgaa   60
tcctggcttt acca                                                    74

SEQ ID NO: 177        moltype = RNA   length = 72
FEATURE               Location/Qualifiers
source                1..72
```

-continued

```
                           mol_type = other RNA
                           organism = synthetic construct
tRNA                       1..72
                           note = tRNA
SEQUENCE: 177
tccctggtgg tctagtggtt aggattcggc gctttaaccg ccgcggcccg ggttcgattc      60
ccggtcaggg aa                                                          72

SEQ ID NO: 178             moltype = RNA   length = 72
FEATURE                    Location/Qualifiers
source                     1..72
                           mol_type = other RNA
                           organism = synthetic construct
tRNA                       1..72
                           note = tRNA
SEQUENCE: 178
tccctggtgg tctagtggtt aggattcggc gctttaaccg ccgcggcccg ggttcgattc      60
ccggtcagga aa                                                          72

SEQ ID NO: 179             moltype = RNA   length = 72
FEATURE                    Location/Qualifiers
source                     1..72
                           mol_type = other RNA
                           organism = synthetic construct
tRNA                       1..72
                           note = tRNA
SEQUENCE: 179
cccctggtgg tctagtgctt aggattcggt gctttaaccg ctgctgcctg cgttcgattc      60
ccggtcaggg aa                                                          72

SEQ ID NO: 180             moltype = RNA   length = 71
FEATURE                    Location/Qualifiers
source                     1..71
                           mol_type = other RNA
                           organism = synthetic construct
tRNA                       1..71
                           note = tRNA
SEQUENCE: 180
tccttgatgt ctagtggtta ggatttggtg ctttaactgc agcagcctgg gttcatttct      60
cagtcaggga a                                                           71

SEQ ID NO: 181             moltype = RNA   length = 72
FEATURE                    Location/Qualifiers
source                     1..72
                           mol_type = other RNA
                           organism = synthetic construct
tRNA                       1..72
                           note = tRNA
SEQUENCE: 181
tcccatatgg tctagcggtt aggattcctg gtttttaaccc aggtggcccg ggttcgactc     60
ccggtatggg aa                                                          72

SEQ ID NO: 182             moltype = RNA   length = 73
FEATURE                    Location/Qualifiers
source                     1..73
                           mol_type = other RNA
                           organism = synthetic construct
tRNA                       1..73
                           note = tRNA
SEQUENCE: 182
tccgtggtgg tctagtggct aggattcggc gctttaaccg cctgcagctc gagttcgatt      60
cctggtcagg gaa                                                         73

SEQ ID NO: 183             moltype = RNA   length = 69
FEATURE                    Location/Qualifiers
source                     1..69
                           mol_type = other RNA
                           organism = synthetic construct
tRNA                       1..69
                           note = tRNA
SEQUENCE: 183
ccctgtggtc tagtggctaa gactttgtgc tttaattgct gcatcctagg ttcaattccc      60
agtcaggga                                                              69

SEQ ID NO: 184             moltype = RNA   length = 72
FEATURE                    Location/Qualifiers
source                     1..72
                           mol_type = other RNA
                           organism = synthetic construct
```

```
tRNA                      1..72
                          note = tRNA
SEQUENCE: 184
tcccacatgg tctagcggtt aggattcctg gttttaaccc aggcggcccg ggttcgactc   60
ccggtgtggg aa                                                       72

SEQ ID NO: 185           moltype = RNA   length = 72
FEATURE                  Location/Qualifiers
source                   1..72
                         mol_type = other RNA
                         organism = synthetic construct
tRNA                     1..72
                         note = tRNA
SEQUENCE: 185
tccctggtgg tctagtggct aggattcggc gctttaaccg ccgcggcccg ggttcgattc   60
ccggccaggg aa                                                       72

SEQ ID NO: 186           moltype = RNA   length = 72
FEATURE                  Location/Qualifiers
source                   1..72
                         mol_type = other RNA
                         organism = synthetic construct
tRNA                     1..72
                         note = tRNA
SEQUENCE: 186
tccctggtgg tctagtggct aggattcggc gctttaaccg ccgcggcccg ggttcgattc   60
ccggtcaggg aa                                                       72

SEQ ID NO: 187           moltype = RNA   length = 72
FEATURE                  Location/Qualifiers
source                   1..72
                         mol_type = other RNA
                         organism = synthetic construct
tRNA                     1..72
                         note = tRNA
SEQUENCE: 187
gcgttggtgg tgtagtggtg agcacagctg cctttaaagc agttaacgcg ggttcgattc   60
ccgggtaacg aa                                                       72

SEQ ID NO: 188           moltype = RNA   length = 72
FEATURE                  Location/Qualifiers
source                   1..72
                         mol_type = other RNA
                         organism = synthetic construct
tRNA                     1..72
                         note = tRNA
SEQUENCE: 188
tccttggtgg tctagtggct aggattcggt gctttaacct gtgcggcccg ggttcaattc   60
ccgatgaagg aa                                                       72

SEQ ID NO: 189           moltype = RNA   length = 72
FEATURE                  Location/Qualifiers
source                   1..72
                         mol_type = other RNA
                         organism = synthetic construct
tRNA                     1..72
                         note = tRNA
SEQUENCE: 189
tgtctggtgg tcaagtggct aggatttggc gctttaactg ccgcggcccg cgttcgattc   60
ccggtcaggg aa                                                       72

SEQ ID NO: 190           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 190
tccctggtgg tctagtggct aggattcggc gctttaaccg cctgcagctc gagttcgatt   60
cctggtcagg gaa                                                      73

SEQ ID NO: 191           moltype = RNA   length = 71
FEATURE                  Location/Qualifiers
source                   1..71
                         mol_type = other RNA
                         organism = synthetic construct
tRNA                     1..71
                         note = tRNA
```

-continued

```
SEQUENCE: 191
gcaatggtgg ttcagtggta gaattctcgc ctttaacaca ggagacccgg gttcaattcc   60
tgacccatgt a                                                         71

SEQ ID NO: 192          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 192
tccctggtgg tctagtggtt aggattcggc gctctaaccg ccgcggcccg ggttcgattc   60
ccggtcaggg aa                                                        72

SEQ ID NO: 193          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 193
tccctggtgg tctagtggtt aggattcggc gctctaaccg ccgcggcccg ggttcgattc   60
ccggtcagga aa                                                        72

SEQ ID NO: 194          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 194
cccctggtgg tctagtgctt aggattcggt gctctaaccg ctgctgcctg cgttcgattc   60
ccggtcaggg aa                                                        72

SEQ ID NO: 195          moltype = RNA   length = 71
FEATURE                 Location/Qualifiers
source                  1..71
                        mol_type = other RNA
                        organism = synthetic construct
tRNA                    1..71
                        note = tRNA
SEQUENCE: 195
tccttgatgt ctagtggtta ggatttggtg ctctaactgc agcagcctgg gttcatttct   60
cagtcaggga a                                                         71

SEQ ID NO: 196          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 196
tcccatatgg tctagcggtt aggattcctg gttctaaccc aggtggcccg ggttcgactc   60
ccggtatggg aa                                                        72

SEQ ID NO: 197          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 197
tccgtggtgg tctagtggct aggattcggc gctctaaccg cctgcagctc gagttcgatt   60
cctggtcagg gaa                                                       73

SEQ ID NO: 198          moltype = RNA   length = 69
FEATURE                 Location/Qualifiers
source                  1..69
                        mol_type = other RNA
                        organism = synthetic construct
tRNA                    1..69
                        note = tRNA
SEQUENCE: 198
ccctgtggtc tagtggctaa gactttgtgc tctaattgct gcatcctagg ttcaattccc   60
```

-continued

```
agtcaggga                                                                    69

SEQ ID NO: 199          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 199
tcccacatgg tctagcggtt aggattcctg gttctaaccc aggcggcccg ggttcgactc   60
ccggtgtggg aa                                                        72

SEQ ID NO: 200          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 200
tccctggtgg tctagtggct aggattcggc gctctaaccg ccgcggcccg ggttcgattc   60
ccggccaggg aa                                                        72

SEQ ID NO: 201          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 201
tccctggtgg tctagtggct aggattcggc gctctaaccg ccgcggcccg ggttcgattc   60
ccggtcaggg aa                                                        72

SEQ ID NO: 202          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 202
gcgttggtgg tgtagtggtg agcacagctg cctctaaagc agttaacgcg ggttcgattc   60
ccgggtaacg aa                                                        72

SEQ ID NO: 203          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 203
tccttggtgg tctagtggct aggattcggt gctctaacct gtgcggcccg ggttcaattc   60
ccgatgaagg aa                                                        72

SEQ ID NO: 204          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 204
tgtctggtgg tcaagtggct aggatttggc gctctaactg ccgcggcccg cgttcgattc   60
ccggtcaggg aa                                                        72

SEQ ID NO: 205          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 205
tccctggtgg tctagtggct aggattcggc gctctaaccg cctgcagctc gagttcgatt   60
cctggtcagg gaa                                                       73
```

```
SEQ ID NO: 206          moltype = RNA   length = 74
FEATURE                 Location/Qualifiers
source                  1..74
                        mol_type = other RNA
                        organism = synthetic construct
tRNA                    1..74
                        note = tRNA
SEQUENCE: 206
gcaatggtgg ttcagtggta gaattctcgc ctctactaac acaggagacc cgggttcaat   60
tcctgaccca tgta                                                      74

SEQ ID NO: 207          moltype = RNA   length = 93
FEATURE                 Location/Qualifiers
source                  1..93
                        mol_type = other RNA
                        organism = synthetic construct
tRNA                    1..93
                        note = tRNA
SEQUENCE: 207
ccttcaatag ttcagctggt agagcagagg actttagcta cttcctcagt aggagacgtc   60
cttaggttgc tggttcgatt ccagcttgaa gga                                 93

SEQ ID NO: 208          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 208
ccttcaatag ttcagctggt agagcagagg actttaggtc cttaggttgc tggttcgatt   60
ccagcttgaa gga                                                       73

SEQ ID NO: 209          moltype = RNA   length = 65
FEATURE                 Location/Qualifiers
source                  1..65
                        mol_type = other RNA
                        organism = synthetic construct
tRNA                    1..65
                        note = tRNA
SEQUENCE: 209
ggtaaaatgg ctgagtaagc tttagacttt aaaatctaaa gagagattga gctctctttt   60
tacca                                                                65

SEQ ID NO: 210          moltype = RNA   length = 66
FEATURE                 Location/Qualifiers
source                  1..66
                        mol_type = other RNA
                        organism = synthetic construct
tRNA                    1..66
                        note = tRNA
SEQUENCE: 210
ggtaaaatga ctgagtaagc attagacttt aaatctaaag acagaggtca agacctcttt   60
ttacca                                                               66

SEQ ID NO: 211          moltype = RNA   length = 66
FEATURE                 Location/Qualifiers
source                  1..66
                        mol_type = other RNA
                        organism = synthetic construct
tRNA                    1..66
                        note = tRNA
SEQUENCE: 211
ggtaaaatgg ctgagtaagc attagacttt aaatctaaag acagaggtca aggcctcttt   60
ttacca                                                               66

SEQ ID NO: 212          moltype = RNA   length = 64
FEATURE                 Location/Qualifiers
source                  1..64
                        mol_type = other RNA
                        organism = synthetic construct
tRNA                    1..64
                        note = tRNA
SEQUENCE: 212
ggtaaaatgg ctgagtaagc attagacttt aaatctaaag acagaggtca aggccttttt   60
acca                                                                 64

SEQ ID NO: 213          moltype = RNA   length = 91
FEATURE                 Location/Qualifiers
```

-continued

```
source                  1..91
                        mol_type = other RNA
                        organism = synthetic construct
tRNA                    1..91
                        note = tRNA
SEQUENCE: 213
ccttcgatag ctcagttggt agagcggagg actttagttg gctgtgtcct tagacatcct   60
taggtcgctg gttcgaatcc ggctcgaagg a                                  91

SEQ ID NO: 214          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 214
ccttcgatag ctcagttggt agagcggagg actttagatc cttaggtcgc tggttcgaat   60
ccggctcgaa gga                                                     73

SEQ ID NO: 215          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 215
gggggtatag ctcagggcta gagctttttg actttagagc aagaggtccc tggttcaaat   60
ccaggttctc cct                                                     73

SEQ ID NO: 216          moltype = RNA   length = 61
FEATURE                 Location/Qualifiers
source                  1..61
                        mol_type = other RNA
                        organism = synthetic construct
tRNA                    1..61
                        note = tRNA
SEQUENCE: 216
tatagctcag tggtagagca tttaacttta gatcaagagg tccctggatc aactctgggt   60
g                                                                  61

SEQ ID NO: 217          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 217
gtcagtgttg cacaacggtt aagtgaagag gctttaaacc cagactggat gggttcaatt   60
cccatctctg ccg                                                     73

SEQ ID NO: 218          moltype = RNA   length = 89
FEATURE                 Location/Qualifiers
source                  1..89
                        mol_type = other RNA
                        organism = synthetic construct
tRNA                    1..89
                        note = tRNA
SEQUENCE: 218
ccttcgatag ctcagttggt agagcggagg actttagtgg atagggcgtg gcaatcctta   60
ggtcgctggt tcgattccgg ctcgaagga                                    89

SEQ ID NO: 219          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 219
ccttcgatag ctcagttggt agagcggagg actttagatc cttaggtcgc tggttcgatt   60
ccggctcgaa gga                                                     73

SEQ ID NO: 220          moltype = RNA   length = 89
FEATURE                 Location/Qualifiers
source                  1..89
                        mol_type = other RNA
```

```
                         organism = synthetic construct
tRNA                     1..89
                         note = tRNA
SEQUENCE: 220
ccttcgatag ctcagttggt agagcggagg actttaggct cattaagcaa ggtatcctta  60
ggtcgctggt tcgaatccgg ctcggagga                                     89

SEQ ID NO: 221           moltype = RNA  length = 73
FEATURE                  Location/Qualifiers
source                   1..73
                         mol_type = other RNA
                         organism = synthetic construct
tRNA                     1..73
                         note = tRNA
SEQUENCE: 221
ccttcgatag ctcagttggt agagcggagg actttagatc cttaggtcgc tggttcgaat  60
ccggctcgga gga                                                      73

SEQ ID NO: 222           moltype = RNA  length = 94
FEATURE                  Location/Qualifiers
source                   1..94
                         mol_type = other RNA
                         organism = synthetic construct
tRNA                     1..94
                         note = tRNA
SEQUENCE: 222
ccttcgatag ctcagctggt agagcggagg actttagatt gtatagacat ttgcggacat  60
ccttaggtcg ctggttcgat tccagctcga agga                               94

SEQ ID NO: 223           moltype = RNA  length = 73
FEATURE                  Location/Qualifiers
source                   1..73
                         mol_type = other RNA
                         organism = synthetic construct
tRNA                     1..73
                         note = tRNA
SEQUENCE: 223
ccttcgatag ctcagctggt agagcggagg actttagatc cttaggtcgc tggttcgatt  60
ccagctcgaa gga                                                      73

SEQ ID NO: 224           moltype = RNA  length = 93
FEATURE                  Location/Qualifiers
source                   1..93
                         mol_type = other RNA
                         organism = synthetic construct
tRNA                     1..93
                         note = tRNA
SEQUENCE: 224
ccttcgatag ctcagctggt agagcggagg actttagcta cttcctcagc aggagacatc  60
cttaggtcgc tggttcgatt ccggctcgaa gga                                93

SEQ ID NO: 225           moltype = RNA  length = 73
FEATURE                  Location/Qualifiers
source                   1..73
                         mol_type = other RNA
                         organism = synthetic construct
tRNA                     1..73
                         note = tRNA
SEQUENCE: 225
ccttcgatag ctcagctggt agagcggagg actttagatc cttaggtcgc tggttcgatt  60
ccggctcgaa gga                                                      73

SEQ ID NO: 226           moltype = RNA  length = 89
FEATURE                  Location/Qualifiers
source                   1..89
                         mol_type = other RNA
                         organism = synthetic construct
tRNA                     1..89
                         note = tRNA
SEQUENCE: 226
ccttcgatag ctcagctggt agagcggagg actttaggcg cgcgcccgtg gccatcctta  60
ggtcgctggt tcgattccgg ctcgaagga                                     89

SEQ ID NO: 227           moltype = RNA  length = 73
FEATURE                  Location/Qualifiers
source                   1..73
                         mol_type = other RNA
                         organism = synthetic construct
tRNA                     1..73
```

-continued

```
                              note = tRNA
SEQUENCE: 227
ccttcgatag ctcagctggt agagcggagg actttagatc cttaggtcgc tggttcgatt    60
ccggctcgaa gga                                                      73

SEQ ID NO: 228               moltype = RNA   length = 95
FEATURE                      Location/Qualifiers
source                       1..95
                             mol_type = other RNA
                             organism = synthetic construct
tRNA                         1..95
                             note = tRNA
SEQUENCE: 228
ccttcgatag ctcagctggt agagcggagg actttaagcc tgtagaaaca tttgtggaca    60
tccttaggtc gctggttcga ttccggctcg aagga                              95

SEQ ID NO: 229               moltype = RNA   length = 73
FEATURE                      Location/Qualifiers
source                       1..73
                             mol_type = other RNA
                             organism = synthetic construct
tRNA                         1..73
                             note = tRNA
SEQUENCE: 229
ccttcgatag ctcagctggt agagcggagg actttagatc cttaggtcgc tggttcgatt    60
ccggctcgaa gga                                                      73

SEQ ID NO: 230               moltype = RNA   length = 94
FEATURE                      Location/Qualifiers
source                       1..94
                             mol_type = other RNA
                             organism = synthetic construct
tRNA                         1..94
                             note = tRNA
SEQUENCE: 230
ccttcgatag ctcagctggt agagcggagg actttagatt gtacagacat ttgcggacat    60
ccttaggtcg ctggttcgat tccggctcga agga                               94

SEQ ID NO: 231               moltype = RNA   length = 73
FEATURE                      Location/Qualifiers
source                       1..73
                             mol_type = other RNA
                             organism = synthetic construct
tRNA                         1..73
                             note = tRNA
SEQUENCE: 231
ccttcgatag ctcagctggt agagcggagg actttagatc cttaggtcgc tggttcgatt    60
ccggctcgaa gga                                                      73

SEQ ID NO: 232               moltype = RNA   length = 89
FEATURE                      Location/Qualifiers
source                       1..89
                             mol_type = other RNA
                             organism = synthetic construct
tRNA                         1..89
                             note = tRNA
SEQUENCE: 232
ccttcgatag ctcagctggt agagcggagg actttagtac ttaatgtgtg gtcatcctta    60
ggtcgctggt tcgattccgg ctcgaagga                                     89

SEQ ID NO: 233               moltype = RNA   length = 73
FEATURE                      Location/Qualifiers
source                       1..73
                             mol_type = other RNA
                             organism = synthetic construct
tRNA                         1..73
                             note = tRNA
SEQUENCE: 233
ccttcgatag ctcagctggt agagcggagg actttagatc cttaggtcgc tggttcgatt    60
ccggctcgaa gga                                                      73

SEQ ID NO: 234               moltype = RNA   length = 89
FEATURE                      Location/Qualifiers
source                       1..89
                             mol_type = other RNA
                             organism = synthetic construct
tRNA                         1..89
                             note = tRNA
SEQUENCE: 234
```

-continued

```
ccttcgatag ctcagctggt agagcggagg actttagggg tttgaatgtg gtcatcctta   60
ggtcgctggt tcgaatccgg ctcggagga                                      89

SEQ ID NO: 235          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 235
ccttcgatag ctcagctggt agagcggagg actttagatc cttaggtcgc tggttcgaat   60
ccggctcgga gga                                                       73

SEQ ID NO: 236          moltype = RNA   length = 94
FEATURE                 Location/Qualifiers
source                  1..94
                        mol_type = other RNA
                        organism = synthetic construct
tRNA                    1..94
                        note = tRNA
SEQUENCE: 236
ccttcgatag ctcagctggt agagcggagg actttagact gcggaaacgt ttgtggacat   60
ccttaggtcg ctggttcaat tccggctcga agga                                94

SEQ ID NO: 237          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 237
ccttcgatag ctcagctggt agagcggagg actttagatc cttaggtcgc tggttcaatt   60
ccggctcgaa gga                                                       73

SEQ ID NO: 238          moltype = RNA   length = 90
FEATURE                 Location/Qualifiers
source                  1..90
                        mol_type = other RNA
                        organism = synthetic construct
tRNA                    1..90
                        note = tRNA
SEQUENCE: 238
ctttcgatag ctcagttggt agagcggagg actttaggtt cattaaacta aggcatcctt   60
aggtcgctgg ttcgaatccg gctcgaagga                                     90

SEQ ID NO: 239          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 239
ctttcgatag ctcagttggt agagcggagg actttagatc cttaggtcgc tggttcgaat   60
ccggctcgaa gga                                                       73

SEQ ID NO: 240          moltype = RNA   length = 89
FEATURE                 Location/Qualifiers
source                  1..89
                        mol_type = other RNA
                        organism = synthetic construct
tRNA                    1..89
                        note = tRNA
SEQUENCE: 240
tcttcaatag ctcagctggt agagcggagg actttaaggt gcacgcccgt ggccattctt   60
aggtgctggt ttgattccga cttggagag                                      89

SEQ ID NO: 241          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 241
tcttcaatag ctcagctggt agagcggagg actttagatt cttaggtgct ggtttgattc   60
cgacttggag ag                                                        72
```

-continued

```
SEQ ID NO: 242          moltype = RNA   length = 66
FEATURE                 Location/Qualifiers
source                  1..66
                        mol_type = other RNA
                        organism = synthetic construct
tRNA                    1..66
                        note = tRNA
SEQUENCE: 242
ggtaaaatgg ctgagtgaag cattggactt taaatctaaa gacaggggtt aagcctcttt    60
ttacca                                                               66

SEQ ID NO: 243          moltype = RNA   length = 66
FEATURE                 Location/Qualifiers
source                  1..66
                        mol_type = other RNA
                        organism = synthetic construct
tRNA                    1..66
                        note = tRNA
SEQUENCE: 243
ggtaaaatgg ctgagcaagc attggacttt aaatctaaag acagatgttg agccatcttt    60
ttagca                                                               66

SEQ ID NO: 244          moltype = RNA   length = 66
FEATURE                 Location/Qualifiers
source                  1..66
                        mol_type = other RNA
                        organism = synthetic construct
tRNA                    1..66
                        note = tRNA
SEQUENCE: 244
ggtaaaatgg ctgagtgaag cattggactt taaatctaaa gacaggggct aagcctcttt    60
ttacca                                                               66

SEQ ID NO: 245          moltype = RNA   length = 66
FEATURE                 Location/Qualifiers
source                  1..66
                        mol_type = other RNA
                        organism = synthetic construct
tRNA                    1..66
                        note = tRNA
SEQUENCE: 245
ggtaaaatgg ctgagcaagc attagacttt aaatctaaag acagaggtta aggcctcttt    60
ttacca                                                               66

SEQ ID NO: 246          moltype = RNA   length = 66
FEATURE                 Location/Qualifiers
source                  1..66
                        mol_type = other RNA
                        organism = synthetic construct
tRNA                    1..66
                        note = tRNA
SEQUENCE: 246
ggtaaaatgg ctgagtaagc attagacttt aaatctaaag acagaggtca aggcctcttt    60
tttcct                                                               66

SEQ ID NO: 247          moltype = RNA   length = 67
FEATURE                 Location/Qualifiers
source                  1..67
                        mol_type = other RNA
                        organism = synthetic construct
tRNA                    1..67
                        note = tRNA
SEQUENCE: 247
ggtaaaatgg ctgagcaagc attagacttt aaatctgaaa acagaggtca aaggtctctt    60
tttacca                                                              67

SEQ ID NO: 248          moltype = RNA   length = 66
FEATURE                 Location/Qualifiers
source                  1..66
                        mol_type = other RNA
                        organism = synthetic construct
tRNA                    1..66
                        note = tRNA
SEQUENCE: 248
ggtaaaatgg ctgagtaagc attagacttt aaatctaaag acagaggtca aggcctcttt    60
ttacca                                                               66

SEQ ID NO: 249          moltype = RNA   length = 66
```

```
FEATURE                 Location/Qualifiers
source                  1..66
                        mol_type = other RNA
                        organism = synthetic construct
tRNA                    1..66
                        note = tRNA
SEQUENCE: 249
ggtaaaatga ctgaataagc cttagacttt aaatctgaag acagaggtca aggcctcttt  60
ttacca                                                             66

SEQ ID NO: 250          moltype = RNA   length = 66
FEATURE                 Location/Qualifiers
source                  1..66
                        mol_type = other RNA
                        organism = synthetic construct
tRNA                    1..66
                        note = tRNA
SEQUENCE: 250
ggtaaaatgg ctgagtaagc attggacttt aaatctaaag acagaggtca agacctcttt  60
ttacca                                                             66

SEQ ID NO: 251          moltype = RNA   length = 66
FEATURE                 Location/Qualifiers
source                  1..66
                        mol_type = other RNA
                        organism = synthetic construct
tRNA                    1..66
                        note = tRNA
SEQUENCE: 251
ggtaaaatgg ctgagtaaag cattagactt taaatctaag gacagaggct aaacctcttt  60
ttacca                                                             66

SEQ ID NO: 252          moltype = RNA   length = 93
FEATURE                 Location/Qualifiers
source                  1..93
                        mol_type = other RNA
                        organism = synthetic construct
tRNA                    1..93
                        note = tRNA
SEQUENCE: 252
ccttcaatag ttcagctggt agagcagagg actctagcta cttcctcagt aggagacgtc  60
cttaggttgc tggttcgatt ccagcttgaa gga                               93

SEQ ID NO: 253          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 253
ccttcaatag ttcagctggt agagcagagg actctaggtc cttaggttgc tggttcgatt  60
ccagcttgaa gga                                                     73

SEQ ID NO: 254          moltype = RNA   length = 65
FEATURE                 Location/Qualifiers
source                  1..65
                        mol_type = other RNA
                        organism = synthetic construct
tRNA                    1..65
                        note = tRNA
SEQUENCE: 254
ggtaaaatgg ctgagtaagc tttagactct aaaatctaaa gagagattga gctctctttt  60
tacca                                                              65

SEQ ID NO: 255          moltype = RNA   length = 66
FEATURE                 Location/Qualifiers
source                  1..66
                        mol_type = other RNA
                        organism = synthetic construct
tRNA                    1..66
                        note = tRNA
SEQUENCE: 255
ggtaaaatga ctgagtaagc attagactct aaatctaaag acagaggtca agacctcttt  60
ttacca                                                             66

SEQ ID NO: 256          moltype = RNA   length = 66
FEATURE                 Location/Qualifiers
source                  1..66
```

-continued

```
                         mol_type = other RNA
                         organism = synthetic construct
tRNA                     1..66
                         note = tRNA
SEQUENCE: 256
ggtaaaatgg ctgagtaagc attagactct aaatctaaag acagaggtca aggcctcttt   60
ttacca                                                              66

SEQ ID NO: 257           moltype = RNA   length = 64
FEATURE                  Location/Qualifiers
source                   1..64
                         mol_type = other RNA
                         organism = synthetic construct
tRNA                     1..64
                         note = tRNA
SEQUENCE: 257
ggtaaaatgg ctgagtaagc attagactct aaatctaaag acagaggtca aggccttttt   60
acca                                                                64

SEQ ID NO: 258           moltype = RNA   length = 91
FEATURE                  Location/Qualifiers
source                   1..91
                         mol_type = other RNA
                         organism = synthetic construct
tRNA                     1..91
                         note = tRNA
SEQUENCE: 258
ccttcgatag ctcagttggt agagcggagg actctagttg ctgtgtcct tagacatcct    60
taggtcgctg gttcgaatcc ggctcgaagg a                                  91

SEQ ID NO: 259           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 259
ccttcgatag ctcagttggt agagcggagg actctagatc cttaggtcgc tggttcgaat   60
ccggctcgaa gga                                                      73

SEQ ID NO: 260           moltype = RNA   length = 74
FEATURE                  Location/Qualifiers
source                   1..74
                         mol_type = other RNA
                         organism = synthetic construct
tRNA                     1..74
                         note = tRNA
SEQUENCE: 260
gggggtatag ctcagggcta gagcttttg actctaagag caagaggtcc ctggttcaaa    60
tccaggttct ccct                                                     74

SEQ ID NO: 261           moltype = RNA   length = 61
FEATURE                  Location/Qualifiers
source                   1..61
                         mol_type = other RNA
                         organism = synthetic construct
tRNA                     1..61
                         note = tRNA
SEQUENCE: 261
tatagctcag tggtagagca tttaactcta gatcaagagg tccctggatc aactctgggt   60
g                                                                   61

SEQ ID NO: 262           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 262
gtcagtgttg cacaacggtt aagtgaagag gctctaaacc cagactggat gggttcaatt   60
cccatctctg ccg                                                      73

SEQ ID NO: 263           moltype = RNA   length = 89
FEATURE                  Location/Qualifiers
source                   1..89
                         mol_type = other RNA
                         organism = synthetic construct
```

-continued

```
tRNA                     1..89
                         note = tRNA
SEQUENCE: 263
ccttcgatag ctcagttggt agagcggagg actctagtgg atagggcgtg gcaatcctta   60
ggtcgctggt tcgattccgg ctcgaagga                                     89

SEQ ID NO: 264           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 264
ccttcgatag ctcagttggt agagcggagg actctagatc cttaggtcgc tggttcgatt   60
ccggctcgaa gga                                                      73

SEQ ID NO: 265           moltype = RNA   length = 89
FEATURE                  Location/Qualifiers
source                   1..89
                         mol_type = other RNA
                         organism = synthetic construct
tRNA                     1..89
                         note = tRNA
SEQUENCE: 265
ccttcgatag ctcagttggt agagcggagg actctaggct cattaagcaa ggtatcctta   60
ggtcgctggt tcgaatccgg ctcggagga                                     89

SEQ ID NO: 266           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 266
ccttcgatag ctcagttggt agagcggagg actctagatc cttaggtcgc tggttcgaat   60
ccggctcgga gga                                                      73

SEQ ID NO: 267           moltype = RNA   length = 94
FEATURE                  Location/Qualifiers
source                   1..94
                         mol_type = other RNA
                         organism = synthetic construct
tRNA                     1..94
                         note = tRNA
SEQUENCE: 267
ccttcgatag ctcagctggt agagcggagg actctagatt gtatagacat ttgcggacat   60
ccttaggtcg ctggttcgat tccagctcga agga                               94

SEQ ID NO: 268           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 268
ccttcgatag ctcagctggt agagcggagg actctagatc cttaggtcgc tggttcgatt   60
ccagctcgaa gga                                                      73

SEQ ID NO: 269           moltype = RNA   length = 93
FEATURE                  Location/Qualifiers
source                   1..93
                         mol_type = other RNA
                         organism = synthetic construct
tRNA                     1..93
                         note = tRNA
SEQUENCE: 269
ccttcgatag ctcagctggt agagcggagg actctagcta cttcctcagc aggagacatc   60
cttaggtcgc tggttcgatt ccggctcgaa gga                                93

SEQ ID NO: 270           moltype = RNA   length = 73
FEATURE                  Location/Qualifiers
source                   1..73
                         mol_type = other RNA
                         organism = synthetic construct
tRNA                     1..73
                         note = tRNA
```

-continued

```
SEQUENCE: 270
ccttcgatag ctcagctggt agagcggagg actctagatc cttaggtcgc tggttcgatt   60
ccggctcgaa gga                                                      73

SEQ ID NO: 271          moltype = RNA   length = 89
FEATURE                 Location/Qualifiers
source                  1..89
                        mol_type = other RNA
                        organism = synthetic construct
tRNA                    1..89
                        note = tRNA
SEQUENCE: 271
ccttcgatag ctcagctggt agagcggagg actctaggcg cgcgcccgtg gccatcctta   60
ggtcgctggt tcgattccgg ctcgaagga                                     89

SEQ ID NO: 272          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 272
ccttcgatag ctcagctggt agagcggagg actctagatc cttaggtcgc tggttcgatt   60
ccggctcgaa gga                                                      73

SEQ ID NO: 273          moltype = RNA   length = 94
FEATURE                 Location/Qualifiers
source                  1..94
                        mol_type = other RNA
                        organism = synthetic construct
tRNA                    1..94
                        note = tRNA
SEQUENCE: 273
ccttcgatag ctcagctggt agagcggagg actctagcct gtagaaacat ttgtggacat   60
ccttaggtcg ctggttcgat tccggctcga agga                               94

SEQ ID NO: 274          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 274
ccttcgatag ctcagctggt agagcggagg actctagatc cttaggtcgc tggttcgatt   60
ccggctcgaa gga                                                      73

SEQ ID NO: 275          moltype = RNA   length = 94
FEATURE                 Location/Qualifiers
source                  1..94
                        mol_type = other RNA
                        organism = synthetic construct
tRNA                    1..94
                        note = tRNA
SEQUENCE: 275
ccttcgatag ctcagctggt agagcggagg actctagatt gtacagacat ttgcggacat   60
ccttaggtcg ctggttcgat tccggctcga agga                               94

SEQ ID NO: 276          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 276
ccttcgatag ctcagctggt agagcggagg actctagatc cttaggtcgc tggttcgatt   60
ccggctcgaa gga                                                      73

SEQ ID NO: 277          moltype = RNA   length = 89
FEATURE                 Location/Qualifiers
source                  1..89
                        mol_type = other RNA
                        organism = synthetic construct
tRNA                    1..89
                        note = tRNA
SEQUENCE: 277
ccttcgatag ctcagctggt agagcggagg actctagtac ttaatgtgtg gtcatcctta   60
```

-continued

```
ggtcgctggt tcgattccgg ctcgaagga                                       89

SEQ ID NO: 278          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 278
ccttcgatag ctcagctggt agagcggagg actctagatc cttaggtcgc tggttcgatt   60
ccggctcgaa gga                                                       73

SEQ ID NO: 279          moltype = RNA   length = 89
FEATURE                 Location/Qualifiers
source                  1..89
                        mol_type = other RNA
                        organism = synthetic construct
tRNA                    1..89
                        note = tRNA
SEQUENCE: 279
ccttcgatag ctcagctggt agagcggagg actctagggg tttgaatgtg gtcatcctta   60
ggtcgctggt tcgaatccgg ctcggagga                                      89

SEQ ID NO: 280          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 280
ccttcgatag ctcagctggt agagcggagg actctagatc cttaggtcgc tggttcgaat   60
ccggctcgga gga                                                       73

SEQ ID NO: 281          moltype = RNA   length = 94
FEATURE                 Location/Qualifiers
source                  1..94
                        mol_type = other RNA
                        organism = synthetic construct
tRNA                    1..94
                        note = tRNA
SEQUENCE: 281
ccttcgatag ctcagctggt agagcggagg actctagact gcggaaacgt ttgtggacat   60
ccttaggtcg ctggttcaat tccggctcga agga                                94

SEQ ID NO: 282          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 282
ccttcgatag ctcagctggt agagcggagg actctagatc cttaggtcgc tggttcaatt   60
ccggctcgaa gga                                                       73

SEQ ID NO: 283          moltype = RNA   length = 90
FEATURE                 Location/Qualifiers
source                  1..90
                        mol_type = other RNA
                        organism = synthetic construct
tRNA                    1..90
                        note = tRNA
SEQUENCE: 283
ctttcgatag ctcagttggt agagcggagg actctaggtt cattaaacta aggcatcctt   60
aggtcgctgg ttcgaatccg gctcgaagga                                     90

SEQ ID NO: 284          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 284
ctttcgatag ctcagttggt agagcggagg actctagatc cttaggtcgc tggttcgaat   60
ccggctcgaa gga                                                       73
```

-continued

```
SEQ ID NO: 285            moltype = RNA   length = 88
FEATURE                   Location/Qualifiers
source                    1..88
                          mol_type = other RNA
                          organism = synthetic construct
tRNA                      1..88
                          note = tRNA
SEQUENCE: 285
tcttcaatag ctcagctggt agagcggagg actctaggtg cacgcccgtg gccattctta   60
ggtgctggtt tgattccgac ttggagag                                      88

SEQ ID NO: 286            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 286
tcttcaatag ctcagctggt agagcggagg actctagatt cttaggtgct ggtttgattc   60
cgacttggag ag                                                       72

SEQ ID NO: 287            moltype = RNA   length = 66
FEATURE                   Location/Qualifiers
source                    1..66
                          mol_type = other RNA
                          organism = synthetic construct
tRNA                      1..66
                          note = tRNA
SEQUENCE: 287
ggtaaaatgg ctgagtgaag cattggactc taaatctaaa gacaggggtt aagcctcttt   60
ttacca                                                              66

SEQ ID NO: 288            moltype = RNA   length = 66
FEATURE                   Location/Qualifiers
source                    1..66
                          mol_type = other RNA
                          organism = synthetic construct
tRNA                      1..66
                          note = tRNA
SEQUENCE: 288
ggtaaaatgg ctgagcaagc attggactct aaatctaaag acagatgttg agccatcttt   60
ttagca                                                              66

SEQ ID NO: 289            moltype = RNA   length = 66
FEATURE                   Location/Qualifiers
source                    1..66
                          mol_type = other RNA
                          organism = synthetic construct
tRNA                      1..66
                          note = tRNA
SEQUENCE: 289
ggtaaaatgg ctgagtgaag cattggactc taaatctaaa gacaggggct aagcctcttt   60
ttacca                                                              66

SEQ ID NO: 290            moltype = RNA   length = 66
FEATURE                   Location/Qualifiers
source                    1..66
                          mol_type = other RNA
                          organism = synthetic construct
tRNA                      1..66
                          note = tRNA
SEQUENCE: 290
ggtaaaatgg ctgagcaagc attagactct aaatctaaag acagaggtta aggcctcttt   60
ttacca                                                              66

SEQ ID NO: 291            moltype = RNA   length = 66
FEATURE                   Location/Qualifiers
source                    1..66
                          mol_type = other RNA
                          organism = synthetic construct
tRNA                      1..66
                          note = tRNA
SEQUENCE: 291
ggtaaaatgg ctgagtaagc attagactct aaatctaaag acagaggtca aggcctcttt   60
tttcct                                                              66

SEQ ID NO: 292            moltype = RNA   length = 67
FEATURE                   Location/Qualifiers
```

-continued

```
source                 1..67
                       mol_type = other RNA
                       organism = synthetic construct
tRNA                   1..67
                       note = tRNA
SEQUENCE: 292
ggtaaaatgg ctgagcaagc attagactct aaatctgaaa acagaggtca aaggtctctt   60
tttacca                                                               67

SEQ ID NO: 293         moltype = RNA  length = 66
FEATURE                Location/Qualifiers
source                 1..66
                       mol_type = other RNA
                       organism = synthetic construct
tRNA                   1..66
                       note = tRNA
SEQUENCE: 293
ggtaaaatgg ctgagtaagc attagactct aaatctaaag acagaggtca aggcctcttt   60
ttacca                                                                66

SEQ ID NO: 294         moltype = RNA  length = 66
FEATURE                Location/Qualifiers
source                 1..66
                       mol_type = other RNA
                       organism = synthetic construct
tRNA                   1..66
                       note = tRNA
SEQUENCE: 294
ggtaaaatga ctgaataagc cttagactct aaatctgaag acagaggtca aggcctcttt   60
ttacca                                                                66

SEQ ID NO: 295         moltype = RNA  length = 66
FEATURE                Location/Qualifiers
source                 1..66
                       mol_type = other RNA
                       organism = synthetic construct
tRNA                   1..66
                       note = tRNA
SEQUENCE: 295
ggtaaaatgg ctgagtaagc attggactct aaatctaaag acagaggtca agacctcttt   60
ttacca                                                                66

SEQ ID NO: 296         moltype = RNA  length = 66
FEATURE                Location/Qualifiers
source                 1..66
                       mol_type = other RNA
                       organism = synthetic construct
tRNA                   1..66
                       note = tRNA
SEQUENCE: 296
ggtaaaatgg ctgagtaaag cattagactc taaatctaag gacagaggct aaacctcttt   60
ttacca                                                                66

SEQ ID NO: 297         moltype = RNA  length = 75
FEATURE                Location/Qualifiers
source                 1..75
                       mol_type = other RNA
                       organism = synthetic construct
tRNA                   1..75
                       note = tRNA
SEQUENCE: 297
gttaagatgg cagagcctgg taattgcatt aaacttaaaa ttttataatc agaggttcaa   60
ctcctcttct taaca                                                      75

SEQ ID NO: 298         moltype = RNA  length = 75
FEATURE                Location/Qualifiers
source                 1..75
                       mol_type = other RNA
                       organism = synthetic construct
tRNA                   1..75
                       note = tRNA
SEQUENCE: 298
gttaagatgg cagagcccgg caattgcatt agacttaaaa ctttataatc agaggttcaa   60
ctcctctcat taaca                                                      75

SEQ ID NO: 299         moltype = RNA  length = 82
FEATURE                Location/Qualifiers
source                 1..82
                       mol_type = other RNA
```

```
                                 organism = synthetic construct
tRNA                             1..82
                                 note = tRNA
SEQUENCE: 299
ggtagcgtgg ccgagcggtc taaggcgctg gattttagct ccagtctctt cggggggcgtg   60
ggttcaaatc ccaccgctgc ca                                             82

SEQ ID NO: 300          moltype = RNA   length = 82
FEATURE                 Location/Qualifiers
source                  1..82
                        mol_type = other RNA
                        organism = synthetic construct
tRNA                    1..82
                        note = tRNA
SEQUENCE: 300
ggtagcgtgg ccgagtggtc taagacgctg gattttagct ccagtctctt cggggggcgtg   60
ggtttgaatc ccaccgctgc ca                                             82

SEQ ID NO: 301          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 301
gggccagtgg ctcaatggat aatgcgtctg actttaaatc agaagattcc agccttgact   60
cctggctggc tca                                                       73

SEQ ID NO: 302          moltype = RNA   length = 82
FEATURE                 Location/Qualifiers
source                  1..82
                        mol_type = other RNA
                        organism = synthetic construct
tRNA                    1..82
                        note = tRNA
SEQUENCE: 302
ggtagggtgg ccgagcggtc taaggcactg tattttaact ccagtctctt cagaggcatg   60
ggtttgaatc ccactgctgc ca                                             82

SEQ ID NO: 303          moltype = RNA   length = 65
FEATURE                 Location/Qualifiers
source                  1..65
                        mol_type = other RNA
                        organism = synthetic construct
tRNA                    1..65
                        note = tRNA
SEQUENCE: 303
gccgagcggt ctaaggctcc ggattttagc gccggtgtct cggaggcat gggttcgaat    60
tccac                                                                65

SEQ ID NO: 304          moltype = RNA   length = 106
FEATURE                 Location/Qualifiers
source                  1..106
                        mol_type = other RNA
                        organism = synthetic construct
tRNA                    1..106
                        note = tRNA
SEQUENCE: 304
gtcaggatgg ccgagtggtc taaggcgcca gacttagct aagcttcctc cgcggtgggg    60
attctggtct ccaatggagg cgtgggttcg aatcccactt ctgaca                  106

SEQ ID NO: 305          moltype = RNA   length = 83
FEATURE                 Location/Qualifiers
source                  1..83
                        mol_type = other RNA
                        organism = synthetic construct
tRNA                    1..83
                        note = tRNA
SEQUENCE: 305
gtcaggatgg ccgagtggtc taaggcgcca gactttagtt ctggtctcca atggaggcgt   60
gggttcgaat cccacttctg aca                                            83

SEQ ID NO: 306          moltype = RNA   length = 105
FEATURE                 Location/Qualifiers
source                  1..105
                        mol_type = other RNA
                        organism = synthetic construct
tRNA                    1..105
```

-continued

```
                            note = tRNA
SEQUENCE: 306
gtcaggatgg ccgagtggtc taaggcgcca gactttagct tggcttcctc gtgttgagga    60
ttctggtctc caatggaggc gtgggttcga atcccacttc tgaca                   105

SEQ ID NO: 307         moltype = RNA   length = 83
FEATURE                Location/Qualifiers
source                 1..83
                       mol_type = other RNA
                       organism = synthetic construct
tRNA                   1..83
                       note = tRNA
SEQUENCE: 307
gtcaggatgg ccgagtggtc taaggcgcca gactttagtt ctggtctcca atggaggcgt    60
gggttcgaat cccacttctg aca                                            83

SEQ ID NO: 308         moltype = RNA   length = 108
FEATURE                Location/Qualifiers
source                 1..108
                       mol_type = other RNA
                       organism = synthetic construct
tRNA                   1..108
                       note = tRNA
SEQUENCE: 308
gtcaggatgg ccgagtggtc taaggcgcca gactttagct tactgcttcc tgtgttcggg    60
tcttctggtc tccgtatgga ggcgtgggtt cgaatcccac ttctgaca                108

SEQ ID NO: 309         moltype = RNA   length = 84
FEATURE                Location/Qualifiers
source                 1..84
                       mol_type = other RNA
                       organism = synthetic construct
tRNA                   1..84
                       note = tRNA
SEQUENCE: 309
gtcaggatgg ccgagtggtc taaggcgcca gactttagtt ctggtctccg tatggaggcg    60
tgggttcgaa tcccacttct gaca                                           84

SEQ ID NO: 310         moltype = RNA   length = 107
FEATURE                Location/Qualifiers
source                 1..107
                       mol_type = other RNA
                       organism = synthetic construct
tRNA                   1..107
                       note = tRNA
SEQUENCE: 310
gtcaggatgg ccgagtggtc taaggcgcca gactttagtt gctacttccc aggtttgggg    60
cttctggtct ccgcatggag gcgtgggttc gaatcccact tctgaca                 107

SEQ ID NO: 311         moltype = RNA   length = 84
FEATURE                Location/Qualifiers
source                 1..84
                       mol_type = other RNA
                       organism = synthetic construct
tRNA                   1..84
                       note = tRNA
SEQUENCE: 311
gtcaggatgg ccgagtggtc taaggcgcca gactttagtt ctggtctccg catggaggcg    60
tgggttcgaa tcccacttct gaca                                           84

SEQ ID NO: 312         moltype = RNA   length = 106
FEATURE                Location/Qualifiers
source                 1..106
                       mol_type = other RNA
                       organism = synthetic construct
tRNA                   1..106
                       note = tRNA
SEQUENCE: 312
gtcaggatgg ccgagtggtc taaggcgcca gactttaggt aagcaccttg cctgcgggct    60
ttctggtctc cggatggagg cgtgggttcg aatcccactt ctgaca                  106

SEQ ID NO: 313         moltype = RNA   length = 85
FEATURE                Location/Qualifiers
source                 1..85
                       mol_type = other RNA
                       organism = synthetic construct
tRNA                   1..85
                       note = tRNA
SEQUENCE: 313
```

-continued

```
gtcaggatgg ccgagtggtc taaggcgcca gactttagtt tctggtctcc ggatggaggc    60
gtgggttcga atcccacttc tgaca                                          85

SEQ ID NO: 314            moltype = RNA   length = 74
FEATURE                   Location/Qualifiers
source                    1..74
                          mol_type = other RNA
                          organism = synthetic construct
tRNA                      1..74
                          note = tRNA
SEQUENCE: 314
gcctccttag tgcagtaggt agcgcatcag tctttaaatc tgaatggtcc tgagttcaag    60
cctcagaggg ggca                                                      74

SEQ ID NO: 315            moltype = RNA   length = 84
FEATURE                   Location/Qualifiers
source                    1..84
                          mol_type = other RNA
                          organism = synthetic construct
tRNA                      1..84
                          note = tRNA
SEQUENCE: 315
gtcaggatgg ccgagcagtc ttaaggcgct gcgttttaat cgcaccctcc gctggaggcg    60
tgggttcgaa tcccactttt gaca                                           84

SEQ ID NO: 316            moltype = RNA   length = 60
FEATURE                   Location/Qualifiers
source                    1..60
                          mol_type = other RNA
                          organism = synthetic construct
tRNA                      1..60
                          note = tRNA
SEQUENCE: 316
ggttccatgg tgtaatggtg agcactctgg actttaaatc cagaagtagt gctggaacaa    60

SEQ ID NO: 317            moltype = RNA   length = 83
FEATURE                   Location/Qualifiers
source                    1..83
                          mol_type = other RNA
                          organism = synthetic construct
tRNA                      1..83
                          note = tRNA
SEQUENCE: 317
gtcagggtgg ctgagcagtc tgaggggctg cgttttagtc gcagtctgcc ctggaggcgt    60
gggttcgaat cccactcctg aaa                                            83

SEQ ID NO: 318            moltype = RNA   length = 83
FEATURE                   Location/Qualifiers
source                    1..83
                          mol_type = other RNA
                          organism = synthetic construct
tRNA                      1..83
                          note = tRNA
SEQUENCE: 318
accaggatgg ccgagtggtt aaggcgttgg actttagatc caatggacat atgtccgcgt    60
gggttcgaac cccactcctg gta                                            83

SEQ ID NO: 319            moltype = RNA   length = 83
FEATURE                   Location/Qualifiers
source                    1..83
                          mol_type = other RNA
                          organism = synthetic construct
tRNA                      1..83
                          note = tRNA
SEQUENCE: 319
accgggatgg ccgagtggtt aaggcgttgg actttagatc caatgggctg gtgcccgcgt    60
gggttcgaac cccactctcg gta                                            83

SEQ ID NO: 320            moltype = RNA   length = 83
FEATURE                   Location/Qualifiers
source                    1..83
                          mol_type = other RNA
                          organism = synthetic construct
tRNA                      1..83
                          note = tRNA
SEQUENCE: 320
accagaatgg ccgagtggtt aaggcgttgg actttagatc caatggattc atatccgcgt    60
gggttcgaac cccacttctg gta                                            83
```

-continued

```
SEQ ID NO: 321            moltype = RNA   length = 83
FEATURE                   Location/Qualifiers
source                    1..83
                          mol_type = other RNA
                          organism = synthetic construct
tRNA                      1..83
                          note = tRNA
SEQUENCE: 321
accgggatgg ctgagtggtt aaggcgttgg actttagatc caatggacag gtgtccgcgt     60
gggttcgagc cccactcccg gta                                            83

SEQ ID NO: 322            moltype = RNA   length = 83
FEATURE                   Location/Qualifiers
source                    1..83
                          mol_type = other RNA
                          organism = synthetic construct
tRNA                      1..83
                          note = tRNA
SEQUENCE: 322
actcatttgg ctgagtggtt aaggcattgg actttagatc caatggagta gtggctgtgt     60
gggtttaaac cccactactg gta                                            83

SEQ ID NO: 323            moltype = RNA   length = 69
FEATURE                   Location/Qualifiers
source                    1..69
                          mol_type = other RNA
                          organism = synthetic construct
tRNA                      1..69
                          note = tRNA
SEQUENCE: 323
gagaaagtca tcgtagttac gaagttggct ttaacccagt tttgggaggt tcaattcctt     60
cctttctct                                                            69

SEQ ID NO: 324            moltype = RNA   length = 84
FEATURE                   Location/Qualifiers
source                    1..84
                          mol_type = other RNA
                          organism = synthetic construct
tRNA                      1..84
                          note = tRNA
SEQUENCE: 324
accaggatgg ccaagtagtt aaaggcactg gactttagag ccaatggaca tatgtctgtg     60
tgggtttgaa ccccactcct ggtg                                           84

SEQ ID NO: 325            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 325
ggtagcgtgg ccgagcggtc taaggcgctg gatttagct ccagtctctt cggaggcgtg      60
ggttcgaatc ccaccgctgc ca                                             82

SEQ ID NO: 326            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 326
ggtagtgtgg ccgagcggtc taaggcgctg gatttagct ccagtctctt cggggggcgtg     60
ggttcgaatc ccaccactgc ca                                             82

SEQ ID NO: 327            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 327
ggtagcgtgg ccgagtggtc taaggcgctg gatttagct ccagtcattt cgatggcgtg      60
ggttcgaatc ccaccgctgc ca                                             82

SEQ ID NO: 328            moltype = RNA   length = 82
FEATURE                   Location/Qualifiers
```

-continued

```
source                    1..82
                          mol_type = other RNA
                          organism = synthetic construct
tRNA                      1..82
                          note = tRNA
SEQUENCE: 328
ggtagtgtgg ttgaatggtc taaggcactg aattttagct ccagtctctt tggggacgtg    60
ggtttaaatc ccactgctgc aa                                              82

SEQ ID NO: 329           moltype = RNA   length = 75
FEATURE                  Location/Qualifiers
source                    1..75
                          mol_type = other RNA
                          organism = synthetic construct
tRNA                      1..75
                          note = tRNA
SEQUENCE: 329
gttaagatgg cagagcctgg taattgcact aaacttaaaa ttttataatc agaggttcaa    60
ctcctcttct taaca                                                      75

SEQ ID NO: 330           moltype = RNA   length = 75
FEATURE                  Location/Qualifiers
source                    1..75
                          mol_type = other RNA
                          organism = synthetic construct
tRNA                      1..75
                          note = tRNA
SEQUENCE: 330
gttaagatgg cagagcccgg caattgcact agacttaaaa ctttataatc agaggttcaa    60
ctcctctcat taaca                                                      75

SEQ ID NO: 331           moltype = RNA   length = 82
FEATURE                  Location/Qualifiers
source                    1..82
                          mol_type = other RNA
                          organism = synthetic construct
tRNA                      1..82
                          note = tRNA
SEQUENCE: 331
ggtagcgtgg ccgagcggtc taaggcgctg gattctagct ccagtctctt cggggcgtg     60
ggttcaaatc ccaccgctgc ca                                              82

SEQ ID NO: 332           moltype = RNA   length = 82
FEATURE                  Location/Qualifiers
source                    1..82
                          mol_type = other RNA
                          organism = synthetic construct
tRNA                      1..82
                          note = tRNA
SEQUENCE: 332
ggtagcgtgg ccgagtggtc taagacgctg gattctagct ccagtctctt cggggcgtg     60
ggtttgaatc ccaccgctgc ca                                              82

SEQ ID NO: 333           moltype = RNA   length = 73
FEATURE                  Location/Qualifiers
source                    1..73
                          mol_type = other RNA
                          organism = synthetic construct
tRNA                      1..73
                          note = tRNA
SEQUENCE: 333
gggccagtgg ctcaatggat aatgcgtctg actctaaatc agaagattcc agccttgact    60
cctggctggc tca                                                        73

SEQ ID NO: 334           moltype = RNA   length = 82
FEATURE                  Location/Qualifiers
source                    1..82
                          mol_type = other RNA
                          organism = synthetic construct
tRNA                      1..82
                          note = tRNA
SEQUENCE: 334
ggtagggtgg ccgagcggtc taaggcactg tattctaact ccagtctctt cagaggcatg    60
ggtttgaatc ccactgctgc ca                                              82

SEQ ID NO: 335           moltype = RNA   length = 65
FEATURE                  Location/Qualifiers
source                    1..65
                          mol_type = other RNA
```

-continued

```
                        organism = synthetic construct
tRNA                    1..65
                        note = tRNA
SEQUENCE: 335
gccgagcggt ctaaggctcc ggattctagc gccggtgtct tcggaggcat gggttcgaat    60
tccac                                                                 65

SEQ ID NO: 336          moltype = RNA  length = 106
FEATURE                 Location/Qualifiers
source                  1..106
                        mol_type = other RNA
                        organism = synthetic construct
tRNA                    1..106
                        note = tRNA
SEQUENCE: 336
gtcaggatgg ccgagtggtc taaggcgcca gactctagct aagcttcctc cgcggtgggg    60
attctggtct ccaatggagg cgtgggttcg aatcccactt ctgaca                  106

SEQ ID NO: 337          moltype = RNA  length = 83
FEATURE                 Location/Qualifiers
source                  1..83
                        mol_type = other RNA
                        organism = synthetic construct
tRNA                    1..83
                        note = tRNA
SEQUENCE: 337
gtcaggatgg ccgagtggtc taaggcgcca gactctagtt ctggtctcca atggaggcgt    60
gggttcgaat cccacttctg aca                                            83

SEQ ID NO: 338          moltype = RNA  length = 105
FEATURE                 Location/Qualifiers
source                  1..105
                        mol_type = other RNA
                        organism = synthetic construct
tRNA                    1..105
                        note = tRNA
SEQUENCE: 338
gtcaggatgg ccgagtggtc taaggcgcca gactctagct tggcttcctc gtgttgagga    60
ttctggtctc caatggaggc gtgggttcga atcccacttc tgaca                   105

SEQ ID NO: 339          moltype = RNA  length = 83
FEATURE                 Location/Qualifiers
source                  1..83
                        mol_type = other RNA
                        organism = synthetic construct
tRNA                    1..83
                        note = tRNA
SEQUENCE: 339
gtcaggatgg ccgagtggtc taaggcgcca gactctagtt ctggtctcca atggaggcgt    60
gggttcgaat cccacttctg aca                                            83

SEQ ID NO: 340          moltype = RNA  length = 108
FEATURE                 Location/Qualifiers
source                  1..108
                        mol_type = other RNA
                        organism = synthetic construct
tRNA                    1..108
                        note = tRNA
SEQUENCE: 340
gtcaggatgg ccgagtggtc taaggcgcca gactctagct tactgcttcc tgtgttcggg    60
tcttctggtc tccgtatgga ggcgtgggtt cgaatcccac ttctgaca               108

SEQ ID NO: 341          moltype = RNA  length = 84
FEATURE                 Location/Qualifiers
source                  1..84
                        mol_type = other RNA
                        organism = synthetic construct
tRNA                    1..84
                        note = tRNA
SEQUENCE: 341
gtcaggatgg ccgagtggtc taaggcgcca gactctagtt ctggtctccg tatggaggcg    60
tgggttcgaa tcccacttct gaca                                           84

SEQ ID NO: 342          moltype = RNA  length = 107
FEATURE                 Location/Qualifiers
source                  1..107
                        mol_type = other RNA
                        organism = synthetic construct
tRNA                    1..107
```

-continued

```
                            note = tRNA
SEQUENCE: 342
gtcaggatgg ccgagtggtc taaggcgcca gactctagtt gctacttccc aggtttgggg   60
cttctggtct ccgcatggag gcgtgggttc gaatcccact tctgaca                107

SEQ ID NO: 343           moltype = RNA   length = 84
FEATURE                  Location/Qualifiers
source                   1..84
                         mol_type = other RNA
                         organism = synthetic construct
tRNA                     1..84
                         note = tRNA
SEQUENCE: 343
gtcaggatgg ccgagtggtc taaggcgcca gactctagtt ctggtctccg catggaggcg   60
tgggttcgaa tcccacttct gaca                                           84

SEQ ID NO: 344           moltype = RNA   length = 106
FEATURE                  Location/Qualifiers
source                   1..106
                         mol_type = other RNA
                         organism = synthetic construct
tRNA                     1..106
                         note = tRNA
SEQUENCE: 344
gtcaggatgg ccgagtggtc taaggcgcca gactctaggt aagcaccttg cctgcgggct   60
ttctggtctc cggatggagg cgtgggttcg aatcccactt ctgaca                  106

SEQ ID NO: 345           moltype = RNA   length = 85
FEATURE                  Location/Qualifiers
source                   1..85
                         mol_type = other RNA
                         organism = synthetic construct
tRNA                     1..85
                         note = tRNA
SEQUENCE: 345
gtcaggatgg ccgagtggtc taaggcgcca gactctagtt ctggtctcc ggatggaggc    60
gtgggttcga atcccacttc tgaca                                          85

SEQ ID NO: 346           moltype = RNA   length = 74
FEATURE                  Location/Qualifiers
source                   1..74
                         mol_type = other RNA
                         organism = synthetic construct
tRNA                     1..74
                         note = tRNA
SEQUENCE: 346
gcctccttag tgcagtaggt agcgcatcag tctctaaatc tgaatggtcc tgagttcaag    60
cctcagaggg ggca                                                      74

SEQ ID NO: 347           moltype = RNA   length = 84
FEATURE                  Location/Qualifiers
source                   1..84
                         mol_type = other RNA
                         organism = synthetic construct
tRNA                     1..84
                         note = tRNA
SEQUENCE: 347
gtcaggatgg ccgagcagtc ttaaggcgct gcgttctaat cgcaccctcc gctggaggcg    60
tgggttcgaa tcccactttt gaca                                           84

SEQ ID NO: 348           moltype = RNA   length = 60
FEATURE                  Location/Qualifiers
source                   1..60
                         mol_type = other RNA
                         organism = synthetic construct
tRNA                     1..60
                         note = tRNA
SEQUENCE: 348
ggttccatgg tgtaatggtg agcactctgg actctaaatc cagaagtagt gctggaacaa    60

SEQ ID NO: 349           moltype = RNA   length = 83
FEATURE                  Location/Qualifiers
source                   1..83
                         mol_type = other RNA
                         organism = synthetic construct
tRNA                     1..83
                         note = tRNA
SEQUENCE: 349
gtcagggtgg ctgagcagtc tgaggggctg cgttctagtc gcagtctgcc ctggaggcgt    60
```

-continued

```
gggttcgaat cccactcctg aaa                                            83

SEQ ID NO: 350            moltype = RNA   length = 83
FEATURE                   Location/Qualifiers
source                    1..83
                          mol_type = other RNA
                          organism = synthetic construct
tRNA                      1..83
                          note = tRNA
SEQUENCE: 350
accaggatgg ccgagtggtt aaggcgttgg actctagatc caatggacat atgtccgcgt    60
gggttcgaac cccactcctg gta                                            83

SEQ ID NO: 351            moltype = RNA   length = 83
FEATURE                   Location/Qualifiers
source                    1..83
                          mol_type = other RNA
                          organism = synthetic construct
tRNA                      1..83
                          note = tRNA
SEQUENCE: 351
accgggatgg ccgagtggtt aaggcgttgg actctagatc caatgggctg gtgcccgcgt    60
gggttcgaac cccactctcg gta                                            83

SEQ ID NO: 352            moltype = RNA   length = 83
FEATURE                   Location/Qualifiers
source                    1..83
                          mol_type = other RNA
                          organism = synthetic construct
tRNA                      1..83
                          note = tRNA
SEQUENCE: 352
accagaatgg ccgagtggtt aaggcgttgg actctagatc caatggattc atatccgcgt    60
gggttcgaac cccacttctg gta                                            83

SEQ ID NO: 353            moltype = RNA   length = 83
FEATURE                   Location/Qualifiers
source                    1..83
                          mol_type = other RNA
                          organism = synthetic construct
tRNA                      1..83
                          note = tRNA
SEQUENCE: 353
accgggatgg ctgagtggtt aaggcgttgg actctagatc caatggacag gtgtccgcgt    60
gggttcgagc cccactcccg gta                                            83

SEQ ID NO: 354            moltype = RNA   length = 84
FEATURE                   Location/Qualifiers
source                    1..84
                          mol_type = other RNA
                          organism = synthetic construct
tRNA                      1..84
                          note = tRNA
SEQUENCE: 354
actcatttgg ctgagtggtt aaggcattgg actctaagat ccaatggagt agtggctgtg    60
tgggtttaaa ccccactact ggta                                           84

SEQ ID NO: 355            moltype = RNA   length = 69
FEATURE                   Location/Qualifiers
source                    1..69
                          mol_type = other RNA
                          organism = synthetic construct
tRNA                      1..69
                          note = tRNA
SEQUENCE: 355
gagaaagtca tcgtagttac gaagttggct ctaacccagt tttgggaggt tcaattcctt    60
cctttctct                                                            69

SEQ ID NO: 356            moltype = RNA   length = 84
FEATURE                   Location/Qualifiers
source                    1..84
                          mol_type = other RNA
                          organism = synthetic construct
tRNA                      1..84
                          note = tRNA
SEQUENCE: 356
accaggatgg ccaagtagtt aaaggcactg gactctagag ccaatggaca tatgtctgtg    60
tgggtttgaa ccccactcct ggtg                                           84
```

```
SEQ ID NO: 357            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 357
ggtagcgtgg ccgagcggtc taaggcgctg gattctagct ccagtctctt cggaggcgtg   60
ggttcgaatc ccaccgctgc ca                                            82

SEQ ID NO: 358            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 358
ggtagtgtgg ccgagcggtc taaggcgctg gattctagct ccagtctctt cggggncgtg   60
ggttcgaatc ccaccactgc ca                                            82

SEQ ID NO: 359            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 359
ggtagcgtgg ccgagtggtc taaggcgctg gattctagct ccagtcattt cgatggcgtg   60
ggttcgaatc ccaccgctgc ca                                            82

SEQ ID NO: 360            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 360
ggtagtgtgg ttgaatggtc taaggcactg aattctagct ccagtctctt tggggacgtg   60
ggtttaaatc ccactgctgc aa                                            82

SEQ ID NO: 361            moltype = RNA   length = 70
FEATURE                   Location/Qualifiers
source                    1..70
                          mol_type = other RNA
                          organism = synthetic construct
tRNA                      1..70
                          note = tRNA
SEQUENCE: 361
gagaaggtca cagaggttat gggattggct ctaaaccagt ctgtgggggg ttcgattccc   60
tcctttttca                                                          70

SEQ ID NO: 362            moltype = RNA   length = 70
FEATURE                   Location/Qualifiers
source                    1..70
                          mol_type = other RNA
                          organism = synthetic construct
tRNA                      1..70
                          note = tRNA
SEQUENCE: 362
gagaaggtca tagaggttat gggattggct ctaaaccagt ctctgggggg ttcgattccc   60
tcctttttca                                                          70

SEQ ID NO: 363            moltype = RNA   length = 69
FEATURE                   Location/Qualifiers
source                    1..69
                          mol_type = other RNA
                          organism = synthetic construct
tRNA                      1..69
                          note = tRNA
SEQUENCE: 363
gaaaaagtca taggggttat gaggctggct ctaaaccagc cttaggaggt tcaattcctt   60
cctttttttg                                                          69

SEQ ID NO: 364            moltype = RNA   length = 74
FEATURE                   Location/Qualifiers
```

-continued

```
source                    1..74
                          mol_type = other RNA
                          organism = synthetic construct
tRNA                      1..74
                          note = tRNA
SEQUENCE: 364
ggccggttag ctcagttggt tagagcgtgc tgctctaaat gccagggtcg aggtttcgat    60
ccccgtacgg gcct                                                      74

SEQ ID NO: 365            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 365
gtagtcgtgg ccgagtggtt aaggcgatgg actctaaatc cattggggtt tccccgcgca    60
ggttcgaatc ctgccgacta cg                                             82

SEQ ID NO: 366            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 366
gtagtcgtgg ccgagtggtt aaggcgatgg actctaaatc cattggggtt tccccacgca    60
ggttcgaatc ctgccgacta cg                                             82

SEQ ID NO: 367            moltype = RNA   length = 83
FEATURE                   Location/Qualifiers
source                    1..83
                          mol_type = other RNA
                          organism = synthetic construct
tRNA                      1..83
                          note = tRNA
SEQUENCE: 367
gtagtcgtgg ccgagtggtt aaggtgatgg actctaaaac ccattggggt ctccccgcgc    60
aggttcgaat cctgccgact acg                                            83

SEQ ID NO: 368            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 368
gggtgtatgg ctcaggggta gagaatttga ctctagatca agaggtccct ggttcaaatc    60
caggtgcccc ct                                                        72

SEQ ID NO: 369            moltype = RNA   length = 78
FEATURE                   Location/Qualifiers
source                    1..78
                          mol_type = other RNA
                          organism = synthetic construct
tRNA                      1..78
                          note = tRNA
SEQUENCE: 369
agttgtagct gagtggttaa ggcaacgagc tctaaattcg ttggtttctc tctgtgcagg    60
tttgaatcct gctaatta                                                  78

SEQ ID NO: 370            moltype = RNA   length = 70
FEATURE                   Location/Qualifiers
source                    1..70
                          mol_type = other RNA
                          organism = synthetic construct
tRNA                      1..70
                          note = tRNA
SEQUENCE: 370
caagaaattc atagaggtta tgggattggc tctaaaccag tttcaggagg ttcgattcct    60
tcctttttgg                                                           70

SEQ ID NO: 371            moltype = RNA   length = 82
FEATURE                   Location/Qualifiers
source                    1..82
                          mol_type = other RNA
```

-continued

```
                         organism = synthetic construct
tRNA                     1..82
                         note = tRNA
SEQUENCE: 371
gctgtgatgg ccgagtggtt aaggcgttgg actctaaatc caatggggtc tccccgcgca   60
ggttcgaatc ctgctcacag cg                                            82

SEQ ID NO: 372          moltype = RNA  length = 82
FEATURE                 Location/Qualifiers
source                  1..82
                         mol_type = other RNA
                         organism = synthetic construct
tRNA                     1..82
                         note = tRNA
SEQUENCE: 372
gctgtgatgg ccgagtggtt aaggcgttgg actctaaatc caatggggtc tccccgcgca   60
ggttcaaatc ctgctcacag cg                                            82

SEQ ID NO: 373          moltype = RNA  length = 82
FEATURE                 Location/Qualifiers
source                  1..82
                         mol_type = other RNA
                         organism = synthetic construct
tRNA                     1..82
                         note = tRNA
SEQUENCE: 373
gctgtgatgg ccgagtggtt aaggtgttgg actctaaatc caatgggggt tccccgcgca   60
ggttcaaatc ctgctcacag cg                                            82

SEQ ID NO: 374          moltype = RNA  length = 82
FEATURE                 Location/Qualifiers
source                  1..82
                         mol_type = other RNA
                         organism = synthetic construct
tRNA                     1..82
                         note = tRNA
SEQUENCE: 374
gtcacggtgg ccgagtggtt aaggcgttgg actctaaatc caatggggtt tccccgcaca   60
ggttcgaatc ctgttcgtga cg                                            82

SEQ ID NO: 375          moltype = RNA  length = 82
FEATURE                 Location/Qualifiers
source                  1..82
                         mol_type = other RNA
                         organism = synthetic construct
tRNA                     1..82
                         note = tRNA
SEQUENCE: 375
gacgaggtgg ccgagtggtt aaggcgatgg actctaaatc cattgtgctc tgcacgcgtg   60
ggttcgaatc ccaccctcgt cg                                            82

SEQ ID NO: 376          moltype = RNA  length = 82
FEATURE                 Location/Qualifiers
source                  1..82
                         mol_type = other RNA
                         organism = synthetic construct
tRNA                     1..82
                         note = tRNA
SEQUENCE: 376
gacgaggtgg ccgagtggtt aaggcgatgg actctaaatc cattgtgctc tgcacgcgtg   60
ggttcgaatc ccaccttcgt cg                                            82

SEQ ID NO: 377          moltype = RNA  length = 74
FEATURE                 Location/Qualifiers
source                  1..74
                         mol_type = other RNA
                         organism = synthetic construct
tRNA                     1..74
                         note = tRNA
SEQUENCE: 377
ggccggttag ctcagttggt tagagcgtgc tctaactaat gccagggtcg aggtttcgat   60
ccccgtacgg gcct                                                     74

SEQ ID NO: 378          moltype = RNA  length = 82
FEATURE                 Location/Qualifiers
source                  1..82
                         mol_type = other RNA
                         organism = synthetic construct
tRNA                     1..82
```

-continued

```
                              note = tRNA
SEQUENCE: 378
gacgaggtgg ccgagtggtt aaggcgatgg actctaaatc cattgtgctc tgcacacgtg   60
ggttcgaatc ccatcctcgt cg                                            82

SEQ ID NO: 379          moltype = RNA   length = 78
FEATURE                 Location/Qualifiers
source                  1..78
                        mol_type = other RNA
                        organism = synthetic construct
tRNA                    1..78
                        note = tRNA
SEQUENCE: 379
gaggcctggc cgagtggtta aggcgatgga ctctaaatcc attgtgctct gcacgcgtgg   60
gttcgaatcc catcctcg                                                 78

SEQ ID NO: 380          moltype = RNA   length = 82
FEATURE                 Location/Qualifiers
source                  1..82
                        mol_type = other RNA
                        organism = synthetic construct
tRNA                    1..82
                        note = tRNA
SEQUENCE: 380
gcagcgatgg ccgagtggtt aaggcgttgg actctaaatc caatggggtc tccccgcgca   60
ggttcgaacc ctgctcgctg cg                                            82

SEQ ID NO: 381          moltype = RNA   length = 82
FEATURE                 Location/Qualifiers
source                  1..82
                        mol_type = other RNA
                        organism = synthetic construct
tRNA                    1..82
                        note = tRNA
SEQUENCE: 381
gtagtcgtgg ccgagtggtt aaggcgatgg actctaaatc cattggggtt tccccgcgca   60
ggttcgaatc ctgccgacta cg                                            82

SEQ ID NO: 382          moltype = RNA   length = 82
FEATURE                 Location/Qualifiers
source                  1..82
                        mol_type = other RNA
                        organism = synthetic construct
tRNA                    1..82
                        note = tRNA
SEQUENCE: 382
gtagtcgtgg ccgagtggtt aaggcgatgg actctaaatc cattggggtc tccccgcgca   60
ggttcgaatc ctgccgacta cg                                            82

SEQ ID NO: 383          moltype = RNA   length = 82
FEATURE                 Location/Qualifiers
source                  1..82
                        mol_type = other RNA
                        organism = synthetic construct
tRNA                    1..82
                        note = tRNA
SEQUENCE: 383
gtagtcgtgg ccgagtggtt aaggcgatgg actctaaatc cattggggtt tccccgcgca   60
ggttcgaatc ctgtcggcta cg                                            82

SEQ ID NO: 384          moltype = RNA   length = 70
FEATURE                 Location/Qualifiers
source                  1..70
                        mol_type = other RNA
                        organism = synthetic construct
tRNA                    1..70
                        note = tRNA
SEQUENCE: 384
gagaaggtca cagaggttat gggattggct tcaaaccagt ctgtgggggg ttcgattccc   60
tcctttttca                                                          70

SEQ ID NO: 385          moltype = RNA   length = 70
FEATURE                 Location/Qualifiers
source                  1..70
                        mol_type = other RNA
                        organism = synthetic construct
tRNA                    1..70
                        note = tRNA
SEQUENCE: 385
```

```
gagaaggtca tagaggttat gggattggct tcaaaccagt ctctgggggg ttcgattccc   60
tcctttttca                                                          70

SEQ ID NO: 386          moltype = RNA   length = 69
FEATURE                 Location/Qualifiers
source                  1..69
                        mol_type = other RNA
                        organism = synthetic construct
tRNA                    1..69
                        note = tRNA
SEQUENCE: 386
gaaaaagtca tagggttat gaggctggct tcaaaccagc cttaggaggt tcaattcctt   60
cctttttttg                                                          69

SEQ ID NO: 387          moltype = RNA   length = 74
FEATURE                 Location/Qualifiers
source                  1..74
                        mol_type = other RNA
                        organism = synthetic construct
tRNA                    1..74
                        note = tRNA
SEQUENCE: 387
ggccggttag ctcagttggt tagagcgtgc tgcttcaaat gccagggtcg aggtttcgat   60
ccccgtacgg gcct                                                     74

SEQ ID NO: 388          moltype = RNA   length = 82
FEATURE                 Location/Qualifiers
source                  1..82
                        mol_type = other RNA
                        organism = synthetic construct
tRNA                    1..82
                        note = tRNA
SEQUENCE: 388
gtagtcgtgg ccgagtggtt aaggcgatgg acttcaaatc cattggggtt tccccgcgca   60
ggttcgaatc ctgccgacta cg                                            82

SEQ ID NO: 389          moltype = RNA   length = 82
FEATURE                 Location/Qualifiers
source                  1..82
                        mol_type = other RNA
                        organism = synthetic construct
tRNA                    1..82
                        note = tRNA
SEQUENCE: 389
gtagtcgtgg ccgagtggtt aaggcgatgg acttcaaatc cattggggtt tccccacgca   60
ggttcgaatc ctgccgacta cg                                            82

SEQ ID NO: 390          moltype = RNA   length = 82
FEATURE                 Location/Qualifiers
source                  1..82
                        mol_type = other RNA
                        organism = synthetic construct
tRNA                    1..82
                        note = tRNA
SEQUENCE: 390
gtagtcgtgg ccgagtggtt aaggtgatgg acttcaaacc cattggggtc tccccgcgca   60
ggttcgaatc ctgccgacta cg                                            82

SEQ ID NO: 391          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 391
gggtgtatgg ctcaggggta gagaatttga cttcagatca agaggtccct ggttcaaatc   60
caggtgcccc ct                                                       72

SEQ ID NO: 392          moltype = RNA   length = 78
FEATURE                 Location/Qualifiers
source                  1..78
                        mol_type = other RNA
                        organism = synthetic construct
tRNA                    1..78
                        note = tRNA
SEQUENCE: 392
agttgtagct gagtggttaa ggcaacgagc ttcaaattcg ttggtttctc tctgtgcagg   60
tttgaatcct gctaatta                                                 78
```

-continued

```
SEQ ID NO: 393            moltype = RNA   length = 70
FEATURE                   Location/Qualifiers
source                    1..70
                          mol_type = other RNA
                          organism = synthetic construct
tRNA                      1..70
                          note = tRNA
SEQUENCE: 393
caagaaattc atagaggtta tgggattggc ttcaaaccag tttcaggagg ttcgattcct   60
tcctttttgg                                                          70

SEQ ID NO: 394            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 394
gctgtgatgg ccgagtggtt aaggcgttgg acttcaaatc caatggggtc tccccgcgca   60
ggttcgaatc ctgctcacag cg                                            82

SEQ ID NO: 395            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 395
gctgtgatgg ccgagtggtt aaggcgttgg acttcaaatc caatggggtc tccccgcgca   60
ggttcaaatc ctgctcacag cg                                            82

SEQ ID NO: 396            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 396
gctgtgatgg ccgagtggtt aaggtgttgg acttcaaatc caatgggggt tccccgcgca   60
ggttcaaatc ctgctcacag cg                                            82

SEQ ID NO: 397            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 397
gtcacggtgg ccgagtggtt aaggcgttgg acttcaaatc caatggggtt tccccgcaca   60
ggttcgaatc ctgttcgtga cg                                            82

SEQ ID NO: 398            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 398
gacgaggtgg ccgagtggtt aaggcgatgg acttcaaatc cattgtgctc tgcacgcgtg   60
ggttcgaatc ccaccctcgt cg                                            82

SEQ ID NO: 399            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 399
gacgaggtgg ccgagtggtt aaggcgatgg acttcaaatc cattgtgctc tgcacgcgtg   60
ggttcgaatc ccaccttcgt cg                                            82

SEQ ID NO: 400            moltype = RNA   length = 74
```

-continued

```
FEATURE                  Location/Qualifiers
source                   1..74
                         mol_type = other RNA
                         organism = synthetic construct
tRNA                     1..74
                         note = tRNA
SEQUENCE: 400
ggccggttag ctcagttggt tagagcgtgc ttcaactaat gccagggtcg aggtttcgat    60
ccccgtacgg gcct                                                      74

SEQ ID NO: 401           moltype = RNA   length = 82
FEATURE                  Location/Qualifiers
source                   1..82
                         mol_type = other RNA
                         organism = synthetic construct
tRNA                     1..82
                         note = tRNA
SEQUENCE: 401
gacgaggtgg ccgagtggtt aaggcgatgg acttcaaatc cattgtgctc tgcacacgtg    60
ggttcgaatc ccatcctcgt cg                                             82

SEQ ID NO: 402           moltype = RNA   length = 78
FEATURE                  Location/Qualifiers
source                   1..78
                         mol_type = other RNA
                         organism = synthetic construct
tRNA                     1..78
                         note = tRNA
SEQUENCE: 402
gaggcctggc cgagtggtta aggcgatgga cttcaaatcc attgtgctct gcacgcgtgg    60
gttcgaatcc catcctcg                                                  78

SEQ ID NO: 403           moltype = RNA   length = 82
FEATURE                  Location/Qualifiers
source                   1..82
                         mol_type = other RNA
                         organism = synthetic construct
tRNA                     1..82
                         note = tRNA
SEQUENCE: 403
gcagcgatgg ccgagtggtt aaggcgttgg acttcaaatc caatggggtc tccccgcgca    60
ggttcgaacc ctgctcgctg cg                                             82

SEQ ID NO: 404           moltype = RNA   length = 82
FEATURE                  Location/Qualifiers
source                   1..82
                         mol_type = other RNA
                         organism = synthetic construct
tRNA                     1..82
                         note = tRNA
SEQUENCE: 404
gtagtcgtgg ccgagtggtt aaggcgatgg acttcaaatc cattgggggtt tccccgcgca   60
ggttcgaatc ctgccgacta cg                                             82

SEQ ID NO: 405           moltype = RNA   length = 82
FEATURE                  Location/Qualifiers
source                   1..82
                         mol_type = other RNA
                         organism = synthetic construct
tRNA                     1..82
                         note = tRNA
SEQUENCE: 405
gtagtcgtgg ccgagtggtt aaggcgatgg acttcaaatc cattggggtc tccccgcgca    60
ggttcgaatc ctgccgacta cg                                             82

SEQ ID NO: 406           moltype = RNA   length = 82
FEATURE                  Location/Qualifiers
source                   1..82
                         mol_type = other RNA
                         organism = synthetic construct
tRNA                     1..82
                         note = tRNA
SEQUENCE: 406
gtagtcgtgg ccgagtggtt aaggcgatgg acttcaaatc cattggggtt tccccgcgca    60
ggttcgaatc ctgtcggcta cg                                             82

SEQ ID NO: 407           moltype = RNA   length = 73
FEATURE                  Location/Qualifiers
source                   1..73
```

-continued

```
                         mol_type = other RNA
                         organism = synthetic construct
tRNA                     1..73
                         note = tRNA
SEQUENCE: 407
gcccagctag ctcagtcggt agagcataag actttaaatc tcagggttgt ggattcgtgc   60
cccatgctgg gtg                                                      73

SEQ ID NO: 408           moltype = RNA  length = 71
FEATURE                  Location/Qualifiers
source                   1..71
                         mol_type = other RNA
                         organism = synthetic construct
tRNA                     1..71
                         note = tRNA
SEQUENCE: 408
ctgcagctag ctcagtcggt agagcatgag actttaaatc tcagggtcat gggttcgtgc   60
cccatgttgg g                                                        71

SEQ ID NO: 409           moltype = RNA  length = 70
FEATURE                  Location/Qualifiers
source                   1..70
                         mol_type = other RNA
                         organism = synthetic construct
tRNA                     1..70
                         note = tRNA
SEQUENCE: 409
ccagcatgtc tcagtcggta tagtgtgaga ctttaaatct cagggtcgtg ggttcaagcc   60
ccacattggg                                                          70

SEQ ID NO: 410           moltype = RNA  length = 73
FEATURE                  Location/Qualifiers
source                   1..73
                         mol_type = other RNA
                         organism = synthetic construct
tRNA                     1..73
                         note = tRNA
SEQUENCE: 410
gtctagctag atcagttggt agagcataag actttaaatc tcagggtcat gggtttgagc   60
cctacgttgg gcg                                                      73

SEQ ID NO: 411           moltype = RNA  length = 73
FEATURE                  Location/Qualifiers
source                   1..73
                         mol_type = other RNA
                         organism = synthetic construct
tRNA                     1..73
                         note = tRNA
SEQUENCE: 411
gcccagctag ctcagccggt agagcacaag actttaaatc tcagggtcgt gggtttgagc   60
cctgtgttga gca                                                      73

SEQ ID NO: 412           moltype = RNA  length = 69
FEATURE                  Location/Qualifiers
source                   1..69
                         mol_type = other RNA
                         organism = synthetic construct
tRNA                     1..69
                         note = tRNA
SEQUENCE: 412
ccgaatagct tagttgatga agcgtgagac tttaaatctc agggtagtgg gttcaagccc   60
cacattgga                                                           69

SEQ ID NO: 413           moltype = RNA  length = 74
FEATURE                  Location/Qualifiers
source                   1..74
                         mol_type = other RNA
                         organism = synthetic construct
tRNA                     1..74
                         note = tRNA
SEQUENCE: 413
gcctggctac ctcagttggt agagcatggg actttaaatc ccagagtcag tgggttcaag   60
cctcacattg agtg                                                     74

SEQ ID NO: 414           moltype = RNA  length = 73
FEATURE                  Location/Qualifiers
source                   1..73
                         mol_type = other RNA
                         organism = synthetic construct
```

```
tRNA                     1..73
                         note = tRNA
SEQUENCE: 414
gcccggctag ctcagtcggt agagcatgag accttaaatc tcagggtcgt gggttcgagc   60
cccacgttgg gcg                                                      73

SEQ ID NO: 415          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 415
gcccggctag ctcagtcggt agagcatggg actttaaatc tcagggtcgt gggttcgagc   60
cccacgttgg gcg                                                      73

SEQ ID NO: 416          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 416
gcccggctag ctcagtcgat agagcatgag actttaaatc tcagggtcgt gggttcgagc   60
cgcacgttgg gcg                                                      73

SEQ ID NO: 417          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 417
gcccagctag ctcagtcggt agagcatgag actttaaatc tcagggtcat gggtttgagc   60
cccacgtttg gtg                                                      73

SEQ ID NO: 418          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 418
gcctggctag ctcagtcggc aaagcatgag actttaaatc tcagggtcgt gggctcgagc   60
tccatgttgg gcg                                                      73

SEQ ID NO: 419          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 419
gcccgactac ctcagtcggt ggagcatggg actttacatc ccagggttgt gggttcgagc   60
cccacattgg gca                                                      73

SEQ ID NO: 420          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 420
ccccggctgg ctcagtcagt agatcatgag actttaaatc tcagggtcgt gggttcacgc   60
cccacactgg gcg                                                      73

SEQ ID NO: 421          moltype = RNA   length = 65
FEATURE                 Location/Qualifiers
source                  1..65
                        mol_type = other RNA
                        organism = synthetic construct
tRNA                    1..65
                        note = tRNA
```

```
SEQUENCE: 421
gcgctagtca gtagagcatg agactttaaa tctcagggtc gtgggttcga gccccacatc    60
gggcg                                                                65

SEQ ID NO: 422            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 422
gcctggatag ctcagttggt agagcatcag actttaaatc tgagggtcca gggttcaagt    60
ccctgttcag gca                                                       73

SEQ ID NO: 423            moltype = RNA   length = 74
FEATURE                   Location/Qualifiers
source                    1..74
                          mol_type = other RNA
                          organism = synthetic construct
tRNA                      1..74
                          note = tRNA
SEQUENCE: 423
gccaggatag ttcaggtggt agagcatcag actttaaaac ctgagggttc agggttcaag    60
tctctgtttg ggcg                                                      74

SEQ ID NO: 424            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 424
acccagatag ctcagtcagt agagcatcag actttaaatc tgagggtcca aggttcatgt    60
ccctttttgg gtg                                                       73

SEQ ID NO: 425            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 425
acctgggtag cttagttggt agagcattgg actttaaatt tgagggccca ggtttcaagt    60
ccctgtttgg gtg                                                       73

SEQ ID NO: 426            moltype = RNA   length = 74
FEATURE                   Location/Qualifiers
source                    1..74
                          mol_type = other RNA
                          organism = synthetic construct
tRNA                      1..74
                          note = tRNA
SEQUENCE: 426
gcctgggtag ctcagtcggt agagctatca gactttaagc ctgaggattc agggttcaat    60
ccccttgctgg ggcg                                                     74

SEQ ID NO: 427            moltype = RNA   length = 62
FEATURE                   Location/Qualifiers
source                    1..62
                          mol_type = other RNA
                          organism = synthetic construct
tRNA                      1..62
                          note = tRNA
SEQUENCE: 427
gatagctcag ttgatagagc atcagacttt aaatctgagg gtccagggtt catgtccctg    60
tt                                                                   62

SEQ ID NO: 428            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 428
gttggggtaa ctcagttggt agagtagcag actttacatc tgagggtcca gggtttaagt    60
```

-continued

```
ccatgtccag gca                                                       73

SEQ ID NO: 429            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 429
gcctggatag ctcagttggt agagcatcag actttaaatc tgagggtcca gggttcaagt   60
ccctgttcag gcg                                                       73

SEQ ID NO: 430            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 430
gcctggatag ctcagtcggt agagcatcag actttaaatc tgagggtcca gggttcaagt   60
ccctgttcag gcg                                                       73

SEQ ID NO: 431            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 431
gcccggatag ctcagtcggt agagcatcag actttaaatc tgagggtccg gggttcaagt   60
ccctgttcgg gcg                                                       73

SEQ ID NO: 432            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 432
gcctgggtag ctcagtcggt agagcatcag actttaaatc tgagggtcca gggttcaagt   60
ccctgtccag gcg                                                       73

SEQ ID NO: 433            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 433
gcctggatag ctcagttggt agaacatcag actttaaatc tgacggtgca gggttcaagt   60
ccctgttcag gcg                                                       73

SEQ ID NO: 434            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 434
gcccggagag ctcagtgggt agagcatcag actttaaatc tgagggtcca gggttcaagt   60
cctcgttcgg gca                                                       73

SEQ ID NO: 435            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 435
acctgggtag ctcagtaggt agaacatcag actttaaatc tgagggtcta gggttcaagt   60
ccctgtccag gcg                                                       73
```

-continued

```
SEQ ID NO: 436            moltype = RNA   length = 76
FEATURE                   Location/Qualifiers
source                    1..76
                          mol_type = other RNA
                          organism = synthetic construct
tRNA                      1..76
                          note = tRNA
SEQUENCE: 436
gcctggatag ctccttcggt agagcatcat cagactttaa atgtgagggt ccagggttca  60
agttcctgtt tgggcg                                                  76

SEQ ID NO: 437            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 437
gcccagctag ctcagtcggt agagcataag actctaaatc tcagggttgt ggattcgtgc  60
cccatgctgg gtg                                                     73

SEQ ID NO: 438            moltype = RNA   length = 71
FEATURE                   Location/Qualifiers
source                    1..71
                          mol_type = other RNA
                          organism = synthetic construct
tRNA                      1..71
                          note = tRNA
SEQUENCE: 438
ctgcagctag ctcagtcggt agagcatgag actctaaatc tcagggtcat gggttcgtgc  60
cccatgttgg g                                                       71

SEQ ID NO: 439            moltype = RNA   length = 70
FEATURE                   Location/Qualifiers
source                    1..70
                          mol_type = other RNA
                          organism = synthetic construct
tRNA                      1..70
                          note = tRNA
SEQUENCE: 439
ccagcatgtc tcagtcggta tagtgtgaga ctctaaatct cagggtcgtg ggttcaagcc  60
ccacattggg                                                         70

SEQ ID NO: 440            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 440
gtctagctag atcagttggt agagcataag actctaaatc tcagggtcat gggtttgagc  60
cctacgttgg gcg                                                     73

SEQ ID NO: 441            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 441
gcccagctag ctcagccggt agagcacaag actctaaatc tcagggtcgt gggtttgagc  60
cctgtgttga gca                                                     73

SEQ ID NO: 442            moltype = RNA   length = 69
FEATURE                   Location/Qualifiers
source                    1..69
                          mol_type = other RNA
                          organism = synthetic construct
tRNA                      1..69
                          note = tRNA
SEQUENCE: 442
ccgaatagct tagttgatga agcgtgagac tctaaatctc agggtagtgg gttcaagccc  60
cacattgga                                                          69

SEQ ID NO: 443            moltype = RNA   length = 74
FEATURE                   Location/Qualifiers
```

-continued

```
source                  1..74
                        mol_type = other RNA
                        organism = synthetic construct
tRNA                    1..74
                        note = tRNA
SEQUENCE: 443
gcctggctac ctcagttggt agagcatggg actctaaatc ccagagtcag tgggttcaag   60
cctcacattg agtg                                                      74

SEQ ID NO: 444          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 444
gcccggctag ctcagtcggt agagcatgag accctaaatc tcagggtcgt gggttcgagc   60
cccacgttgg gcg                                                       73

SEQ ID NO: 445          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 445
gcccggctag ctcagtcggt agagcatggg actctaaatc tcagggtcgt gggttcgagc   60
cccacgttgg gcg                                                       73

SEQ ID NO: 446          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 446
gcccggctag ctcagtcgat agagcatgag actctaaatc tcagggtcgt gggttcgagc   60
cgcacgttgg gcg                                                       73

SEQ ID NO: 447          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 447
gcccagctag ctcagtcggt agagcatgag actctaaatc tcagggtcat gggtttgagc   60
cccacgtttg gtg                                                       73

SEQ ID NO: 448          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 448
gcctggctag ctcagtcggc aaagcatgag actctaaatc tcagggtcgt gggctcgagc   60
tccatgttgg gcg                                                       73

SEQ ID NO: 449          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 449
gcccgactac ctcagtcggt ggagcatggg actctacatc ccagggttgt gggttcgagc   60
cccacattgg gca                                                       73

SEQ ID NO: 450          moltype = RNA   length = 73
FEATURE                 Location/Qualifiers
source                  1..73
                        mol_type = other RNA
```

```
                              organism = synthetic construct
tRNA                          1..73
                              note = tRNA
SEQUENCE: 450
ccccggctgg ctcagtcagt agatcatgag actctaaatc tcagggtcgt gggttcacgc   60
cccacactgg gcg                                                       73

SEQ ID NO: 451        moltype = RNA  length = 65
FEATURE               Location/Qualifiers
source                1..65
                      mol_type = other RNA
                      organism = synthetic construct
tRNA                  1..65
                      note = tRNA
SEQUENCE: 451
gcgctagtca gtagagcatg agactctaaa tctcagggtc gtgggttcga gccccacatc   60
gggcg                                                                65

SEQ ID NO: 452        moltype = RNA  length = 73
FEATURE               Location/Qualifiers
source                1..73
                      mol_type = other RNA
                      organism = synthetic construct
tRNA                  1..73
                      note = tRNA
SEQUENCE: 452
gcctggatag ctcagttggt agagcatcag actctaaatc tgagggtcca gggttcaagt   60
ccctgttcag gca                                                       73

SEQ ID NO: 453        moltype = RNA  length = 73
FEATURE               Location/Qualifiers
source                1..73
                      mol_type = other RNA
                      organism = synthetic construct
tRNA                  1..73
                      note = tRNA
SEQUENCE: 453
gccaggatag ttcaggtggt agagcatcag actctaaacc tgagggttca gggttcaagt   60
ctctgtttgg gcg                                                       73

SEQ ID NO: 454        moltype = RNA  length = 73
FEATURE               Location/Qualifiers
source                1..73
                      mol_type = other RNA
                      organism = synthetic construct
tRNA                  1..73
                      note = tRNA
SEQUENCE: 454
acccagatag ctcagtcagt agagcatcag actctaaatc tgagggtcca aggttcatgt   60
ccctttttgg gtg                                                       73

SEQ ID NO: 455        moltype = RNA  length = 73
FEATURE               Location/Qualifiers
source                1..73
                      mol_type = other RNA
                      organism = synthetic construct
tRNA                  1..73
                      note = tRNA
SEQUENCE: 455
acctgggtag cttagttggt agagcattgg actctaaatt tgagggccca ggtttcaagt   60
ccctgtttgg gtg                                                       73

SEQ ID NO: 456        moltype = RNA  length = 75
FEATURE               Location/Qualifiers
source                1..75
                      mol_type = other RNA
                      organism = synthetic construct
tRNA                  1..75
                      note = tRNA
SEQUENCE: 456
gcctgggtag ctcagtcggt agagctatca gactctaaag cctgaggatt cagggttcaa   60
tcccttgctg gggcg                                                     75

SEQ ID NO: 457        moltype = RNA  length = 62
FEATURE               Location/Qualifiers
source                1..62
                      mol_type = other RNA
                      organism = synthetic construct
tRNA                  1..62
```

-continued

```
                           note = tRNA
SEQUENCE: 457
gatagctcag ttgatagagc atcagactct aaatctgagg gtccagggtt catgtccctg   60
tt                                                                  62

SEQ ID NO: 458           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 458
gttggggtaa ctcagttggt agagtagcag actctacatc tgagggtcca gggtttaagt   60
ccatgtccag gca                                                      73

SEQ ID NO: 459           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 459
gcctggatag ctcagttggt agagcatcag actctaaatc tgagggtcca gggttcaagt   60
ccctgttcag gcg                                                      73

SEQ ID NO: 460           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 460
gcctggatag ctcagtcggt agagcatcag actctaaatc tgagggtcca gggttcaagt   60
ccctgttcag gcg                                                      73

SEQ ID NO: 461           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 461
gcccggatag ctcagtcggt agagcatcag actctaaatc tgagggtccg gggttcaagt   60
ccctgttcgg gcg                                                      73

SEQ ID NO: 462           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 462
gcctgggtag ctcagtcggt agagcatcag actctaaatc tgagggtcca gggttcaagt   60
ccctgtccag gcg                                                      73

SEQ ID NO: 463           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 463
gcctggatag ctcagttggt agaacatcag actctaaatc tgacggtgca gggttcaagt   60
ccctgttcag gcg                                                      73

SEQ ID NO: 464           moltype = RNA   length = 73
FEATURE                  Location/Qualifiers
source                   1..73
                         mol_type = other RNA
                         organism = synthetic construct
tRNA                     1..73
                         note = tRNA
SEQUENCE: 464
```

-continued

```
gcccggagag ctcagtgggt agagcatcag actctaaatc tgagggtcca gggttcaagt   60
cctcgttcgg gca                                                      73

SEQ ID NO: 465          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 465
acctgggtag ctcagtaggt agaacatcag actctaaatc tgagggtcta gggttcaagt   60
ccctgtccag gcg                                                      73

SEQ ID NO: 466          moltype = RNA   length = 76
FEATURE                 Location/Qualifiers
source                  1..76
                        mol_type = other RNA
                        organism = synthetic construct
tRNA                    1..76
                        note = tRNA
SEQUENCE: 466
gcctggatag ctccttcggt agagcatcat cagactctaa atgtgagggt ccagggttca   60
agttcctgtt tgggcg                                                   76

SEQ ID NO: 467          moltype = RNA   length = 75
FEATURE                 Location/Qualifiers
source                  1..75
                        mol_type = other RNA
                        organism = synthetic construct
tRNA                    1..75
                        note = tRNA
SEQUENCE: 467
ggcagaatgg tgcagcggtt cagcacccag gctcttcagc cagctgttgc ctgggctcaa   60
atcccagctc tgcca                                                    75

SEQ ID NO: 468          moltype = RNA   length = 176
FEATURE                 Location/Qualifiers
source                  1..176
                        mol_type = other RNA
                        organism = synthetic construct
tRNA                    1..176
                        note = tRNA
SEQUENCE: 468
ggctgtatag ctcagtggta gagcatttga cttcagaatc ctatactcag gggaaggaga   60
actgggggtt tctcagtggg tcaaaggact tgtagtggta aatcaaaagc aactctataa  120
gctatgtaac aaactttaaa gtcatatgta gctgggttca atcctgtttt ctgcca       176

SEQ ID NO: 469          moltype = RNA   length = 79
FEATURE                 Location/Qualifiers
source                  1..79
                        mol_type = other RNA
                        organism = synthetic construct
tRNA                    1..79
                        note = tRNA
SEQUENCE: 469
ggctgtatag ctcagtggta gagcatttga cttcagcttt aaagtcatat gtagctgggt   60
tcaaatcctt tttctgcca                                                79

SEQ ID NO: 470          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 470
ggggggcatag ctcagtggta gagcatttga cttcagatca agaggtccct ggttcaaatc  60
caggtgcccc ct                                                       72

SEQ ID NO: 471          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 471
gggggtatag ctcaggggta gagcatttga cttcagatca agaggtccct ggttcaaatc   60
```

-continued

```
caggtgcccc cc                                                         72

SEQ ID NO: 472            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 472
gggggtatag cttagcggta gagcatttga cttcagatca agaggtcccc ggttcaaatc   60
cgggtgcccc ct                                                        72

SEQ ID NO: 473            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 473
gggggtatag cttagggta gagcatttga cttcagatca aaaggtccct ggttcaaatc    60
caggtgcccc tt                                                        72

SEQ ID NO: 474            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 474
gggggtatag ctcaggggta gagcatttga cttcagatca agaggtcccc agttcaaatc   60
tgggtgcccc ct                                                        72

SEQ ID NO: 475            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 475
gggggtatag ctcaggggta gagcatttga cttcagatca agaagtcccc ggttcaaatc   60
cgggtgcccc ct                                                        72

SEQ ID NO: 476            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 476
gggggtatag ctcaggggta gagcatttga cttcagatca agaggtctct ggttcaaatc   60
caggtgcccc ct                                                        72

SEQ ID NO: 477            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 477
gggggtatag ctcaggggta gagcacttga cttcagatca agaagtcctt ggttcaaatc   60
caggtgcccc ct                                                        72

SEQ ID NO: 478            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 478
ggggatatag ctcaggggta gagcatttga cttcagatca agaggtcccc ggttcaaatc   60
cgggtgcccc cc                                                        72
```

-continued

```
SEQ ID NO: 479          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 479
gggggtatag ttcaggggta gagcatttga cttcagatca agaggtccct ggttcaaatc  60
caggtgcccc ct                                                      72

SEQ ID NO: 480          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 480
gggggtatag ctcaggggta gagcatttga cttcaaatca agaggtccct gattcaaatc  60
caggtgcccc ct                                                      72

SEQ ID NO: 481          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 481
gggcgtatag ctcaggggta gagcatttga cttcagatca agaggtcccc agttcaaatc  60
tgggtgcccc ct                                                      72

SEQ ID NO: 482          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 482
gggggtatag ctcacaggta gagcatttga cttcagatca agaggtcccc ggttcaaatc  60
tgggtgcccc ct                                                      72

SEQ ID NO: 483          moltype = RNA   length = 70
FEATURE                 Location/Qualifiers
source                  1..70
                        mol_type = other RNA
                        organism = synthetic construct
tRNA                    1..70
                        note = tRNA
SEQUENCE: 483
gggcgtatag ctcaggggta gagcatttga cttcagatca agaggtcccc agttcaaatc  60
tgggtgccca                                                         70

SEQ ID NO: 484          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 484
gggggtatag ctcacaggta gagcatttga cttcagatca agaggtcccc ggttcaaatc  60
cggttactcc ct                                                      72

SEQ ID NO: 485          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 485
gggggtaggg ctcagggata gagcatttga cttcagatca agaggtcccc ggttcgaatc  60
taggtgcccc ct                                                      72

SEQ ID NO: 486          moltype = RNA   length = 66
FEATURE                 Location/Qualifiers
```

-continued

```
source               1..66
                     mol_type = other RNA
                     organism = synthetic construct
tRNA                 1..66
                     note = tRNA
SEQUENCE: 486
ggtatatctc agggggcaga gcatttgact tcagatcaag aggtccccgg ttgaaatccg   60
ggtgct                                                               66

SEQ ID NO: 487       moltype = RNA   length = 72
FEATURE              Location/Qualifiers
source               1..72
                     mol_type = other RNA
                     organism = synthetic construct
tRNA                 1..72
                     note = tRNA
SEQUENCE: 487
gggggtatag ctcaggggta gagcacttga cttcagatca agaggtccct ggttcaaatc   60
caggtgcccc ct                                                        72

SEQ ID NO: 488       moltype = RNA   length = 72
FEATURE              Location/Qualifiers
source               1..72
                     mol_type = other RNA
                     organism = synthetic construct
tRNA                 1..72
                     note = tRNA
SEQUENCE: 488
gggggtatag ctcagtggta gagcatttga cttcagatca agaggtccct ggttcaaatc   60
cgggtgcccc ct                                                        72

SEQ ID NO: 489       moltype = RNA   length = 73
FEATURE              Location/Qualifiers
source               1..73
                     mol_type = other RNA
                     organism = synthetic construct
tRNA                 1..73
                     note = tRNA
SEQUENCE: 489
gggggtatag ctcagtgggt agagcatttg acttcagatc aagaggtccc cggttcaaat   60
ccgggtgccc cct                                                       73

SEQ ID NO: 490       moltype = RNA   length = 72
FEATURE              Location/Qualifiers
source               1..72
                     mol_type = other RNA
                     organism = synthetic construct
tRNA                 1..72
                     note = tRNA
SEQUENCE: 490
gggggtgtag ctcagtggta gagcatttga cttcagatca agaggtccct ggttcaaatc   60
caggtgcccc ct                                                        72

SEQ ID NO: 491       moltype = RNA   length = 72
FEATURE              Location/Qualifiers
source               1..72
                     mol_type = other RNA
                     organism = synthetic construct
tRNA                 1..72
                     note = tRNA
SEQUENCE: 491
gggggtatag ctcaggggta gagcatttga cttcagatca agaggtcccc ggttcaaatc   60
cgggtgcccc ct                                                        72

SEQ ID NO: 492       moltype = RNA   length = 72
FEATURE              Location/Qualifiers
source               1..72
                     mol_type = other RNA
                     organism = synthetic construct
tRNA                 1..72
                     note = tRNA
SEQUENCE: 492
gggggtatag ctcaggggta gagcatttga cttcagatca agaggtccct ggttcaaatc   60
caggtgcccc ct                                                        72

SEQ ID NO: 493       moltype = RNA   length = 72
FEATURE              Location/Qualifiers
source               1..72
                     mol_type = tRNA
```

```
                             organism = Mus musculus
tRNA                         1..72
                             note = tRNA
SEQUENCE: 493
gacctcgtgg cgcaatggta gcgcgtctga cttcagatca gaaggttgcg tgttcaaatc   60
acgtcggggt ca                                                        72

SEQ ID NO: 494         moltype = RNA   length = 72
FEATURE                Location/Qualifiers
source                 1..72
                       mol_type = tRNA
                       organism = Mus musculus
tRNA                   1..72
                       note = tRNA
SEQUENCE: 494
gacctcgtgg cacaatggta gcacgtctga cttcagatca gaaggttgcg tgttcaaatc   60
acgtcggggt ca                                                        72

SEQ ID NO: 495         moltype = RNA   length = 106
FEATURE                Location/Qualifiers
source                 1..106
                       mol_type = tRNA
                       organism = Saccharomyces cerevisiae
tRNA                   1..106
                       note = tRNA
SEQUENCE: 495
gaagcggtgg ctcaatggta gagctttcga cttcaattaa atcttggaaa ttccacggaa   60
taagattgca atcgaagggt tgcaggttca attcctgtcc gtttca                  106

SEQ ID NO: 496         moltype = RNA   length = 72
FEATURE                Location/Qualifiers
source                 1..72
                       mol_type = tRNA
                       organism = Saccharomyces cerevisiae
tRNA                   1..72
                       note = tRNA
SEQUENCE: 496
gaagcggtgg ctcaatggta gagctttcga cttcaaatcg aagggttgca ggttcaattc   60
ctgtccgttt ca                                                        72

SEQ ID NO: 497         moltype = RNA   length = 72
FEATURE                Location/Qualifiers
source                 1..72
                       mol_type = tRNA
                       organism = Pan troglodytes
tRNA                   1..72
                       note = tRNA
SEQUENCE: 497
ggcctcatgg tgcaacagta gtgtgtctga cttcagatca gaaggttgta tgttcaaatc   60
acataggggt ca                                                        72

SEQ ID NO: 498         moltype = RNA   length = 72
FEATURE                Location/Qualifiers
source                 1..72
                       mol_type = tRNA
                       organism = Oryctolagus cuniculus
tRNA                   1..72
                       note = tRNA
SEQUENCE: 498
gacctcgtgg tgaaatggta gcatgtttga cttcaaatca ggaggttgtg tgttcaagtc   60
acatcagggt ca                                                        72

SEQ ID NO: 499         moltype = RNA   length = 72
FEATURE                Location/Qualifiers
source                 1..72
                       mol_type = tRNA
                       organism = Oryctolagus cuniculus
tRNA                   1..72
                       note = tRNA
SEQUENCE: 499
gaccttgtgg cgcaatggta gcatgtttga cttcaaatca ggaggttgtg tgttcaagtc   60
acatcagggt ca                                                        72

SEQ ID NO: 500         moltype = RNA   length = 72
FEATURE                Location/Qualifiers
source                 1..72
                       mol_type = tRNA
                       organism = Oryctolagus cuniculus
tRNA                   1..72
```

-continued

```
                              note = tRNA
SEQUENCE: 500
gacctcgtgg cgcaacggta gcgcgtctga cttcagatca gaaggctgcg tgttcgaatc    60
acgccggggt ca                                                        72

SEQ ID NO: 501          moltype = RNA   length = 72
FEATURE                 Location/Qualifiers
source                  1..72
                        mol_type = tRNA
                        organism = Rattus norvegicus
tRNA                    1..72
                        note = tRNA
SEQUENCE: 501
gaccttgtgg ctcaatggta gcgcatctga cttcagatca ggaggttgca cgttcaaatc    60
atgccggggt ca                                                        72

SEQ ID NO: 502          moltype = RNA   length = 72
FEATURE                 Location/Qualifiers
source                  1..72
                        mol_type = tRNA
                        organism = Rattus norvegicus
tRNA                    1..72
                        note = tRNA
SEQUENCE: 502
gaccttgtgg cgcaacggta gcgcgtctga cttcagatca gaaggttgcg tgttcaaatc    60
acgtcggggt ca                                                        72

SEQ ID NO: 503          moltype = RNA   length = 72
FEATURE                 Location/Qualifiers
source                  1..72
                        mol_type = tRNA
                        organism = Xenopus tropicalis
tRNA                    1..72
                        note = tRNA
SEQUENCE: 503
gacctcgtgg cgcaacggta gcgcgtctga cttcagatca gaaggttgcg tattcaaatc    60
acgtcggggt ca                                                        72

SEQ ID NO: 504          moltype = RNA   length = 72
FEATURE                 Location/Qualifiers
source                  1..72
                        mol_type = tRNA
                        organism = Xenopus tropicalis
tRNA                    1..72
                        note = tRNA
SEQUENCE: 504
gacctcgtgg cgcaacggca gcgcgtctga cttcacatta gaaggttgcg tgttcaaatc    60
acgtcggggt ca                                                        72

SEQ ID NO: 505          moltype = RNA   length = 72
FEATURE                 Location/Qualifiers
source                  1..72
                        mol_type = tRNA
                        organism = Xenopus tropicalis
tRNA                    1..72
                        note = tRNA
SEQUENCE: 505
gacctcatgg cgcaacggta gcgcgtctga cttcagatca gaaggttgcg tgttcaaatc    60
acatcggggt ca                                                        72

SEQ ID NO: 506          moltype = RNA   length = 72
FEATURE                 Location/Qualifiers
source                  1..72
                        mol_type = tRNA
                        organism = Xenopus tropicalis
tRNA                    1..72
                        note = tRNA
SEQUENCE: 506
gacctcgtgg tgcaacggta gcgcgtatga tttcagatca gaaggttgcg tgttcaaatc    60
acgtcggggt ca                                                        72

SEQ ID NO: 507          moltype = RNA   length = 72
FEATURE                 Location/Qualifiers
source                  1..72
                        mol_type = tRNA
                        organism = Xenopus tropicalis
tRNA                    1..72
                        note = tRNA
SEQUENCE: 507
```

```
gacctcgtag cgcaacggta gcgcgtctga cttcagatca gaaggttgcg tgttcaaatc    60
acgtcggggt ca                                                        72

SEQ ID NO: 508          moltype = RNA   length = 76
FEATURE                 Location/Qualifiers
source                  1..76
                        mol_type = tRNA
                        organism = Xenopus tropicalis
tRNA                    1..76
                        note = tRNA
SEQUENCE: 508
aggggtatag ctcaattggc agagcgtcgg tcttcaaaac cgaaggttgt aggttcgatt    60
cctactgccc ctgcca                                                    76

SEQ ID NO: 509          moltype = RNA   length = 72
FEATURE                 Location/Qualifiers
source                  1..72
                        mol_type = tRNA
                        organism = Xenopus tropicalis
tRNA                    1..72
                        note = tRNA
SEQUENCE: 509
gacctcatgg cgcaacggta gcgcgtctga cttcagatca gaaggttgcg tgttcaaatc    60
acgtcggggt ca                                                        72

SEQ ID NO: 510          moltype = RNA   length = 72
FEATURE                 Location/Qualifiers
source                  1..72
                        mol_type = tRNA
                        organism = Xenopus tropicalis
tRNA                    1..72
                        note = tRNA
SEQUENCE: 510
gacctcgtgg cgcaacggta gcgcgtctaa cttcagatca gaaggttgcg tgttcaaatc    60
acgtcggggt ca                                                        72

SEQ ID NO: 511          moltype = RNA   length = 73
FEATURE                 Location/Qualifiers
source                  1..73
                        mol_type = tRNA
                        organism = Xenopus tropicalis
tRNA                    1..73
                        note = tRNA
SEQUENCE: 511
acgggagtag ctcagttggt agagcaccgg tcttcaaaac cgggtgtcgg gagttcgagc    60
ctctcctccc gtg                                                       73

SEQ ID NO: 512          moltype = RNA   length = 72
FEATURE                 Location/Qualifiers
source                  1..72
                        mol_type = tRNA
                        organism = Xenopus tropicalis
tRNA                    1..72
                        note = tRNA
SEQUENCE: 512
gacctcgtgg cgcaacggta gcgcgtctga cttcagatca gaaggttgca tgttcaaatc    60
acgtcggggt ca                                                        72

SEQ ID NO: 513          moltype = RNA   length = 72
FEATURE                 Location/Qualifiers
source                  1..72
                        mol_type = tRNA
                        organism = Drosophila melanogaster
tRNA                    1..72
                        note = tRNA
SEQUENCE: 513
gactccgtgg cgcaacggta gcgcgtccga cttcagatcg gaaggttgcg tgttcaaatc    60
acgtcggggt ca                                                        72

SEQ ID NO: 514          moltype = RNA   length = 72
FEATURE                 Location/Qualifiers
source                  1..72
                        mol_type = tRNA
                        organism = Drosophila melanogaster
tRNA                    1..72
                        note = tRNA
SEQUENCE: 514
gactccgtgg cgcaacggta gcgcgtctga cttcagatca gaaggttgcg tgttcaaatc    60
acgtcggggt ca                                                        72
```

-continued

```
SEQ ID NO: 515          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 515
ggcctcgtgg cgcaacggta gcgcgtctga ctccagatca gaaggttgcg tgttcaaatc   60
acgtcggggt ca                                                       72

SEQ ID NO: 516          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 516
ggcctcgtgg cgcaacggta gcacgtctga ctccagatca gaaggttgcg tgttcaaatc   60
acgtcggggt ca                                                       72

SEQ ID NO: 517          moltype = RNA   length = 73
FEATURE                 Location/Qualifiers
source                  1..73
                        mol_type = other RNA
                        organism = synthetic construct
tRNA                    1..73
                        note = tRNA
SEQUENCE: 517
cggcctcgtg gcgcaacggt agcacgtctg acttcagatc agaaggttgc gtgttcaaat   60
cacgtcgggg tca                                                      73

SEQ ID NO: 518          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 518
ggcctcgtcg cgcaacggta gcgcgtctga ctccagatca gaaggttgcg tgttcaaatc   60
acgtcggggt ca                                                       72

SEQ ID NO: 519          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 519
ggcctcgtcg cgcaacggta gcgcgtctga cttcagatca gaaggttgcg tgttcaaatc   60
acgtcggggt ca                                                       72

SEQ ID NO: 520          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 520
ggcctcgtcg cgcaacggta gcacgtctga ctccagatca gaaggttgcg tgttcaaatc   60
acgtcggggt ca                                                       72

SEQ ID NO: 521          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 521
ggcctcgtcg cgcaacggta gcacgtctga cttcagatca gaaggttgcg tgttcaaatc   60
acgtcggggt ca                                                       72

SEQ ID NO: 522          moltype =    length =
```

-continued

```
SEQUENCE: 522
000

SEQ ID NO: 523            moltype = RNA   length = 75
FEATURE                   Location/Qualifiers
source                    1..75
                          mol_type = other RNA
                          organism = synthetic construct
tRNA                      1..75
                          note = tRNA
SEQUENCE: 523
gttaagatgg cagagcctgg taattgcatc aaacttaaaa ttttataatc agaggttcaa   60
ctcctcttct taaca                                                    75

SEQ ID NO: 524            moltype = RNA   length = 75
FEATURE                   Location/Qualifiers
source                    1..75
                          mol_type = other RNA
                          organism = synthetic construct
tRNA                      1..75
                          note = tRNA
SEQUENCE: 524
gttaagatgg cagagcccgg caattgcatc agacttaaaa ctttataatc agaggttcaa   60
ctcctctcat taaca                                                    75

SEQ ID NO: 525            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 525
ggtagcgtgg ccgagcggtc taaggcgctg gatttcagct ccagtctctt cggggggcgtg   60
ggttcaaatc ccaccgctgc ca                                            82

SEQ ID NO: 526            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 526
ggtagcgtgg ccgagtggtc taagacgctg gatttcagct ccagtctctt cggggggcgtg   60
ggtttgaatc ccaccgctgc ca                                            82

SEQ ID NO: 527            moltype = RNA   length = 73
FEATURE                   Location/Qualifiers
source                    1..73
                          mol_type = other RNA
                          organism = synthetic construct
tRNA                      1..73
                          note = tRNA
SEQUENCE: 527
gggccagtgg ctcaatggat aatgcgtctg acttcaaatc agaagattcc agccttgact   60
cctggctggc tca                                                      73

SEQ ID NO: 528            moltype = RNA   length = 82
FEATURE                   Location/Qualifiers
source                    1..82
                          mol_type = other RNA
                          organism = synthetic construct
tRNA                      1..82
                          note = tRNA
SEQUENCE: 528
ggtagggtgg ccgagcggtc taaggcactg tatttcaact ccagtctctt cagaggcatg   60
ggtttgaatc ccactgctgc ca                                            82

SEQ ID NO: 529            moltype = RNA   length = 65
FEATURE                   Location/Qualifiers
source                    1..65
                          mol_type = other RNA
                          organism = synthetic construct
tRNA                      1..65
                          note = tRNA
SEQUENCE: 529
gccgagcggt ctaaggctcc ggatttcagc gccggtgtct tcggaggcat gggttcgaat   60
tccac                                                               65
```

-continued

```
SEQ ID NO: 530          moltype = RNA  length = 106
FEATURE                 Location/Qualifiers
source                  1..106
                        mol_type = other RNA
                        organism = synthetic construct
tRNA                    1..106
                        note = tRNA
SEQUENCE: 530
gtcaggatgg ccgagtggtc taaggcgcca gacttcagct aagcttcctc cgcggtgggg   60
attctggtct ccaatggagg cgtgggttcg aatcccactt ctgaca                 106

SEQ ID NO: 531          moltype =    length =
SEQUENCE: 531
000

SEQ ID NO: 532          moltype = RNA  length = 83
FEATURE                 Location/Qualifiers
source                  1..83
                        mol_type = other RNA
                        organism = synthetic construct
tRNA                    1..83
                        note = tRNA
SEQUENCE: 532
gtcaggatgg ccgagtggtc taaggcgcca gacttcagtt ctggtctcca atggaggcgt   60
gggttcgaat cccacttctg aca                                           83

SEQ ID NO: 533          moltype = RNA  length = 105
FEATURE                 Location/Qualifiers
source                  1..105
                        mol_type = other RNA
                        organism = synthetic construct
tRNA                    1..105
                        note = tRNA
SEQUENCE: 533
gtcaggatgg ccgagtggtc taaggcgcca gacttcagct tggcttcctc gtgttgagga   60
ttctggtctc caatggaggc gtgggttcga atcccacttc tgaca                  105

SEQ ID NO: 534          moltype = RNA  length = 83
FEATURE                 Location/Qualifiers
source                  1..83
                        mol_type = other RNA
                        organism = synthetic construct
tRNA                    1..83
                        note = tRNA
SEQUENCE: 534
gtcaggatgg ccgagtggtc taaggcgcca gacttcagtt ctggtctcca atggaggcgt   60
gggttcgaat cccacttctg aca                                           83

SEQ ID NO: 535          moltype = RNA  length = 108
FEATURE                 Location/Qualifiers
source                  1..108
                        mol_type = other RNA
                        organism = synthetic construct
tRNA                    1..108
                        note = tRNA
SEQUENCE: 535
gtcaggatgg ccgagtggtc taaggcgcca gacttcagct tactgcttcc tgtgttcggg   60
tcttctggtc tccgtatgga ggcgtgggtt cgaatcccac ttctgaca               108

SEQ ID NO: 536          moltype = RNA  length = 84
FEATURE                 Location/Qualifiers
source                  1..84
                        mol_type = other RNA
                        organism = synthetic construct
tRNA                    1..84
                        note = tRNA
SEQUENCE: 536
gtcaggatgg ccgagtggtc taaggcgcca gacttcagtt ctggtctccg tatggaggcg   60
tgggttcgaa tcccacttct gaca                                          84

SEQ ID NO: 537          moltype = RNA  length = 107
FEATURE                 Location/Qualifiers
source                  1..107
                        mol_type = other RNA
                        organism = synthetic construct
tRNA                    1..107
                        note = tRNA
SEQUENCE: 537
```

```
gtcaggatgg ccgagtggtc taaggcgcca gacttcagtt gctacttccc aggtttgggg   60
cttctggtct ccgcatggag gcgtgggttc gaatcccact tctgaca                  107

SEQ ID NO: 538              moltype = RNA   length = 84
FEATURE                     Location/Qualifiers
source                      1..84
                            mol_type = other RNA
                            organism = synthetic construct
tRNA                        1..84
                            note = tRNA
SEQUENCE: 538
gtcaggatgg ccgagtggtc taaggcgcca gacttcagtt ctggtctccg catggaggcg   60
tgggttcgaa tcccacttct gaca                                            84

SEQ ID NO: 539              moltype = RNA   length = 106
FEATURE                     Location/Qualifiers
source                      1..106
                            mol_type = other RNA
                            organism = synthetic construct
tRNA                        1..106
                            note = tRNA
SEQUENCE: 539
gtcaggatgg ccgagtggtc taaggcgcca gacttcaggt aagcaccttg cctgcgggct   60
ttctggtctc cggatggagg cgtgggttcg aatcccactt ctgaca                   106

SEQ ID NO: 540              moltype = RNA   length = 85
FEATURE                     Location/Qualifiers
source                      1..85
                            mol_type = other RNA
                            organism = synthetic construct
tRNA                        1..85
                            note = tRNA
SEQUENCE: 540
gtcaggatgg ccgagtggtc taaggcgcca gacttcagtt tctggtctcc ggatggaggc   60
gtgggttcga atcccacttc tgaca                                           85

SEQ ID NO: 541              moltype = RNA   length = 74
FEATURE                     Location/Qualifiers
source                      1..74
                            mol_type = other RNA
                            organism = synthetic construct
tRNA                        1..74
                            note = tRNA
SEQUENCE: 541
gcctccttag tgcagtaggt agcgcatcag tcttcaaatc tgaatggtcc tgagttcaag   60
cctcagaggg ggca                                                       74

SEQ ID NO: 542              moltype = RNA   length = 84
FEATURE                     Location/Qualifiers
source                      1..84
                            mol_type = other RNA
                            organism = synthetic construct
tRNA                        1..84
                            note = tRNA
SEQUENCE: 542
gtcaggatgg ccgagcagtc ttaaggcgct gcgtttcaat cgcaccctcc gctggaggcg   60
tgggttcgaa tcccactttt gaca                                            84

SEQ ID NO: 543              moltype = RNA   length = 60
FEATURE                     Location/Qualifiers
source                      1..60
                            mol_type = other RNA
                            organism = synthetic construct
tRNA                        1..60
                            note = tRNA
SEQUENCE: 543
ggttccatgg tgtaatggtg agcactctgg acttcaaatc cagaagtagt gctggaacaa   60

SEQ ID NO: 544              moltype = RNA   length = 83
FEATURE                     Location/Qualifiers
source                      1..83
                            mol_type = other RNA
                            organism = synthetic construct
tRNA                        1..83
                            note = tRNA
SEQUENCE: 544
gtcagggtgg ctgagcagtc tgaggggctg cgtttcagtc gcagtctgcc ctggaggcgt   60
gggttcgaat cccactcctg aaa                                             83
```

-continued

```
SEQ ID NO: 545          moltype = RNA   length = 83
FEATURE                 Location/Qualifiers
source                  1..83
                        mol_type = other RNA
                        organism = synthetic construct
tRNA                    1..83
                        note = tRNA
SEQUENCE: 545
accaggatgg ccgagtggtt aaggcgttgg acttcagatc caatggacat atgtccgcgt    60
gggttcgaac cccactcctg gta                                           83

SEQ ID NO: 546          moltype = RNA   length = 83
FEATURE                 Location/Qualifiers
source                  1..83
                        mol_type = other RNA
                        organism = synthetic construct
tRNA                    1..83
                        note = tRNA
SEQUENCE: 546
accgggatgg ccgagtggtt aaggcgttgg acttcagatc caatgggctg gtgcccgcgt    60
gggttcgaac cccactctcg gta                                           83

SEQ ID NO: 547          moltype =    length =
SEQUENCE: 547
000

SEQ ID NO: 548          moltype = RNA   length = 83
FEATURE                 Location/Qualifiers
source                  1..83
                        mol_type = other RNA
                        organism = synthetic construct
tRNA                    1..83
                        note = tRNA
SEQUENCE: 548
accagaatgg ccgagtggtt aaggcgttgg acttcagatc caatggattc atatccgcgt    60
gggttcgaac cccacttctg gta                                           83

SEQ ID NO: 549          moltype = RNA   length = 83
FEATURE                 Location/Qualifiers
source                  1..83
                        mol_type = other RNA
                        organism = synthetic construct
tRNA                    1..83
                        note = tRNA
SEQUENCE: 549
accgggatgg ctgagtggtt aaggcgttgg acttcagatc caatggacag gtgtccgcgt    60
gggttcgagc cccactcccg gta                                           83

SEQ ID NO: 550          moltype = RNA   length = 83
FEATURE                 Location/Qualifiers
source                  1..83
                        mol_type = other RNA
                        organism = synthetic construct
tRNA                    1..83
                        note = tRNA
SEQUENCE: 550
actcatttgg ctgagtggtt aaggcattgg acttcagatc caatggagta gtggctgtgt    60
gggtttaaac cccactactg gta                                           83

SEQ ID NO: 551          moltype = RNA   length = 69
FEATURE                 Location/Qualifiers
source                  1..69
                        mol_type = other RNA
                        organism = synthetic construct
tRNA                    1..69
                        note = tRNA
SEQUENCE: 551
gagaaagtca tcgtagttac gaagttggct tcaacccagt tttgggaggt tcaattcctt    60
cctttctct                                                           69

SEQ ID NO: 552          moltype = RNA   length = 84
FEATURE                 Location/Qualifiers
source                  1..84
                        mol_type = other RNA
                        organism = synthetic construct
tRNA                    1..84
                        note = tRNA
SEQUENCE: 552
accaggatgg ccaagtagtt aaaggcactg gacttcagag ccaatggaca tatgtctgtg    60
```

-continued

```
tgggtttgaa ccccactcct ggtg                                              84

SEQ ID NO: 553          moltype = RNA  length = 82
FEATURE                 Location/Qualifiers
source                  1..82
                        mol_type = other RNA
                        organism = synthetic construct
tRNA                    1..82
                        note = tRNA
SEQUENCE: 553
ggtagcgtgg ccgagcggtc taaggcgctg gatttcagct ccagtctctt cggaggcgtg     60
ggttcgaatc ccaccgctgc ca                                                82

SEQ ID NO: 554          moltype = RNA  length = 82
FEATURE                 Location/Qualifiers
source                  1..82
                        mol_type = other RNA
                        organism = synthetic construct
tRNA                    1..82
                        note = tRNA
SEQUENCE: 554
ggtagtgtgg ccgagcggtc taaggcgctg gatttcagct ccagtctctt cgggggcgtg     60
ggttcgaatc ccaccactgc ca                                                82

SEQ ID NO: 555          moltype = RNA  length = 82
FEATURE                 Location/Qualifiers
source                  1..82
                        mol_type = other RNA
                        organism = synthetic construct
tRNA                    1..82
                        note = tRNA
SEQUENCE: 555
ggtagcgtgg ccgagtggtc taaggcgctg gatttcagct ccagtcattt cgatggcgtg     60
ggttcgaatc ccaccgctgc ca                                                82

SEQ ID NO: 556          moltype = RNA  length = 82
FEATURE                 Location/Qualifiers
source                  1..82
                        mol_type = other RNA
                        organism = synthetic construct
tRNA                    1..82
                        note = tRNA
SEQUENCE: 556
ggtagtgtgg ttgaatggtc taaggcactg aatttcagct ccagtctctt tggggacgtg     60
ggtttaaatc ccactgctgc aa                                                82

SEQ ID NO: 557          moltype = RNA  length = 70
FEATURE                 Location/Qualifiers
source                  1..70
                        mol_type = other RNA
                        organism = synthetic construct
tRNA                    1..70
                        note = tRNA
SEQUENCE: 557
gagaaggtca cagaggttat gggattggct ttaaaccagt ctgtgggggg ttcgattccc     60
tccttttttca                                                             70

SEQ ID NO: 558          moltype = RNA  length = 70
FEATURE                 Location/Qualifiers
source                  1..70
                        mol_type = other RNA
                        organism = synthetic construct
tRNA                    1..70
                        note = tRNA
SEQUENCE: 558
gagaaggtca tagaggttat gggattggct ttaaaccagt ctctgggggg ttcgattccc     60
tccttttttca                                                             70

SEQ ID NO: 559          moltype = RNA  length = 69
FEATURE                 Location/Qualifiers
source                  1..69
                        mol_type = other RNA
                        organism = synthetic construct
tRNA                    1..69
                        note = tRNA
SEQUENCE: 559
gaaaaagtca taggggttat gaggctggct ttaaaccagc cttaggaggt tcaattcctt     60
ccttttttg                                                               69
```

-continued

```
SEQ ID NO: 560          moltype = RNA   length = 74
FEATURE                 Location/Qualifiers
source                  1..74
                        mol_type = other RNA
                        organism = synthetic construct
tRNA                    1..74
                        note = tRNA
SEQUENCE: 560
ggccggttag ctcagttggt tagagcgtgc tgctttaaat gccagggtcg aggtttcgat  60
ccccgtacgg gcct                                                    74

SEQ ID NO: 561          moltype = RNA   length = 82
FEATURE                 Location/Qualifiers
source                  1..82
                        mol_type = other RNA
                        organism = synthetic construct
tRNA                    1..82
                        note = tRNA
SEQUENCE: 561
gtagtcgtgg ccgagtggtt aaggcgatgg actttaaatc cattggggtt tccccgcgca  60
ggttcgaatc ctgccgacta cg                                           82

SEQ ID NO: 562          moltype = RNA   length = 82
FEATURE                 Location/Qualifiers
source                  1..82
                        mol_type = other RNA
                        organism = synthetic construct
tRNA                    1..82
                        note = tRNA
SEQUENCE: 562
gtagtcgtgg ccgagtggtt aaggcgatgg actttaaatc cattggggtt tccccacgca  60
ggttcgaatc ctgccgacta cg                                           82

SEQ ID NO: 563          moltype = RNA   length = 82
FEATURE                 Location/Qualifiers
source                  1..82
                        mol_type = other RNA
                        organism = synthetic construct
tRNA                    1..82
                        note = tRNA
SEQUENCE: 563
gtagtcgtgg ccgagtggtt aaggtgatgg actttaaacc cattggggtc tccccgcgca  60
ggttcgaatc ctgccgacta cg                                           82

SEQ ID NO: 564          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 564
gggtgtatgg ctcaggggta gagaatttga ctttagatca agaggtccct ggttcaaatc  60
caggtgcccc ct                                                      72

SEQ ID NO: 565          moltype = RNA   length = 78
FEATURE                 Location/Qualifiers
source                  1..78
                        mol_type = other RNA
                        organism = synthetic construct
tRNA                    1..78
                        note = tRNA
SEQUENCE: 565
agttgtagct gagtggttaa ggcaacgagc tttaaattcg ttggtttctc tctgtgcagg  60
tttgaatcct gctaatta                                                78

SEQ ID NO: 566          moltype = RNA   length = 70
FEATURE                 Location/Qualifiers
source                  1..70
                        mol_type = other RNA
                        organism = synthetic construct
tRNA                    1..70
                        note = tRNA
SEQUENCE: 566
caagaaattc atagaggtta tgggattggc tttaaaccag tttcaggagg ttcgattcct  60
tcctttttgg                                                         70

SEQ ID NO: 567          moltype = RNA   length = 82
FEATURE                 Location/Qualifiers
```

```
source                    1..82
                          mol_type = other RNA
                          organism = synthetic construct
tRNA                      1..82
                          note = tRNA
SEQUENCE: 567
gctgtgatgg ccgagtggtt aaggcgttgg actttaaatc caatggggtc tccccgcgca  60
ggttcgaatc ctgctcacag cg                                           82

SEQ ID NO: 568           moltype = RNA   length = 82
FEATURE                  Location/Qualifiers
source                    1..82
                          mol_type = other RNA
                          organism = synthetic construct
tRNA                      1..82
                          note = tRNA
SEQUENCE: 568
gctgtgatgg ccgagtggtt aaggcgttgg actttaaatc caatggggtc tccccgcgca  60
ggttcaaatc ctgctcacag cg                                           82

SEQ ID NO: 569           moltype = RNA   length = 82
FEATURE                  Location/Qualifiers
source                    1..82
                          mol_type = other RNA
                          organism = synthetic construct
tRNA                      1..82
                          note = tRNA
SEQUENCE: 569
gctgtgatgg ccgagtggtt aaggtgttgg actttaaatc caatgggggt tccccgcgca  60
ggttcaaatc ctgctcacag cg                                           82

SEQ ID NO: 570           moltype = RNA   length = 82
FEATURE                  Location/Qualifiers
source                    1..82
                          mol_type = other RNA
                          organism = synthetic construct
tRNA                      1..82
                          note = tRNA
SEQUENCE: 570
gtcacggtgg ccgagtggtt aaggcgttgg actttaaatc caatggggtt tccccgcaca  60
ggttcgaatc ctgttcgtga cg                                           82

SEQ ID NO: 571           moltype = RNA   length = 82
FEATURE                  Location/Qualifiers
source                    1..82
                          mol_type = other RNA
                          organism = synthetic construct
tRNA                      1..82
                          note = tRNA
SEQUENCE: 571
gacgaggtgg ccgagtggtt aaggcgatgg actttaaatc cattgtgctc tgcacgcgtg  60
ggttcgaatc ccaccctcgt cg                                           82

SEQ ID NO: 572           moltype = RNA   length = 82
FEATURE                  Location/Qualifiers
source                    1..82
                          mol_type = other RNA
                          organism = synthetic construct
tRNA                      1..82
                          note = tRNA
SEQUENCE: 572
gacgaggtgg ccgagtggtt aaggcgatgg actttaaatc cattgtgctc tgcacgcgtg  60
ggttcgaatc ccaccttcgt cg                                           82

SEQ ID NO: 573           moltype = RNA   length = 74
FEATURE                  Location/Qualifiers
source                    1..74
                          mol_type = other RNA
                          organism = synthetic construct
tRNA                      1..74
                          note = tRNA
SEQUENCE: 573
ggccggttag ctcagttggt tagagcgtgc tttaactaat gccagggtcg aggtttcgat  60
ccccgtacgg gcct                                                    74

SEQ ID NO: 574           moltype = RNA   length = 82
FEATURE                  Location/Qualifiers
source                    1..82
                          mol_type = other RNA
```

US 12,559,749 B2

-continued

```
                              organism = synthetic construct
tRNA                          1..82
                              note = tRNA
SEQUENCE: 574
gacgaggtgg ccgagtggtt aaggcgatgg actttaaatc cattgtgctc tgcacacgtg   60
ggttcgaatc ccatcctcgt cg                                            82

SEQ ID NO: 575        moltype = RNA  length = 78
FEATURE               Location/Qualifiers
source                1..78
                      mol_type = other RNA
                      organism = synthetic construct
tRNA                  1..78
                      note = tRNA
SEQUENCE: 575
gaggcctggc cgagtggtta aggcgatgga ctttaaatcc attgtgctct gcacgcgtgg   60
gttcgaatcc catcctcg                                                 78

SEQ ID NO: 576        moltype = RNA  length = 82
FEATURE               Location/Qualifiers
source                1..82
                      mol_type = other RNA
                      organism = synthetic construct
tRNA                  1..82
                      note = tRNA
SEQUENCE: 576
gcagcgatgg ccgagtggtt aaggcgttgg actttaaatc caatggggtc tccccgcgca   60
ggttcgaacc ctgctcgctg cg                                            82

SEQ ID NO: 577        moltype = RNA  length = 82
FEATURE               Location/Qualifiers
source                1..82
                      mol_type = other RNA
                      organism = synthetic construct
tRNA                  1..82
                      note = tRNA
SEQUENCE: 577
gtagtcgtgg ccgagtggtt aaggcgatgg actttaaatc cattggggtt tccccgcgca   60
ggttcgaatc ctgccgacta cg                                            82

SEQ ID NO: 578        moltype = RNA  length = 82
FEATURE               Location/Qualifiers
source                1..82
                      mol_type = other RNA
                      organism = synthetic construct
tRNA                  1..82
                      note = tRNA
SEQUENCE: 578
gtagtcgtgg ccgagtggtt aaggcgatgg actttaaatc cattggggtc tccccgcgca   60
ggttcgaatc ctgccgacta cg                                            82

SEQ ID NO: 579        moltype = RNA  length = 82
FEATURE               Location/Qualifiers
source                1..82
                      mol_type = other RNA
                      organism = synthetic construct
tRNA                  1..82
                      note = tRNA
SEQUENCE: 579
gtagtcgtgg ccgagtggtt aaggcgatgg actttaaatc cattggggtt tccccgcgca   60
ggttcgaatc ctgtcggcta cg                                            82

SEQ ID NO: 580        moltype = RNA  length = 76
FEATURE               Location/Qualifiers
source                1..76
                      mol_type = other RNA
                      organism = synthetic construct
modified_base         10
                      mod_base = m2g
modified_base         26
                      mod_base = m2g
modified_base         32
                      mod_base = cm
modified_base         34
                      mod_base = gm
modified_base         39
                      mod_base = p
modified_base         40
                      mod_base = m5c
```

-continued

```
modified_base         46
                      mod_base = m7g
modified_base         49
                      mod_base = m5c
modified_base         55
                      mod_base = p
modified_base         58
                      mod_base = m1a
tRNA                  1..76
                      note = tRNA
modified_base         54
                      mod_base = OTHER
                      note = Thymine
SEQUENCE: 580
gcggatttag ctcagddggg agagcgccag actgaayatc tggaggtcct gtgttcgatc   60
cacagaattc gcacca                                                   76

SEQ ID NO: 581        moltype = RNA  length = 73
FEATURE               Location/Qualifiers
source                1..73
                      mol_type = tRNA
                      organism = Homo sapiens
tRNA                  1..73
                      note = tRNA
modified_base         34
                      mod_base = OTHER
                      note = Thymine
SEQUENCE: 581
gacctcgtgg cgcaacggtt agcgcgtctg acttcagatc agaaggctgc gtgttcgaat   60
cacgtcgggg tca                                                      73

SEQ ID NO: 582        moltype = AA  length = 10
FEATURE               Location/Qualifiers
source                1..10
                      mol_type = protein
                      organism = synthetic construct
SEQUENCE: 582
NIETFHTAQK                                                           10

SEQ ID NO: 583        moltype = AA  length = 8
FEATURE               Location/Qualifiers
source                1..8
                      mol_type = protein
                      organism = synthetic construct
SEQUENCE: 583
ETFHTAQK                                                              8

SEQ ID NO: 584        moltype = AA  length = 8
FEATURE               Location/Qualifiers
source                1..8
                      mol_type = protein
                      organism = synthetic construct
SEQUENCE: 584
QATHFTEN                                                              8

SEQ ID NO: 585        moltype = AA  length = 8
FEATURE               Location/Qualifiers
source                1..8
                      mol_type = protein
                      organism = synthetic construct
SEQUENCE: 585
ETFHTAQK                                                              8

SEQ ID NO: 586        moltype = AA  length = 7
FEATURE               Location/Qualifiers
source                1..7
                      mol_type = protein
                      organism = synthetic construct
SEQUENCE: 586
QATHFTE                                                               7

SEQ ID NO: 587        moltype = RNA  length = 27
FEATURE               Location/Qualifiers
source                1..27
                      mol_type = other RNA
                      organism = synthetic construct
tRNA                  1..27
                      note = tRNA
SEQUENCE: 587
```

-continued

```
nnnnnngtat tcatcgaaga cnnnnnn                                        27

SEQ ID NO: 588          moltype = RNA   length = 27
FEATURE                 Location/Qualifiers
source                  1..27
                        mol_type = other RNA
                        organism = synthetic construct
tRNA                    1..27
                        note = tRNA
SEQUENCE: 588
nnnnnngtct tcgatgaata cnnnnnn                                        27

SEQ ID NO: 589          moltype = RNA   length = 73
FEATURE                 Location/Qualifiers
source                  1..73
                        mol_type = other RNA
                        organism = synthetic construct
modified_base           34
                        mod_base = OTHER
                        note = Thymine
tRNA                    1..73
                        note = tRNA
SEQUENCE: 589
gacctcgtgg cgcaacggtt agcgcgtctg acttcagatc agaaggctcc gggttcgaat   60
cccggcgggg tca                                                      73

SEQ ID NO: 590          moltype = AA   length = 10
FEATURE                 Location/Qualifiers
source                  1..10
                        mol_type = protein
                        organism = synthetic construct
REGION                  1
                        note = Suppressed PTC codon
SEQUENCE: 590
XIETPHTAQK                                                          10

SEQ ID NO: 591          moltype = RNA   length = 71
FEATURE                 Location/Qualifiers
source                  1..71
                        mol_type = other RNA
                        organism = synthetic construct
tRNA                    1..71
                        note = tRNA
SEQUENCE: 591
gcattggtgg ttcagtggta gaattctcgc cttcaacgcg ggagacccgg gttcaattcc   60
cggccaatgc a                                                        71

SEQ ID NO: 592          moltype = RNA   length = 71
FEATURE                 Location/Qualifiers
source                  1..71
                        mol_type = other RNA
                        organism = synthetic construct
tRNA                    1..71
                        note = tRNA
SEQUENCE: 592
gcgccgctgg tgtagtggta tcatgcaaga tttcaattct tgcgacccgg gttcgattcc   60
cgggcggcgc a                                                        71

SEQ ID NO: 593          moltype = RNA   length = 71
FEATURE                 Location/Qualifiers
source                  1..71
                        mol_type = other RNA
                        organism = synthetic construct
tRNA                    1..71
                        note = tRNA
SEQUENCE: 593
gcattggtgg ttcaatggta gaattctcgc cttcaacgca ggagacccag gttcgattcc   60
tggccaatgc a                                                        71

SEQ ID NO: 594          moltype = RNA   length = 71
FEATURE                 Location/Qualifiers
source                  1..71
                        mol_type = other RNA
                        organism = synthetic construct
tRNA                    1..71
                        note = tRNA
SEQUENCE: 594
gcgttggtgg tttagtggta gaattctcgc cttcaatgcg ggagacccgg gttcaattcc   60
cggccactgc a                                                        71
```

-continued

```
SEQ ID NO: 595           moltype = RNA   length = 71
FEATURE                  Location/Qualifiers
source                   1..71
                         mol_type = other RNA
                         organism = synthetic construct
tRNA                     1..71
                         note = tRNA
SEQUENCE: 595
gccttggtgg tgcagtggta gaattctcgc cttcaacgtg ggagacccgg gttcaattcc   60
cggccaatgc a                                                         71

SEQ ID NO: 596           moltype = RNA   length = 61
FEATURE                  Location/Qualifiers
source                   1..61
                         mol_type = other RNA
                         organism = synthetic construct
tRNA                     1..61
                         note = tRNA
SEQUENCE: 596
ggtggttcag tggtagaatt ctcgccttca acgcgggaga cccgggttta attcccggtc   60
a                                                                    61

SEQ ID NO: 597           moltype = RNA   length = 61
FEATURE                  Location/Qualifiers
source                   1..61
                         mol_type = other RNA
                         organism = synthetic construct
tRNA                     1..61
                         note = tRNA
SEQUENCE: 597
gtggtctagt ggttaggatt cagcgcttca accgccgcag cccgggttcg attcccggtc   60
a                                                                    61

SEQ ID NO: 598           moltype = RNA   length = 71
FEATURE                  Location/Qualifiers
source                   1..71
                         mol_type = other RNA
                         organism = synthetic construct
tRNA                     1..71
                         note = tRNA
SEQUENCE: 598
gcgtcagtgg tttagtggtg gaattcctgc cttcaatgca cgagatccgt gttcaactcc   60
tggttggtgc a                                                         71

SEQ ID NO: 599           moltype = RNA   length = 72
FEATURE                  Location/Qualifiers
source                   1..72
                         mol_type = other RNA
                         organism = synthetic construct
tRNA                     1..72
                         note = tRNA
SEQUENCE: 599
gcgtcagtgg ttttagtggt ggaattcctg ccttcaatgc acgagatccg tgttcaactc   60
ctggttggtg ca                                                        72

SEQ ID NO: 600           moltype = RNA   length = 71
FEATURE                  Location/Qualifiers
source                   1..71
                         mol_type = other RNA
                         organism = synthetic construct
tRNA                     1..71
                         note = tRNA
SEQUENCE: 600
gcgttggcag ttcagtggta gaattctcgc cttcaacccg ggagacctgg attccatttc   60
cggcaaatgc a                                                         71

SEQ ID NO: 601           moltype = RNA   length = 71
FEATURE                  Location/Qualifiers
source                   1..71
                         mol_type = other RNA
                         organism = synthetic construct
tRNA                     1..71
                         note = tRNA
SEQUENCE: 601
gcatgggtgg ttcagtggta gaattctcgc cttcaacgcg ggaggcccgg gttcgattcc   60
cggcccatgc a                                                         71

SEQ ID NO: 602           moltype = RNA   length = 71
```

-continued

```
FEATURE                Location/Qualifiers
source                 1..71
                       mol_type = other RNA
                       organism = synthetic construct
tRNA                   1..71
                       note = tRNA
SEQUENCE: 602
gcattggtgg ttcagtggta gaattctcgc cttcaacgcg ggaggcccgg gttcgattcc   60
cggccaatgc a                                                        71

SEQ ID NO: 603         moltype = RNA   length = 71
FEATURE                Location/Qualifiers
source                 1..71
                       mol_type = other RNA
                       organism = synthetic construct
tRNA                   1..71
                       note = tRNA
SEQUENCE: 603
gcattggtgg ttcagtggta gaattctcgc cttcaacgcg ggaggcccgg gtttgattcc   60
cggccagtgc a                                                        71

SEQ ID NO: 604         moltype = RNA   length = 71
FEATURE                Location/Qualifiers
source                 1..71
                       mol_type = other RNA
                       organism = synthetic construct
tRNA                   1..71
                       note = tRNA
SEQUENCE: 604
gcataggtgg ttcagtggta gaattcttgc cttcaacgca ggaggcccag gtttgattcc   60
tggcccatgc a                                                        71

SEQ ID NO: 605         moltype = RNA   length = 71
FEATURE                Location/Qualifiers
source                 1..71
                       mol_type = other RNA
                       organism = synthetic construct
tRNA                   1..71
                       note = tRNA
SEQUENCE: 605
gcattggtgg ttcagtggta gaattctcgc cttcaatgcg ggcggccggg cttcgattcc   60
tggccaatgc a                                                        71

SEQ ID NO: 606         moltype = RNA   length = 71
FEATURE                Location/Qualifiers
source                 1..71
                       mol_type = other RNA
                       organism = synthetic construct
tRNA                   1..71
                       note = tRNA
SEQUENCE: 606
gcatgggtga ttcagtggta gaattttcac cttcaatgca ggaggtccag gttcatttcc   60
tggcctatgc a                                                        71

SEQ ID NO: 607         moltype = RNA   length = 72
FEATURE                Location/Qualifiers
source                 1..72
                       mol_type = other RNA
                       organism = synthetic construct
tRNA                   1..72
                       note = tRNA
SEQUENCE: 607
gcgttggtgg tatagtggtt agcatagctg ccttcaaagc agttgacccg ggttcgattc   60
ccggccaacg ca                                                       72

SEQ ID NO: 608         moltype = RNA   length = 72
FEATURE                Location/Qualifiers
source                 1..72
                       mol_type = other RNA
                       organism = synthetic construct
tRNA                   1..72
                       note = tRNA
SEQUENCE: 608
gcgttggtgg tatagtggtg agcatagctg ccttcaaagc agttgacccg ggttcgattc   60
ccggccaacg ca                                                       72

SEQ ID NO: 609         moltype = RNA   length = 72
FEATURE                Location/Qualifiers
source                 1..72
```

-continued

```
                               mol_type = other RNA
                               organism = synthetic construct
tRNA                           1..72
                               note = tRNA
SEQUENCE: 609
gcgttggtgg tatagtggta agcatagctg ccttcaaagc agttgacccg ggttcgattc   60
ccggccaacg ca                                                        72

SEQ ID NO: 610            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 610
gcgttggtgg tatagtggtg agcatagttg ccttcaaagc agttgacccg ggctcgattc   60
ccgcccaacg ca                                                        72

SEQ ID NO: 611            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 611
gcgttggtgg tatagtggtg agcatagttg ccttcaaagc agttgacccg ggctcgattc   60
ccggccaacg ca                                                        72

SEQ ID NO: 612            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 612
gacctcgtgg cgcaacggca gcgcgtctga cttcagatca gaaggttgcg tgttcaaatc   60
acgtcggggt ca                                                        72

SEQ ID NO: 613            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 613
gacctcgtgg cgcaacggta gcgcgtctga cttcagatca gaaggttgcg tgttcaaatc   60
acgtcggggt ca                                                        72

SEQ ID NO: 614            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 614
ggcctcatgg tgcaacagta gtgtgtctga cttcagatca gaaggttgta tgttcaaatc   60
acgtaggggt ca                                                        72

SEQ ID NO: 615            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 615
gacctcgtgg cgcaatggta gcgcgtctga cttcagatca gaaggttgcg tgttcaagtc   60
acgtcggggt ca                                                        72

SEQ ID NO: 616            moltype = RNA   length = 72
FEATURE                   Location/Qualifiers
source                    1..72
                          mol_type = other RNA
                          organism = synthetic construct
```

```
tRNA                       1..72
                           note = tRNA
SEQUENCE: 616
ggcctcgtgg cgcaacggta gcgcgtctga cttcagatca gaaggttgcg tgttcaaatc    60
acgtcggggt ca                                                        72

SEQ ID NO: 617          moltype = RNA   length = 72
FEATURE                 Location/Qualifiers
source                  1..72
                        mol_type = other RNA
                        organism = synthetic construct
tRNA                    1..72
                        note = tRNA
SEQUENCE: 617
gacctcgtgg cgcaacggta gcgcgtctga cttcagatca gaaggctgcg tgttcgaatc    60
acgtcggggt ca                                                        72

SEQ ID NO: 618          moltype = RNA   length = 72
FEATURE                 Location/Qualifiers
source                  1..72
                        mol_type = other RNA
                        organism = Mus musculus
tRNA                    1..72
                        note = tRNA
SEQUENCE: 618
gacctcgtgg cgcaatggta gcgcgtctga cttcagatca gaaggttgcg tgttcaaatc    60
acgtcggggt ca                                                        72

SEQ ID NO: 619          moltype = RNA   length = 72
FEATURE                 Location/Qualifiers
source                  1..72
                        mol_type = other RNA
                        organism = Mus musculus
tRNA                    1..72
                        note = tRNA
SEQUENCE: 619
gacctcgtgg cacaatggta gcacgtctga cttcagatca gaaggttgcg tgttcaaatc    60
acgtcggggt ca                                                        72

SEQ ID NO: 620          moltype = RNA   length = 106
FEATURE                 Location/Qualifiers
source                  1..106
                        mol_type = other RNA
                        organism = Saccharomyces cerevisiae
tRNA                    1..106
                        note = tRNA
SEQUENCE: 620
gaagcggtgg ctcaatggta gagctttcga cttcaattaa atcttggaaa ttccacggaa    60
taagattgca atcgaagggt tgcaggttca attcctgtcc gtttca                  106

SEQ ID NO: 621          moltype = RNA   length = 72
FEATURE                 Location/Qualifiers
source                  1..72
                        mol_type = other RNA
                        organism = Saccharomyces cerevisiae
tRNA                    1..72
                        note = tRNA
SEQUENCE: 621
gaagcggtgg ctcaatggta gagctttcga cttcaaatcg aagggttgca ggttcaattc    60
ctgtcggttt ca                                                        72

SEQ ID NO: 622          moltype = RNA   length = 72
FEATURE                 Location/Qualifiers
source                  1..72
                        mol_type = other RNA
                        organism = Pan troglodytes
tRNA                    1..72
                        note = tRNA
SEQUENCE: 622
ggcctcatgg tgcaacagta gtgtgtctga cttcagatca gaaggttgta tgttcaaatc    60
acataggggt ca                                                        72

SEQ ID NO: 623          moltype = RNA   length = 72
FEATURE                 Location/Qualifiers
source                  1..72
                        mol_type = other RNA
                        organism = Oryctolagus cuniculus
tRNA                    1..72
                        note = tRNA
```

```
SEQUENCE: 623
gacctcgtgg tgaaatggta gcatgtttga cttcaaatca ggaggttgtg tgttcaagtc   60
acatcagggt ca                                                       72

SEQ ID NO: 624          moltype = RNA   length = 72
FEATURE                 Location/Qualifiers
source                  1..72
                        mol_type = other RNA
                        organism = Oryctolagus cuniculus
tRNA                    1..72
                        note = tRNA
SEQUENCE: 624
gaccttgtgg cgcaatggta gcatgtttga cttcaaatca ggaggttgtg tgttcaagtc   60
acatcagggt ca                                                       72

SEQ ID NO: 625          moltype = RNA   length = 72
FEATURE                 Location/Qualifiers
source                  1..72
                        mol_type = other RNA
                        organism = Oryctolagus cuniculus
tRNA                    1..72
                        note = tRNA
SEQUENCE: 625
gacctcgtgg cgcaacggta gcgcgtctga cttcagatca gaaggctgcg tgttcgaatc   60
acgccggggt ca                                                       72

SEQ ID NO: 626          moltype = RNA   length = 72
FEATURE                 Location/Qualifiers
source                  1..72
                        mol_type = other RNA
                        organism = Rattus norvegicus
tRNA                    1..72
                        note = tRNA
SEQUENCE: 626
gaccttgtgg ctcaatggta gcgcatctga cttcagatca ggaggttgca cgttcaaatc   60
atgccggggt ca                                                       72

SEQ ID NO: 627          moltype = RNA   length = 72
FEATURE                 Location/Qualifiers
source                  1..72
                        mol_type = other RNA
                        organism = Rattus norvegicus
tRNA                    1..72
                        note = tRNA
SEQUENCE: 627
gaccttgtgg cgcaacggta gcgcgtctga cttcagatca gaaggttgcg tgttcaaatc   60
acgtcggggt ca                                                       72

SEQ ID NO: 628          moltype = RNA   length = 72
FEATURE                 Location/Qualifiers
source                  1..72
                        mol_type = other RNA
                        organism = Xenopus tropicalis
tRNA                    1..72
                        note = tRNA
SEQUENCE: 628
gacctcgtgg cgcaacggta gcgcgtctga cttcagatca gaaggttgcg tattcaaatc   60
acgtcggggt ca                                                       72

SEQ ID NO: 629          moltype = RNA   length = 72
FEATURE                 Location/Qualifiers
source                  1..72
                        mol_type = other RNA
                        organism = Xenopus tropicalis
tRNA                    1..72
                        note = tRNA
SEQUENCE: 629
gacctcgtgg cgcaacggca gcgcgtctga cttcacatta gaaggttgcg tgttcaaatc   60
acgtcggggt ca                                                       72

SEQ ID NO: 630          moltype = RNA   length = 72
FEATURE                 Location/Qualifiers
source                  1..72
                        mol_type = other RNA
                        organism = Xenopus tropicalis
tRNA                    1..72
                        note = tRNA
SEQUENCE: 630
gacctcatgg cgcaacggta gcgcgtctga cttcagatca gaaggttgcg tgttcaaatc   60
```

-continued

```
acatcggggt ca                                                        72

SEQ ID NO: 631          moltype = RNA   length = 72
FEATURE                 Location/Qualifiers
source                  1..72
                        mol_type = other RNA
                        organism = Xenopus tropicalis
tRNA                    1..72
                        note = tRNA
SEQUENCE: 631
gacctcgtgg tgcaacggta gcgcgtatga tttcagatca gaaggttgcg tgttcaaatc   60
acgtcggggt ca                                                        72

SEQ ID NO: 632          moltype = RNA   length = 72
FEATURE                 Location/Qualifiers
source                  1..72
                        mol_type = other RNA
                        organism = Xenopus tropicalis
tRNA                    1..72
                        note = tRNA
SEQUENCE: 632
gacctcgtag cgcaacggta gcgcgtctga cttcagatca gaaggttgcg tgttcaaatc   60
acgtcggggt ca                                                        72

SEQ ID NO: 633          moltype = RNA   length = 76
FEATURE                 Location/Qualifiers
source                  1..76
                        mol_type = other RNA
                        organism = Xenopus tropicalis
tRNA                    1..76
                        note = tRNA
SEQUENCE: 633
aggggtatag ctcaattggc agagcgtcgg tcttcaaaac cgaaggttgt aggttcgatt   60
cctactgccc ctgcca                                                    76

SEQ ID NO: 634          moltype = RNA   length = 72
FEATURE                 Location/Qualifiers
source                  1..72
                        mol_type = other RNA
                        organism = Xenopus tropicalis
tRNA                    1..72
                        note = tRNA
SEQUENCE: 634
gacctcatgg cgcaacggta gcgcgtctga cttcagatca gaaggttgcg tgttcaaatc   60
acgtcggggt ca                                                        72

SEQ ID NO: 635          moltype = RNA   length = 72
FEATURE                 Location/Qualifiers
source                  1..72
                        mol_type = other RNA
                        organism = Xenopus tropicalis
tRNA                    1..72
                        note = tRNA
SEQUENCE: 635
gacctcgtgg cgcaacggta gcgcgtctaa cttcagatca gaaggttgcg tgttcaaatc   60
acgtcggggt ca                                                        72

SEQ ID NO: 636          moltype = RNA   length = 73
FEATURE                 Location/Qualifiers
source                  1..73
                        mol_type = other RNA
                        organism = Xenopus tropicalis
tRNA                    1..73
                        note = tRNA
SEQUENCE: 636
acgggagtag ctcagttggt agagcaccgg tcttcaaaac cgggtgtcgg gagttcgagc   60
ctctcctccc gtg                                                       73

SEQ ID NO: 637          moltype = RNA   length = 72
FEATURE                 Location/Qualifiers
source                  1..72
                        mol_type = other RNA
                        organism = Xenopus tropicalis
tRNA                    1..72
                        note = tRNA
SEQUENCE: 637
gacctcgtgg cgcaacggta gcgcgtctga cttcagatca gaaggttgca tgttcaaatc   60
acgtcggggt ca                                                        72
```

```
SEQ ID NO: 638            moltype = RNA   length = 72
FEATURE                   Location/Qualifiers
source                    1..72
                          mol_type = other RNA
                          organism = Drosophila melanogaster
tRNA                      1..72
                          note = tRNA
SEQUENCE: 638
gactccgtgg cgcaacggta gcgcgtccga cttcagatcg gaaggttgcg tgttcaaatc  60
acgtcggggt ca                                                       72

SEQ ID NO: 639            moltype = RNA   length = 72
FEATURE                   Location/Qualifiers
source                    1..72
                          mol_type = other RNA
                          organism = Drosophila melanogaster
tRNA                      1..72
                          note = tRNA
SEQUENCE: 639
gactccgtgg cgcaacggta gcgcgtctga cttcagatca gaaggttgcg tgttcaaatc  60
acgtcggggt ca                                                       72

SEQ ID NO: 640            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 640
ggcctcgtgg cgcaacggta gcgcgtctga ctccagatca gaaggttgcg tgttcaaatc  60
acgtcggggt ca                                                       72

SEQ ID NO: 641            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 641
ggcctcgtgg cgcaacggta gcacgtctga ctccagatca gaaggttgcg tgttcaaatc  60
acgtcggggt ca                                                       72

SEQ ID NO: 642            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 642
ggcctcgtcg cgcaacggta gcgcgtctga ctccagatca gaaggttgcg tgttcaaatc  60
acgtcggggt ca                                                       72

SEQ ID NO: 643            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 643
ggcctcgtgg cgcaacggta gcacgtctga cttcagatca gaaggttgcg tgttcaaatc  60
acgtcggggt ca                                                       72

SEQ ID NO: 644            moltype = RNA   length = 72
FEATURE                   Location/Qualifiers
source                    1..72
                          mol_type = other RNA
                          organism = synthetic construct
tRNA                      1..72
                          note = tRNA
SEQUENCE: 644
ggcctcgtcg cgcaacggta gcgcgtctga cttcagatca gaaggttgcg tgttcaaatc  60
acgtcggggt ca                                                       72

SEQ ID NO: 645            moltype = RNA   length = 72
FEATURE                   Location/Qualifiers
```

-continued

```
source                    1..72
                          mol_type = other RNA
                          organism = synthetic construct
tRNA                      1..72
                          note = tRNA
SEQUENCE: 645
ggcctcgtcg cgcaacggta gcacgtctga cttcagatca gaaggttgcg tgttcaaatc    60
acgtcggggt ca                                                        72

SEQ ID NO: 646            moltype = AA  length = 455
FEATURE                   Location/Qualifiers
source                    1..455
                          mol_type = protein
                          organism = synthetic construct
SEQUENCE: 646
MSFNTIIDWN SCTAEQQRQL LMRPAISASE SITRTVNDIL DNVKARGDEA LREYSAKFDK    60
TTVTALKVSA EEIAAASERL SDELKQAMAV AVKNIETFHT AQKLPPVDVE TQPGVRCQQV   120
TRPVASVGLY IPGGSAPLFS TVLMLATPAS IAGCKKVVLC SPPPIADEIL YAAQLCGVQD   180
VFNVGGAQAI AALAFGTESV PKVDKIFGPG NAFVTEAKRQ VSQRLDGAAI DMPAGPSEVL   240
VIADSGATPD FVASDLLSQA EHGPDSQVIL LTPAADMARR VAEAVERQLA ELPRAETARQ   300
ALNASRLIVT KDLAQCVEIS NQYGPEHLII QTRNARELVD SITSAGSVFL GDWSPESAGD   360
YASGTNHVLP TYGYTATCSS LGLADFQKRM TVQELSKEGF SALASTIETL AAAERLTAHK   420
NAVTLRVNAL KEQAHHHHHH HHSGGSAWSH PQFEK                             455

SEQ ID NO: 647            moltype = AA  length = 8
FEATURE                   Location/Qualifiers
source                    1..8
                          mol_type = protein
                          organism = synthetic construct
SEQUENCE: 647
HHHHHHHH                                                              8

SEQ ID NO: 648            moltype = AA  length = 13
FEATURE                   Location/Qualifiers
source                    1..13
                          mol_type = protein
                          organism = synthetic construct
SEQUENCE: 648
KPINQWPANT HER                                                       13

SEQ ID NO: 649            moltype = RNA  length = 73
FEATURE                   Location/Qualifiers
source                    1..73
                          mol_type = other RNA
                          organism = synthetic construct
tRNA                      1..73
                          note = tRNA
SEQUENCE: 649
taatacgact cactatagag cgctccggtt tttctgtgct gaacctcagg ggacgccgac    60
acacgtacac gtc                                                       73

SEQ ID NO: 650            moltype = RNA  length = 10
FEATURE                   Location/Qualifiers
source                    1..10
                          mol_type = other RNA
                          organism = synthetic construct
tRNA                      1..10
                          note = tRNA
SEQUENCE: 650
tagtcttcgg                                                           10

SEQ ID NO: 651            moltype = RNA  length = 10
FEATURE                   Location/Qualifiers
source                    1..10
                          mol_type = other RNA
                          organism = synthetic construct
tRNA                      1..10
                          note = tRNA
SEQUENCE: 651
aagaagaccg                                                           10

SEQ ID NO: 652            moltype = RNA  length = 30
FEATURE                   Location/Qualifiers
source                    1..30
                          mol_type = other RNA
                          organism = synthetic construct
tRNA                      1..30
                          note = tRNA
SEQUENCE: 652
```

-continued

```
gtcctttttt tgctttagtg agggttaatt                                      30

SEQ ID NO: 653          moltype = DNA  length = 59
FEATURE                 Location/Qualifiers
source                  1..59
                        mol_type = other DNA
                        organism = synthetic construct
SEQUENCE: 653
gaattcttcc cgagacgttc caagtcttca tgaagactac aggcgtctcc caggaagct    59

SEQ ID NO: 654          moltype = RNA  length = 92
FEATURE                 Location/Qualifiers
source                  1..92
                        mol_type = other RNA
                        organism = synthetic construct
tRNA                    1..92
                        note = tRNA
SEQUENCE: 654
attatgctga gtgatatccg gagcaccgcg ttgccatcgc gcagactgaa gtctagtctt    60
ccaacgcaca agtttagtgc agccccagtg gt                                   92

SEQ ID NO: 655          moltype = RNA  length = 89
FEATURE                 Location/Qualifiers
source                  1..89
                        mol_type = other RNA
                        organism = synthetic construct
tRNA                    1..89
                        note = tRNA
SEQUENCE: 655
attatgctga gtgatatcgc aaccaccata taccaatcgt atcgaggaag tttcgtaact    60
gggcccaagc taagggccgg ttgcgtggt                                       89

SEQ ID NO: 656          moltype = DNA  length = 17
FEATURE                 Location/Qualifiers
source                  1..17
                        mol_type = other DNA
                        organism = synthetic construct
SEQUENCE: 656
taatacgact cactata                                                    17
```

METHODS OF RESCUING STOP CODONS VIA GENETIC REASSIGNMENT WITH ACE-tRNA

PRIORITY OF INVENTION

This application is a divisional of U.S. patent application Ser. No. 16/761,205, filed May 1, 2020, which is a 35 U.S.C. § 371 application of International Application Serial No. PCT/US2018/059065, filed Nov. 2, 2018; which claims the benefit of U.S. Provisional Application Ser. No. 62/580,887, filed Nov. 2, 2017 and U.S. Provisional Application Ser. No. 62/687,015, filed Jun. 19, 2018. The entire content of the applications referenced above are hereby incorporated by reference herein.

STATEMENT REGARDING FEDERALLY SPONSORED RESEARCH

This invention was made with government support under R01 GM106569 awarded by the National Institutes of Health. The government has certain rights in the invention.

SEQUENCE LISTING

The instant application contains a Sequence Listing which has been submitted electronically in XML format and is hereby incorporated by reference in its entirety. Said XML copy, created on Aug. 9, 2023, is named 17023215US2 and is 851,993 bytes in size.

BACKGROUND

DNA molecules carry genetic information in the form of the sequence of the nucleotide bases that make up the DNA polymer. Only four nucleotide bases are utilized in DNA: adenine, guanine, cytosine, and thymine. This information, in the form of codons of three contiguous bases is transcribed into messenger RNA (mRNA), and then translated by transfer RNA (tRNA) and ribosomes to form proteins. Four nucleotide bases are utilized in RNA: adenine, guanine, cytosine, and uracil. The genetic code is the relation between a triplet codon and a particular amino acid. Sixty-four possible codon triplets form the genetic code, where three stop (also called terminating) codons, which provide a signal to the translation machinery (cellular ribosomes) to stop protein production at the particular codon. The other sixty-one triplets in the code correspond to one of the 20 standard amino acid. See FIG. 1.

DNA is translated by ribosomes, causing each amino acid to be linked together one by one to form polypeptides, according to the genetic instructions specifically provided by the DNA. When the ribosome reaches a stop codon, the elongation of the protein terminates. The three stop codons are UAG (amber), UAA (ochre) and UGA (opal). Mutations that occur that change an amino acid-encoding codon to stop codon are called "nonsense mutations." These nonsense mutations can result in a significant truncation/shortening of the polypeptide sequence, and can cause a profound change in genetic phenotype. Thus, even though a gene directing expression may be present, a crucial protein may not be produced because when the ribosome reaches the mutant stop signal, it terminates translation resulting in an unfinished protein.

Transfer RNAs translate mRNA into a protein on a ribosome. Each tRNA contains an "anti-codon" region that hybridizes with a complementary codon on the mRNA. A tRNA that carries its designated amino acid is called a "charged" tRNA. If the tRNA is one of the 61 amino-acid-associated (i.e., not a stop-signal-associated) tRNAs, it will normally attach its amino acid to the growing peptide. The structural gene of tRNA is about 72-90 nucleotides long and folds into a cloverleaf structure. tRNAs are transcribed by RNA polymerase III and contain their own intragenic split promoters that become a part of the mature tRNA coding sequence (Sharp S. J., Schaack J., Coolen L., Burke D. J. and Soll D., "Structure and transcription of eukaryotic tRNA genes", Crit. Rev. Biochem, 19:107-144 (1985); Geiduschek E. O., and Tocchini-Valentini, "Transcription by RNA polymerase III, Annu. Rev. Biochem. 57:873-914 (1988)).

"Nonsense suppressors" are alleles of tRNA genes that contain an altered anticodon, such that instead of triggering a "stop" signal, they insert an amino acid in response to a termination codon. For example, an ochre mutation results in the creation of a UAA codon in an mRNA. An ochre suppressor gene produces tRNA with an AUU anticodon that inserts an amino acid at the UAA site, which permits the continued translation of the mRNA despite the presence of a codon that would normally trigger a stop in translation.

A number of nonsense suppressor tRNA alleles have been identified in prokaryotes and eukaryotes such as yeast and C. elegans. The different suppressor tRNAs vary in their suppression efficiency. In E. coli and other systems, the amber suppressors are relatively more efficient, ochre suppressors are less efficient while opal are the least, this suggests that the amber codons are used infrequently to terminate protein synthesis, while ochre and opal codons are more frequently used as natural termination signals.

Unwanted errors in the DNA blueprint can cause disease. For example, the occurrence of an unexpected "stop" signal in the middle of the protein, rather than at the end of the blueprint, results in the production of a truncated or shortened protein that has an altered function, or no function at all. Many human diseases, such as cystic fibrosis, muscular dystrophy, β-thalassemia and Liddle's syndrome result from unwanted stop signals in DNA reading frames for proteins that are important for proper lung, blood, muscle or kidney function, respectively.

Accordingly, there is a need to provide novel modified nonsense suppressor tRNAs that are stabilized as compared to corresponding unmodified nonsense suppressor tRNAs, and nonsense suppressor tRNAs that have an increased activity to suppress termination of genes associated with cystic fibrosis.

SUMMARY

In certain embodiments, the present invention provides a modified transfer RNA (tRNA) comprising a T-arm, a D-arm, an anticodon arm and an acceptor arm, wherein the T-arm comprises a T-stem having nucleotides that interact with Elongation Factor 1-alpha 1 (EF1alpha). EF1alpha recruits aminoacyl-tRNA to the ribosome and protects the tRNA from being deacylated. Rational nucleotide replacement results in a tuned tRNA: EF1α interaction that enhances tRNA delivery to the ribosome and protection from deacylation.

In certain embodiments, the present invention provides a modified transfer RNA (tRNA) of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55, wherein the thymidines are replaced with uracils.

In certain embodiments, the present invention provides a modified transfer RNA (tRNA) of any one of SEQ ID NO: 1-538, wherein the thymidines are replaced with uracils.

In certain embodiments, the modified tRNA is any one of SEQ ID NOs: 56-60, 62-66, 84-86, 90-111, 113, 128-143, 147-149, 153-156, 161-174, 176, 178, 181, 184-186, 192, 196-197, 199-201, 205, 213-240, 246, 255-256, 258-285, 299, 305-312, 314, 318-332, 335-344, 346, 350-354, 357-360, 362, 365-370, 372-383, 388-390, 392, 394-401, 403-407, 414-416, 418, 422, 425, 428-433, 437, 444-445, 452, 455, 459-463, 470, 472-474, 476, 487-492, 525, 530-539, 545-550, 553-555, 561-563, and 567-579, wherein the thymidines are replaced with uracils.

In certain embodiments, the present invention provides a modified transfer RNA (tRNA) comprising a T-stem, a D-stem, an anticodon-loop and an acceptor stem, wherein (a) wherein the anticodon-arm comprises a tri-nucleotide anticodon, wherein the anticodon is 5'-UCA-3' and recognizes TGA stop codons, and wherein the acceptor arm is operably linked to a arginine, tryptophan or glycine; (b) wherein the anticodon-arm comprises a tri-nucleotide anticodon, wherein the anticodon is 5'-UUA-3' and recognizes TAA stop codons, and wherein the acceptor arm is operably linked to a glutamine or, glutamate; or (c) wherein the anticodon-arm comprises a tri-nucleotide anticodon, wherein the anticodon is 5'-CUA-3' and recognizes TAG stop codons, and wherein the acceptor arm is operably linked to a tryptophan, glutamate or glutamine. In certain embodiments, the T-arm comprises rationally altered nucleotide sequences that tune the interaction with the EF1α, enhancing its suppression activity and thereby increasing its therapeutic potential. tRNAs with tuned interaction with the EF1alpha have enhanced nonsense suppression and provide enhanced therapeutic properties.

In certain embodiments, the present invention provides an oligonucleotide sequence that encodes the modified tRNA as described above, wherein the oligonucleotide has a total length of less than 150 nucleotides. In certain embodiments, the oligonucleotide is DNA.

In certain embodiments, the present invention provides an oligonucleotide comprising a first oligonucleotide sequence and a second oligonucleotide sequence, wherein the first and second oligonucleotide sequences independently encode a modified tRNA as described above, wherein the first and second oligonucleotides independently have a total length of less than 150 nucleotides, and wherein the two sequences are in tandem.

In certain embodiments, the present invention provides an expression cassette comprising a promoter and a nucleic acid encoding the modified tRNA or oligonucleotides as described above.

In certain embodiments, the present invention provides a vector comprising the oligonucleotide or the expression cassette described above.

In certain embodiments, the vector is a viral or plasmid vector.

In certain embodiments, the present invention provides a composition comprising a modified tRNA, an oligonucleotide, or a vector described above, and a pharmaceutically acceptable carrier.

In certain embodiments, the carrier is a liposome.

In certain embodiments, the invention provides a cell comprising the vector described above.

The present invention provides a method of treating a stop-codon-associated genetic disease, comprising administering the modified tRNA composition described above to a patient in need thereof.

In certain embodiments, the genetic disease associated with a premature stop codon is cystic fibrosis, muscular dystrophy, β-thalassemia or Liddle's syndrome.

In certain embodiments, the present invention provides a method of restoring translation to a nucleotide sequence that includes a nonsense mutation in a cell, comprising introducing to the cell the composition described above.

In certain embodiments, the present invention provides a method of identifying anti-codon edited (ACE) tRNAs by high-throughput cloning and screening using suppression of a nonsense codon in luciferase enzymes including NanoLuc.

BRIEF DESCRIPTION OF DRAWINGS

FIG. 2 discloses SEQ ID NO: 580.

FIG. 3 discloses SEQ ID NO: 581.

FIGS. 6A and 6B. Nonsense codon rescue with human ACE-tRNA. FIG. 6A. Schematic of the Anti-Codon Edited (ACE) Trp tRNA and cherry-TGA-eGFP-HA construct. FIG. 6B. Rescue of the cherry TGA eGFP-HA construct by ACE tryptophan tRNA #4.

FIG. 7. Nonsense codon rationale and prevalence observed in human disease. The twenty natural amino acids codons ranked as to their contribution to human disease, with dark cross-hatched codons being most prevalent (TGG, TAC, TAT, TCA, and TTA) and stippled codons being least prevalent. All cross-hatched codon sequences require a single nucleotide mutation to convert to a stop codon from the intended amino acid. Right panel, the most common disease causative nonsense codons within the cystic fibrosis transmembrane conductance regulator (CFTR). Herein, novel tRNA sequences have been discovered for the repair of the indicated mutation.

FIG. 10A) Co-expression of model protein histidinol dehydrogenase (HDH)-His-Strep N94-TGA and ACE-tRNA$_{Trp}$(left) and ACE-tRNA$_{Gly}$ (right) results in full-length HDH protein (asterisks) that is detectable by silver stain following affinity purification. FIG. 10B) Spectra of WT HDH (top), HDH-N94+ACE-tRNA$_{Gly}$ (middle), and HDH-N94+ACE-tRNA$_{Trp}$ (bottom). Spectra highlight amino acid mass differences at position N94 that match specifically with Glycine (−57 Da) and Tryptophan (+72 Da), indicating insertion of ACE-tRNA cognate amino acids. FIG. 10B discloses SEQ ID NOS 582-585, 584, 583 and 586, respectively, in order of appearance.

FIG. 11 discloses SEQ ID NOS 587-588, respectively, in order of appearance.

FIG. 12A. Trpchr17.tRNA 39 was systematically mutagenized within the t-stem region. FIG. 12A discloses SEQ ID NO: 581. These efforts identified ACE tRNA TS-10 52-62 G-C, (FIG. 12B) and cross-hatched bar in plot, which displays ~250% increased biological activity. FIG. 12B discloses SEQ ID NO: 589.

FIG. 13A) ACE-tRNA$_{Trp}$ #5 and FIG. 13B) ACE-tRNA$_{Gly}$ #16 were cloned into NanoLuc reporter plasmids containing TGA, TAA or TAG nonsense codons. Nonsense suppression was only measured in NanoLuc-TGA constructs following transfection. FIG. 13C & FIG. 13D) Suppression of NanoLuc-TGA by addition of gentamicin (40 uM) and G418 (150 uM) and co-transfection with ACE-tRNA$_{Trp}$ #5 and ACE-tRNA$_{Gly}$ #16, was measured at FIG. 13C) 24 and FIG. 13D) 48 hrs in HEK293 cells. FIG. 13E & FIG. 13F) HEK293 cells stably expressing NanoLuc-TGA were treated with gentamicin (40 uM) and G418 (150 uM) and transfected with ACE-tRNA$_{Trp}$ #5 and ACE-tRNA$_{Gly}$ #16. Nonsense suppression was measured at FIG. 13E) 24 and FIG. 13F) 48 hrs post treatment.

FIG. 20A) CFTR cRNA with G542X or W1282X cystic fibrosis causing nonsense mutations was co-injected in *Xenopus* oocytes with serial dilutions of pre-folded ACE-tRNA$_{Gly}$ and ACE-tRNATrp, respectively. Two-electrode voltage-clamp recordings of CFTR Cl— current were performed after 36 hrs. Current-voltage relationships illustrate that increasing amounts of FIG. 20B) ACE-tRNATrp and FIG. 20C) ACE-tRNA$_{Gly}$ pre-folded RNA results in increased CFTR function (measured CFTR Cl— currents) with WT CFTR achieved in ACE-tRNA$_{Gly}$ experiments. FIG. 20D) Dose response of G542X ACE-tRNA$_{Gly}$ (filled circles) and W1282X ACE-tRNATrp (open squares) rescue (CFTR Cl— currents elicited at +40 mV were normalized to WT CFTR Cl— currents at +40 mV). The dose dependence of ACE-tRNA$_{Gly}$ (EC50=~20 ng; Hill coefficient ~1.4) shows clear saturation at WT CFTR levels, while ACE-tRNATrp is right shifted (EC50=~94 ng; Hill coefficient 1.24).

FIG. 21A, Schematic illustrates requisite interactions of ACE-tRNAs with translational machinery. Following delivery, ACE-tRNAs are recognized by an endogenous aminoacyl-tRNA synthetase and charged (aminoacylated) with their cognate amino acid. The aminoacylated ACE-tRNA is recognized by the endogenous elongation factor 1-alpha, which protects the ACE-tRNA from being de-acylated and delivers the aminoacyl ACE-tRNA to the ribosome for suppression of a premature termination codon, in this instance UGA. FIG. 21B, Individual ACE-tRNAs were cloned into the High Throughput Cloning Nonsense Reporter plasmid using Golden Gate paired with CcdB negative selection. The all-in-one plasmid contains the NLuc luciferase reporter with either a UGA, UAG or UAA PTC at p. 162 between the enzymatic large bit and requisite C-terminal small bit.

FIG. 23A, Tryptic fragment of histidinol dehydrogenase (HDH), where "X" indicates suppressed PTC codon. MS/MS spectra of the tryptic fragment with masses of indicated y and b ions for WT (top), N94G (middle) and N94W (bottom) HDH. b9 ion mass is shifted by the predicted mass of −57 Da and +72 Da from the WT asparagine, indicating the encoding of cognate amino acids glycine and tryptophan by ACE-tRNA$^{Gly}$ and ACE-tRNA$^{Trp}$, respectively. FIG. 23A discloses SEQ ID NOS 590, 583-585, 584, 583 and 586, respectively, in order of appearance. FIG. 23B, ACE-TGA—tRNA$^{Gly}$ (Glychr19.t2) selectively suppresses the UGA stop codon in transiently transfected HEK293 cells. FIG. 23C) ACE-tRNA$^{Gly}$ transfection outperforms both gentamicin (40 uM) and G418 (140 uM) following a 48 hr incubation in Hek293 cells stably expressing NLuc-UGA.

FIG. 24A, Ribosome footprint densities on 3'UTRs are plotted as log 2-fold change for reads of treated cells versus control (puc57GG empty vector) as described in the materials and methods. Transcripts were grouped by their endogenous TAA, TAG, and TGA stop codons. Each point represents the mean of two replicates for a transcript. Error bars show Mean±SD of the log 2-fold changes. FIG. 24B, The average log 2-fold change of normalized ribosome footprint occupancy was plotted for each nucleotide from −50 to +50 nt surrounding stop codons of transcriptome (18,101 sequences). The cartoon illustrates the ~15 nt offset from the 5' end of ribosome footprint to the first base position of stop codon in the ribosome A-site.

FIG. 27 discloses SEQ ID NOS 591-611, respectively, in order of appearance.

Figure 29A:
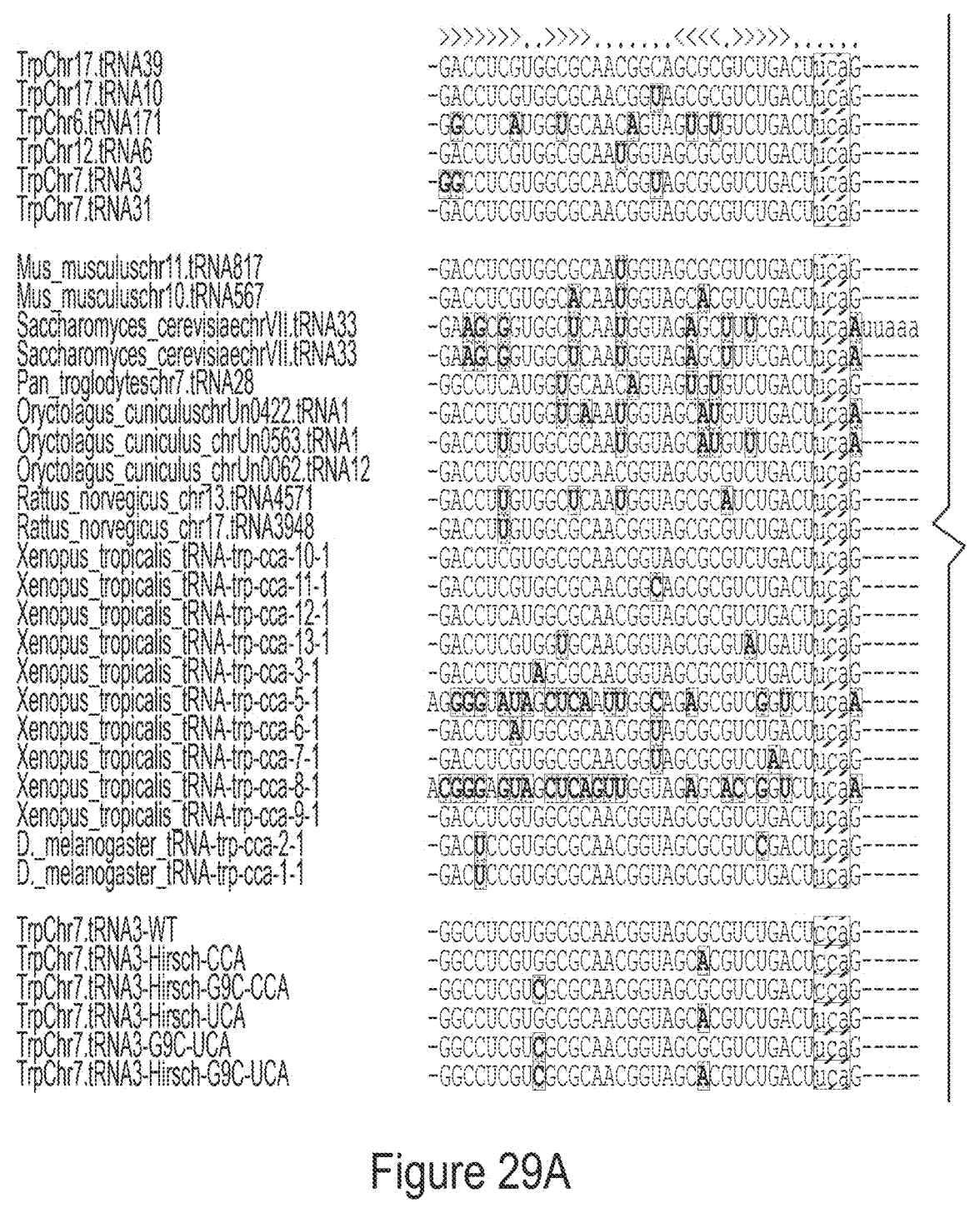

FIGS. 29A-29B. Analysis of ACE-tRNA$^{Trp}$ sequences from multiple species and suppressor tRNA mutations. FIGS. 29A-29B. Sequence alignment. FIG. 29A discloses SEQ ID NOS 612-645, respectively, in order of appearance.

FIGS. 30A-30C. Histidinol dehydrogenase (HDH) His (8)-streptactin expression construct ("His(8)" disclosed as SEQ ID NO: 647) allows for efficient one-step isolation of protein from HEK293 cells. FIG. 30A) Protein sequence of HDH expression construct. Underlined sequence indicates coverage by mass spectrometry. The bold, underlined asparagine (amino acid position 94) is the residue mutated to a TGA PTC for determining ACE-tRNA fidelity. The dual affinity tag is indicated in bold italics. FIG. 30A discloses SEQ ID NO: 646. Silver stain of HDH protein following PTC suppression with FIG. 30B) Trpchr17.trna39 and FIG. 30C) Glychr19.trna2.

FIG. 32A) Raw and FIG. 32B) normalized luminescence measured 24 hrs following addition of gentamicin (40 uM), G418 (150 uM) and transfection with Trpchr17.trna39 and Glychr19.trna2 in HEK293 cells stably expressing PTC reporter Nluc-UGA. FIG. 32C) Raw and FIG. 32D) normalized luminescence measured 24 hrs following addition of gentamicin (40 uM), G418 (150 uM) and co-transfection with Trpchr17.trna39 and Glychr19.trna2 in HEK293 cells.

DETAILED DESCRIPTION OF THE INVENTION

Figures 1, 2:
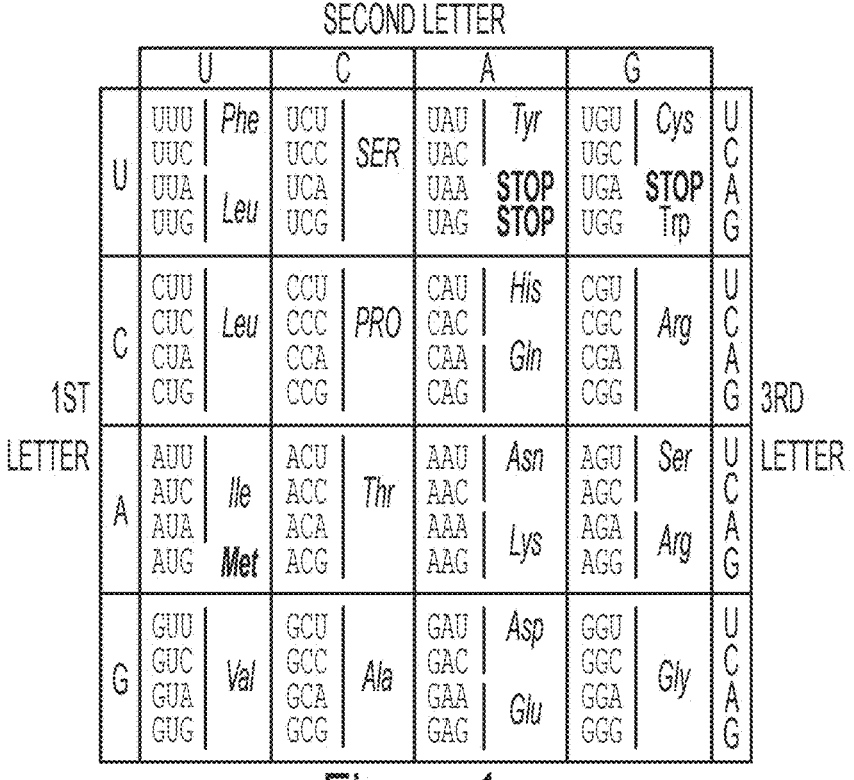
FIG. 1. Table of the Genetic Code.
FIG. 2. tRNAs have a general four-arm structure comprising a T-arm, a D-arm, an anticodon-arm, and an acceptor arm. These arms are also referred to as 'loops' throughout.

Over the years, researchers have identified hundreds of unique point mutations that resulted in nonsense codons being established in human genes. These types of mutations result, for example, in muscular dystrophy, xeroderma pigmentosum, cystic fibrosis, hemophilia, anemia, hypothyroidism, p53 squamal cell carcinoma, p53 hepatocellular carcinoma, p53 ovarian carcinoma, esophageal carcinoma, osteocarcinoma, ovarian carcinoma, esophageal carcinoma, hepatocellular carcinoma, breast cancer, hepatocellular carcinoma, fibrous histiocytoma, ovarian carcinoma, SRY sex reversal, triosephosphate isomerase-anemia, diabetes and rickets. The BRACA-1 and BRACA-2 genes associated with breast cancer also have similar mutations.

The nucleotide sequences encoding several hundred human tRNAs are known and generally available to those of skill in the art through sources such as Genbank. The structure of tRNAs is highly conserved and tRNAs are often functional across species. Thus, bacterial or other eukaryotic tRNA sequences are also potential sources for the oligonucleotides for the stabilized tRNAs of the invention. The determination of whether a particular tRNA sequence is functional in a desired mammalian cell can be ascertained through routine experimentation. Further additional potential tRNA sequences that are not yet known can be modified as described herein in order to be stabilized through routine experimentation.

tRNA genes have strong promoters that are active in all cell types. The promoters for eukaryotic tRNA genes are contained within the structural sequences encoding the tRNA molecule itself. Although there are elements that regulate transcriptional activity within the 5' upstream region, the length of an active transcriptional unit may be considerably less than 500 base pairs and thus accommodation within a delivery vector is straightforward. Once they have been transcribed and processed, tRNAs have low rates of degradation. Finally, gene therapy with a nonsense suppressor maintains the endogenous physiological controls over the target gene that contains the nonsense codon. Nonsense Mutations Transfer RNA (tRNA) is a type of RNA molecule that functions in the decoding of a messenger RNA (mRNA) sequence into a protein. tRNAs function at specific sites in the ribosome during translation, which synthesizes a protein from an mRNA molecule. Nonsense mutations, also called Premature Termination Codons (PTCs), make up ~10-15% of the single base pair mutations that cause human disease, and cystic fibrosis follows suit. (Peitz et al., Annu Rev Med., 64:407-25, 2013). In general, nonsense mutations have more serious ramifications than missense mutations because of the almost complete loss of gene expression and activity and with the possibility of dominant negative effects of truncated products. PTCs result in premature translation termination and accelerated mRNA transcript decay through the Nonsense Mediated Decay (NMD) pathway.

The current studies show that the specific site within an RNA transcript to which a tRNA delivers its amino acid can be changed through molecular editing of the anti-codon sequence within the tRNA. This approach allowed for a premature termination codon (PTC) to be effectively and therapeutically reverted back into the originally lost amino acid. Anticodon-edited tRNA (ACE-tRNA) form a new class of biological therapeutics.

Engineered tRNAs allow for "re-editing" of a disease-causing nonsense codon to a specific amino acid. These engineered tRNAs target only one type of stop codon, such as TGA over TAC or TAA. The small size of these tRNA molecules makes them amenable to ready expression, as the tRNA+the promoter is only ~300 bp. Briefly, an oligonucleotide is synthesized that comprises the structural component of a tRNA gene functional in human cells. The sequence of this oligonucleotide is designed based upon the known sequence with substitutions made in the anticodon region of the tRNA causing the specific tRNA to recognize a nonsense or other specific mutation.

Several small molecule screens have been performed to suppress nonsense stop codons through interactions with the ribosome, the most outstanding molecules being G418, Gentamicin and PTC124. PTC124 or Ataluren has recently been relieved from Phase 3 clinical trials as use for a cystic fibrosis therapeutic. Ataluren and aminoglycosides promote read-through of each of the three nonsense codons by putting in a near cognate amino acid that turn a nonsense mutation into a missense mutation. (Roy et al., PNAS 2016 Nov. 1; 113(44):12508-12513)

Anticodon-Edited tRNA (ACE-tRNA)

tRNAs have a general four-arm structure comprising a T-arm, a D-arm, an anticodon-arm, and an acceptor arm (FIG. 2).

The T-arm is made up of a "T-stem" and a "TΨC loop." In certain embodiments, the T-stem is modified to increase the stability of the tRNA. In certain embodiments, the ACE-tRNA has a modified T-stem that increases the biological activity to suppress stop sites relative to the endogenous T-stem sequence.

The present invention in one embodiment includes compositions comprising stabilized tRNAs, which can be used with higher effectiveness in order to treat a wide variety of nonsense mutation-associated diseases. The following sequences in Tables 1-8 are written as DNA, but as RNA (transcribed DNA) the "T: thymidine" is "U: uracil." Therefore, tRNAs transcribed from the following sequences all contain uracils in place of the thymidines.

In certain embodiments, the tRNA has the following sequences (wherein the thymidines are replaced with uracils):

```
TS-36:
                                    (SEQ ID NO: 1)
GGCCTCGTGGCGCAACGGTAGCGCGTCTGACTtCAGATCAGAAGGtT

GCGgGTTCAAATCcCGTCGGGGTCA

TS-37:
                                    (SEQ ID NO: 2)
GGCCTCGTGGCGCAACGGTAGCGCGTCTGACTtCAGATCAGAAGGtT aCGgGTTCAAATCcCGTCGGGGTCA

TS-38:
                                    (SEQ ID NO: 3)
GGCCTCGTGGCGCAACGGTAGCGCGTCTGACTtCAGATCAGAAGGtT cCGgGTTCAAATCcCGgCGGGGTCA
```

TABLE 1

| Ranking | Identifier | Sequence | SEQ ID NO. |
|---|---|---|---|
| #1 | ArgTGAchr9.trna6/ nointron | CGTCGGCTCTGTGGCGCAATGGATAGCGCATTGGACTTC AAATTCAAAGGTTGTGGGTTCGAGTCCCACCAGAGTCG | 4 |
| #2 | ArgTGAchr17.trna19 | CGTCGCCCCAGTGGCCTAATGGATAAGGCACTGGCCTTC AAAGCCAGGGATTGTGGGTTCGAGTCCCACCTGGGGTG | 5 |
| #3 | ArgTGAchr1.trna10/ nointron | CGTCGGCTCCGTGGCGCAATGGATAGCGCATTGGACTTC AAATTCAAAGGTTCCGGGTTCGAGTCCCGGCGGAGTCG | 6 |
| #4 | ArgTGAchr7.trna5 | CGTCGCCCCAGTGGCCTAATGGATAAGGCATTGGCCTTC AAAGCCAGGGATTGTGGGTTCGAGTCCCATCTGGGGTG | 7 |
| #4 | ArgTGAchr17.trna3/ nointron | CGTCGGCTCTGTGGCGCAATGGATAGCGCATTGGACTTC AAATTCAAAGGTTGTGGGTTCGAATCCCACCAGAGTCG | 8 |
| #5 | ArgTGAchr9.trna6/ withintron | CGTCGGCTCTGTGGCGCAATGGATAGCGCATTGGACTTC AAGCTGAGCCTAGTGTGGTCATTCAAAGGTTGTGGGTTC GAGTCCCACCAGAGTCG | 9 |
| #5 | ArgTGAchr16.trna3 | CGTCGCCCCGGTGGCCTAATGGATAAGGCATTGGCCTTC AAAGCCAGGGATTGTGGGTTCGAGTCCCACCCGGGGTA | 10 |
| #6 | ArgTGAchr1.trna10/ withintron | CGTCGGCTCCGTGGCGCAATGGATAGCGCATTGGACTTC AAGAGGCTGAAGGCATTCAAAGGTTCCGGGTTCGAGTCC CGGCGGAGTCG | 11 |
| #7 | ArgTGAchr17.trna3/ withinron | CGTCGGCTCTGTGGCGCAATGGATAGCGCATTGGACTTC AAGTGACGAATAGAGCAATTCAAAGGTTGTGGGTTCGAA TCCCACCAGAGTCG | 12 |
| | ArgTGAchr15.trna4 | CGTCGGCCGCGTGGCCTAATGGATAAGGCGTCTGACTTC AGATCAGAAGATTGCAGGTTCGAGTCCTGCCGCGGTCG | 13 |
| | ArgTGAchr17.trna17 | CGTCGACCGCGTGGCCTAATGGATAAGGCGTCTGACTTC AGATCAGAAGATTGAGGGTTCGAGTCCCTTCGTGGTCG | 14 |
| | ArgTGAchr11.trna3/ withintron | CGTCGGCTCTGTGGCGCAATGGATAGCGCATTGGACTTC AAGATAGTTAGAGAAATTCAAAGGTTGTGGGTTCGAGTC CCACCAGAGTCG | 15 |

TABLE 2

| Ranking | Identifier | Sequence | SEQ ID NO. |
|---|---|---|---|
| #1 | GlnTAGchr1.trna17 | CGTCGGTTCCATGGTGTAATGGTgAGCACTCTGGACTctaAATCCAGCGaTCCGAGTTCGAGTCTCGGTGGAACCT | 16 |
| #2 | GlnTAGchr6.trna175 | CGTCGGCCCCATGGTGTAATGGTtAGCACTCTGGACTctaAATCCAGCGaTCCGAGTTCAAATCTCGGTGGGACCT | 17 |
| #3 | GlnTAGchr6.trna63 | CGTCGGTCCCATGGTGTAATGGTtAGCACTCTGGACTctaAATCCAGCAaTCCGAGTTCGAATCTCGGTGGGACCT | 18 |
| #4 | GlnTAGchr17.trna14 | CGTCGGTCCCATGGTGTAATGGTtAGCACTCTGGACTctaAATCCAGCGaTCCGAGTTCAAATCTCGGTGGGACCT | 19 |
| #5 | GlnTAGchr6.trna132 | CGTCGGCCCCATGGTGTAATGGTcAGCACTCTGGACTctaAATCCAGCGaTCCGAGTTCAAATCTCGGTGGGACCC | 20 |
| | GlnTAGchr1.trna101 | CGTCGGTTCCATGGTGTAATGGTaAGCACTCTGGACTctaAATCCAGCGaTCCGAGTTCGAGTCTCGGTGGAACCT | 21 |
| | GlnTAGchr6.trna42 | CGTCGGTTCCATGGTGTAATGGTtAGCACTCTGGACTctaAATCCGGTAaTCCGAGTTCAAATCTCGGTGGAACCT | 22 |
| | GlnTAGchr6.trna147 | CGTCGGTTCCATGGTGTAATGGTtAGCACTCTGGACTctaAATCCAGCGaTCCGAGTTCAAGTCTCGGTGGAACCT | 23 |

TABLE 3

| Ranking | Identifier | Sequence | SEQ ID NO. |
|---|---|---|---|
| #1 | GlnTAAchr1.trna101 | CGTCGGTTCCATGGTGTAATGGTaAGCACTCTGGACTtttaAATCCAGCGaTCCGAGTTCGAGTCTCGGTGGAACCT | 24 |
| #2 | GlnTAAchr6.trna175 | CGTCGGCCCCATGGTGTAATGGTtAGCACTCTGGACTtttaAATCCAGCGaTCCGAGTTCAAATCTCGGTGGGACCT | 25 |
| #3 | GlnTAAchr1.trna17 | CGTCGGTTCCATGGTGTAATGGTgAGCACTCTGGACTtttaAATCCAGCGaTCCGAGTTCGAGTCTCGGTGGAACCT | 26 |
| #4 | GlnTAAchr6.trna1 | CGTCGGTTCCATGGTGTAATGGTtAGCACTCTGGACTtttaAATCCAGCGaTCCGAGTTCAAATCTCGGTGGAACCT | 27 |
| #5 | GlnTAAchr17.trna14 | CGTCGGTCCCATGGTGTAATGGTtAGCACTCTGGACTtttaAATCCAGCGaTCCGAGTTCAAATCTCGGTGGGACCT | 28 |
| #5.2 | GlnTAAchr6.trna63 | CGTCGGTCCCATGGTGTAATGGTtAGCACTCTGGACTtttaAATCCAGCAaTCCGAGTTCGAATCTCGGTGGGACCT | 29 |

TABLE 3-continued

| Ranking | Identifier | Sequence | SEQ ID NO. |
|---|---|---|---|
| | GlnTAAchr6.trna42 | CGTCGGTTCCATGGTGTAATGGTtAGCACTCTGGACTtttaAATCCGGTAaTCCGAGTTCAAATCTCGGTGGAACCT | 30 |
| | GlnTAAchr6.trna132 | CGTCGGCCCCATGGTGTAATGGTcAGCACTCTGGACTtttaAATCCAGCGaTCCGAGTTCAAATCTCGGTGGGACCC | 31 |
| | GlnTAAchr6.trna147 | CGTCGGTTCCATGGTGTAATGGTtAGCACTCTGGACTtttaAATCCAGCGaTCCGAGTTCAAGTCTCGGTGGAACCT | 32 |

TABLE 4

| Ranking | Identifier | Sequence | SEQ ID NO. |
|---|---|---|---|
| #1 | TrpTAGchr17.trna10 | CGTCGACCTCGTGGCGCAATGGTAGCGCGTCTGACTctAGATCAGAAGGtTGCGTGTTCAAGTCACGTCGGGGTCA | 33 |
| #2 | TrpTAGchr6.trna171 | CGTCGACCTCGTGGCGCAACGGTAGCGCGTCTGACTctAGATCAGAAGGtTGCGTGTTCAAATCACGTCGGGGTCA | 34 |
| #3 | TrpTAGchr17.trna39 | CGTCGGCCTCGTGGCGCAACGGTAGCGCGTCTGACTctAGATCAGAAGGtTGCGTGTTCAAATCACGTCGGGGTCA | 35 |
| #4 | TrpTAGchr12.trna6 | CGTCGACCTCGTGGCGCAACGGTAGCGCGTCTGACTctAGATCAGAAGGcTGCGTGTTCGAATCACGTCGGGGTCA | 36 |
| | TrpTAGchr7.trna3 | CGTCGACCTCGTGGCGCAACGGCAGCGCGTCTGACTctAGATCAGAAGGtTGCGTGTTCAAATCACGTCGGGGTCA | 37 |

TABLE 5

| Ranking | Identifier | Sequence | SEQ ID NO. |
|---|---|---|---|
| #1 | GluTAGchr13.trna2 | CGTCTCCCACATGGTCTAGCGGTtAGGATTCCTGGTTctaACCCAGGCGGCCCGGGTTCGACTCCCGGTGTGGGAA | 38 |
| #2 | GluTAGchr2.trna18 | CGTCTCCCATATGGTCTAGCGGTtAGGATTCCTGGTTctaACCCAGGTGGCCCGGGTTCGACTCCCGGTATGGGAA | 39 |
| #3 | GluTAGchr1.trna123 | CGTCTCCCTGGTGGTCTAGTGGCtAGGATTCGGCGCTctaACCGCCGCGGCCCGGGTTCGATTCCCGGTCAGGGAA | 40 |
| #4 | GluTAGchr1.trna106 | CGTCTCCCTGGTGGTCTAGTGGTtAGGATTCGGCGCTctaACCGCCGCGGCCCGGGTTCGATTCCCGGTCAGGGAA | 41 |

TABLE 5-continued

| Ranking | Identifier | Sequence | SEQ ID NO. |
|---|---|---|---|
| | GluTAGchr1.trna5 | CGTCTCCCTGGTGGTCTAGTG GCtAGGATTCGGCGCTctaAC CGCCGCGGCCCGGGTTCGATT CCCGGCCAGGGAA | 42 |

TABLE 6

| Ranking | Identifier | Sequence | SEQ ID NO. |
|---|---|---|---|
| | GluTAAchr13.trna2 | CGTCTCCCACATGGTCTAGCG GTtAGGATTCCTGGTTctaAC CCAGGCGGCCCGGGTTCGACT CCCGGTGTGGGAA | 43 |
| | GluTAAchr2.trna18 | CGTCTCCCATATGGTCTAGCG GTtAGGATTCCTGGTTctaAC CCAGGTGGCCCGGGTTCGACT CCCGGTATGGGAA | 44 |
| | GluTAAchr1.trna106 | CGTCTCCCTGGTGGTCTAGTG GTtAGGATTCGGCGCTctaAC CGCCGCGGCCCGGGTTCGATT CCCGGTCAGGGAA | 45 |
| | GluTAAchr1.trna55 | CGTCTCCCTGGTGGTCTAGTG GTtAGGATTCGGCGCTctaAC CGCCGCGGCCCGGGTTCGATT CCCGGTCAGGAAA | 46 |
| | GluTAAchr1.trna5 | CGTCTCCCTGGTGGTCTAGTG GCtAGGATTCGGCGCTctaAC CGCCGCGGCCCGGGTTCGATT CCCGGCCAGGGAA | 47 |

TABLE 7

| Ranking | Identifier | Sequence | SEQ ID NO. |
|---|---|---|---|
| #1 | TrpTGAchr17.trna39 | GGCCTCGTGGCGCAACGGTA GCGCGTCTGACTtCAGATCA GAAGGtTGCGTGTTCAAATC ACGTCGGGGTCA | 48 |
| #2 | TrpTGAchr17.trna10 | GACCTCGTGGCGCAATGGTA GCGCGTCTGACTtCAGATCA GAAGGtTGCGTGTTCAAGTC ACGTCGGGGTCA | 49 |
| #3 | TrpTGAchr6.trna171 | GACCTCGTGGCGCAACGGTA GCGCGTCTGACTtCAGATCA GAAGGtTGCGTGTTCAAATC ACGTCGGGGTCA | 50 |
| | TrpTGAchr12.trna6 | GACCTCGTGGCGCAACGGTA GCGCGTCTGACTtCAGATCA GAAGGcTGCGTGTTCGAATC ACGTCGGGGTCA | 51 |
| | TrpTGAchr7.trna3 | GACCTCGTGGCGCAACGGCA GCGCGTCTGACTtCAGATCA GAAGGtTGCGTGTTCAAATC ACGTCGGGGTCA | 52 |

TABLE 8

| Ranking | Identifier | Sequence | SEQ ID NO. |
|---|---|---|---|
| #1 | GlyTGAchr19.trna2 | GCGTTGGTGGTATAGTGGT tAGCATAGCTGCCTTCaAA GCAGTTGaCCCGGGTTCGA TTCCCGGCCAACGCA | 53 |
| #2 | GlyTGAchr1.trna107 | GCGTTGGTGGTATAGTGGT gAGCATAGCTGCCTTCaAA GCAGTTGaCCCGGGTTCGA TTCCCGGCCAACGCA | 54 |
| #3 | GlyTGAchr17.trna9 | GCGTTGGTGGTATAGTGGT aAGCATAGCTGCCTTCaAA GCAGTTGaCCCGGGTTCGA TTCCCGGCCAACGCA | 55 |

Figure 3:
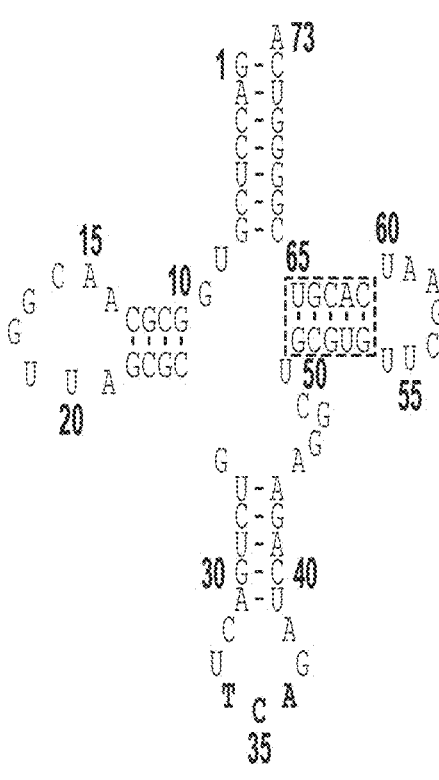
FIG. 3. ACE-tRNA for nonsense suppression (*H. sapiens* tRNA$^{Trp}_{TGA}$).

In one embodiment, the ACE-tRNA for nonsense suppression is as depicted in FIG. 3 (*H. sapiens* tRNA$^{Trp}$ TGA).

According to the invention, human UAA, UAG, and UGA suppressor tRNAs have been designed. The screen has identified codon edited tRNA for the repair of Trp-TGA, Trp-TAG, Arg-TGA, Gln-TAG, Gln-TA, Glu-TAG, Glu-TAA. The tRNAs are approximately 100 nucleotides in length and can be introduced to cells to suppress nonsense codons mutations where the wild-type amino acid should be present. The oligonucleotides can be introduced directly to recipient cells or can be ligated in tandem to increase efficacy of the oligonucleotide.

Expression Cassettes and Vectors

In certain embodiments, the ACT-tRNA is encoded by an expression cassette. In yet another embodiment, the suppressor tRNA of the invention may be introduced to the cells using standard conventional genetic engineering techniques through use of vectors. Because of the internal promoter sequences of tRNA encoding sequences, the tRNA sequence need not be included in a separate transcription unit, although one may be provided.

In one embodiment of the present invention, the nucleotide expression system of the invention is included within an appropriate gene transfer vehicle which is then used to transduce cells to express the suppressor tRNA. The gene delivery vehicle can be any delivery vehicle known in the art, and can include naked DNA that is facilitated by a receptor and/or lipid mediated transfection, as well as any of a number of vectors. Such vectors include but are not limited to eukaryotic vectors, prokaryotic vectors (such as for example bacterial vectors) and viral vectors including, but not limited to, retroviral vectors, adenoviral vectors, adeno-associated viral vectors, lentivirus vectors (human and other including porcine), Herpes virus vectors, Epstein-Barr viral vectors, SV40 virus vectors, pox virus vectors, and pseudo-typed viral vectors.

Figure 4:
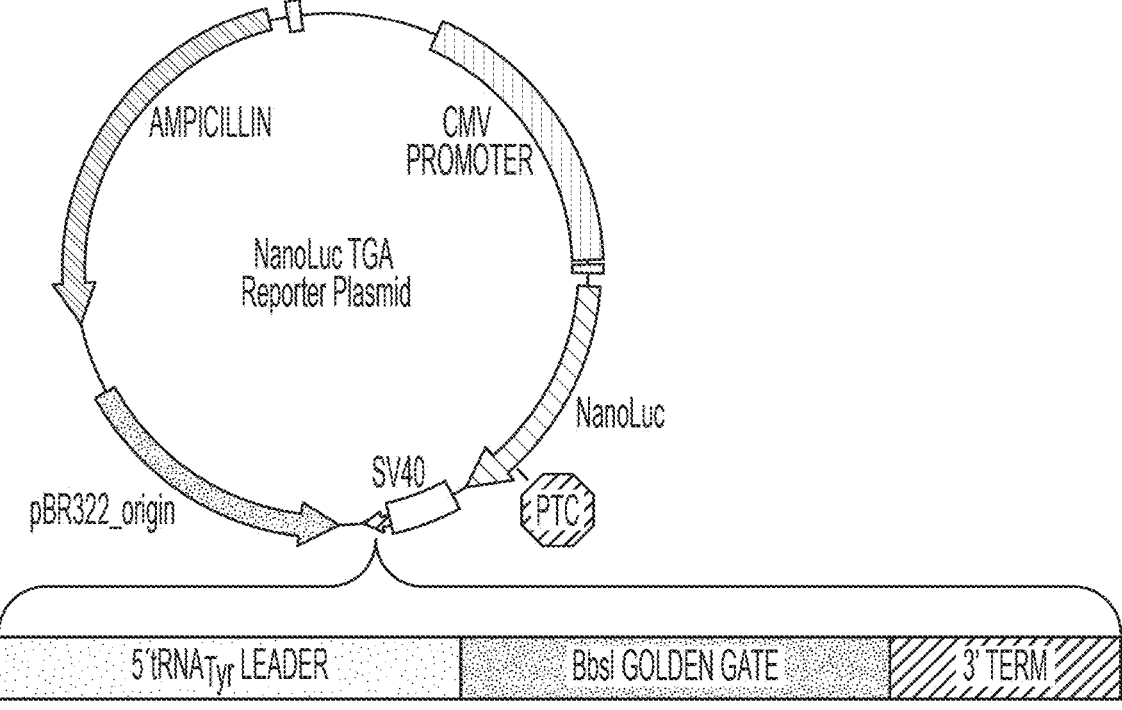
FIG. 4. Anti-codon edited (ACE)-tRNA encoded in a vector used to identify functional ACE tRNA sequences. This vector sequence includes a Nanoluciferase reporter system. The depicted vector was used to identify ACE tRNA with TGA suppression. TAA and TAG variants were used for the appropriate tRNA screens (see FIGS. 14 through 17).
Figure 5:
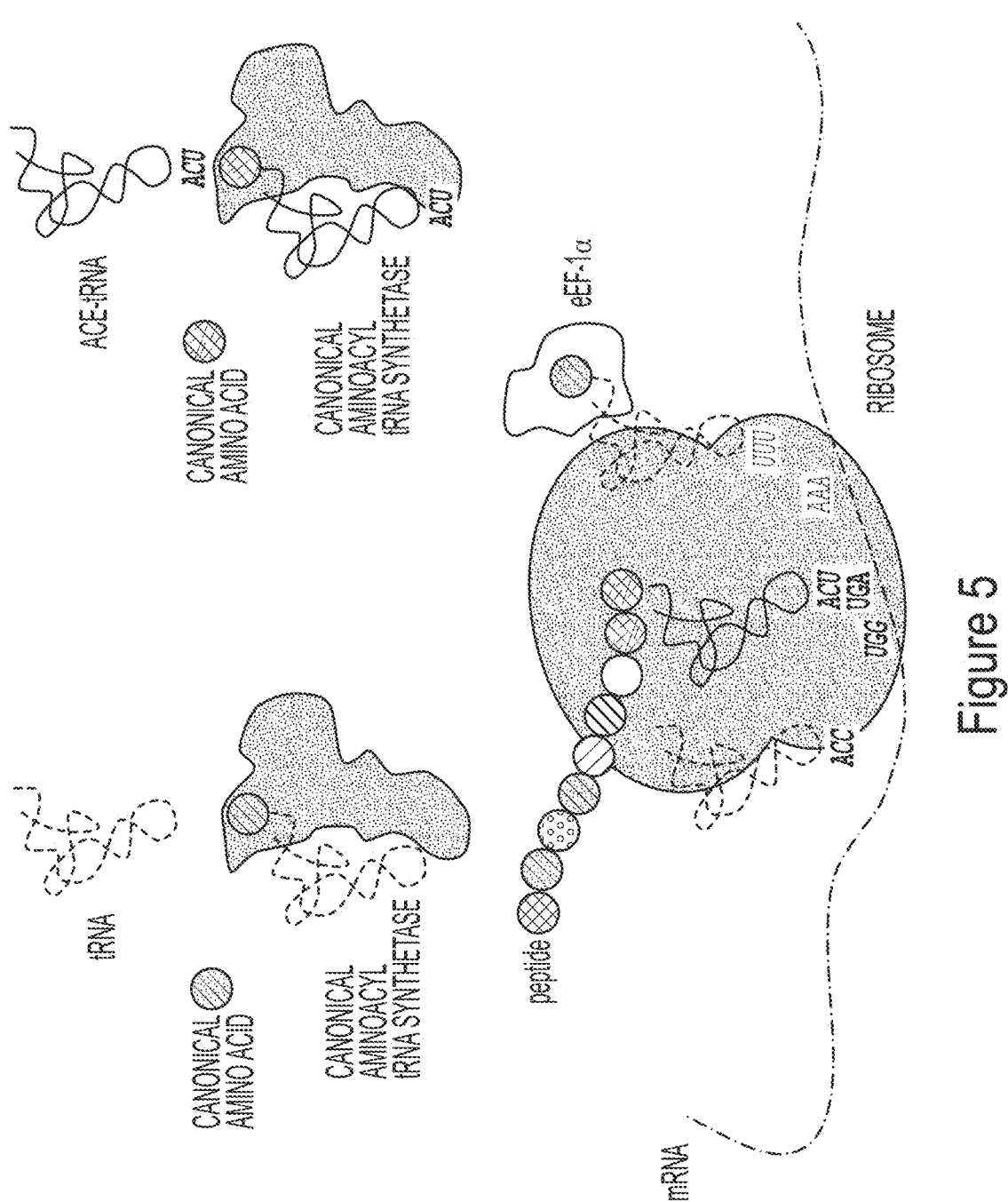
FIG. 5. Schematic of the rescue of proteins and ion channels with stop codons via suppressor tRNA.

In certain embodiments, the ACT-tRNA (PTC) is encoded in a vector. FIG. 4. In certain embodiments, the viral vector is a retroviral or adenoviral vector. Examples of retroviral vectors that may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus.

Retroviruses; Retroviral Vectors

The term "retrovirus" is used in reference to RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules that encode the structural proteins and enzymes needed to produce new viral particles. At each end of the provirus are structures called "long terminal repeats" or "LTRs." The LTR contains numerous regulatory signals including transcriptional control elements, polyadenylation signals and sequences needed for replication and integration of the viral genome. There are several genera included within the family Retroviridae, including Cisterna virus A, Oncovirus A, Oncovirus B, Oncovirus C, Oncovirus D, Lentivirus, and Spumavirus. Some of the retroviruses are oncogenic (i.e., tumorigenic), while others are not. The oncoviruses induce sarcomas, leukemias, lymphomas, and mammary carcinomas in susceptible species. Retroviruses infect a wide variety of species, and may be transmitted both horizontally and vertically. They are integrated into the host DNA, and are capable of transmitting sequences of host DNA from cell to cell. This has led to the development of retroviruses as vectors for various purposes including gene therapy.

Retroviruses, including human foamy virus (HFV) and human immunodeficiency virus (HIV) have gained much recent attention, as their target cells are not limited to dividing cells and their restricted host cell tropism can be readily expanded via pseudotyping with vesicular stomatitis virus G (VSV-G) envelope glycoproteins (See e.g., J. C. Burns et al., Proc. Natl. Acad. Sci. USA 90:8033-8037 [1993]; A. M. L. Lever, Gene Therapy. 3:470-471 [1996]; and D. Russell and A. D. Miller, J. Virol., 70:217-222 [1996]).

Vector systems generally have a DNA vector containing a small portion of the retroviral sequence (the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the viral proteins required for particle assembly (D. Markowitz et al., J. Virol., 62:1120 [1988]). In one embodiment of the present invention, an FIV system employing a three-plasmid transfection production method in 293T cells was used (Johnston et al., J Virol. 1999 73:4991-5000). Replication incompetent virus was successfully produced.

The vector DNA is introduced into the packaging cell by any of a variety of techniques (e.g., calcium phosphate coprecipitation, lipofection, electroporation). The viral proteins produced by the packaging cell mediate the insertion of the vector sequences in the form of RNA into viral particles, which are shed into the culture supernatant.

For cells that are naturally dividing, or are stimulated to divide by growth factors, simple retroviruses like murine leukemia virus (MLV) vectors are suitable delivery systems. A major limitation in the use of many commonly used retroviral vectors in gene transfer, however, is that many of the vectors are restricted to dividing cells. If a non-dividing cell is the target cell, then a lentivirus, which is capable of infecting non-dividing cells, may be used.

As used herein, the term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, that causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells).

Lentiviruses including HIV, SIV, FIV and equine infectious anemia virus (EIAV) depend on several viral regulatory genes in addition to the simple structural gag-pol-env genes for efficient intracellular replication. Thus, lentiviruses use more complex strategies than classical retroviruses for gene regulation and viral replication, with the packaging signals apparently spreading across the entire viral genome. These additional genes display a web of regulatory functions during the lentiviral life cycle. For example, upon HIV-1 infection, transcription is up-regulated by the expression of Tat through interaction with an RNA target (TAR) in the LTR. Expression of the full-length and spliced mRNAs is then regulated by the function of Rev, which interacts with RNA elements present in the gag region and in the env region (RRE) (S. Schwartz et al., J. Virol., 66:150-159 [1992]). Nuclear export of gag-pol and env mRNAs is dependent on the Rev function. In addition to these two essential regulatory genes, a list of accessory genes, including vif, vpr, vpx, vpu, and nef, are also present in the viral genome and their effects on efficient virus production and infectivity have been demonstrated, although they are not absolutely required for virus replication (K. and F. Wong-Staal, Microbiol. Rev., 55:193-205 (1991]; R. A. Subbramanian and E. A. Cohen, J. Virol. 68:6831-6835 [1994]; and D. Trono, Cell 82:189-192 [1995]). A detailed description of the structure of an exemplary lentivirus, HIV-1, is given in U.S. Pat. No. 6,531,123.

A "source" or "original" retrovirus is a wild-type retrovirus from which a pseudotyped retrovirus is derived, or is used as a starting point, during construction of the packaging or transgene vector, for the preparation of one or more of the genetic elements of the vector. The genetic element may be employed unchanged, or it may be mutated (but not beyond the point where it lacks a statistically significant sequence similarity to the original element). A vector may have more than one source retrovirus, and the different source retroviruses may be, e.g., MLV, FIV, HIV-1 and HIV-2, or HIV and SIV. The term "genetic element" includes but is not limited to a gene.

A cognate retrovirus is the wild-type retrovirus with which the vector in question has the greatest percentage sequence identity at the nucleic acid level. Normally, this will be the same as the source retrovirus. However, if a source retrovirus is extensively mutated, it is conceivable that the vector will then more closely resemble some other retrovirus. It is not necessary that the cognate retrovirus be the physical starting point for the construction; one may choose to synthesize a genetic element, especially a mutant element, directly, rather than to first obtain the original element and then modify it. The term "cognate" may similarly be applied to a protein, gene, or genetic element (e.g., splice donor site or packaging signal). When referring to a cognate protein, percentage sequence identities are determined at the amino acid level.

The term "cognate" retrovirus may be difficult to interpret in the extreme case, i.e., if all retroviral genetic elements have been replaced with surrogate non-lentiviral genetic elements. In this case, the source retrovirus strain mentioned previously is arbitrarily considered to be the cognate retrovirus.

The term "replication" as used herein in reference to a virus or vector, refers not to the normal replication of proviral DNA in a chromosome as a consequence of cell reproduction, or the autonomous replication of a plasmid DNA as a result of the presence of a functional origin of replication. Instead "replication" refers to the completion of a complete viral life cycle, wherein infectious viral particles containing viral RNA enter a cell, the RNA is reverse transcribed into DNA, the DNA integrates into the host chromosome as a provirus, the infected cell produces virion proteins and assembles them with full length viral genomic RNA into new, equally infectious particles.

The term "replication-competent" refers to a wild-type virus or mutant virus that is capable of replication, such that replication of the virus in an infected cell result in the production of infectious virions that, after infecting another, previously uninfected cell, causes the latter cell to likewise produce such infectious virions. The present invention contemplates the use of replication-defective virus.

As used herein, the term "attenuated virus" refers to any virus (e.g., an attenuated lentivirus) that has been modified so that its pathogenicity in the intended subject is substantially reduced. The virus may be attenuated to the point it is nonpathogenic from a clinical standpoint, i.e., that subjects exposed to the virus do not exhibit a statistically significant increased level of pathology relative to control subjects.

The present invention contemplates the preparation and use of a modified retrovirus. In some embodiments, the retrovirus is an mutant of murine leukemia virus, human immunodeficiency virus type 1, human immunodeficiency virus type 2, feline immunodeficiency virus, simian immunodeficiency virus, visna-maedi, caprine arthritis-encephalitis virus, equine infectious anemia virus, and bovine immune deficiency virus, or a virus comprised of portions of more than one retroviral species (e.g., a hybrid, comprised of portions of MLV, FIV, HIV-1 and HIV-2, or HIV-1 and/or SIV).

A reference virus is a virus whose genome is used in describing the components of a mutant virus. For example, a particular genetic element of the mutant virus may be said to differ from the cognate element of the reference virus by various substitutions, deletions or insertions. It is not necessary that the mutant virus actually be derived from the reference virus.

The preferred reference FIV sequence is found in Talbott et al., Proc Natl Acad Sci USA. 1989 86:5743-7; Genbank access #NC 001482. In certain embodiments, a three-plasmid transient transfection method can be used to produce replication incompetent pseudotyped retroviruses (e.g., FIV). General methods are described in Wang et al., J Clin Invest. 1999 104:R55-62 and Johnston et al., J Virol. 1999 73:4991-5000.

Retroviral Vector System

The present invention contemplates a retroviral gene amplification and transfer system comprising a transgene vector, one or more compatible packaging vectors, an envelope vector, and a suitable host cell. The vectors used may be derived from a retrovirus (e.g., a lentivirus). Retrovirus vectors allow (1) transfection of the packaging vectors and envelope vectors into the host cell to form a packaging cell line that produces essentially packaging-vector-RNA-free viral particles, (2) transfection of the transgene vector into the packaging cell line, (3) the packaging of the transgene vector RNA by the packaging cell line into infectious viral particles, and (4) the administration of the particles to target cells so that such cells are transduced and subsequently express a transgene.

Either the particles are administered directly to the subject, in vivo, or the subject's cells are removed, infected in vitro with the particles, and returned to the body of the subject.

The packaging vectors and transgene vectors of the present invention will generate replication-incompetent viruses. The vectors chosen for incorporation into a given vector system of the present invention are such that it is not possible, without further mutation of the packaging vector(s) or transgene vector, for the cotransfected cells to generate a replication-competent virus by homologous recombination of the packaging vector(s) and transgene vector alone. The envelope protein used in the present system can be a retroviral envelope, a synthetic or chimeric envelope, or the envelope from a non-retroviral enveloped virus (e.g., baculovirus).

Packaging Signal

As used herein, the term "packaging signal" or "packaging sequence" refers to sequences located within the retroviral genome or a vector that are required for, or at least facilitate, insertion of the viral or vector RNA into the viral capsid or particle. The packaging signals in an RNA identify that RNA as one that is to be packaged into a virion. The term "packaging signal" is also used for convenience to refer to a vector DNA sequence that is transcribed into a functional packaging signal. Certain packaging signals may be part of a gene, but are recognized in the form of RNA, rather than as a peptide moiety of the encoded protein.

The key distinction between a packaging vector and a transgene vector is that in the packaging vector, the major packaging signal is inactivated, and, in the transgene vector, the major packaging sign al is functional. Ideally, in the packaging vector, all packaging signals would be inactivated, and, in the transgene vector, all packaging signals would be functional. However, countervailing considerations, such as maximizing viral titer, or inhibiting homologous recombination, may lend such constructs less desirable.

Packaging System; Packaging Vectors; Packaging Cell Line

A packaging system is a vector, or a plurality of vectors, which collectively provide in expressible form all of the genetic information required to produce a virion that can encapsidate suitable RNA, transport it from the virion-producing cell, transmit it to a target cell, and, in the target cell, cause the RNA to be reverse transcribed and integrated into the host genome in a such a manner that a transgene incorporated into the aforementioned RNA can be expressed. However, the packaging system must be substantially incapable of packaging itself. Rather, it packages a separate transgene vector.

In the present invention, the packaging vector will provide functional equivalents of the gag and pol genes (a "GP" vector). The env gene(s) will be provided by the envelope vector. In theory, a three vector system ("G", "P", and "E" vectors) is possible if one is willing to construct distinct gag and pol genes on separate vectors, and operably link them to different regulatable promoters (or one to a regulatable and the other to a constitutive promoter) such that their relative levels of expression can be adjusted appropriately.

A packaging cell line is a suitable host cell transfected by a packaging system that, under achievable conditions, produces viral particles. As used herein, the term "packaging cell lines" is typically used in reference to cell lines that express viral structural proteins (e.g., gag, pol and env), but do not contain a packaging signal. For example, a cell line has been genetically engineered to carry at one chromosomal site within its genome, a 5'-LTR-gag-pol-3'-LTR fragment that lacks a functional psi+ sequence (designated as Δ-psi), and a 5'-LTR-env-3'-LTR fragment that is also Δ-psi located at another chromosomal site. While both of these segments are transcribed constitutively, because the psi region is missing and the viral RNA molecules produced are less than full-size, empty viral particles are formed.

If a host cell is transfected by the packaging vector(s) alone, it produces substantially only viral particles without the full-length packaging vector. In one example, less than 10% of the viral particles produced by the packaging cell contain full length packaging vector-derived RNA. However, since the packaging vector lacks a functional primer-binding site, even if these particles infect a new cell, the packaging vector RNA will not be reverse transcribed back into DNA and therefore the new cell will not produce virion. Thus, by itself, the packaging vector is a replication-incompetent virus.

In some embodiments, the packaging cell and/or cell line contains a transgene vector. The packaging cell line will package the transgene vector into infectious particles. Such a cell line is referred to herein as a "transgenic virion production cell line."

It is contemplated that packaging may be inducible, as well as non-inducible. In inducible packaging cells and packaging cell lines, retroviral particles are produced in response to at least one inducer. In non-inducible packaging cell lines and packaging cells, no inducer is required in order for retroviral particle production to occur.

The packaging vectors necessarily differ from wild-type, replication-competent retroviral genomes by virtue of the inactivation of at least one packaging signal of the cognate wild-type genome. More than one packaging signal may be inactivated. In one example, only the retroviral genes provided by the packaging vector are those encoding structural, or essential regulatory, proteins.

Transgene Vectors

A transgene vector is an expression vector that bears an expressible non-retroviral gene of interest and includes at least one functional retroviral packaging signal, so that, after the transgene vector is transfected into a packaging cell line, the transgene vector is transcribed into RNA, and this RNA is packaged into an infectious viral particle. These particles, in turn, infect target cells, their RNA is reverse transcribed into DNA, and the DNA is incorporated into the host cell genome as a proviral element, thereby transmitting the gene of interest to the target cells.

As used herein, the term "transduction" refers to the delivery of a gene(s) using a viral or retroviral vector by means of infection rather than by transfection. In certain embodiments, retroviral vectors are transduced. Thus, a "transduced gene" is a gene that has been introduced into the cell via retroviral or vector infection and provirus integration. In certain embodiments, viral vectors (e.g., "transgene vectors") transduce genes into "target cells" or host cells. The, present invention encompasses transgene vectors that are suitable for use in the present invention that are linked to any gene of interest (or a "marker gene" or "reporter gene," used to indicate infection or expression of a gene).

As used herein, the term "long-term transduction" refers to vectors that are capable of remaining transduced in host or target cells for time periods that are longer than those observed with other vectors. For example, the present invention provides retroviral vectors that are capable of remaining transduced for at least 120 days, at least one year, or for the life of the subject or the necessary time course of treatment. The duration of expression is a function of the choice of promoter and the target cell type, more so than the choice of vector.

The term "stable transduction" or "stably transduced" refers to the introduction and integration of foreign DNA into the genome of the transducted cell. The term "stable transductant" refers to a cell that has stably integrated foreign DNA into the genomic DNA.

The term "transient transduction" or "transiently transduced" refers to the introduction of foreign DNA into a cell where the foreign DNA fails to integrate into the genome of the transducted cell. The foreign DNA persists in the nucleus of the transducted cell for several days. During this time the foreign DNA is subject to the regulatory controls that govern the expression of endogenous genes in the chromosomes. The term "transient transductant" refers to cells that have taken up foreign DNA but have failed to integrate this DNA.

In some embodiments, the target and/or host cells of the present invention are "non-dividing" cells. These cells include cells such as neuronal cells that do not normally divide. However, it is not intended that the present invention be limited to non-dividing cells (including, but not limited to muscle cells, white blood cells, spleen cells, liver cells, eye cells, epithelial cells).

In some embodiments, the vector and the vector progeny are capable of transducing a plurality of target cells so as to achieve vector titers of at least $10^5$ cfu/ml. The multiplicity of infection (MOI) may be at least one (i.e., one hit on average per cell), or even at least two.

Expression Cassettes and Vectors

The present invention also provides an expression cassette comprising a sequence encoding ACE-tRNA.

In certain embodiments, the expression cassette further contains a promoter. In certain embodiments, the promoter is a regulatable promoter. In certain embodiments, the promoter is a constitutive promoter. In certain embodiments, the promoter is a PGK, CMV, RSV, H1 or U6 promoter (Pol II and Pol III promoters).

The present invention provides a vector containing the expression cassette described above. In certain embodiments, the vector is a viral vector. In certain embodiments, the viral vector is an adenoviral, lentiviral, adeno-associated viral (AAV), poliovirus, HSV, or murine Maloney-based viral vector.

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. It also may include sequences required for proper translation of the nucleotide sequence. The coding region usually codes for a protein of interest. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

Adeno Associated Virus (AAV)

Adeno associated virus (AAV) is a small nonpathogenic virus of the parvoviridae family. AAV is distinct from the other members of this family by its dependence upon a helper virus for replication. In the absence of a helper virus, AAV may integrate in a locus specific manner into the q arm of chromosome 19. The approximately 5 kb genome of AAV consists of one segment of single stranded DNA of either plus or minus polarity. The ends of the genome are short inverted terminal repeats that can fold into hairpin structures and serve as the origin of viral DNA replication. Physically, the parvovirus virion is non-enveloped and its icosahedral capsid is approximately 20 nm in diameter.

To date, numerous serologically distinct AAVs have been identified, and more than a dozen have been isolated from humans or primates. The genome of AAV2 is 4680 nucleotides in length and contains two open reading frames (ORFs). The left ORF encodes the non-structural Rep proteins, Rep 40, Rep 52, Rep 68 and Rep 78, which are involved in regulation of replication and transcription in addition to the production of single-stranded progeny genomes. Furthermore, two of the Rep proteins have been associated with the preferential integration of AAV genomes into a region of the q arm of human chromosome 19. Rep68/78 has also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats (ITR) which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs, which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The AAV virion is a non-enveloped, icosohedral particle approximately 25 nm in diameter, consisting of three related proteins referred to as VP1, VP2 and VP3. The right ORF encodes the capsid proteins VP1, VP2, and VP3. These proteins are found in a ratio of 1:1:10 respectively and are all derived from the right-hand ORF. The capsid proteins differ from each other by the use of alternative splicing and an unusual start codon. Deletion analysis has shown that removal or alteration of VP1 which is translated from an alternatively spliced message results in a reduced yield of infections particles. Mutations within the VP3 coding region result in the failure to produce any single-stranded progeny DNA or infectious particles. An AAV particle is a viral particle comprising an AAV capsid protein. An AAV capsid polypeptide can encode the entire VP1, VP2 and VP3 polypeptide. The particle can be a particle comprising AAV2 and other AAV capsid proteins (i.e., a chimeric protein, such as AAV1 and AAV2). Variations in the amino acid sequence of the AAV2 capsid protein are contemplated herein, as long as the resulting viral particle comprises the AAV2 capsid remains antigenically or immunologically distinct from AAV1, as can be routinely determined by standard methods. Specifically, for example, ELISA and Western blots can be used to determine whether a viral particle is antigenically or immunologically distinct from AAV1. Furthermore, the AAV2 viral particle preferably retains tissue tropism distinct from AAV1.

An AAV2 particle is a viral particle comprising an AAV2 capsid protein. An AAV2 capsid polypeptide encoding the entire VP1, VP2, and VP3 polypeptide can overall have at least about 63% homology (or identity) to the polypeptide having the amino acid sequence encoded by nucleotides set forth in NC 001401 (nucleotide sequence encoding AAV2 capsid protein). The capsid protein can have about 70% homology, about 75% homology, 80% homology, 85% homology, 90% homology, 95% homology, 98% homology, 99% homology, or even 100% homology to the protein encoded by the nucleotide sequence set forth in NC 001401. The capsid protein can have about 70% identity, about 75% identity, 80% identity, 85% identity, 90% identity, 95% identity, 98% identity, 99% identity, or even 100% identity to the protein encoded by the nucleotide sequence set forth in NC 001401. The particle can be a particle comprising another AAV and AAV2 capsid protein, i.e., a chimeric protein. Variations in the amino acid sequence of the AAV2 capsid protein are contemplated herein, as long as the resulting viral particle comprising the AAV2 capsid remains antigenically or immunologically distinct from AAV4, as can be routinely determined by standard methods. Specifically, for example, ELISA and Western blots can be used to determine whether a viral particle is antigenically or immunologically distinct from AAV1. Furthermore, the AAV2 viral particle preferably retains tissue tropism distinction from AAV1, such as that exemplified in the examples herein, though an AAV2 chimeric particle comprising at least one AAV2 coat protein may have a different tissue tropism from that of an AAV2 particle consisting only of AAV2 coat proteins.

In certain embodiments, the invention further provides an AAV2 particle containing, i.e., encapsidating, a vector comprising a pair of AAV2 inverted terminal repeats. The nucleotide sequence of AAV2 ITRs is known in the art. Furthermore, the particle can be a particle comprising both AAV1 and AAV2 capsid protein, i.e., a chimeric protein. Moreover, the particle can be a particle encapsidating a vector comprising a pair of AAV inverted terminal repeats from other AAVs (e.g., AAV1-AAV9 and AAVrh10). The vector encapsidated in the particle can further comprise an exogenous nucleic acid inserted between the inverted terminal repeats.

The following features of AAV have made it an attractive vector for gene transfer. AAV vectors have been shown in vitro to stably integrate into the cellular genome; possess a broad host range; transduce both dividing and non-dividing cells in vitro and in vivo and maintain high levels of
expression of the transduced genes. Viral particles are heat
stable, resistant to solvents, detergents, changes in pH,
temperature, and can be concentrated on CsCl gradients or
by other means. The present invention provides methods of
administering AAV particles, recombinant AAV vectors, and
recombinant AAV virions. For example, an AAV2 particle is
a viral particle comprising an AAV2 capsid protein, or an
AAV1 particle is a viral particle comprising an AAV1 capsid
protein. A recombinant AAV2 vector is a nucleic acid
construct that comprises at least one unique nucleic acid of
AAV2. A recombinant AAV2 virion is a particle containing
a recombinant AAV2 vector. To be considered within the
term "AAV2 ITRs" the nucleotide sequence must retain one
or both features described herein that distinguish the AAV2
ITR from the AAV1 ITR: (1) three (rather than four as in
AAV1) "GAGC" repeats and (2) in the AAV2 ITR Rep
binding site the fourth nucleotide in the first two "GAGC"
repeats is a C rather than a T.

The promoter to drive expression of the sequence encod-
ing the tRNA to be delivered can be any desired promoter,
selected by known considerations, such as the level of
expression of a nucleic acid functionally linked to the
promoter and the cell type in which the vector is to be used.
Promoters can be an exogenous or an endogenous promoter.
Promoters can include, for example, known strong promot-
ers such as SV40 or the inducible metallothionein promoter,
or an AAV promoter, such as an AAV p5 promoter. Addi-
tional examples of promoters include promoters derived
from actin genes, immunoglobulin genes, cytomegalovirus
(CMV), adenovirus, bovine papilloma virus, adenoviral
promoters, such as the adenoviral major late promoter, an
inducible heat shock promoter, respiratory syncytial virus,
Rous sarcomas virus (RSV), etc. Additional examples
include regulated promoters.

The AAV vector can further comprise an exogenous
(heterologous) nucleic acid functionally linked to the pro-
moter. By "heterologous nucleic acid" is meant that any
heterologous or exogenous nucleic acid can be inserted into
the vector for transfer into a cell, tissue or organism. The
nucleic acid can encode a tRNA, for example. By "func-
tionally linked" is meant such that the promoter can promote
expression of the heterologous nucleic acid, as is known in
the art, such as appropriate orientation of the promoter
relative to the heterologous nucleic acid. Furthermore, the
heterologous nucleic acid preferably has all appropriate
sequences for expression of the nucleic acid, as known in the
art, to functionally encode, i.e., allow the nucleic acid to be
expressed. The nucleic acid can include, for example,
expression control sequences, such as an enhancer. The
nucleic acid can encode more than one gene product, limited
only by the size of nucleic acid that can be packaged.

An AAV1 particle is a viral particle comprising an AAV1
capsid protein. Variations in the amino acid sequence of the
AAV1 capsid protein are contemplated herein, as long as the
resulting viral particle comprising the AAV1 capsid remains
antigenically or immunologically distinct from other AAV
capsids, as can be routinely determined by standard meth-
ods. Specifically, for example, ELISA and Western blots can
be used to determine whether a viral particle is antigenically
or immunologically distinct from other AAV serotypes.

The term "polypeptide" as used herein refers to a polymer
of amino acids and includes full-length proteins and frag-
ments thereof. Thus, "protein" and "polypeptide" are often
used interchangeably herein.

The present method provides a method of delivering a
nucleic acid to a cell comprising administering to the cell an AAV particle containing a vector comprising the nucleic
acid inserted between a pair of AAV inverted terminal
repeats, thereby delivering the nucleic acid to the cell.
Administration to the cell can be accomplished by any
means, including simply contacting the particle, optionally
contained in a desired liquid such as tissue culture medium,
or a buffered saline solution, with the cells. The particle can
be allowed to remain in contact with the cells for any desired
length of time, and typically, the particle is administered and
allowed to remain indefinitely. For such in vitro methods,
the virus can be administered to the cell by standard viral
transduction methods, as known in the art and as exemplified
herein. Titers of virus to administer can vary, particularly
depending upon the cell type, but will be typical of that used
for AAV transduction in general. Additionally the titers used
to transduce the particular cells in the present examples can
be utilized. The cells can include any desired cell in humans
as well as other large (non-rodent) mammals, such as
primates, horse, sheep, goat, pig, and dog.

The present invention further provides a method of deliv-
ering a nucleic acid to a cell in a subject comprising
administering to the subject an AAV particle comprising the
nucleic acid inserted between a pair of AAV inverted ter-
minal repeats, thereby delivering the nucleic acid to a cell in
the subject.

Certain embodiments of the present disclosure provide a
cell comprising a viral vector as described herein.

AAV Vectors

In one embodiment, a viral vector of the disclosure is an
AAV vector. An "AAV" vector refers to an adeno-associated
virus, and may be used to refer to the naturally occurring
wild-type virus itself or derivatives thereof. The term covers
all subtypes, serotypes and pseudotypes, and both naturally
occurring and recombinant forms, except where required
otherwise. As used herein, the term "serotype" refers to an
AAV, which is identified by, and distinguished from other
AAVs based on capsid protein reactivity with defined anti-
sera, e.g., there are eight known serotypes of primate AAVs,
AAV-1 to AAV-9 and AAVrh10. For example, serotype
AAV2 is used to refer to an AAV, which contains capsid
proteins encoded from the cap gene of AAV2 and a genome
containing 5' and 3' ITR sequences from the same AAV2
serotype. As used herein, for example, rAAV1 may be used
to refer an AAV having both capsid proteins and 5'-3' ITRs
from the same serotype or it may refer to an AAV having
capsid proteins from one serotype and 5'-3' ITRs from a
different AAV serotype, e.g., capsid from AAV serotype 2
and ITRs from AAV serotype 5. For each example illustrated
herein, the description of the vector design and production
describes the serotype of the capsid and 5'-3' ITR sequences.
The abbreviation "rAAV" refers to recombinant adeno-
associated virus, also referred to as a recombinant AAV
vector (or "rAAV vector").

An "AAV virus" or "AAV viral particle" refers to a viral
particle composed of at least one AAV capsid protein
(preferably by all of the capsid proteins of a wild-type AAV)
and an encapsidated polynucleotide. If the particle com-
prises heterologous polynucleotide (i.e., a polynucleotide
other than a wild-type AAV genome such as a transgene to
be delivered to a mammalian cell), it is typically referred to
as "rAAV".

In one embodiment, the AAV expression vectors are
constructed using known techniques to at least provide as
operatively linked components in the direction of transcrip-
tion, control elements including a transcriptional initiation
region, the DNA of interest and a transcriptional termination
region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

In one embodiment, AAV ITRs can be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

In one embodiment, AAV capsids can be derived from AAV2. Suitable DNA molecules for use in AAV vectors will be less than about 5 kilobases (kb), less than about 4.5 kb, less than about 4 kb, less than about 3.5 kb, less than about 3 kb, less than about 2.5 kb in size and are known in the art.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from non-viral genes, such as the murine metallothionein gene, will also find use herein. Such promoter sequences are commercially available from, e.g., Stratagene (San Diego, Calif.).

In one embodiment, both heterologous promoters and other control elements, such as tissue-specific and inducible promoters, enhancers and the like, will be of particular use. Examples of heterologous promoters include the CMV promoter. Examples of inducible promoters include DNA responsive elements for ecdysone, tetracycline, hypoxia and aufin.

In one embodiment, the AAV expression vector that harbors the DNA molecule of interest bounded by AAV ITRs, can be constructed by directly inserting the selected sequence(s) into an AAV genome, which has had the major AAV open reading frames ("ORFs"), excised therefrom. Other portions of the AAV genome can also be deleted, so long as sufficient portions of the ITRs remain to allow for replication and packaging functions. Such constructs can be designed using techniques well known in the art.

Alternatively, AAV ITRs can be excised from the viral genome or from an AAV vector containing the same and fused 5' and 3' of a selected nucleic acid construct that is present in another vector using standard ligation techniques. For example, ligations can be accomplished in 20 mM Tris-Cl pH 7.5, 10 mM MgCl2, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs.

Additionally, chimeric genes can be produced synthetically to include AAV ITR sequences arranged 5' and 3' of one or more selected nucleic acid sequences. The complete chimeric sequence is assembled from overlapping oligonucleotides prepared by standard methods.

In order to produce rAAV virions, an AAV expression vector is introduced into a suitable host cell using known techniques, such as by transfection. A number of transfection techniques are generally known in the art. See, e.g., Sambrook et al. (1989) Molecular Cloning, a laboratory manual, Cold Spring Harbor Laboratories, New York. Particularly suitable transfection methods include calcium phosphate co-precipitation, direct micro-injection into cultured cells, electroporation, liposome mediated gene transfer, lipid-mediated transduction, and nucleic acid delivery using high-velocity microprojectiles.

In one embodiment, suitable host cells for producing rAAV virions include microorganisms, yeast cells, insect cells, and mammalian cells, that can be, or have been, used as recipients of a heterologous DNA molecule. The term includes the progeny of the original cell that has been transfected. Thus, a "host cell" as used herein generally refers to a cell that has been transfected with an exogenous DNA sequence. Cells from the stable human cell line, 293 (readily available through, e.g., the American Type Culture Collection under Accession Number ATCC CRL1573) can be used in the practice of the present disclosure. Particularly, the human cell line 293 is a human embryonic kidney cell line that has been transformed with adenovirus type-5 DNA fragments, and expresses the adenoviral Ela and E1b genes. The 293 cell line is readily transfected, and provides a particularly convenient platform in which to produce rAAV virions.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Suitable homologues of the AAV rep coding region include the human herpesvirus 6 (HHV-6) rep gene which is also known to mediate AAV-2 DNA replication.

By "AAV cap coding region" is meant the art-recognized region of the AAV genome that encodes the capsid proteins VP1, VP2, and VP3, or functional homologues thereof. These Cap expression products supply the packaging functions, which are collectively required for packaging the viral genome.

In one embodiment, AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 that encode both Rep and Cap expression products. A number of other vectors have been described that encode Rep and/or Cap expression products.

Methods of delivery of viral vectors include injecting the AAV into the subject. Generally, rAAV virions may be introduced into cells using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, pharmaceutical compositions will comprise sufficient genetic material to produce a therapeutically effective amount of the nucleic acid of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., N.J. 1991).

It should be understood that more than one transgene could be expressed by the delivered viral vector. Alternatively, separate vectors, each expressing one or more different transgenes, can also be delivered to the subject as described herein. Furthermore, it is also intended that the viral vectors delivered by the methods of the present disclosure be combined with other suitable compositions and therapies.

As is apparent to those skilled in the art in view of the teachings of this specification, an effective amount of viral vector that must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

In certain embodiments, the rAAV is administered at a dose of about 0.3-2 ml of 1×105–1×1016 vg/ml. In certain embodiments, the rAAV is administered at a dose of about 1-3 ml of 1×107-1×1014 vg/ml. In certain embodiments, the rAAV is administered at a dose of about 1-2 ml of 1×108-1×1013 vg/ml.

Formulations containing the rAAV particles will contain an effective amount of the rAAV particles in a vehicle, the effective amount being readily determined by one skilled in the art. The rAAV particles may typically range from about 1% to about 95% (w/w) of the composition, or even higher or lower if appropriate. The quantity to be administered depends upon factors such as the age, weight and physical condition of the animal or the human subject considered for treatment. Effective dosages can be established by one of ordinary skill in the art through routine trials establishing dose response curves. The subject is treated by administration of the rAAV particles in one or more doses. Multiple doses may be administered as is required to maintain adequate enzyme activity.

Vehicles including water, aqueous saline, artificial CSF, or other known substances can be employed with the subject invention. To prepare a formulation, the purified composition can be isolated, lyophilized and stabilized. The composition may then be adjusted to an appropriate concentration, optionally combined with an anti-inflammatory agent, and packaged for use.

The present invention provides a method of increasing the level of a target protein in a cell by introducing a protein, or nucleic acid molecule encoding a protein described above into a cell in an amount sufficient to increase the level of the target protein in the cell. In certain embodiments, the accumulation of target protein is increased by at least 10%. The accumulation of target protein is increased by at least 10%, 20%, 30%, 40%, 50%, 60%, 70%, 80%, 90% 95%, or 99%.
39

Nucleic Acids Encoding Therapeutic Agents

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides.

A "nucleic acid fragment" is a portion of a given nucleic acid molecule. The term "substantial identity" of polynucleotide sequences means that a polynucleotide comprises a sequence that has at least 70%, 71%, 72%, 73%, 74%, 75%, 76%, 77%, 78%, or 79%, or at least 80%, 81%, 82%, 83%, 84%, 85%, 86%, 87%, 88%, or 89%, or at least 90%, 91%, 92%, 93%, or 94%, or even at least 95%, 96%, 97%, 98%, or 99% sequence identity, compared to a reference sequence using one of the alignment programs described using standard parameters.

Methods for Introducing Genetic Material into Cells

The exogenous genetic material (e.g., a DNA encoding one or more therapeutic ACE-tRNAs) is introduced into the cell in vivo by genetic transfer methods, such as transfection or transduction, to provide a genetically modified cell. Various expression vectors (i.e., vehicles for facilitating delivery of exogenous genetic material into a target cell) are known to one of ordinary skill in the art.

As used herein, "transfection of cells" refers to the acquisition by a cell of new genetic material by incorporation of added DNA. Thus, transfection refers to the insertion of nucleic acid into a cell using physical or chemical methods. Several transfection techniques are known to those of ordinary skill in the art including: calcium phosphate DNA co-precipitation; DEAE-dextran; electroporation; cationic liposome-mediated transfection; and tungsten particle-facilitated microparticle bombardment. Strontium phosphate DNA co-precipitation is another possible transfection method.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous genetic material contained within the retrovirus is incorporated into the genome of the transduced cell. A cell that has been transduced with a chimeric DNA virus (e.g., an adenovirus carrying a cDNA encoding a therapeutic agent), will not have the exogenous genetic material incorporated into its genome but will be capable of expressing the exogenous genetic material that is retained extrachromosomally within the cell.

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion, an "enhancer" is simply any non-translated DNA sequence that works contiguous with the coding sequence (in cis) to change the basal transcription level dictated by the promoter. The exogenous genetic material may introduced into the cell genome immediately downstream from the promoter so that the promoter and coding sequence are operatively linked so as to permit transcription of the coding sequence. A retroviral expression vector may include an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes that encode certain constitutive or "housekeeping" functions:

hypoxanthine phosphoribosyl transferase (HPRT), dihydrofolate reductase (DHFR), adenosine deaminase, phosphoglycerol kinase (PGK), pyruvate kinase, phosphoglycerol mutase, the actin promoter, and other constitutive promoters known to those of skill in the art. In addition, many viral promoters function constitutively in eucaryotic cells. These include the early and late promoters of SV40; the long terminal repeats (LTRs) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified cell. If the gene encoding the therapeutic agent is under the control of an inducible promoter, delivery of the therapeutic agent in situ is triggered by exposing the genetically modified cell in situ to conditions for permitting transcription of the therapeutic agent, e.g., by intraperitoneal injection of specific inducers of the inducible promoters which control transcription of the agent. For example, in situ expression by genetically modified cells of a therapeutic agent encoded by a gene under the control of the metallothionein promoter, is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene, (i.e., whether the promoter is constitutive or inducible, strong or weak); (2) the number of copies of the exogenous gene that are inserted into the cell; (3) the number of transduced/transfected cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the therapeutic agent by the genetically modified cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid encoding the therapeutic agent, the expression vector may include a selection gene, for example, a neomycin resistance gene, for facilitating selection of cells that have been transfected or transduced with the expression vector. Alternatively, the cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the scope of one of ordinary skill in the art without undue experimentation.

Disease Conditions and Methods of Treatment

The present invention in one embodiment includes compositions and methods for treating cystic fibrosis by reversing the effects of mutations present that are associated with nonsense mutations through introduction of the synthetic oligonucleotide suppressor tRNAs of the invention.

Certain embodiments of the present disclosure provide a method of treating a disease in a mammal comprising administering a protein or vector encoding a therapeutic agent (e.g., a modified and/or stabilized ACE-tRNA) as described herein to the mammal. In certain embodiments, the mammal is human.

Certain embodiments of the present disclosure provide a use of a therapeutic agent or vector encoding a therapeutic agent as described herein to prepare a medicament useful for treating disease in a mammal. In certain embodiments, the disease is cystic fibrosis.

The present disclosure also provides a mammalian cell containing a vector described herein. The cell may be human.

Certain aspects of the disclosure relate to polynucleotides, polypeptides, vectors, and genetically engineered cells (modified in vivo), and the use of them. In particular, the disclosure relates to a method for gene therapy that is capable of both systemic delivery of a therapeutically effective dose of the therapeutic agent.

According to one aspect, a cell expression system for expressing a therapeutic agent in a mammalian recipient is provided. The expression system (also referred to herein as a "genetically modified cell") comprises a cell and an expression vector for expressing the therapeutic agent. Expression vectors include, but are not limited to, viruses, plasmids, and other vehicles for delivering heterologous genetic material to cells. Accordingly, the term "expression vector" as used herein refers to a vehicle for delivering heterologous genetic material to a cell. In particular, the expression vector is a recombinant adenoviral, adeno-associated virus, or lentivirus or retrovirus vector.

The expression vector further includes a promoter for controlling transcription of the heterologous gene. The promoter may be an inducible promoter (described herein). The expression system is suitable for administration to the mammalian recipient. The expression system may comprise a plurality of non-immortalized genetically modified cells, each cell containing at least one recombinant gene encoding at least one therapeutic agent.

The cell expression system is formed in vivo. According to yet another aspect, a method for treating a mammalian recipient in vivo is provided. The method includes introducing an expression vector for expressing a heterologous gene product into a cell of the patient in situ, such as via intravenous administration. To form the expression system in vivo, an expression vector for expressing the therapeutic agent is introduced in vivo into the mammalian recipient i.v.

According to yet another aspect, a method for treating a mammalian recipient in vivo is provided. The method includes introducing the target therapeutic agent into the patient in vivo.

The expression vector for expressing the heterologous gene may include an inducible promoter for controlling transcription of the heterologous gene product. Accordingly, delivery of the therapeutic agent in situ is controlled by exposing the cell in situ to conditions, which induce transcription of the heterologous gene.

The present disclosure provides methods of treating a disease in a mammal by administering an expression vector to a cell or patient. For the gene therapy methods, a person having ordinary skill in the art of molecular biology and gene therapy would be able to determine, without undue experimentation, the appropriate dosages and routes of administration of the expression vector used in the novel methods of the present disclosure.

According to one embodiment, the cells are transformed or otherwise genetically modified in vivo. The cells from the mammalian recipient are transformed (i.e., transduced or transfected) in vivo with a vector containing exogenous genetic material for expressing a heterologous (e.g., recombinant) gene encoding a therapeutic agent and the therapeutic agent is delivered in situ.

As used herein, "exogenous genetic material" refers to a nucleic acid or an oligonucleotide, either natural or synthetic, that is not naturally found in the cells; or if it is naturally found in the cells, it is not transcribed or expressed at biologically significant levels by the cells. Thus, "exogenous genetic material" includes, for example, a non-naturally occurring nucleic acid that can be transcribed into a tRNA.

The above-disclosed therapeutic agents and conditions amenable to gene therapy are merely illustrative and are not intended to limit the scope of the instant disclosure. The selection of a suitable therapeutic agent for treating a known condition is deemed to be within the scope of one of ordinary skill of the art without undue experimentation.

In certain embodiments, the therapy has potential use for the treatment/management of diseases that are caused by Premature Termination Codons (PTCs), including, but not limited to, cystic fibrosis, muscular dystrophy, β-thalassemia and Liddle's syndrome. This therapy is advantageous in that it provides improved stop codon suppression specificity. The therapeutic ACE-tRNAs of the present invention target a specific stop-codon, TGA for instance, thus reducing off-target effects at stop-codons unrelated to disease. The present therapy is also advantageous in that it provides amino-acid specificity. The expressed tRNA is engineered to specifically replace the amino acid that was lost via insertion of the disease stop codon, thus negating any spurious effects on protein stability, folding and trafficking.

In certain embodiments, the present system is modular, and thus can be "personalized" to every possible disease PTC. For instance, there are nine individual tryptophan tRNAs in the human genome that are recognized by the Trp synthetase, all of which suppress the mRNA UGG codon. Thus, each of these nine Trp tRNA provides an opportunity for codon re-editing tolerance (UGG UGA). Additionally, given their proximity to stop codons in the genetic code, the mutation of arginine codons to PTC nonsense codons are common in disease. There are over thirty Arg tRNA that could be tested for codon editing tolerance and suppression efficacy.

A further advantage of the present invention is that it provides facile expression and cell specific delivery, because the entire system (tRNA+promoter sequence) is compact.

Dosages, Formulations and Routes of Administration of the Agents of the Invention The agents of the invention are administered so as to result in a reduction in at least one symptom associated with a genetic disease (e.g., cystic fibrosis). The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems that are well known to the art.

The present invention envisions treating genetic disease (e.g., cystic fibrosis) by the administration of an agent, e.g., ACE-tRNA, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation), can be administered by a variety of routes including parenteral, including by intravenous and intramuscular routes, as well as by direct injection into the diseased tissue. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well-known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0 and water.

Definitions

Disease state: For the purposes of the present invention, a "disease state" or "disease phenotype" is a characteristic of a mammalian cell that results from a stop codon within the coding region of a gene inside the cell (e.g., that results from a nonsense mutation). For example, an increasing number of human genetic diseases are thought to be caused by nonsense mutations (see, for example, Atkinson et al., Nuc. Acids Res. 22:1327, 1994). To give but a few examples, β-thalessemia, Duchenne muscular dystrophy, xeroderma pigmentosum, Fanconi's anemia, and cystic fibrosis can all be caused by nonsense mutations in identified genes.

Endogenous tRNA synthetase: A tRNA synthetase is considered to be "endogenous" to a cell if it is present in the cell into which a tRNA is introduced according to the present invention. As will be the apparent to those of ordinary skill in the art, a tRNA synthetase may be considered to be endogenous for these purposes whether it is naturally found in cells of the relevant type, or whether the particular cell at issue has been engineered or otherwise manipulated by the hand of man to contain or express it.

Suppressor tRNA: A "suppressor tRNA" is one whose anti-codon is complementary with a codon that would otherwise terminate translation, so that detectable read-through occurs under the conditions of the experiment. Standard termination codons are amber (UAG), ochre (UAA), and opal (UGA) codons. However, non-standard termination codons (e.g., 4-nucleotide codons) have also been employed in the literature (see, for example, Moore et al., J. Mol. Biol. 298:195, 2000; Hohsaka et al., J. Am. Chem. Soc. 121:12194, 1999).

The invention is now illustrated by the following non-limiting Examples.

Example 1

The genetic code uses four nucleotides that in turn form triplet codons, which form the basis for DNA to protein translation. There are 64 codons in total, 61 of which are used to encode amino acids, and three (TAG, TGA and TAA) of which encode protein termination "stop" or "nonsense" codons.

Five to ten percent of cystic fibrosis cases are caused by "nonsense" mutations that lead to premature truncation of the cystic fibrosis transmembrane conductance regulator (CFTR) protein. An example of this "class 1" mutation is p.Trp1282X, a premature termination codon (PTC) which causes a loss of CFTR function and severe cystic fibrosis phenotypes. Some compounds, such as ataluren, promote stop read-through of disease producing nonsense mutations but have been only modestly successful as therapeutics due to a number of caveats, including poor stop-codon specificity and unexpectedly low efficiency of codon skipping in vivo. However, the widespread use of these compounds and the discovery that endogenous stop-codon read-through is common in metazoans, suggests that assisted suppression could be viable if delivered to a subset of cell types, i.e., airway epithelium. Yet, when therapeutically assisted stop-codon read-through is successful, the nonselective incorporation of an amino acid at the location of the nonsense codon has the potential to affect protein folding, trafficking and function (as is the case with CFTR 1282X); and thus, requires additional therapeutic intervention. Thus, there is an acute unmet need to understand the nature of disease PTCs and potentially therapeutic suppressors and generally, more effective treatments of PTC diseases.

This Example characterizes anticodon edited (ACE) Trp-tRNA for the rescue of CFTR p.Trp1282X channels. Such tRNAs are engineered to 'suppress' the disease-causing TGA stop codon and incorporate the original amino acid, Trp at p.Trp1282X CFTR, in effect, genetically reconstructing the wild-type CFTR protein. Data demonstrate that this general approach (nonsense suppression) produces robust rescue of transcripts that carry in-frame stop codons, through either transient transfection of a tRNA and its cognate synthetase in adherent cells, or their virus-based delivery to more native airway cell-types, such as A549 airway cells. This approach offers a number of significant benefits over existing strategies: 1) Improved codon specificity—the expressed tRNA may be directed towards a specific stop-codon, thus reducing off-target effects at stop-codons unrelated to disease. 2) Amino-acid specificity—the expressed tRNA and/or synthetase can be engineered to replace the amino acid that was lost via insertion of the disease stop codon, thus negating any spurious effects on CFTR stability, folding and trafficking. 3) Tunability—the system can be theoretically personalized for each type of tRNA and PTC mutation. 4) Facile expression—the entire system is compact (<1 kb) and can be easily packaged and expressed transiently or via nanoparticle delivery of tRNA. 5) Proof of principle for a general strategy—in-frame stop codons are a major cause of human disease and few treatment options exist; the experiments performed here on p.Trp1282X are expected to lead to insights into the mechanisms of other CFTR nonsense codons.

Data shows that ACE-tRNA stop-codon suppressor tRNA are efficient at "rescuing" transcripts which contain introduced stop-sites (FIGS. 6A and 6B) suggesting that such tRNA have the potential to interfere with nonsense mediated decay (NMD) as the major biological hurdle in the therapeutic rescue of disease stop sites. Thus opening the possibility for the use of suppressor tRNA to gain more molecular insights into NMD in disease.

Results

We questioned if it might be possible to express eukaryotic tRNA that had been anticodon edited to suppress stop sites, TGA for instance, and not its designated codon. This was tested in five human tryptophan tRNA on a test construct consisting of a fluorescent protein (cherry) in frame with eGFP sequence that are separated by a linker containing a TGA site. To indicate the production of the full-length protein an HA epitope was added to the C-terminus of the eGFP reading frame. This test system is useful because visual appearance of the cherry signal indicates plasmid delivery and expression and in combination with the eGFP rescue shows TGA suppression. Data in FIGS. 6A and 6B show western blot data using this test construct to assay the ability of five anticodon edited Trp tRNA human to suppress the TGA stop site in the short linker between cherry and eGFP reading frames. Of these constructs, the candidates 1, 2, 3 & 5 show modest activity in this regard. This may be due to structural intolerance to the mutation or the possibility that altering the anticodon, even just by a single base, disrupted the ability of the Trp synthetase to recognize and/or acylate the tRNA with tryptophan. However, number 4 of these test tRNA (tRNA #4) shows significant suppression activity of the TGA site, producing a full-length cherry-eGFP-HA protein (FIG. 6B). Further, no read-through was seen in the absence of co-expressed tRNA, last lane, FIG. 6B.

Methods

The Trp tRNA were examined for codon editing tolerance (TGG TGA) and their ability to suppress a targeted TGA test site in a transiently transfected tandem-fluorophore (mCherry-TGA-GFP) and CFTR Trp1282X. Initial screening of 5/6 Trp tRNA discovered an anticodon edited Trp-tRNA that was transiently transfected in HEK cells and has 'stand alone' functionality to rescue a cherry-TGA-eGFP-HA test construct, FIG. 6B. The selective presence of the HA epitope indicates successful rescue, as well as confocal examination of both cherry and eGFP fluorescence at the single cell level (not shown). This result provides proof of principle data that a) some ACE—tRNA can tolerate anticodon editing b) that these tRNA retain the ability to be acylated with Trp by endogenous tryptophan synthetases, and c) these tRNA can suppress TGA sites embedded within open protein reading frames.

The remaining four Trp-tRNA are functionally examined for tolerance of anticodon editing from TAA to TGA suppressors. These anticodon edited tRNA are tested for their ability to rescue the cherry-TGA-eGFPHA clone. Biochemical (western blot) data are obtained for cherry and eGFP signals as well as HA epitopes. Here, cherry expression serves as the positive transfection control. Confocal imaging verifies cherry and eGFP fluorescence at the single cell level.

The fidelity of endogenous Trp synthetases to charge ACE—Trp tRNA with the tryptophan amino acid is determined by mass spectroscopic analysis of tryptic fragments of purified rescued cherry-Trp-eGFPHAprotein. Predicted mass for the tryptic fragment generated from the linker between the cherry and eGFP reading frames is: KPINQW-PANTHER (SEQ ID NO: 648) with a predicted mass of 1590.8135; bold W indicates incorporation site, FIG. 10. Thus, this represents the first example of a nonsense codon repair and replacement with the wild-type amino acid and therefore is a significant advance over existing approaches, such as the therapeutic Ataluran. The later example, the compound promotes read-through of the nonsense codon with the incorrect amino acid, thus the discovery and identification of new tRNA sequences that provide stringent repair is significant.

Rescue of transiently transfected CFTR 1282X channels by ACE— tRNA identified above are assessed by standard biochemical methods for full maturation of the B and C glycosylated CFTR bands 20. Thus, the channel has been repaired with the wildtype amino acid, is fully functional and successfully trafficked to the plasma membrane.

The next step is to functionally characterize CFTR Trp1282X channels rescued with ACE—tRNA systems identified above using electrophysiological (single cell patch clamp and Ussing chamber) and biochemical approaches.

The efficacy of expressed tRNA to diminish nonsense-mediated decay (NMD) of 1282X mRNA would be assessed with quantitative rtPCR. Reprogramed human airway cells are used to test expressed codon edited Trp-tRNA rescue of native 1282X CFTR channels.

It is demonstrated that anticodon editing is tolerated in an identified human Trp tRNA and this 75-base pair transfer RNA is capable of suppressing an in-frame TGA codon within a test construct. These experiments extrapolate this discovery to characterize the ability of this ACE-tRNA to interact with CFTR 1282TGA mRNA and produce functional CFTR channels in model cells (FRT and A549) as well as p. 1282X human reprogrammed airway cells.

Biochemical determination of rescue levels in transiently expressed CFTR 1282X channels as well as those in reprogrammed airway cells. Antibody M3A7 is used to recognize the rescued (epitope is aa 1370-1380) and to detect all CFTR, rescued and non-rescued, antibody binding to the N-terminus like MM13-4 (epitope aa 25-36), available through EMD Millipore. Alternatively, L12B4 (epitope aa 386-412, EMD Millipore) or 660 (epitope aa 576-585) are available through Cystic Fibrosis Foundation Therapeutics.

Surface functionality is examined through electrophysiological approaches, patch-clamp and Ussing chamber recording. 1282X mRNA stability and abundance is assayed by quantitative rtPCR of RNA extracts from transiently expressing cells and reprogrammed airway cells.

Bioinformatic analysis of RNA transcriptome data from human airway cells identifies abundance, context and identity of TGA codon containing transcripts. The top 10 expressing transcripts using TGA for their normal stop sites are followed up at the level of individual transcript with protein biochemistry before and after ACE— tRNA expression. Biochemical and immunohistological probes of cellular apoptosis are also used to examine the impact of ACE-tRNA in cell death.

Figures 9, 10A:
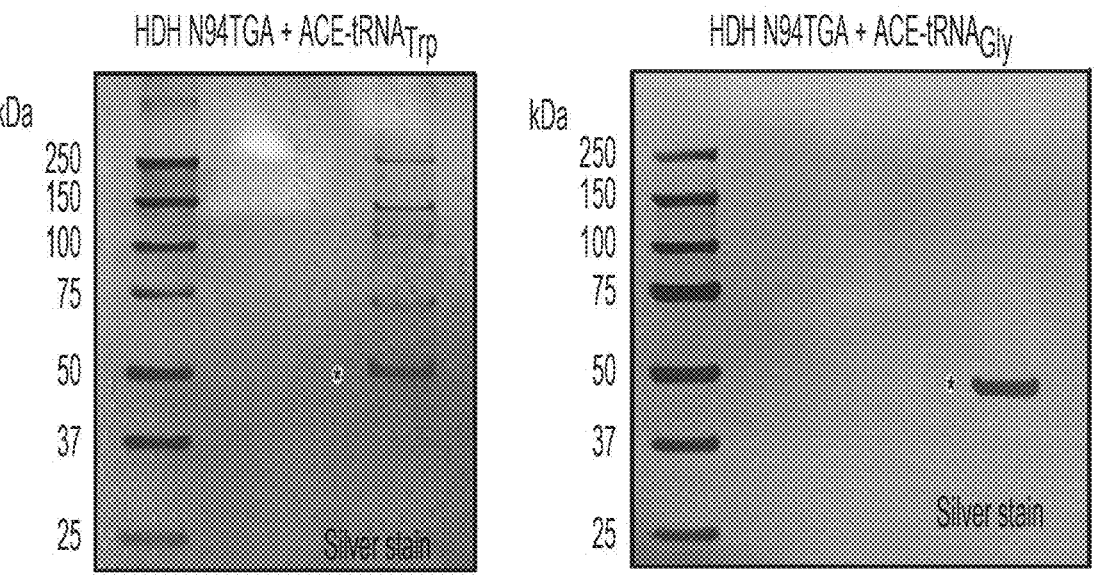
FIG. 9. CFTR 1282x rescue with Trpchr17.trna39 and Glychr19.trna2 ACE-tRNAs. Biochemical western blot data of CFTR W1282X channels co-expressed in HEK cells with the indicated tRNA. Expression vectors containing four copies of the indicated tRNA display higher rescue of the CFTR protein. "C" band indicates rescue of the fully mature, glycosylated CFTR protein. Antibody used was M3A7 from Cystic Fibrosis Therapeutics at a 1:1000 dilution.
FIGS. 10A and 10B. Expression of ACE-tRNA$_{Trp}$ and ACE-tRNA$_{Gly}$ results in specific incorporation of cognate amino acids into nonsense codons.

In conclusion, the data show that ion channel genes with in-frame stop sites are amenable to this type of "rescue" (FIG. 9) and components of the system can be expressed virally in airway cells. Further, a highly simplified form of this idea, an ACE-tRNA of human origin, demonstrates the "stand alone" ability to rescue in-frame CFTR TGA codons in mammalian cell lines (FIG. 9). This approach has many advantages over existing stop-codon strategies and merits closer examination in terms of the ability of ACE-tRNA to 1) abrogate nonsense mediated decay 2) function in lung cell preparations and 3) to specifically rescue CFTR 1282X.

Example 2

Several different nonsense mutations cause CF, thus underlying roughly 10% of all CF disease. FIG. 7. These cases are concentrated into ten specific genetic lesions: E60X, R75X, G542X, R553X, Q890X, Y1092X, R1158X, R1162X and W1282X. We propose that it should be feasible, with the right approach, to screen existing human tRNA sequences for modification and tolerance to anti-codon editing. To this end, roughly 144 ACE-tRNAs were candidates to test for those that could be used to promote the repair of the disease causative nonsense codon and the expression of the full-length protein. Specifically, using the scheme described in FIG. 11, tRNA libraries were generated to identify novel tRNA sequences that encode for ACE tRNA with the ability to repair the top CF causative nonsense mutations. Specifically, 10 ng of annealed oligos encoding the ACE-tRNAs were combined with 50 ng of NanoLuc reporter plasmid, 1 ul 10× CutSmart Buffer (NEB), 1 ul T4 ligase (NEB), 10 mM ATP and 1 ul BbsI (NEB) and cycled in a thermocycler as described in FIG. 11. 1 ul of the reaction was transformed into competent *E. coli* and the transformants were plated on ampicillin agar plates. One transformant was picked per plate was picked, grown in 1 ml of LB under ampicillin selection, miniprepped and sequence verified.

Figure 8:
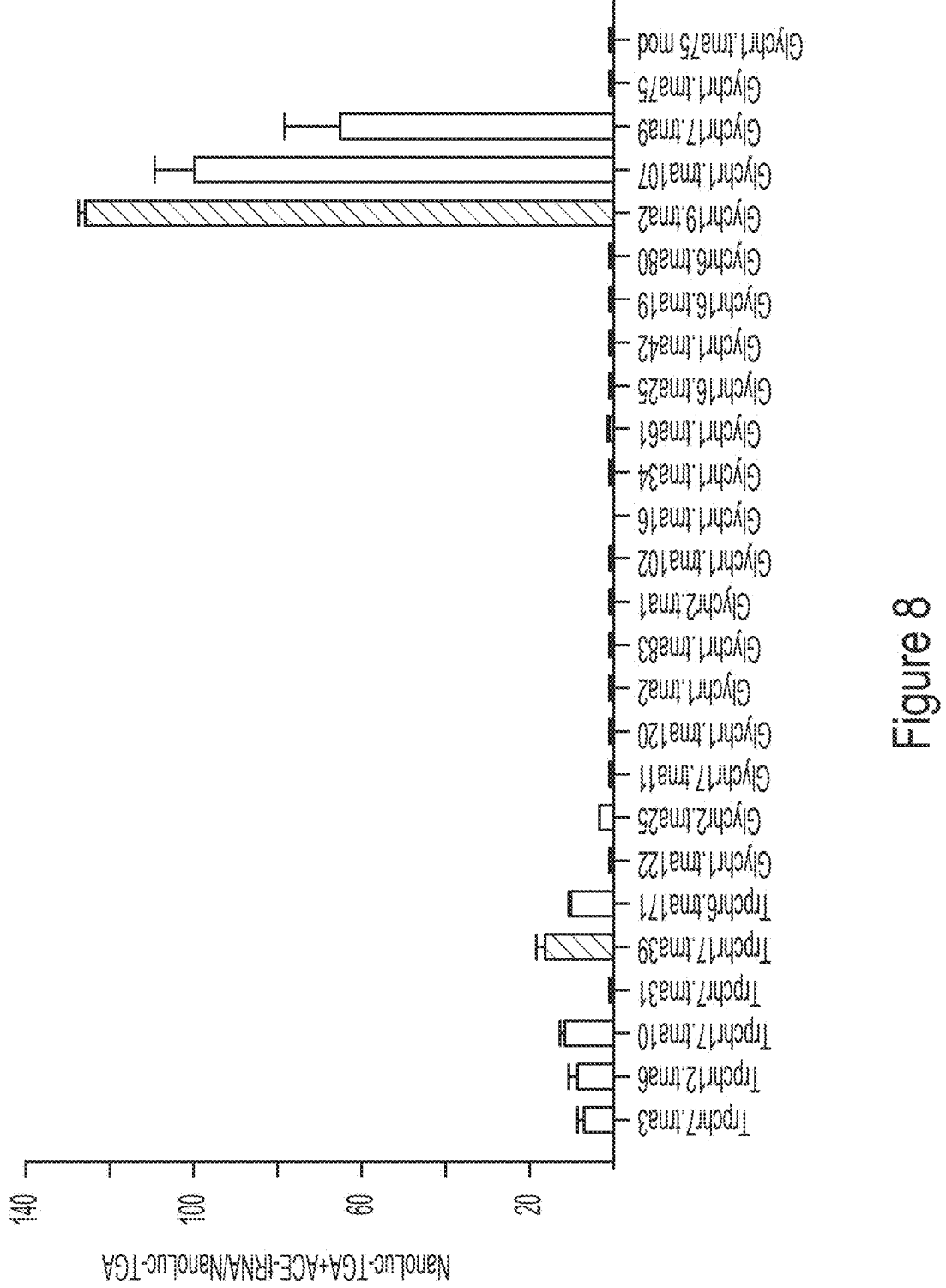
FIG. 8. Identification of tRNA sequences for the repair of tryptophan-TGA and glycine-TGA. Left axis indicates fold above background for luciferase activity. A majority tRNA with mutant anti-codon loops lack rescue activity.

Screening studies were first performed to identify the best ACE-tRNA Candidates from tryptophan and glycine. 125 ng of sequence verified miniprep cDNA of NanoLuc reporter plasmid with ACE-tRNA was transfected into HEK cells using calcium phosphate. HEK cells were plated in 96 well plates at $4 \times 10^4$ the day prior. 24 hrs after transfection the media was replaced with 20 ul of PBS and 15 ul of NanoGlo reagent (Promega) was added. Plates were read on a SpectraMax i3 (Molecular Devices). Data are of replicates of 3 or greater. FIG. 8. The data show that most tRNA demonstrate poor codon editing tolerance. However, clear high-performing tRNA emerge from the screen, with identification of ACE-Trp and ACE-Gly tRNA which demonstrate rescue of nonsense codon containing protein of 20-fold to 130-fold over background.

To assess is these novel tRNA could rescue CFTR channels harboring nonsense codons, they were co-expressed in mammalian HEK cells with a CFTR W1282X cDNA plasmid. The cellular preparations were analyzed by standard biochemical approaches via Western blot assessment of CFTR protein. This method is highly advantageous for this purpose because the CFTR protein displays a multi-banded pattern that is well-established. Specifically, the "B" and "C" bands represent the full-length and fully mature, post-translationally proceeded CFTR protein at the cell surface, respectively. In this case, both rescue with Trpchr17.trna39 and Glychr19.trna2 ACT-tRNAs produce robust populations of 'B' and 'C' CFTR immunopositive (antibody MA37) bands, indicating the promotion by said tRNA of the full-length, successfully trafficked ion channel protein. FIG. 9.

Example 3

Figure 10B:
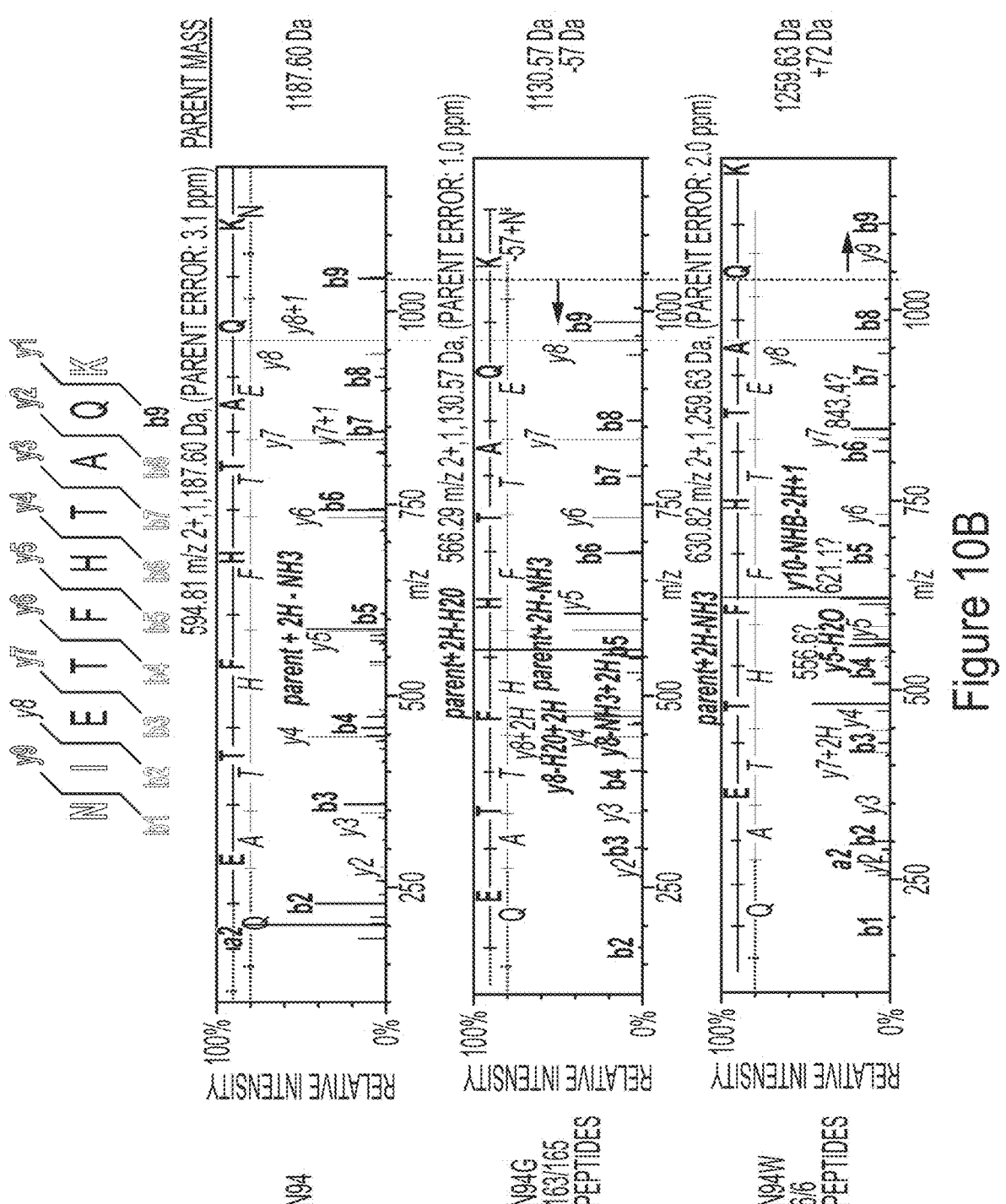
Figure 12A:
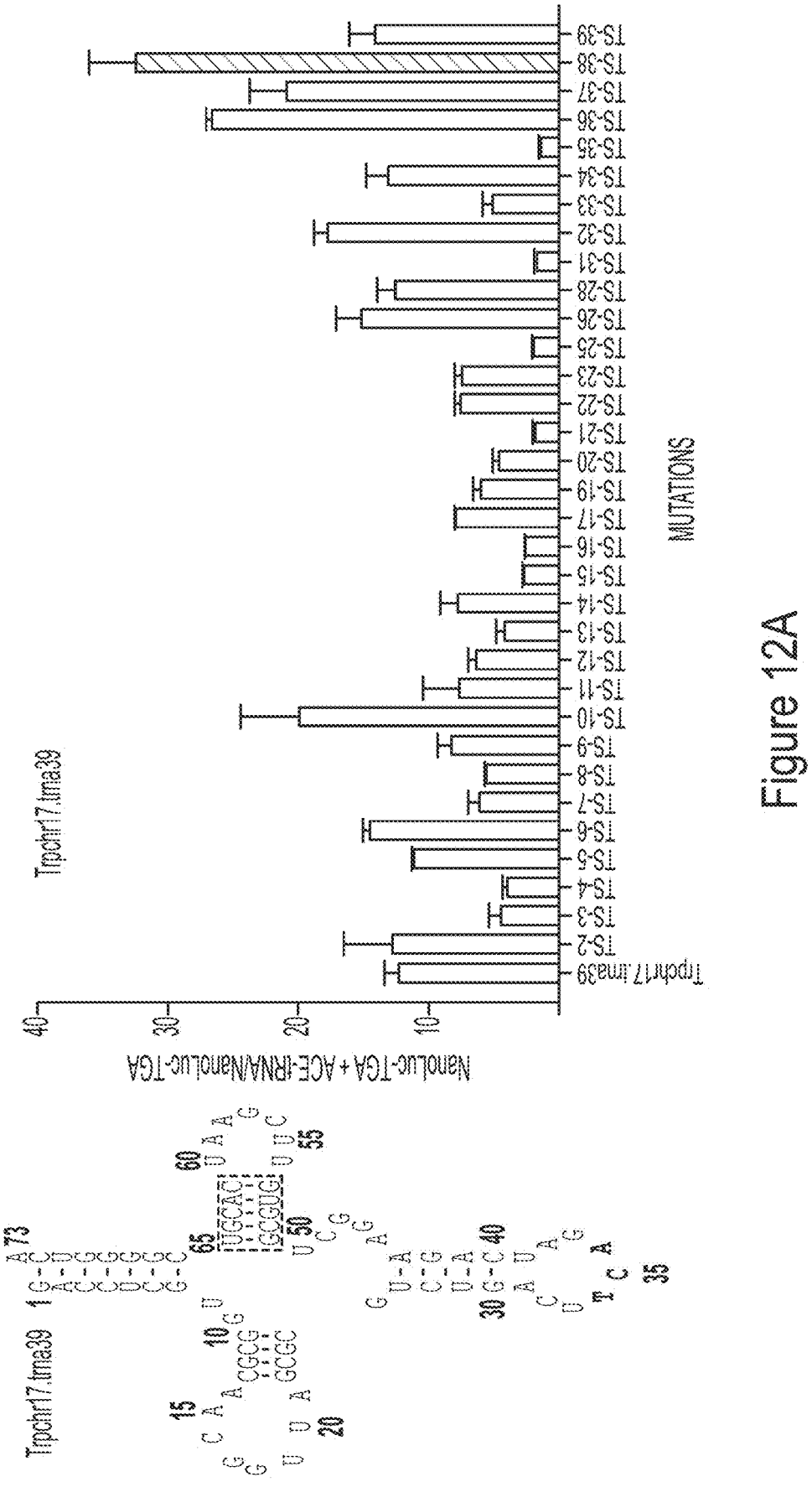
FIGS. 12A-12B. Targeted mutations of nucleotides within the t-stem region further enhance ACE-tRNA rescue function.
Figure 12B:
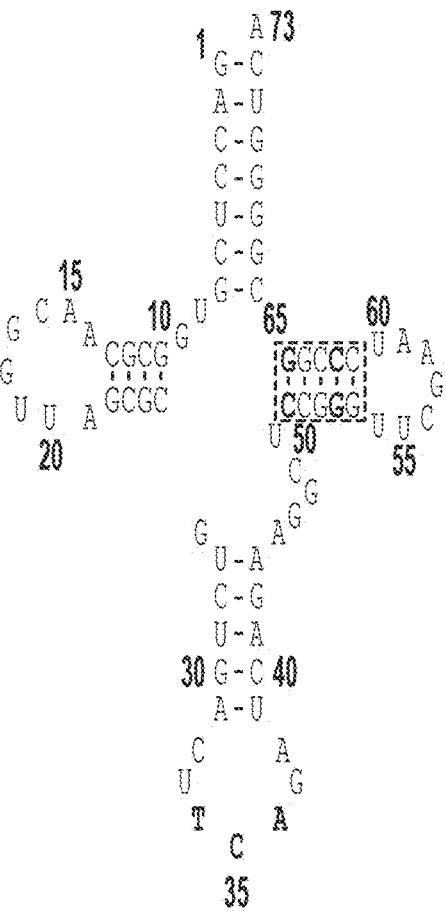

T-stem modification significantly improves nonsense suppression. FIG. 10. Herein we propose an additional modification of the tRNA to further enable their function for the purpose of suppression of nonsense codons and the promotion of protein expression. The hypothesis is based on the possibility that rationally introduced mutations within the tRNA 't-stem' loop, shown in FIG. 10, will yield a tRNA molecule that is more stable and functionally more potent for nonsense codon suppression. To this end, single and double mutations were directly engineered into the t-stem loop of tRNA Trpchr17.trna39—an ACE-tRNA identified with activity for the rescue of tryptophan TGA nonsense codons. Thirty-eight tRNA t-stem variants were thus generated and screened in HEK cells transiently transfected with the nonsense rescue reporter construct shown in FIG. 4. 24 hours post-transfection, cells were assayed for luciferase activity, shown in FIG. 10. The data show strong variation and identify novel tRNA sequences with varied t-stem loop sequences with enhanced suppression activity. Notably, one such mutant, TS-38 52-62 G-C enhances the suppression ability of Trpchr17.trna39 by roughly 250% (FIG. 12). We thus propose this is a generalizable modification, that is, of new tRNA sequences identified, by example 1 and 2, can be made better (for their ability to rescue nonsense codons) through further rationale modifications. Such approaches aid in the therapeutic utility of ACE-tRNA directed to tissue types with low abundance target RNA or where tRNA delivery may be limiting.

Example 4

Figure 11:
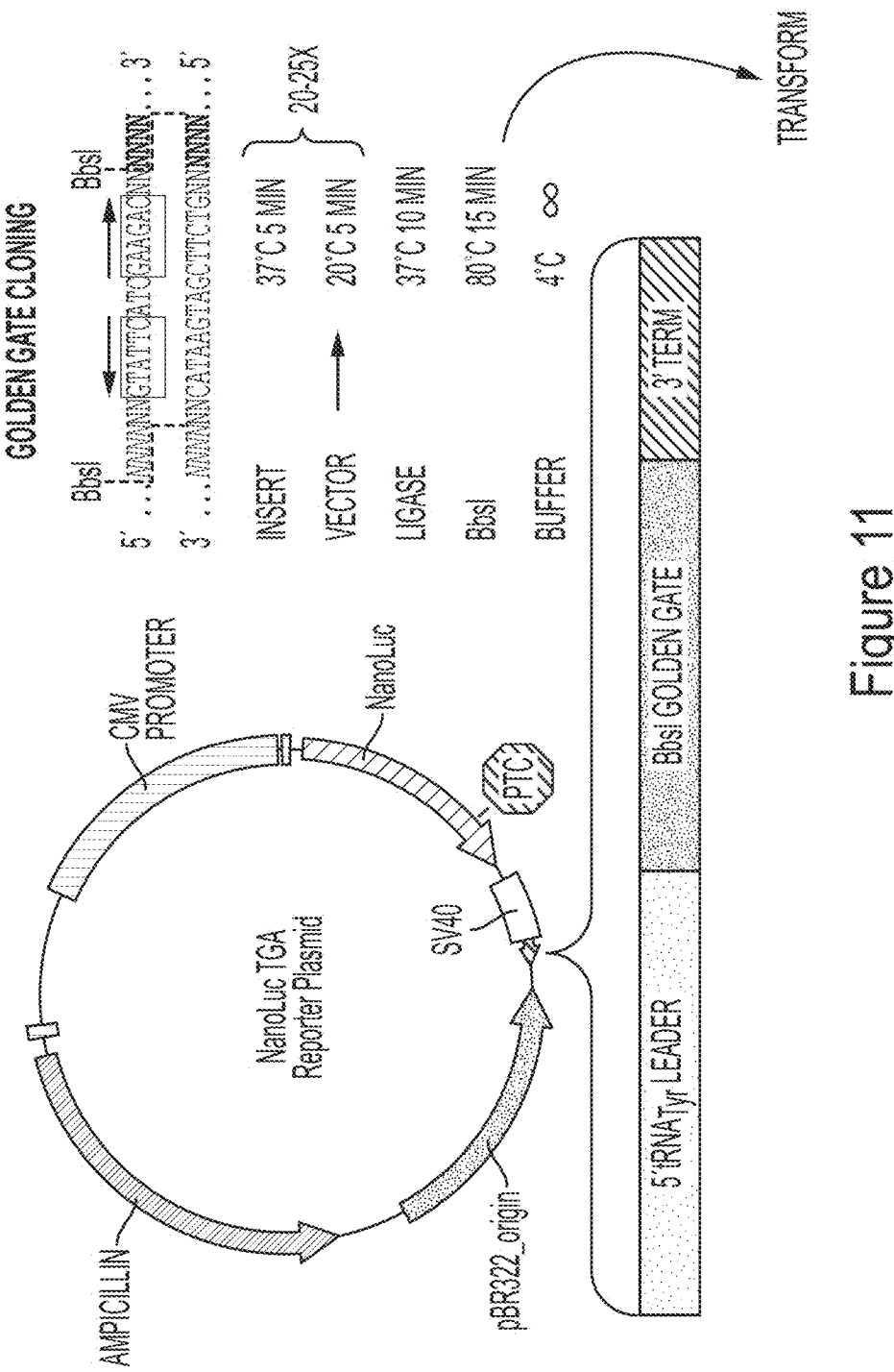
FIG. 11. Cloning workflow for the construction of tRNA libraries.

In order to enable the identification of the nucleotide composition and functional ability to suppress nonsense codons by new types of tRNA, an All-In-One Plasmid With A One Pot Cloning Reaction was invented for High Throughput Cloning FIG. 11. This approach enables the facile investigation of ACE-tRNA activity via luciferase activity in a standard 96 well format. Briefly, synthetic nucleotide sequences encoding for tRNA are ligated into the NanoLuc Reporter plasmid, with an example of the TGA nonsense reporter plasmid variant shown in FIG. 11. TAA (Opal) and TAG (amber) stop codon rescue vectors have been successfully designed and implemented in FIGS. 16-19. The benefits are the approach is that DNA oligos encoding for tRNA libraries can be ligated in the NanoLuc reporter plasmid with the presence of the restriction enzyme and ligase with the reaction pushed to nearly 100% incorporation of tRNA insert (FIG. 11)-thus the 'one-pot' designation. The reaction is transformed into *E. coli*, with the resultant cDNA purified by standard methods. Another benefit of the invented method is that the tRNA and reporter gen are within the single expression cassette, therefore lowering biological variability and improving data quality obtaining in resulting screens of tRNA suppression activity. The purified cDNA plasmids are then screened in high-throughput 96 well format for their ability to repair nonsense codons by inferred luciferase activity. The approach is suitable for the high-throughput screening of hundreds to thousands of tRNA for novel therapeutic activity.

Figures 13A, 13B, 13C, 13D:
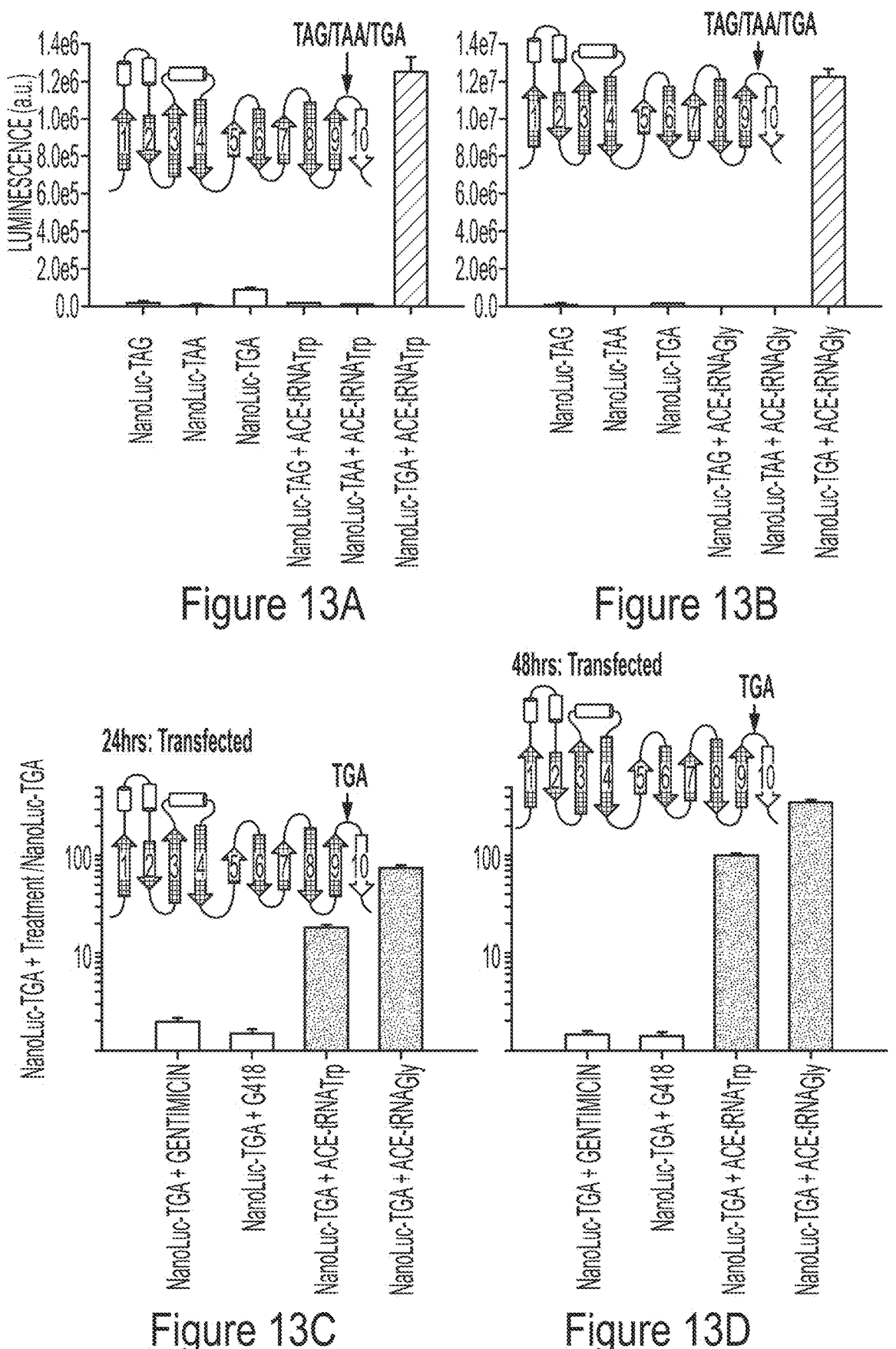
FIGS. 13A-13F. ACE-tRNAs are selective for nonsense codons and more efficient than aminoglycoside nonsense suppression.
Figures 13E, 13F:
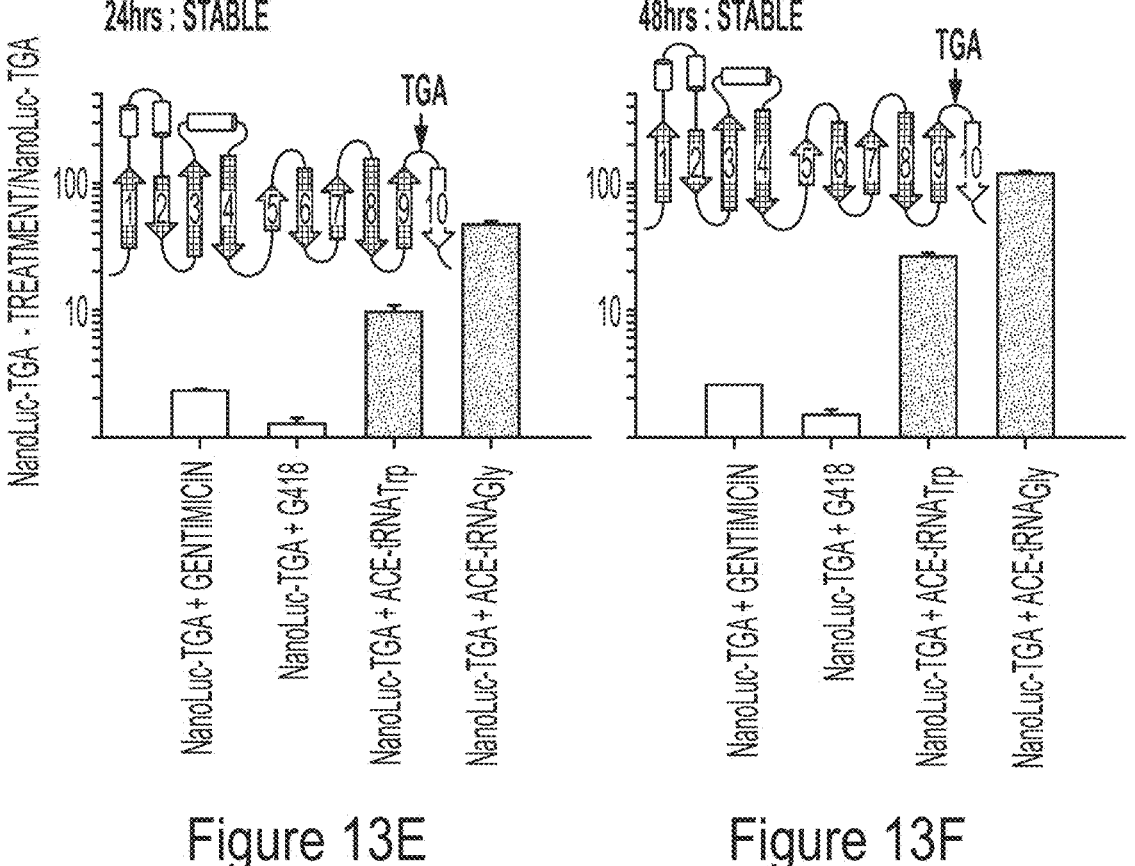
Figure 14:
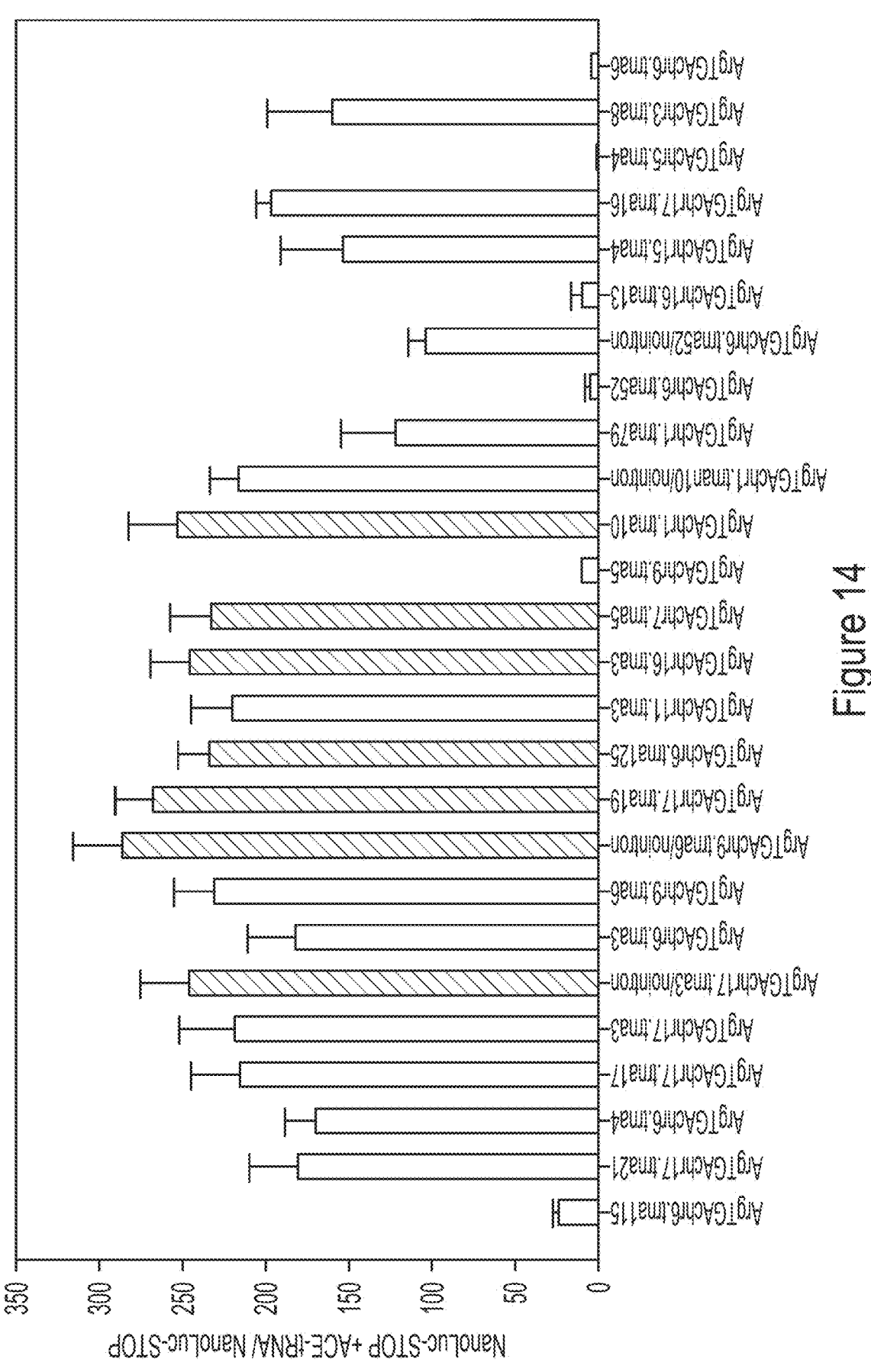
FIG. 14. ACE-tRNA-Arg-TGA. Identification of ACE-tRNA for repair of arginine-TGA nonsense codons.
Figure 15:
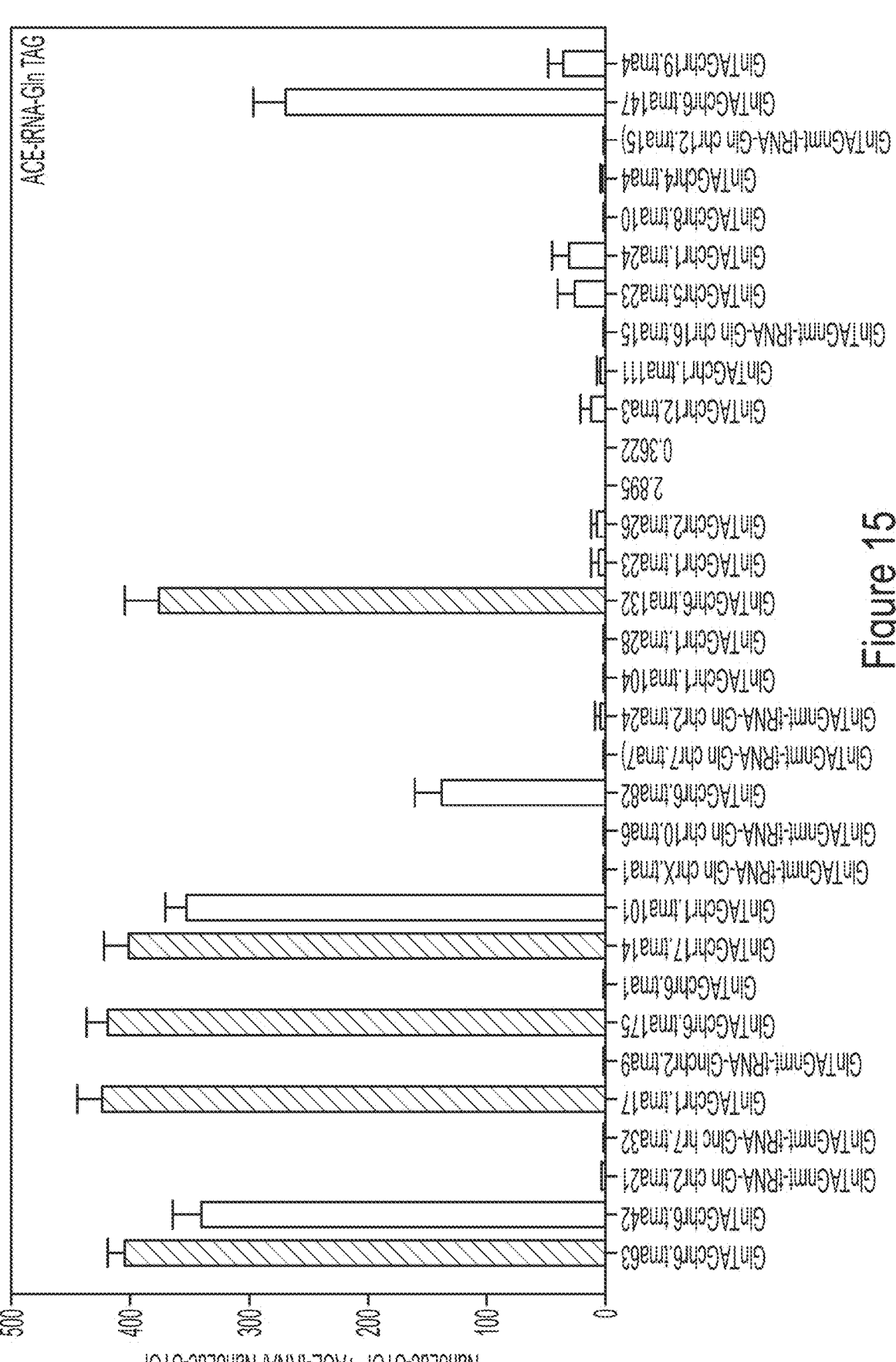
FIG. 15. ACE-tRNA-Gln TAG. Identification of ACE-tRNA for repair of glutamine TAG nonsense codons.
Figure 16:
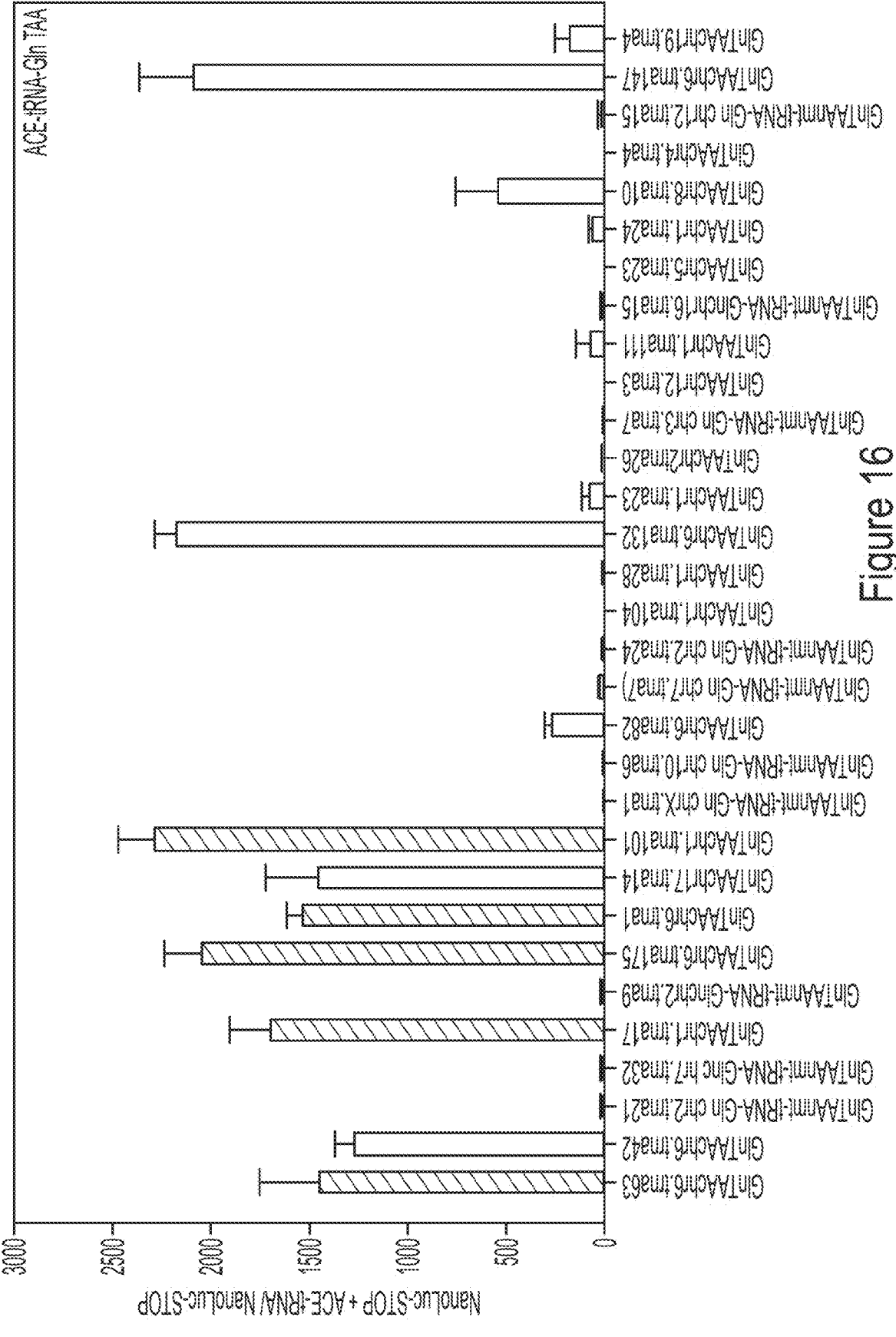
FIG. 16. ACE-tRNA-Gln TAA Identification of ACE-tRNA for repair of glutamine TAA nonsense codons.
Figure 17:
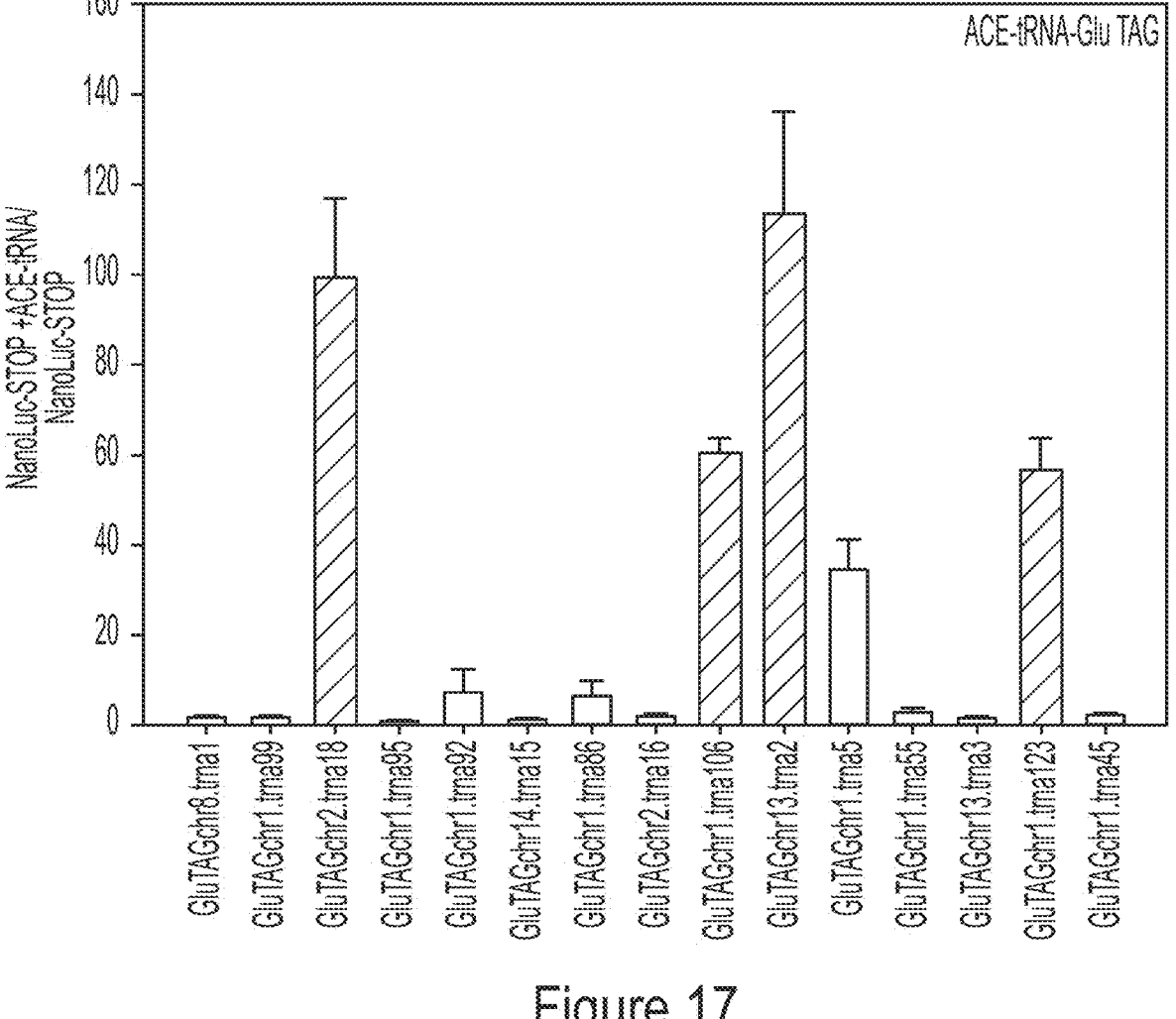
FIG. 17. ACE-tRNA-Glu TAG Identification of ACE-tRNA for repair of glutamate-TAG nonsense codons.
Figure 18:
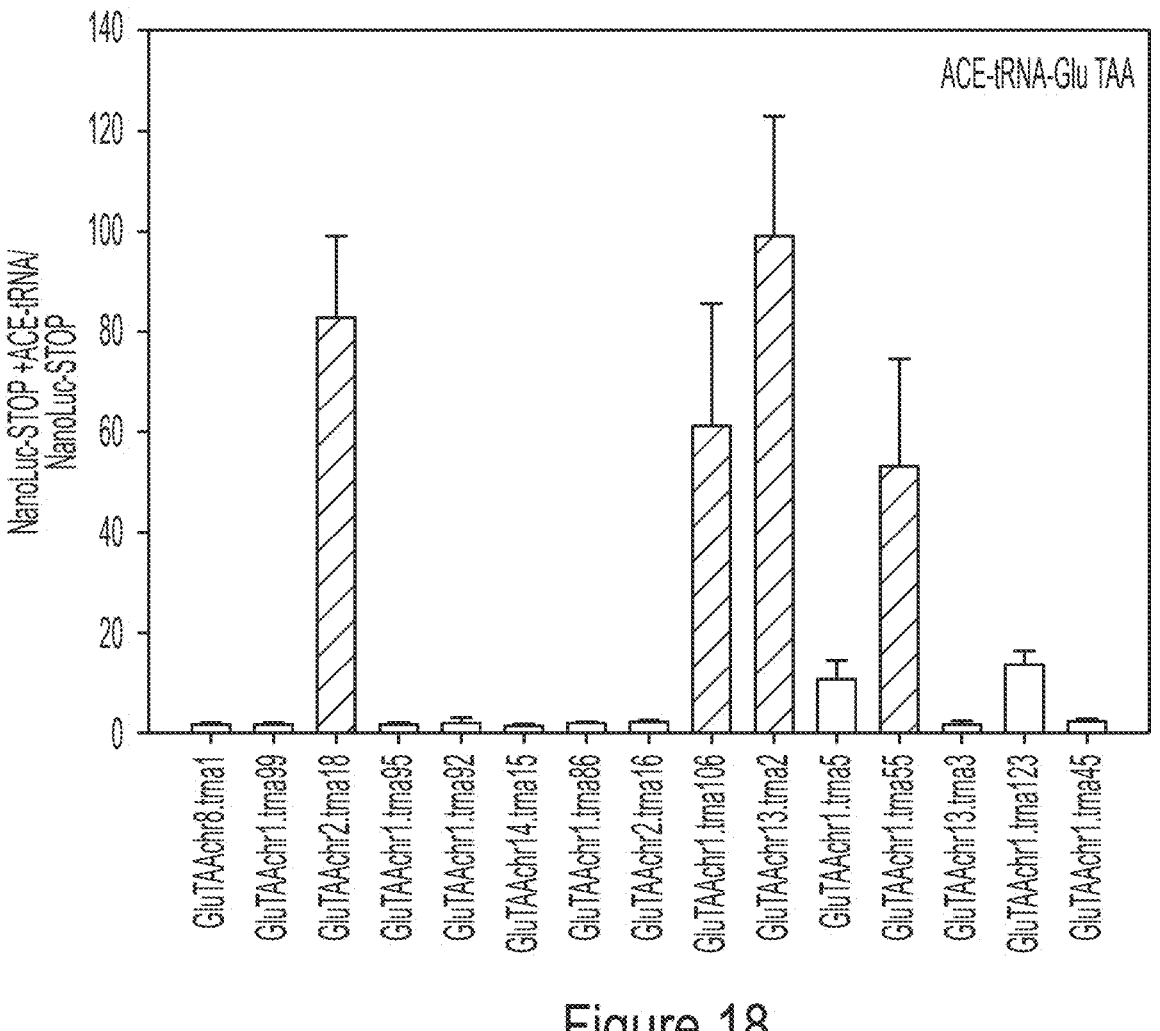
FIG. 18. ACE-tRNA-Gln TAA Identification of ACE-tRNA for repair of glutamate TAA nonsense codons.
Figure 19:
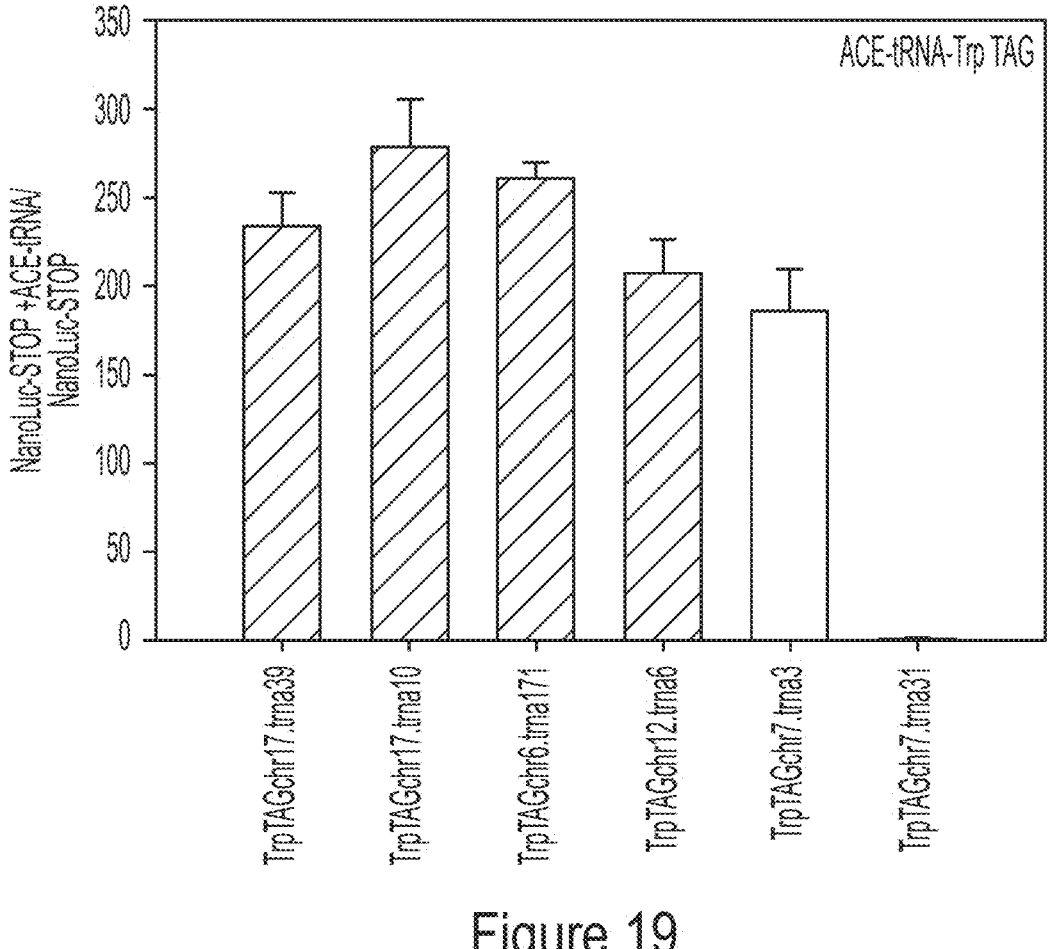
FIG. 19. ACE-tRNA-Trp TAG Identification of ACE tRNA for the repair of tryptophan TAG nonsense codons.
Figure 20A:
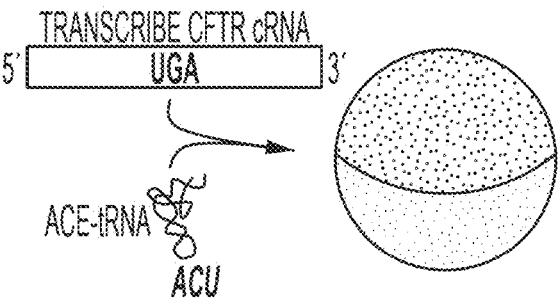
FIGS. 20A-20D. Delivery of ACE-tRNA as small RNA supports robust suppression of G542X and W1282X nonsense mutations.
Figure 20B:
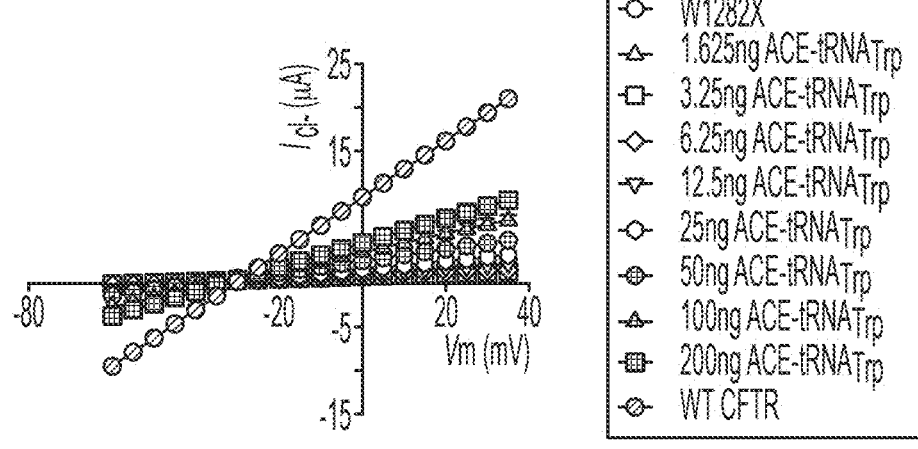
Figure 20C:
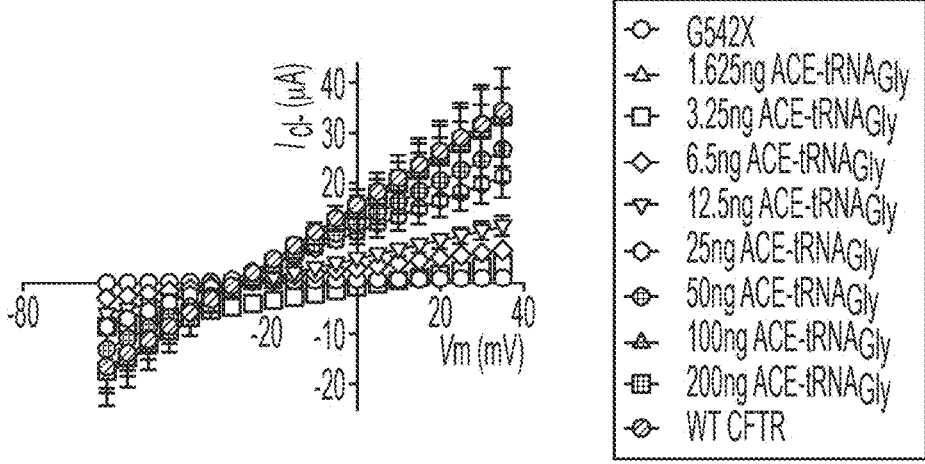
Figure 20D:
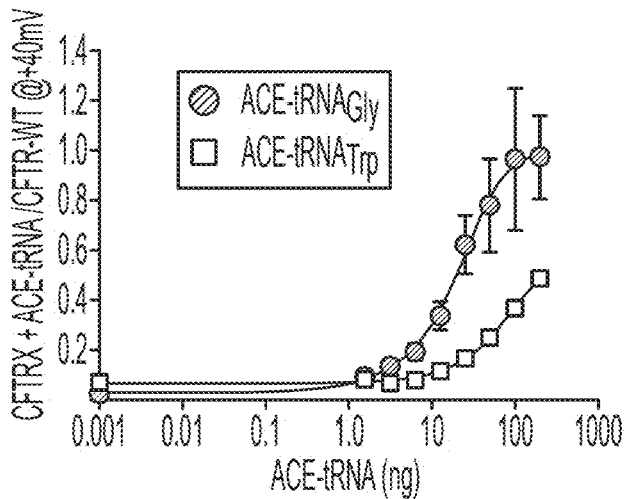

The one-pot' cloning and expression system described in FIG. 11 has been used successfully to identify unique tRNA sequences for the repair of Tryptophan and Glycine ACE-tRNA (FIG. 13), ACE-tRNA-Arg (FIG. 14), ACE-tRNA-Gln TAG (FIG. 15), ACE-tRNA-Gln TAA (FIG. 16), ACE-tRNA-Glu TAG (FIG. 17), ACE-tRNA-Gln TAA (FIG. 18) and ACE-tRNA-Trp TAG (FIG. 19). FIGS. 20A-20D show that delivery of ACE-tRNA as small RNA supports robust suppression of G542X and W1282X nonsense mutations.

Example 5

Engineered Transfer RNAs for Suppression of Premature Termination Codons

Abstract

Premature termination codons (PTCs) are responsible for 10-15% of all inherited disease. PTC suppression during translation offers a promising approach to treat a variety of genetic disorders, yet small molecules that promote PTC read-through have yielded mixed performance in clinical trials. A high-throughput, cell-based assay is presented to identify anticodon engineered transfer RNAs (ACE-tRNA) that can effectively suppress in-frame PTCs and faithfully encode their cognate amino acid. In total, ACE-tRNA were identified with a high degree of suppression activity targeting the most common human disease-causing nonsense codons. Genome-wide transcriptome ribosome profiling of cells expressing ACE-tRNA at levels which repair PTC indicate that there are limited interactions with translation termination codons. These ACE-tRNAs display high suppression potency in mammalian cells, *Xenopus* oocytes and mice in vivo, producing PTC repair in multiple genes, including disease causing mutations within the cystic fibrosis transmembrane conductance regulator (CFTR).

Introduction

Figure 25:
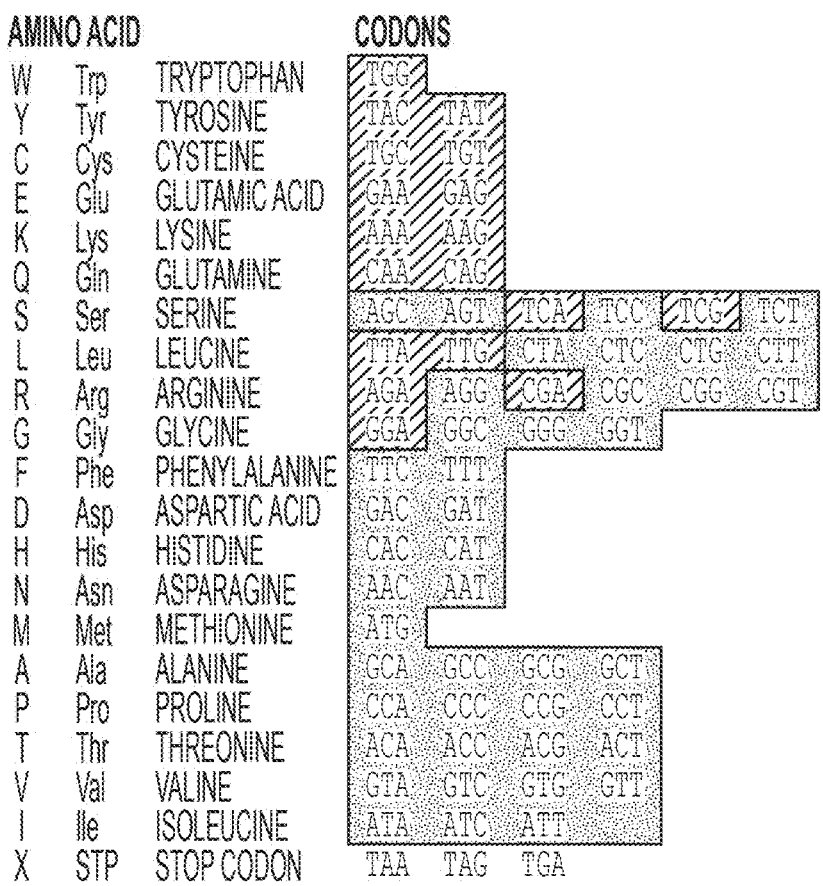
FIG. 25. Codon usage for common PTC. Cross-hatching indicates the most common codons and corresponding amino acid type that can be converted to stop codons via nucleotide substitution. Engineered tRNA have been developed for each type.

Premature termination codons (PTCs) arise from single nucleotide mutations that convert a canonical triplet nucleotide codon into one of three stop codons, e.g., TAG, TGA, or TAA. PTCs are often more deleterious than missense mutations because they result in the loss of protein expression. Additionally, mRNA abundance is reduced through nonsense-mediated decay (NMD) and in some cases, truncated proteins may have a dominant negative function[1-3]. Therefore, it is not surprising that PTCs are associated with many severe disease phenotypes, including cystic fibrosis[4], Duchenne muscular dystrophy, spinal muscular atrophy[5], infantile neuronal ceroid lipofuscinosis[6], β-thalessemia[7], cystinosis[8], X-linked nephrogenic diabetes insipidus[9], Hurler syndrome[10], Usher syndrome[11], and polycystic kidney disease. Additionally, nonsense mutations occur within the tumor suppressor genes p53 and ATM[12], further implicating their role in disease. Amino acid codons most vulnerable to PTC conversion are those with a single nucleotide substitution from a stop codon: tryptophan, tyrosine, cysteine, glutamic acid, lysine, glutamine, serine, leucine, arginine, and glycine (FIG. 25). As such, PTCs represent a unique constellation of diseases which afflict over 30 million people worldwide, accounting for 10-15% of all genetic diseases[13].

Small molecules, such as aminoglycosides[14], dipeptides[15], and oxadiazoles[16], promote the "read-through" or "suppression" of nonsense mutations. These compounds are effective in model organisms[17, 18], mammalian cell lines[19] and some animal disease models[16, 20]. However, this approach results in the encoding of a near-cognate amino acid[21], effectively generating a missense mutation at the PIC, which itself may have deleterious effects on protein folding, trafficking, and function. Furthermore, aminoglycosides are oto- and nephrotoxic[22], and the first-in-class oxadiazole, Ataluren, displayed unexpectedly low efficacy in patient populations (ACT MID Phase 3 clinical trial, NCT01826487; ACT CF, NCT02139306), thus limiting their utility as PTC therapeutics. Recent and ongoing advances in CRISPR/Cas9-mediated genome editing provides potentially a permanent solution for diseases resulting from nonsense mutations. However, aspects of this technology impart hurdles for its rapid use as a therapeutic[23, 24]. This is not limited to the requirement of "precision" or "personalized" diagnostics for each mutation based on the context of each patient's genetic variability.

Figures 21A, 21B:
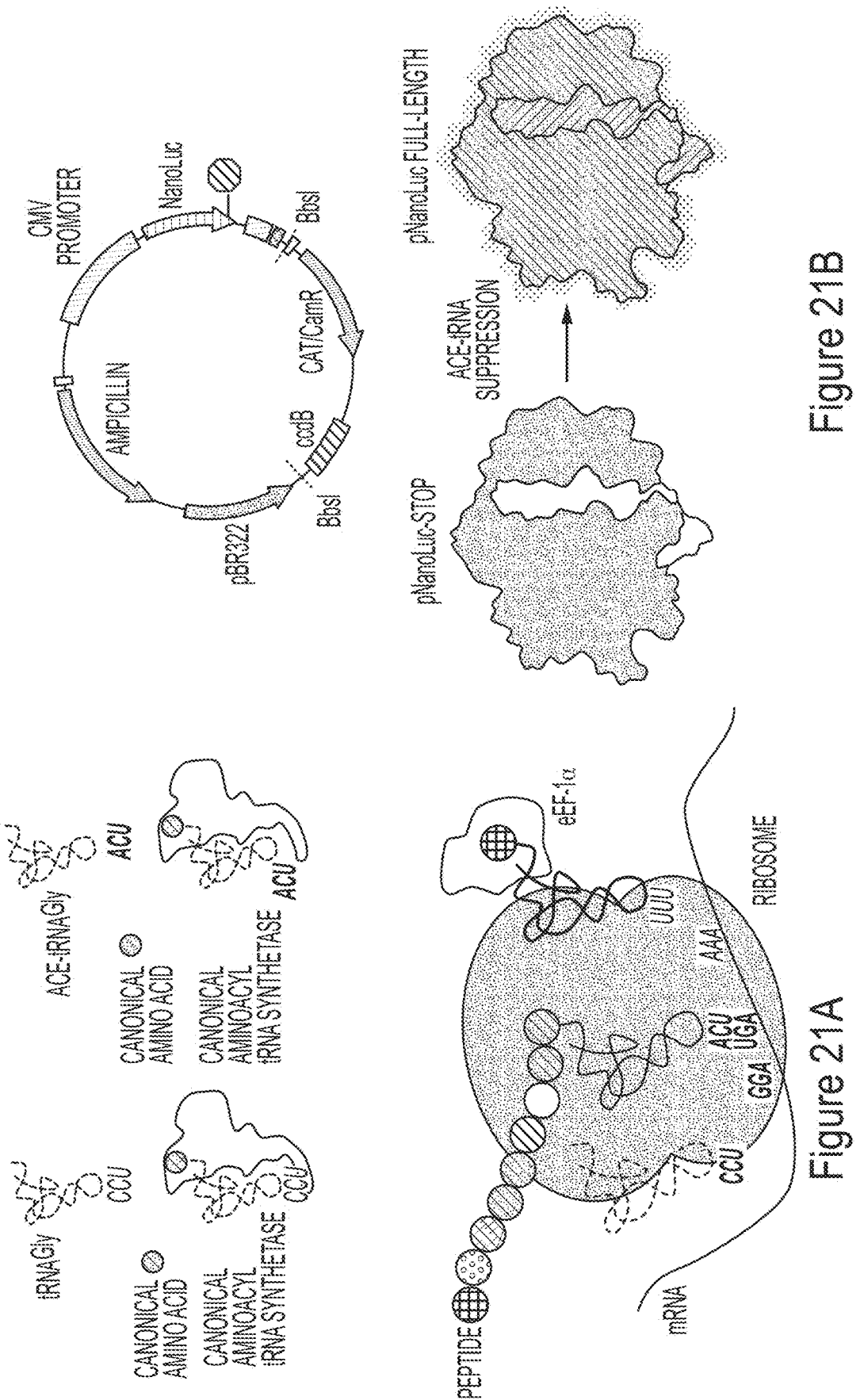
FIGS. 21A-21B. A nonsense mutation suppression screen to identify candidate anticodon edited tRNAs (ACE-tR-NAs).

A PTC repair approach was identified that displays the versatility of small molecules and the precision of gene editing. tRNAs were investigated to fulfill these criteria, whereby their anticodons have been engineered via mutagenesis to recognize and suppress UGA, UAA or UAG PTC codons. In order to be effective, the anticodon edited tRNAs, aka ACE-tRNAs, should still be recognized by the endogenous translation cellular machinery, including the aminoacyl-tRNA synthetase for charging the ACE-tRNA with their cognate amino acid and the eukaryotic elongation factor 1a (eEF-1α) for delivery of the charged tRNA to the ribosome, FIG. 21A. Such suppressor tRNAs have been shown, in a limited manner, to rescue in frame stop codons associated with β-thalassemia[25], xeroderma pigmentosum[26] and a transgenic PIC reporter gene[27].

Here it is shown that an anti-codon editing approach is generalizable to multiple RNA gene families, indicating that many annotated tRNA are biologically viable. Further, it is demonstrate that anti-codon edited suppressor tRNA encode their cognate amino acid, lack significant interactions with termination stop codons and are efficacious in vivo to suppress PTC. In total, the data support the possibility that such engineered tRNA satisfy the broad requirement for coverage of disease-causing PTCs and thus represent a promising new class of RNA therapeutic agent.

Results

Figure 22:
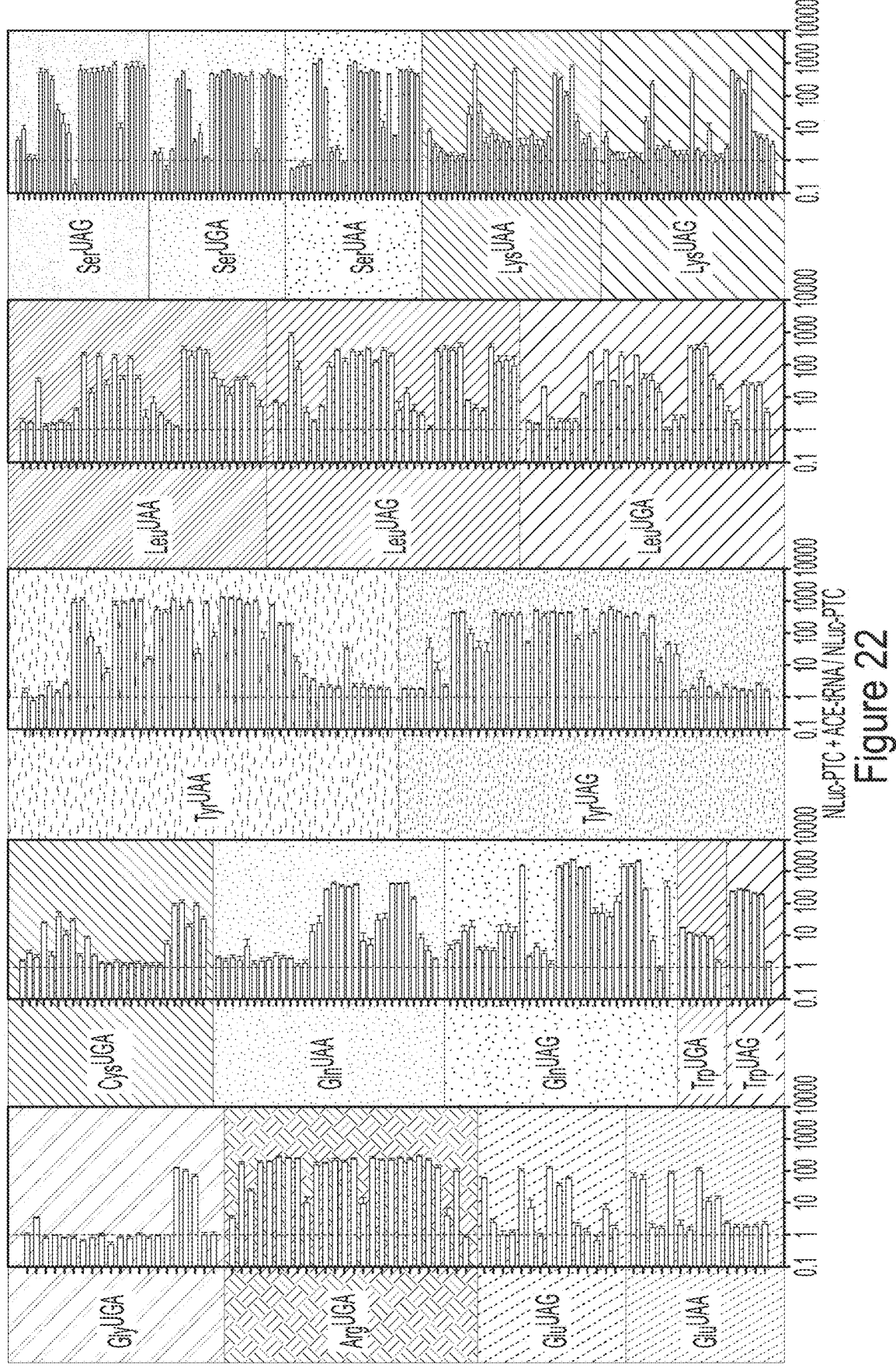
FIG. 22 Screens of ACE-tRNA gene families with the high throughput cloning nonsense mutation reporter platform. The indicated anticodon edited PTC sequences were tested for each ACE-tRNA family that is one nucleotide away from the endogenous anticodon sequence, FIG. 25. Multiple high performing suppressor tRNA were identified for each class. Data are shown in Log 10 scale in terms of normalized NLuc luminescence. Each tRNA dataset were obtained in triplicates and are displayed at SEM, with the corresponding ANOVA statistical analysis in Table 2. Coded identities and corresponding tRNA sequences are shown in FIG. 26 and Table 9, respectively.
Figure 27:
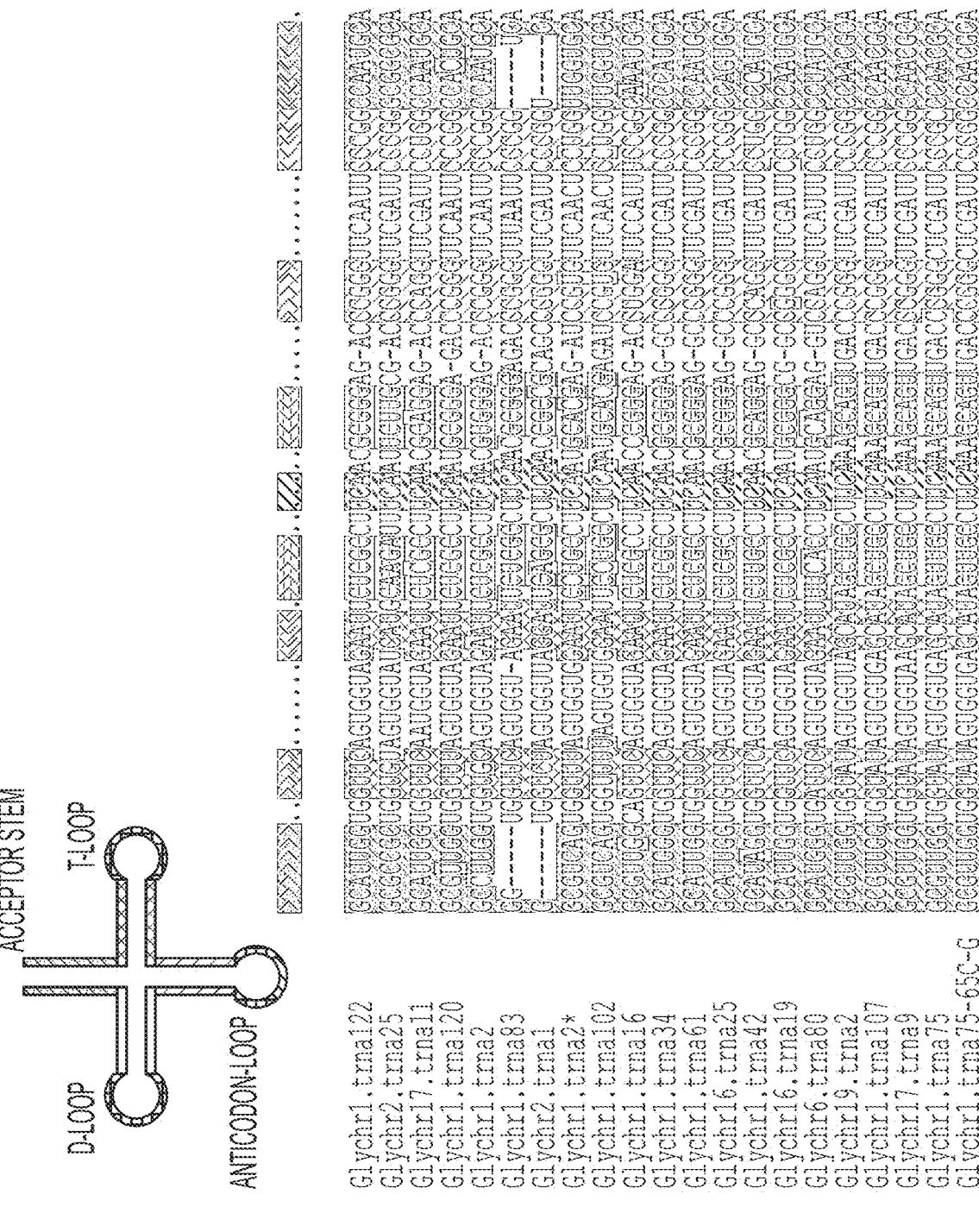
FIG. 27. Alignment of Glycine tRNA sequences. 21 tRNA$_{Gly}$ human sequences demonstrate high sequence homology amongst tRNA clades. Pattern in tRNA image corresponds to patterned boxes in sequences.

The rationale of this study is rooted in the observation that there are multiple tRNA genes with unique sequences (iso-decoders) for a given cognate amino acid (isoacceptors), leading to >400 tRNAs annotated in the human genome (http:lowelab.ucsc.edu/GtRNAdb/)[28, 29]. First, tRNA genes were examined to identify individual ACE-tRNAs that retain suppression efficacy of PTCs in mammalian cells. In order to maximize sequence coverage, an all-in-one cDNA plasmid was generated that supports both high-throughput cloning (HTC) of ACE-tRNAs and quantitative measurement of PTC suppression using luminescence following delivery to mammalian cells, FIG. 21B. ACE-tRNA sequences were cloned as DNA oligos into the HTC plasmid using Golden Gate cloning 30 paired with ccdB negative selection[31]. This strategy produced ~100% cloning efficiency. ACE-tRNA suppression efficiency was read out from a split NanoLuc luciferase (NLuc) NanoBiT platform whereby the PTC of interest (UGA, UAA, or UAG) was introduced in-frame at the junction between the large bit and small bit domains, FIG. 21B, using a 96-well format and normalized to background obtained in NLuc-PTC expressing cells. Twenty-one glycine ACE-tRNAs were first evaluated for suppression of the UGA PTC, FIG. 22, top left, column 1 (violet). A majority of the ACE-tRNA$^{Gly}$ sequences failed to suppress the UGA NLuc PTC, however, three Gly-tR-NA$^{UGA}$ were identified with high suppression yields (~100-fold over background). Given the high sequence conservation among the Gly-tRNAs screened for anti-codon tolerance (FIG. 27), it would be difficult to predict de novo which tRNA would be most amenable to anticodon-editing.

Next, performed screens were performed on codon-edited tRNA for the each of the possible single nucleotide mutations which could produce a disease-causing PTCs: Arg-tRNA$^{UGA}$, Gln-tRNA$^{UAA}$, Gln-tRNA$^{UAG}$Trp-tRNA$^{UGA}$, Trp-tRNA$^{UAG}$, Glu-tRNA$^{UAA}$, Glu-tRNA$^{UAG}$, Cys-tR-NA$^{UGA}$, Tyr-tRNA$^{UAG}$, Tyr-tRNA$^{UAA}$, Ser-tRNAUAG, Leu-tRNA$^{UAG}$, Leu-tRNA$^{UAA}$, Lys-tRNA$^{UAG}$, Lys-tR-NA$^{UGA}$ and Ser-tRNA$^{UAG}$. The enzymatic activity of NLuc was not significantly influenced by the introduced amino acid (FIG. 28), therefore owing the difference in NLuc luminescence to ACE-tRNA suppression ability. The screen identified multiple ACE-tRNAs for each of the amino acids and stop codon type, with suppression coverage for all three stop codons, FIG. 22. Many of these ACE-tRNAs exhibited strong activity with >100-fold PTC suppression over background, which is significantly higher than the aminoglycosides used in this study. Interestingly, some ACE-tRNAs displayed a clear preference for a particular anticodon editing, possibly reflecting altered aminoacyl-tRNA synthetase binding to the tRNA anticodon isoacceptor sequences[33]. For instance, tryptophan conversion to UAG suppression yielded rescue that was ten times higher than that of UGA editing of the same ACE-tRNA$^{Trp}$. Yet the opposite was true for glutamine, where a clear preference was shown for UAA over UAG. Notably, in each case, multiple high performing suppressors were identified, and this was especially evident with Arg$^{UGA}$, a PTC which plays an outsized role in human disease; where twenty efficient ACE-Arg$^{UGA}$ suppressors were identified. In other cases, such as ACE-tRNA$^{Glu}$, of those which exhibited function, the suppression efficiency was roughly equal for UAA and UAG. And a similar pattern was found in ACE-tRNA$^{Lys}$ where encoding via UAG or UGA suppression were strongly mirrored. For Gln-tRNA$^{UAA}$, the suppression activity resulted in suppression signals >2,000-fold over background. Of the ACE-tRNAs identified in the screen, the tryptophan tRNA gene family displayed the weakest suppression activity for UGA PTCs. With only 6 unique human ACE-tRNA$^{Trp}$ sequences available to screen, the UGA suppressing ACE-tRNA$^{Trp}$ library was expanded using tRNA from a range of species. UGA anticodon-editing tolerance was tested for tryptophan tRNA genes with unique sequences from yeast, fly, mouse, rat, rabbit, and frog; in addition to a miscoding A9C tRNA$^{Trp}$ and bacterial Hirsh Trp suppressor[34-36], FIG. 29A-29B. This effort was unsuccessful in identifying ACE-tRNA$^{Trp}$ UGA PTC suppression activity that exceeded that of the human ACE Trp tRNA. Overall, the tRNA screens identified multiple engineered tRNAs (for each amino acid and stop codon type) that displayed potent suppression, thus bearing general tolerance to anticodon editing.

Figure 23A:
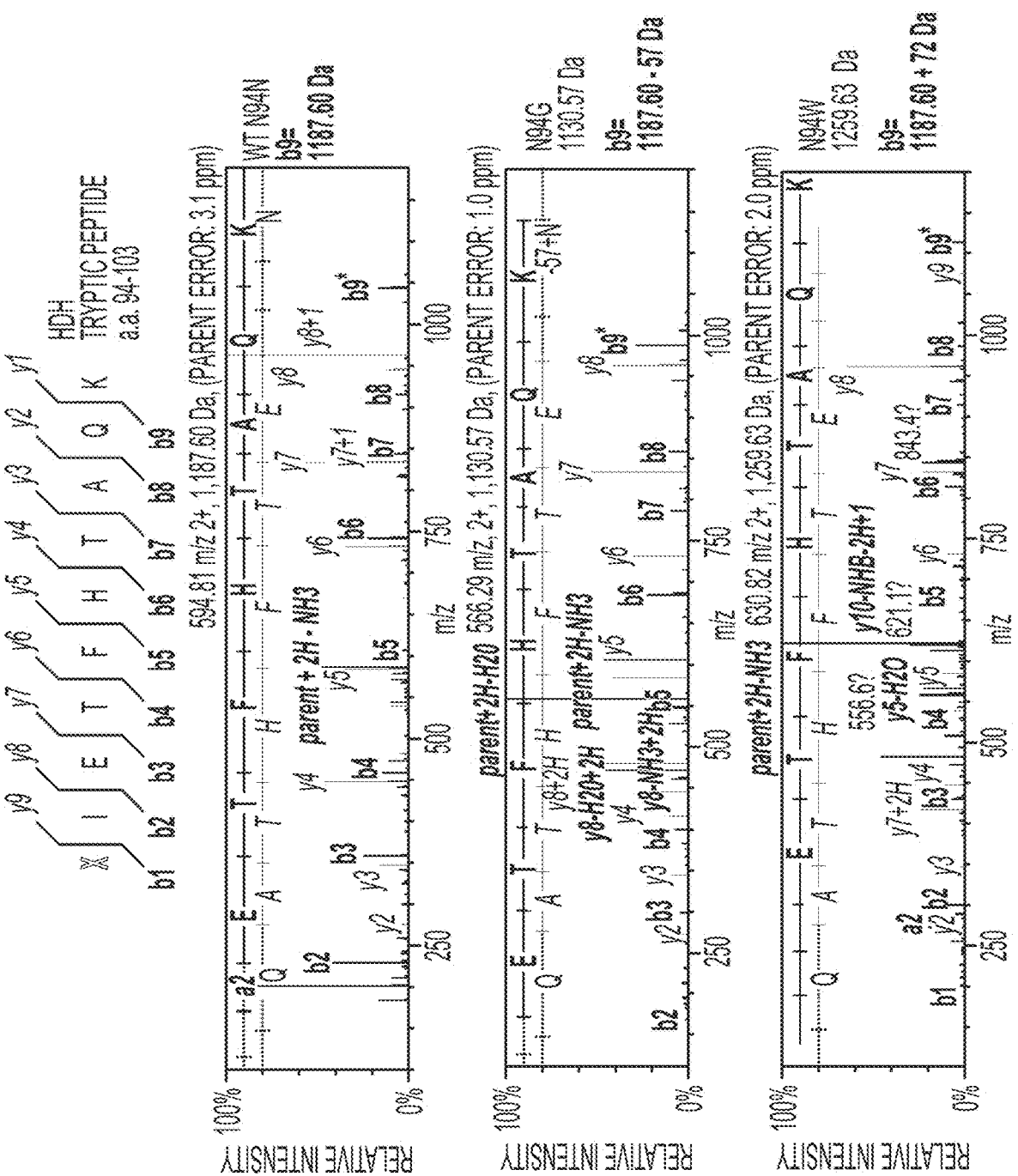
FIGS. 23A-23C Cognate Encoding and High-Fidelity Suppression by Engineered tRNA.
Figure 23B:
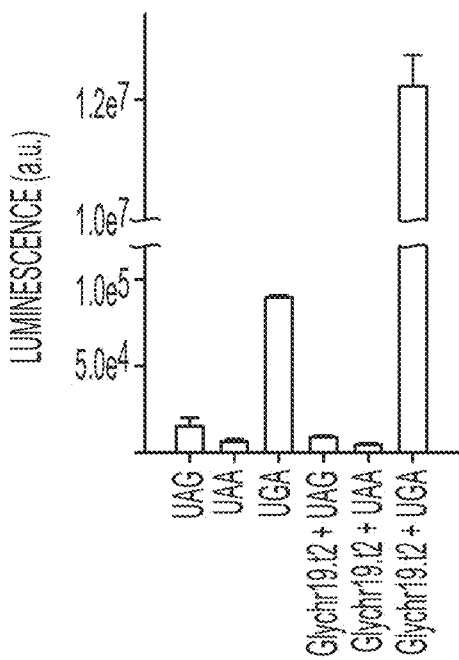
Figure 23C:
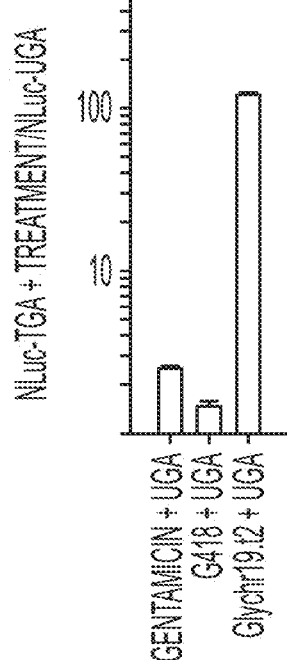
Figure 28:
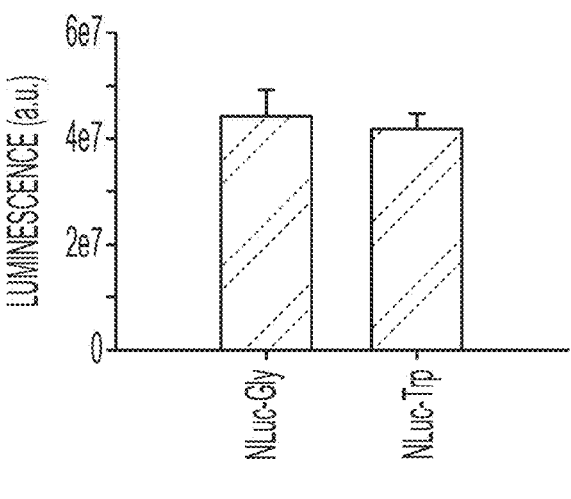
FIG. 28. Side-chain identity at p. 162 in Nanoluciferase does not affect activity. Total luminescence activity is indicated for each mutation at site.
Figure 29B:
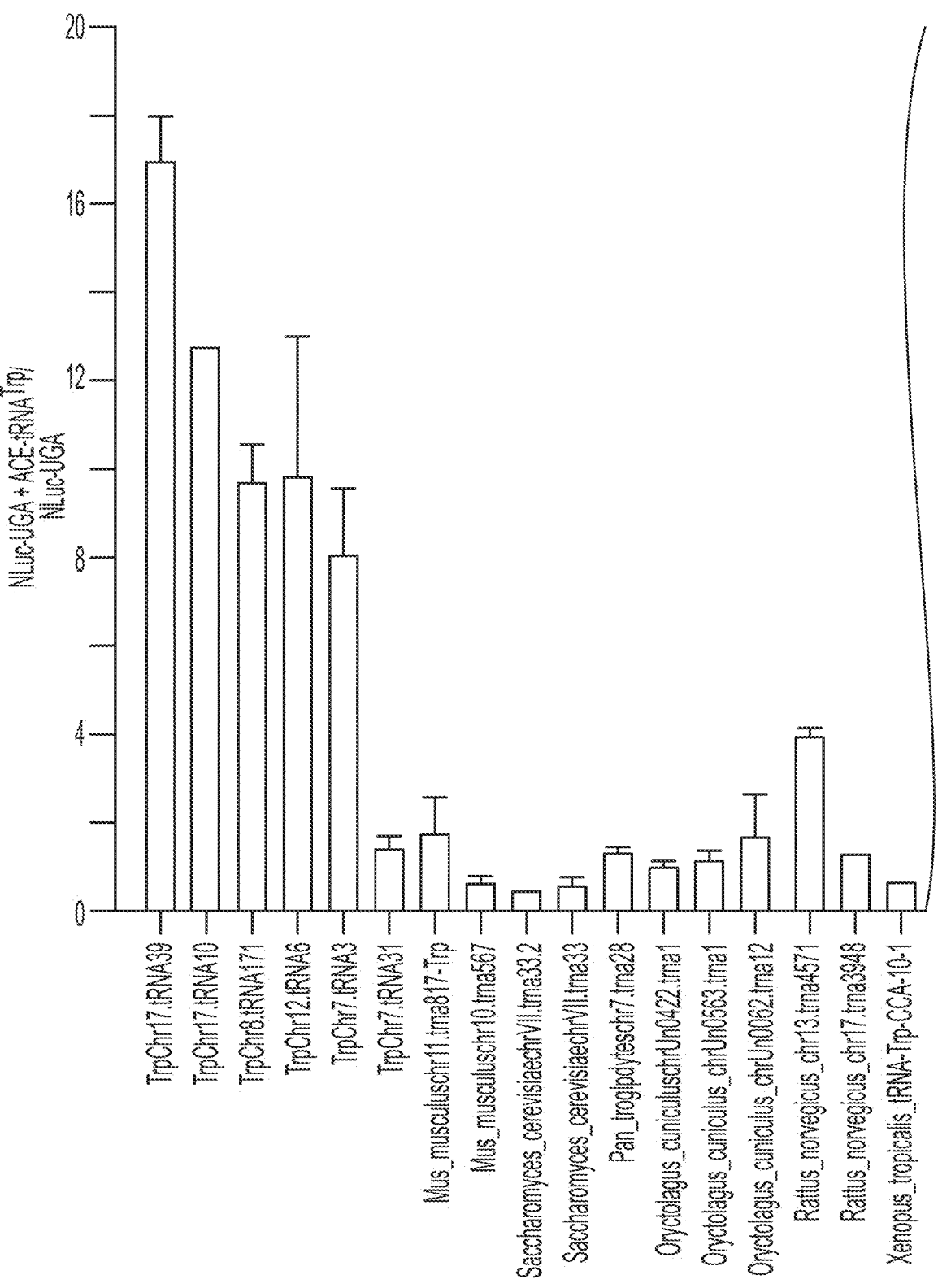
Figure 29B:
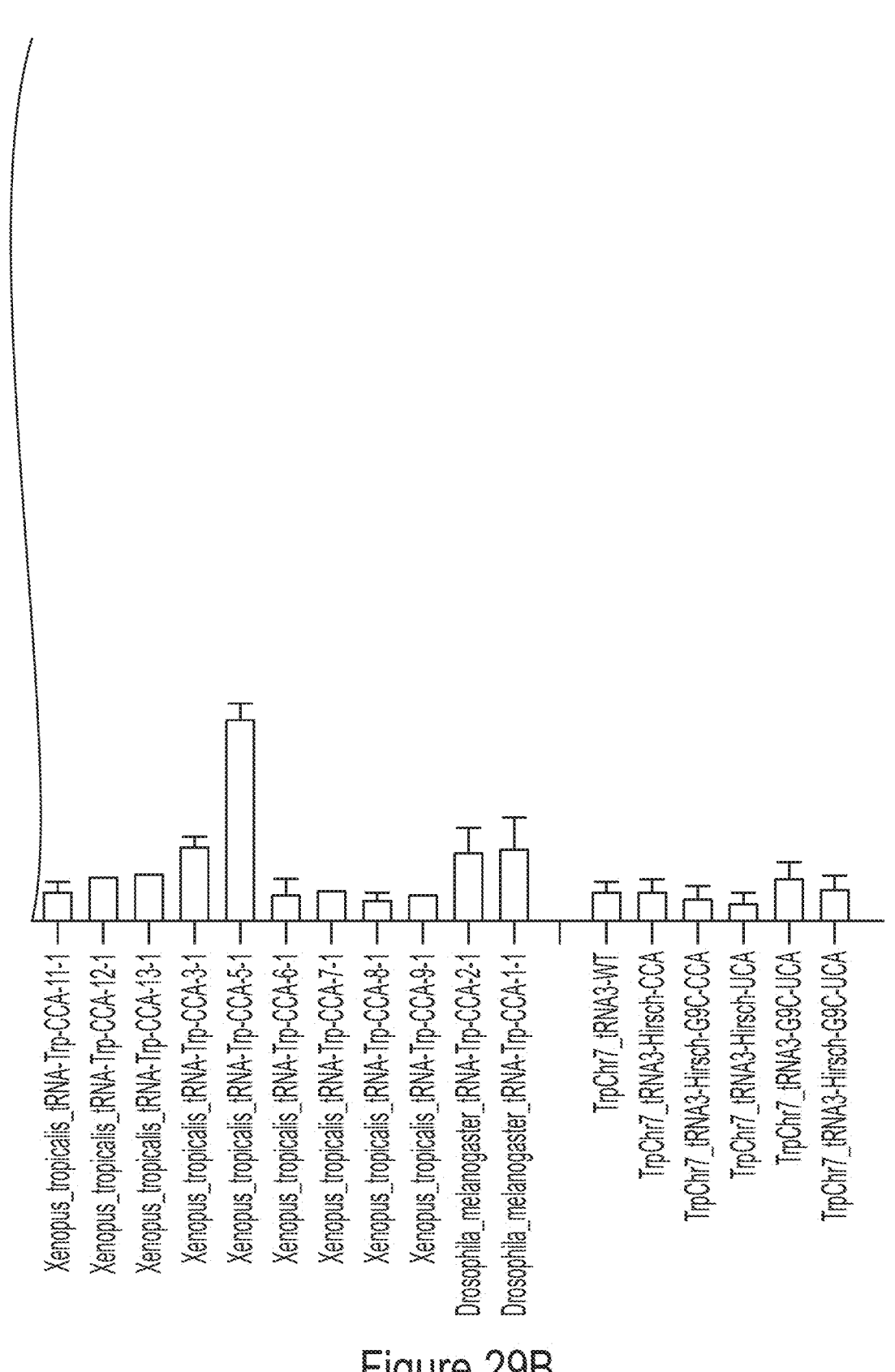
Figure 31:
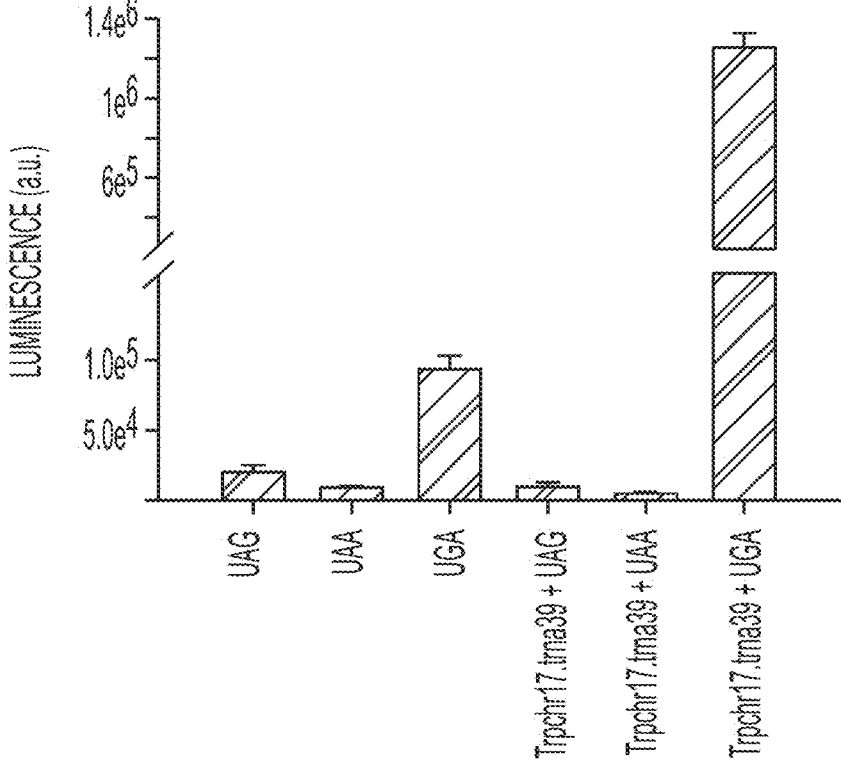
FIG. 31. Stop codon specificity is maintained for ACE-tRNA$^{Trp}$. Suppression activity 36 for tRNA Trp$^{TGA}$ Trpchr17.trna39, the top performing Trp$^{TGA}$ suppressor tRNA, FIG. 22. This tRNA was co-expressed with the indicated pNano-STOP plasmid.
Figures 32A, 32B, 32C, 32D:
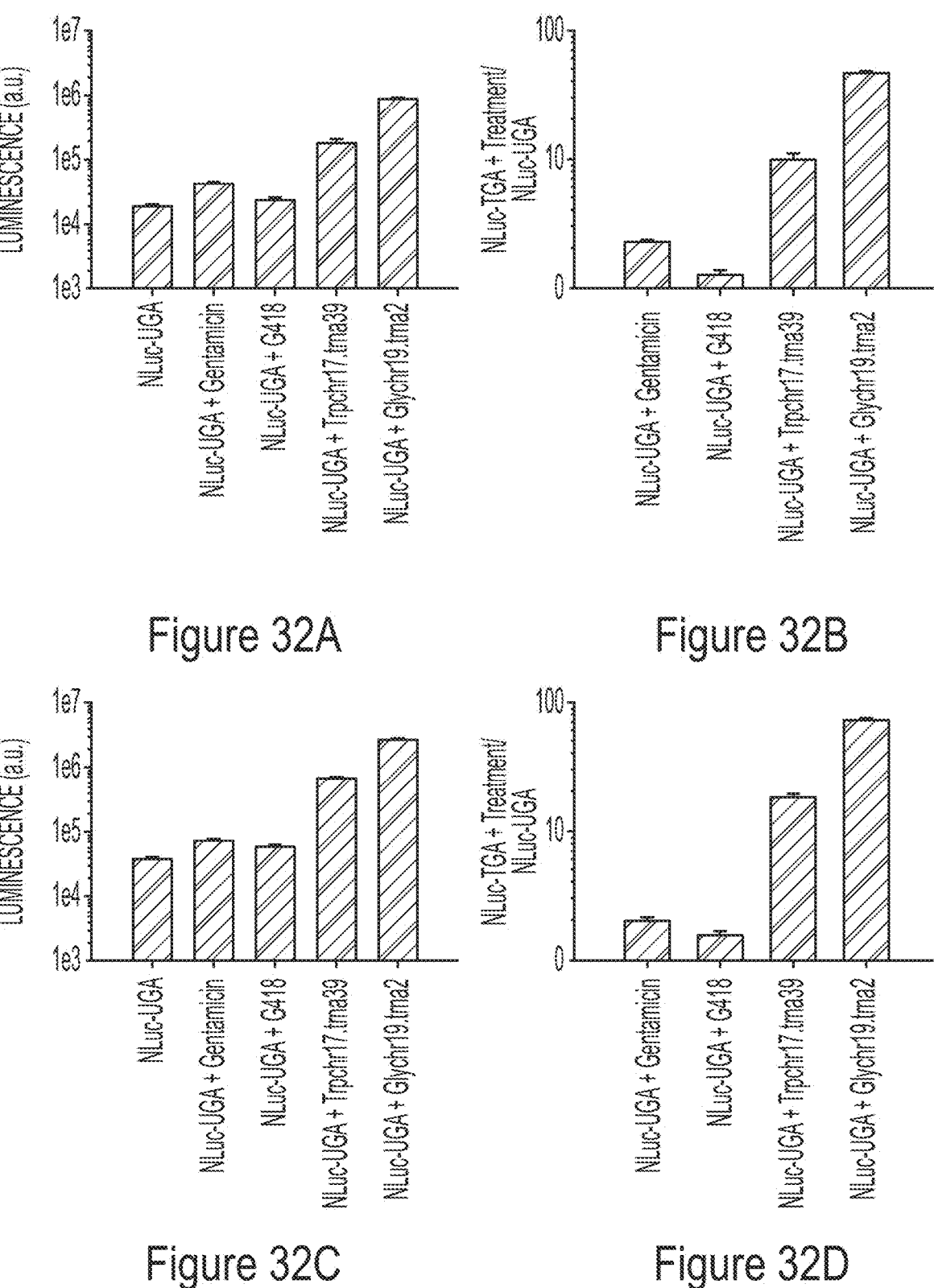
FIGS. 32A-32D. ACE-tRNAs are more efficient than aminoglycoside PTC suppression.
Figure 33:
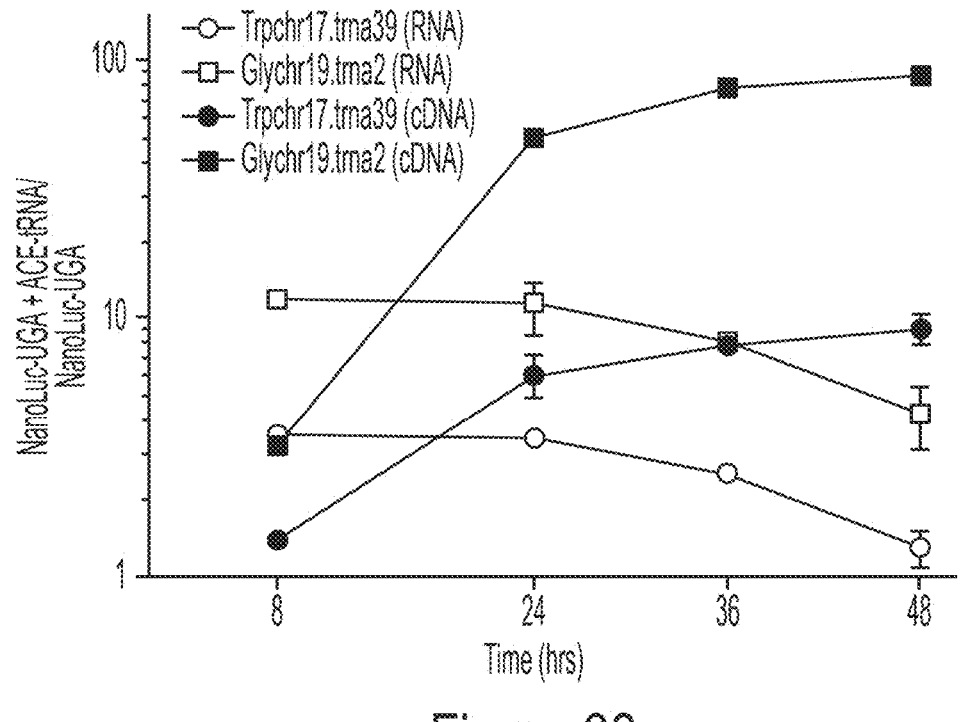
FIG. 33. Comparison of time courses of ACE-tRNA activity following delivery as RNA or cDNA. ACE-tRNAs were delivered to HEK293 cells that stably express pNano-Luc-UGA, however only 5 µl of the reaction mix was added to the cells to reduce the effect of transfection reagents on cell viability. ACE-tRNA delivered as RNA (open symbols), was more rapid in rescuing expression of the PTC reporter than cDNA constructs (close circles). However, ACE-tRNA activity continued to rise over the 48 hours when expressed from cDNA and decreased as an RNA deliverable.

Next it was established whether ACE-tRNAs identified in the screen were functionalized at the expense of aminoacylation stringency by the cognate aminoacyl-tRNA synthetase. To this end, mass spectrometry was used to examine PTC suppression in a model soluble protein, histidinol dehydrogenase (HDH), FIG. 23A. A TGA codon was introduced at asparagine 94 (N94) (FIG. 30A-C) and co-expressed in HEK293 cells in tandem with plasmids encoding Glychr19.trna2 or Trpchr17.trna39 ACE-tRNAs, the top performing glycine and tryptophan ACE-tRNA$^{UGA}$, respectively. The resulting full-length, suppressed, HDH proteins were purified via a Strep-Tactin® C-terminal affinity tag and analyzed by mass spectrometry, FIG. 23A (FIG. 28). Subsequent searches of the data identified the modification of Asn to Trp (+72 Da) for Trp chr17.trna39 and (−57 Da) for Glychr19.trna2, thus confirming the faithful encoding of the cognate amino acid for each ACE-tRNA type. Importantly, in each case >98% of the peptide identified at the HDH p.N94X site had the encoded cognate tryptophan and glycine. Further, both ACE-tRNAs retained selectivity for the UGA stop codon, over UAA and UAG, FIG. 23B (ACE-tRNA$^{Gly}$) and FIG. 31 (ACE-tRNA$^{Trp}$). Lastly, when transiently expressed, the ACE-tRNA$^{Gly}$ outperformed the conventional small molecule suppressors gentamicin (40 μM) and G418 (140 μM) in their ability to suppress NLuc-UGA stably expressed in HEK293 cells, FIG. 23C. The same was true even for ACE-tRNA$^{Trp}$, which had a lower suppression efficiency yet exceeded PTC rescue compared to G418, FIG. 33A-D.

Figure 24A:
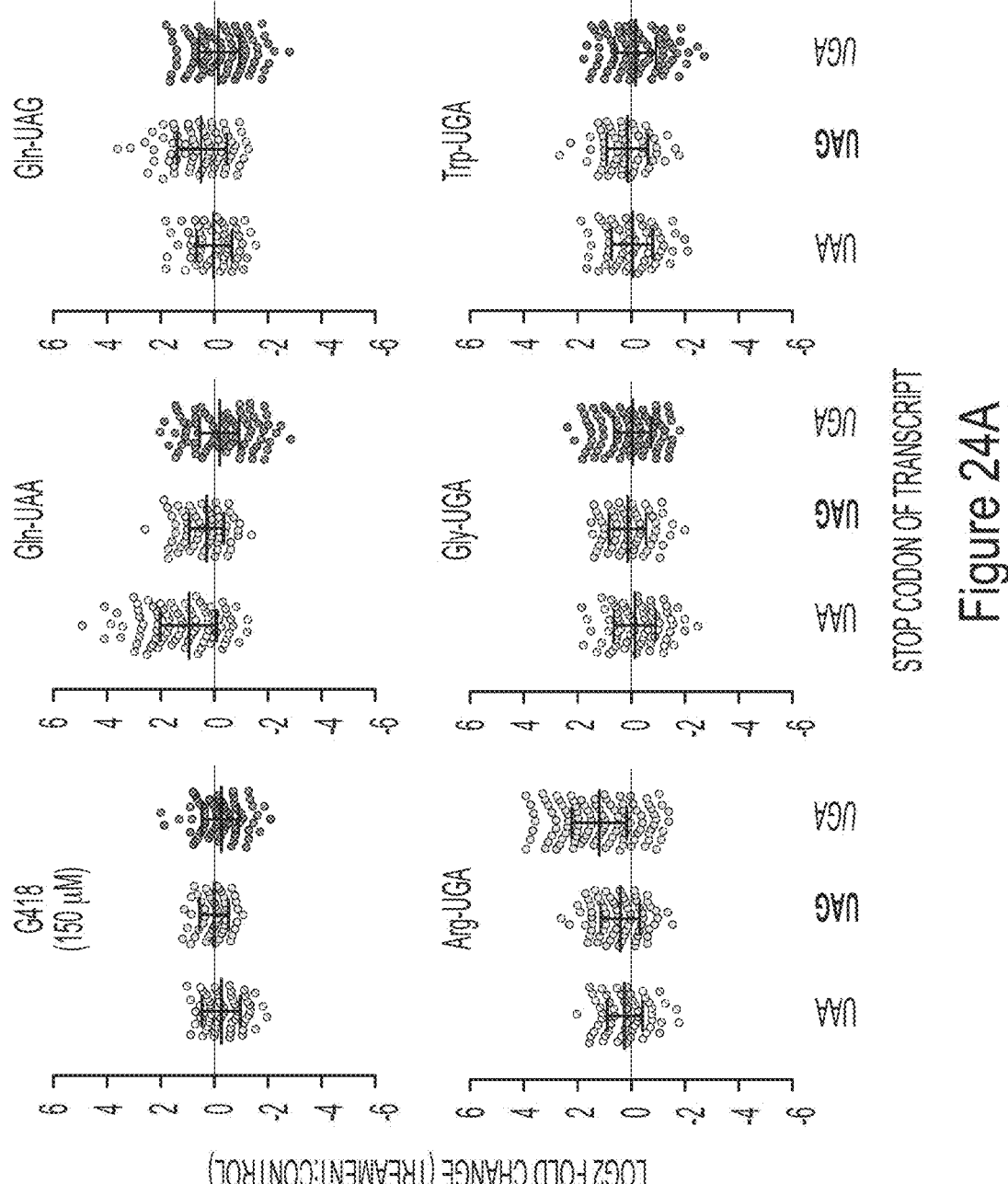
FIGS. 24A-24B. Ribosome profiling of ACE-tRNA on transcriptome-wide 3'UTRs.

The question was raised whether ACE-tRNAs that show efficacious suppression of premature stop codons may also induce global readthrough of native stop codons. To address this potential "off target" suppression, a transcriptome-wide quantitative profile of actively engaged ribosomes on all cellular transcripts was obtained by generating libraries of ribosome footprints from HEK293 cells expressing exogenous ACE-tRNAs or a control mock plasmid (puc57GG). Streptomycin was removed from the growth media to prevent readthrough artifacts. For comparison, the ribosome footprint library was also generated from cells in the presence or absence of G418 (150 μM, 48 h). FIG. 24A shows ribosome footprint densities of G418 and five ACE-tRNAs compared against controls (log 2-fold change) on 3'UTR regions. Only transcripts with a minimum threshold of 5 RPKM in the coding sequence and 0.5 RPKM in the 3'UTR in two replicate libraries were included for the quantitation comparison (254 transcripts in G418 and 495-748 transcripts in ACE-tRNAs). In this system, G418 had no observable effect on transcriptome-wide 3'UTR ribosome density for any of the three endogenous stop codon groups. ACE-tRNAs examined here had no detectable change of 3'UTR ribosome density with the exception of ACE-tRNA Gln-UAA and Arg-UGA which induced approximately a 2-fold increase in 3'UTR ribosome density for the cognate stop codon complimentary to the ACE-tRNA anticodon. Understanding the biological significance of 2-fold readthrough of protein stops will require further study, but this effect is substantially lower compared to the 100- to 1000-fold suppression of PTC for the same ACE-tRNA.

Figure 24B:
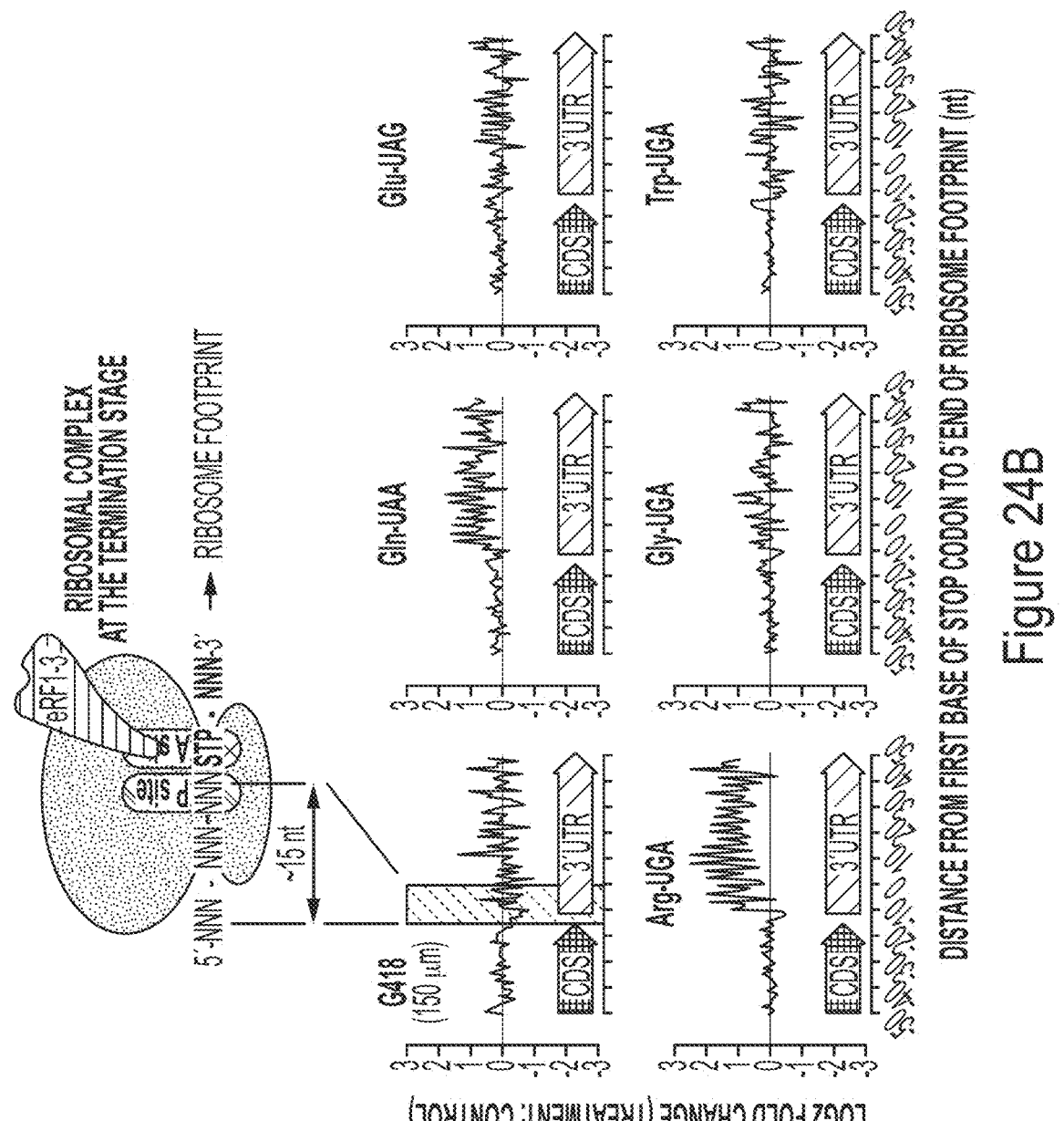

Multiple in-frame stop codons are frequently found at the end of genes 37-39 and may cause a minor difference in overall 3'UTR ribosome density for ACE-tRNA and G418 treatment. Ribosome occupancy was examined at each nucleotide in the 3'UTR within a 60 nt region downstream of the stop codons. FIG. 24B demonstrates the ribosome occupancy surrounding native stop codons for each nucleotide within the region from −35 to +65 nt relative to the first nucleotide of stop codon. Reads were normalized per total million-mapped reads, compared against control cells, and reported as a log 2-fold change as in panel A. More than 5,200 transcripts were mapped to at least 1 footprint in the region of interest. ACE-tRNA Gln-UAA and Arg-UGA showed not only notable increased ribosome occupancy in the early region but also characteristic 3-nt periodicity, indicating that the ribosomes were not randomly distributed but followed codon-by-codon movement. ACE-tRNAs for UGA-Trp, UGA-Gly and UAG-Glu, or G418, consistently showed no observable change of ribosome occupancy even in the early region of 3'UTR. Taken together, the ribosome profiling data argue that efficiency of native stop codon suppression by ACE-tRNAs is generally low, and markedly less than the level of PTC suppression.

Discussion

PTCs cause a multitude of human diseases and there are no established therapeutic options for their therapeutic management. The high-throughput cloning and identification, characterization and functional analysis of anticodon-edited tRNA that display efficacious PTC reversion in eukaryotic cells and mouse skeletal muscle is reported herein. Notably, the screen identifies ACE-tRNA, in total, with the ability to repair a vast majority of known human disease-causing PTC. The engineered tRNA faithfully encode their cognate amino acid, thus abrogating spurious effects on downstream protein stability, folding, and trafficking, and consequently negating the need for tandem therapies involving protein folding or trafficking agents. When transfected as cDNA, ACE-tRNAs rescued multiple full-length proteins via PTC suppression; a NLuc luciferase reporter, a model protein HDH, and two disease nonsense mutations in CFTR. Potent and stable in vivo PTC suppression in mouse skeletal muscle was displayed by an ACE-tRNA$^{Arg}$ cDNA, suggesting a particularly high level of cellular tolerance for ACE-tRNA activity. The identification of an active ACE-tRNA for arginine in muscle is relevant for the treatment of dystrophinopathies caused by nonsense mutations. Following suit with most genetic diseases, greater than 10 percent of dystrophinopathies are caused by nonsense mutations[43], where CGA→TGA mutations are most prevalent[43]. Efficient suppression was also achieved with ACE-tRNAs delivered as synthetic RNA transcripts, thus enabling the development of nanoparticle formulations. Future studies will be needed to assess ideal tRNA delivery strategies for each tissue and disease type, where efforts will likely benefit from rapidly expanding technologies for nucleic acid delivery.

Agents that suppress PTCs have the potential to also produce readthrough of native stop codons. The RNA profiling data presented herein suggest this is, generally, not the case in the cells and for the codon-edited tRNA that were tested. While detectable readthrough was found with Arg-tRNA$^{UGA}$ and Gln-tRNA$^{UAA}$, no significant effect on global translation termination was measured with Glu-tRNA UAG UGA-Gly-tRNA$^{UGA}$ and Trp-tRNA$^{UGA}$. This behavior did not obviously segregate with stop codon type, or the intrinsic PTC suppression activity of the tRNA. One potential reason that ACE-tRNA ineffectually promote readthrough at real stop codons may be due to the contextual sequence landscapes near translation terminations[44]. This possibility is supported by the finding that the composition of termination complexes at PTCs differ from those at native stops[45, 46]. However, in cases where lower level readthrough occurs, there are multiple cellular mechanisms in place to limit both normal stop read-through and damaging effects thereof. Multiple in-frame stop codons are frequently found at the end of genes[37-39] and specialized ubiquitin ligases[47] and ribosome associated pathways[48] are known to identify and degrade proteins with erroneous translation termination. Nonetheless, despite the limited impact seen here in mammalian cells, similar ribosomal profiling experiments should be performed in the desired cell or tissue type for ACE-tRNA delivery and expression.

Previous studies have shown that the surrounding mRNA sequence influences inherent stop codon suppression efficacy of aminoglycosides and Ataluren PTC[49-52], and ACE-tRNA may be similarly affected. Further, while gene addition strategies to replace a PTC containing gene, via viral or non-viral delivery, have achieved short term benefit in some settings, it may be difficult to regulate transgene expression levels. In contrast, the abundance of protein rescue via ACE-tRNA suppression is coupled to native cellular RNA levels, and thus upper levels of expression will be intrinsically regulated. The biological purpose remains unknown for a majority of the variable isoacceptor tRNA sequences in the human genome, and almost half these genes have been speculated to be transcriptionally silent pseudogenes[53], however the data here suggest many annotated tRNA are viable. Consistent with this possibility, a suppression approach has been used to identify functional isodecoder tRNAs within Ser and Leu isoacceptor families[54]. The data presented here further demonstrate that the majority of tRNA gene sequences support viable activity when removed from the genomic context, further deepening the mystery for the biological need for a plurality of tRNA, and codon usage. Thus, the high-throughput suppression strategy described here will be useful to identify new types of tRNA sequences with unique suppression properties, and such studies have the potential to produce new RNA reagents as well as advance the molecular understanding tRNA expression and suppression.

Materials and Methods

Nonsense Reporter HTC Plasmid

The parent plasmid used was pcDNA3.1(+). The cDNA encoding pNLuc was Gibson Assembled (New England Biolabs, USA) into restriction sites HindIII and XhoI. A glycine (codon gga), tryptophan (tgc), amber (tag), opal (tga) and ochre (taa), were added to amino acid position 160 during cDNA per. The pcDNA3.1(+) polyA sequence was replaced for one with no BbsI restriction sites using per based Gibson Assembly. The high throughput ACE-tRNA Golden Gate cloning site was generated by first inserting the 5' leader sequence of the human tRNA$^{Tyr}$ gene (bold) with a T7 promoter sequence upstream (italics)

(*TAATACGACTCACTATAG*AGCGCTCCGGTTTTTCTGTGCTGAACCTCAGGGGACG CCGACACACGTACACGTC (SEQ ID NO: 649)) (Ye et al., 2008) followed by two BbsI restriction sites (bold italics) (TA*GTCTTC*GG (SEQ ID NO: 650) (ccdB cassette) AA*GAAGAC*CG (SEQ ID NO: 651)) and 3' termination sequence (bold) followed by a reverse T3 primer sequence (italics) (GTCCTTTTTTTG*CTTTAGTGAGGGTTAATT* (SEQ ID NO: 652)).

Figure 26:
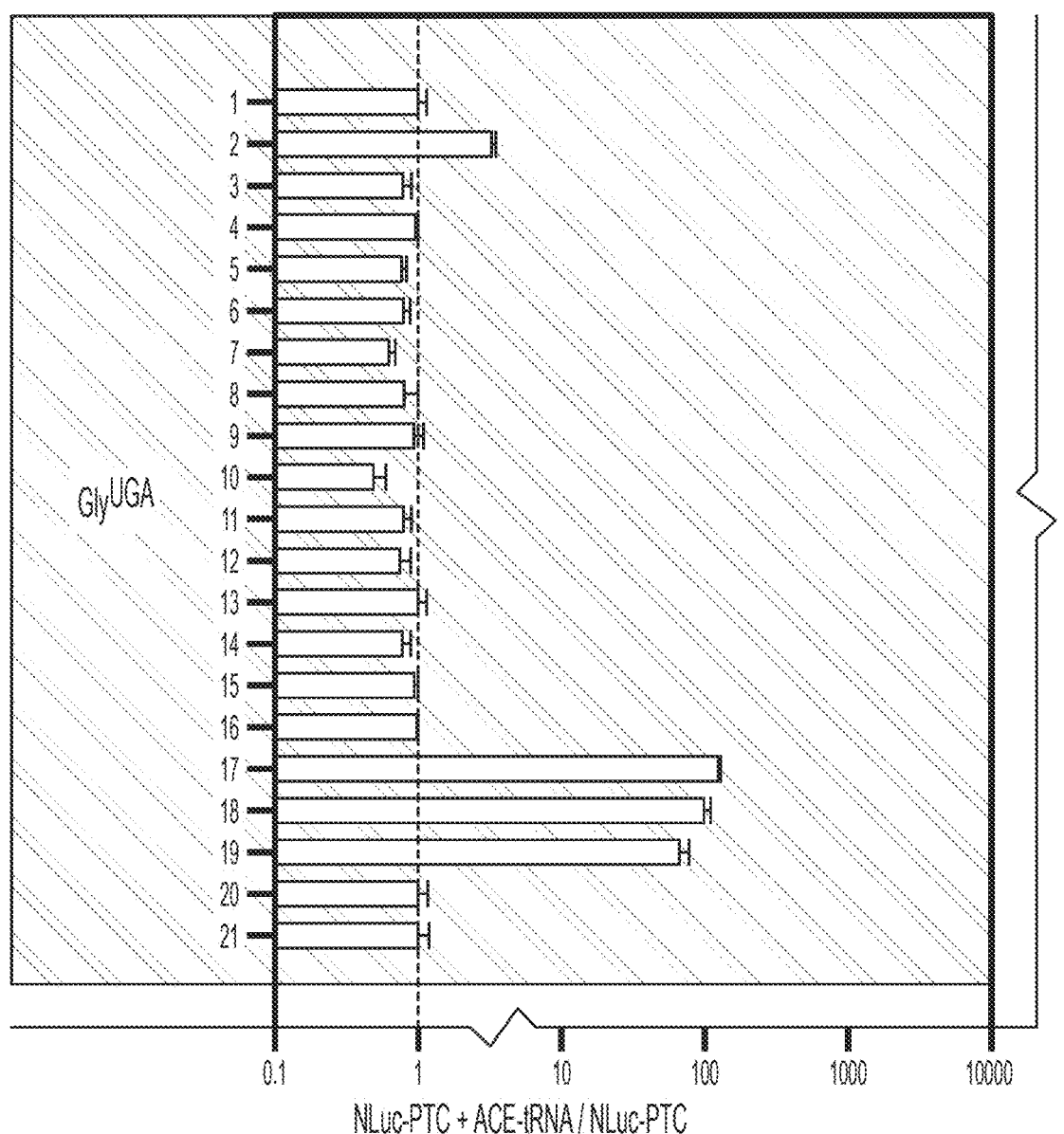
FIG. 26. Number referenced ACE-tRNA activity plot.
Figure 26:
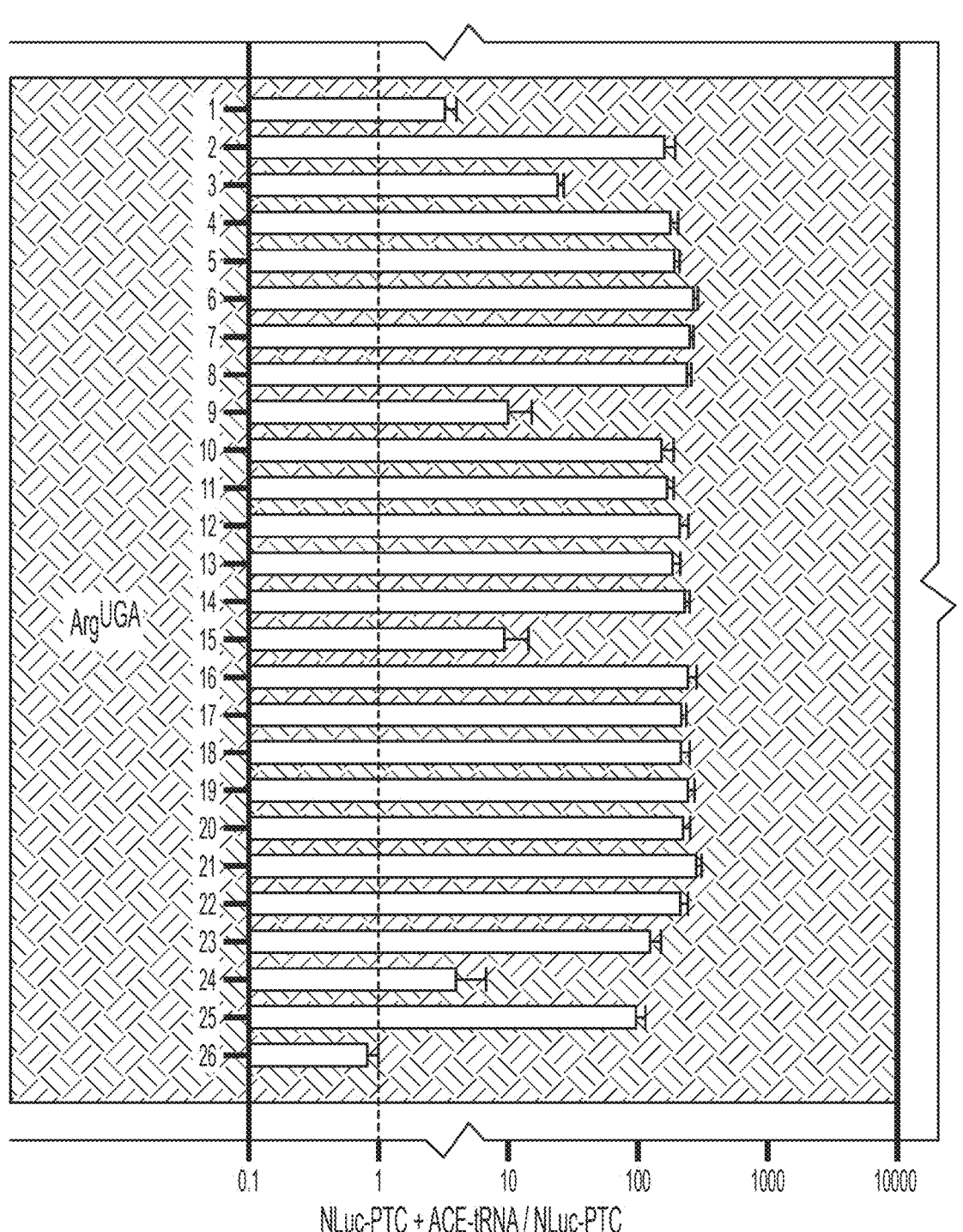
Figure 26:
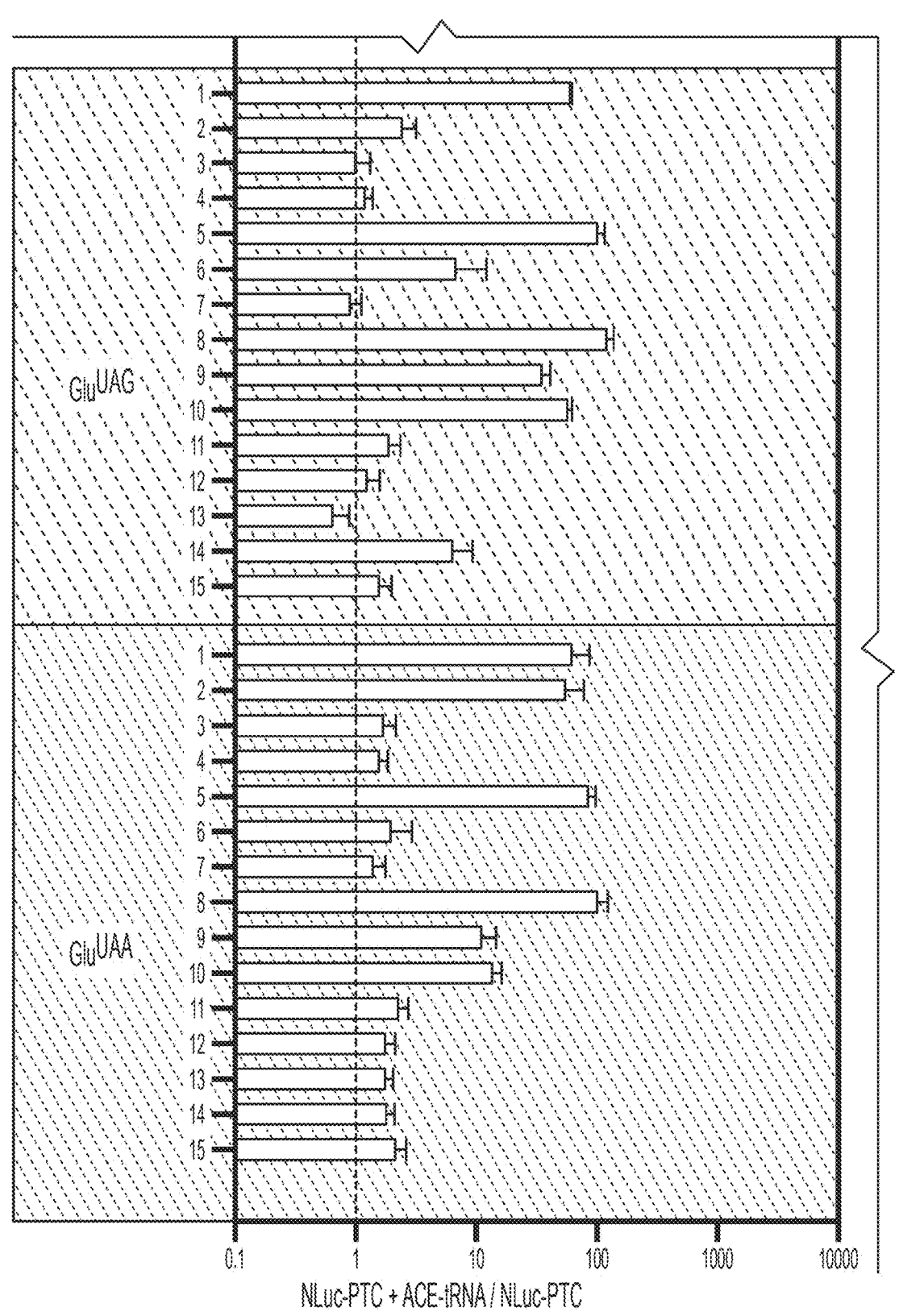
Figure 26:
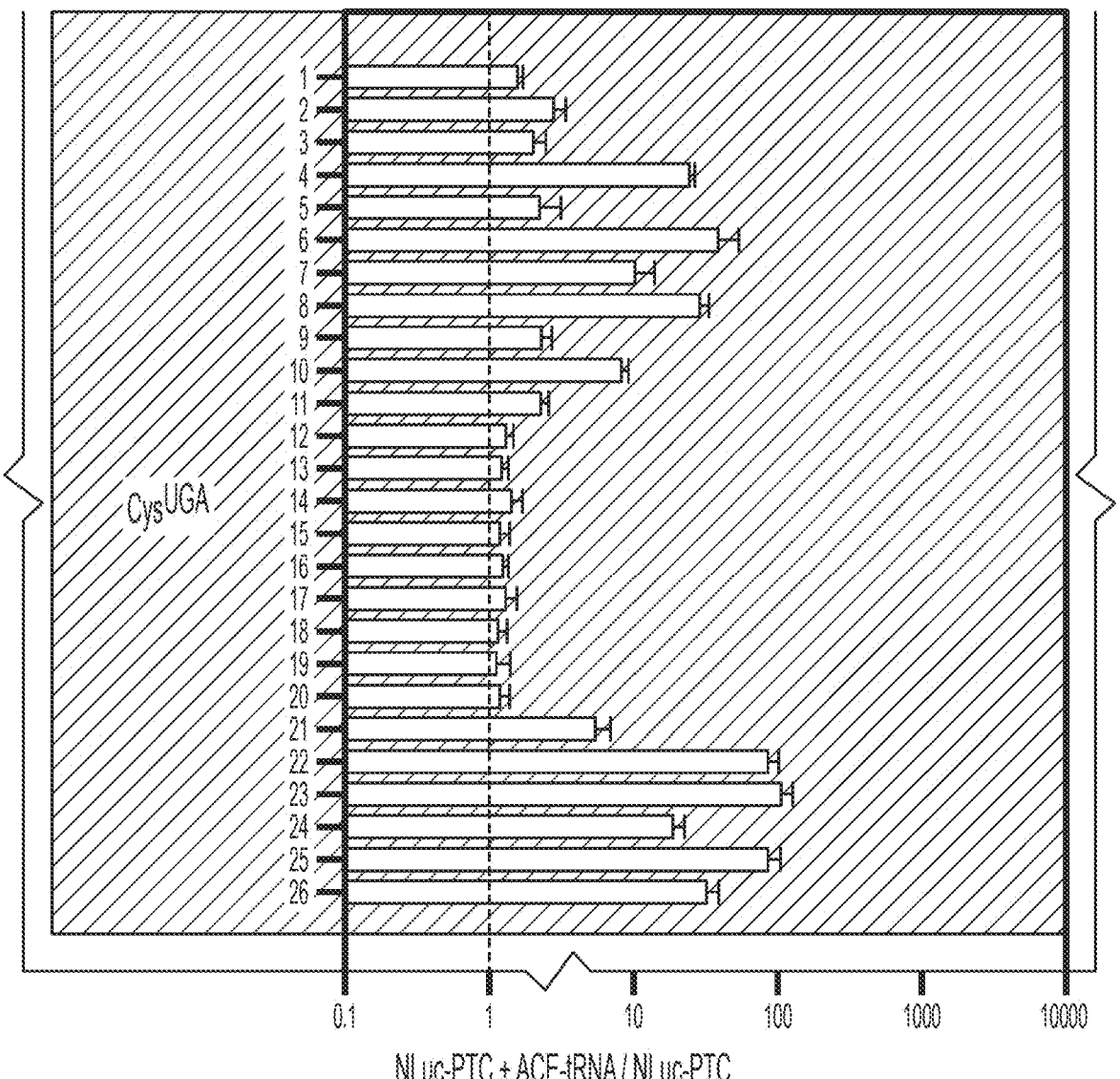
Figure 26:
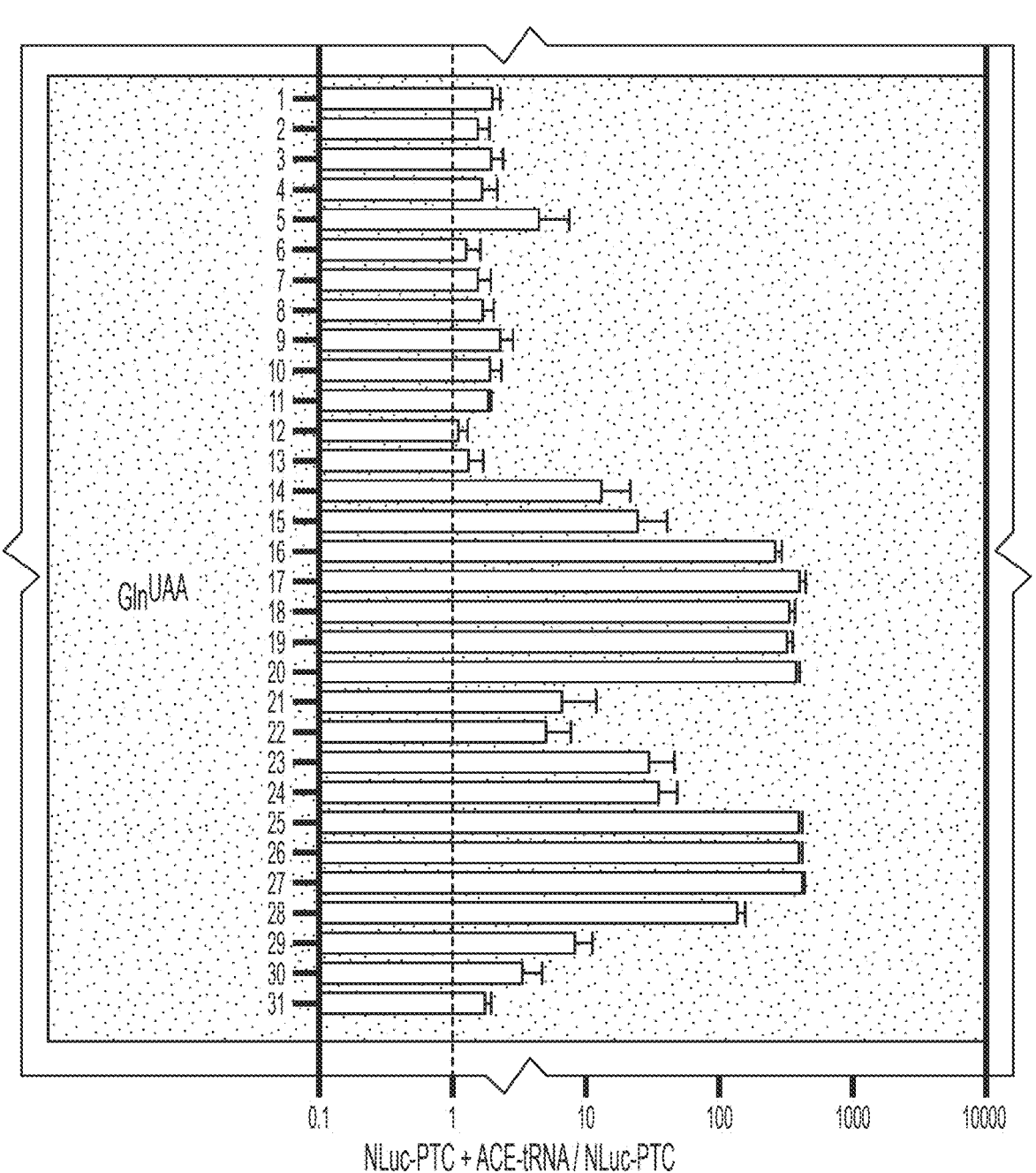
Figure 26:
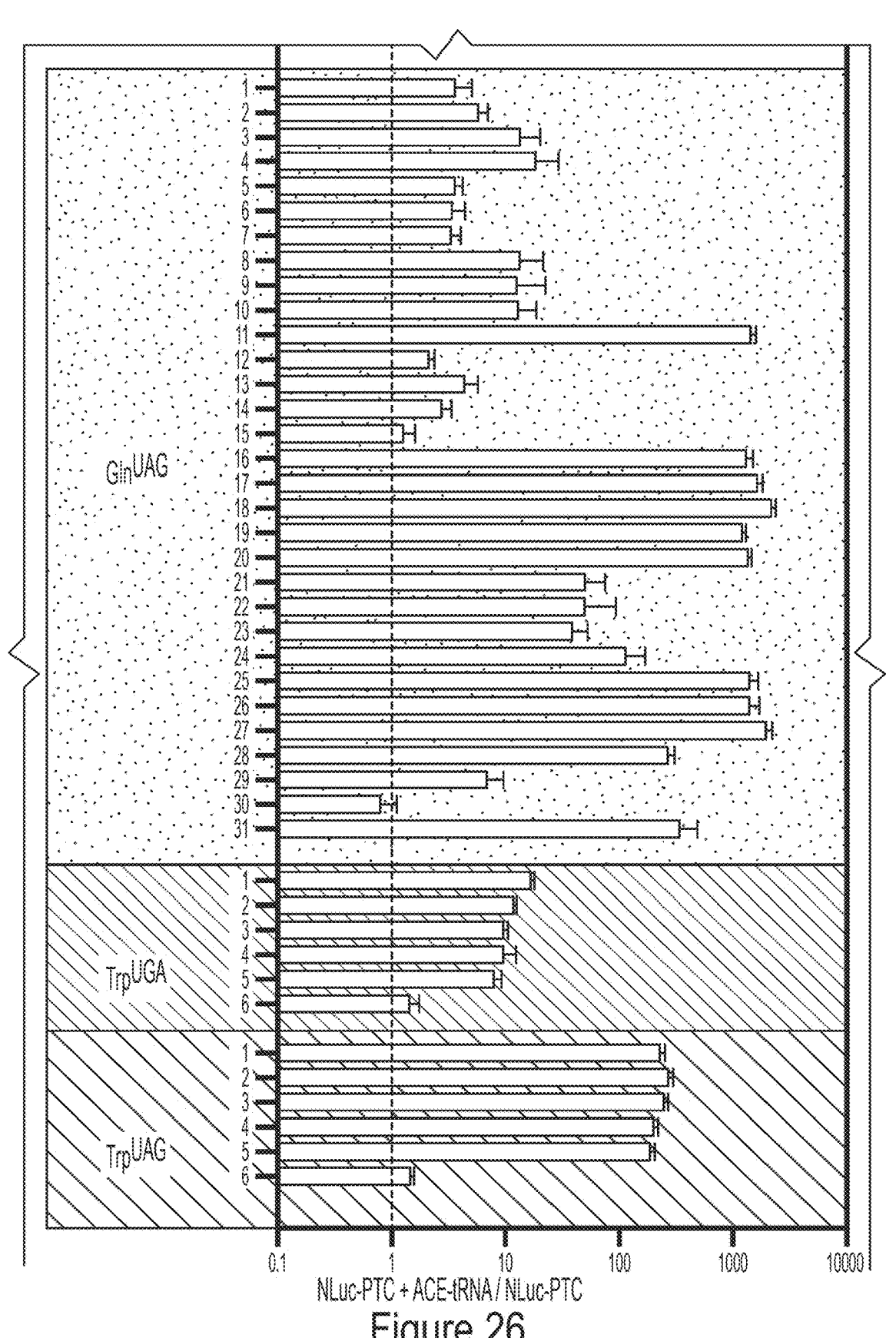
Figure 26:
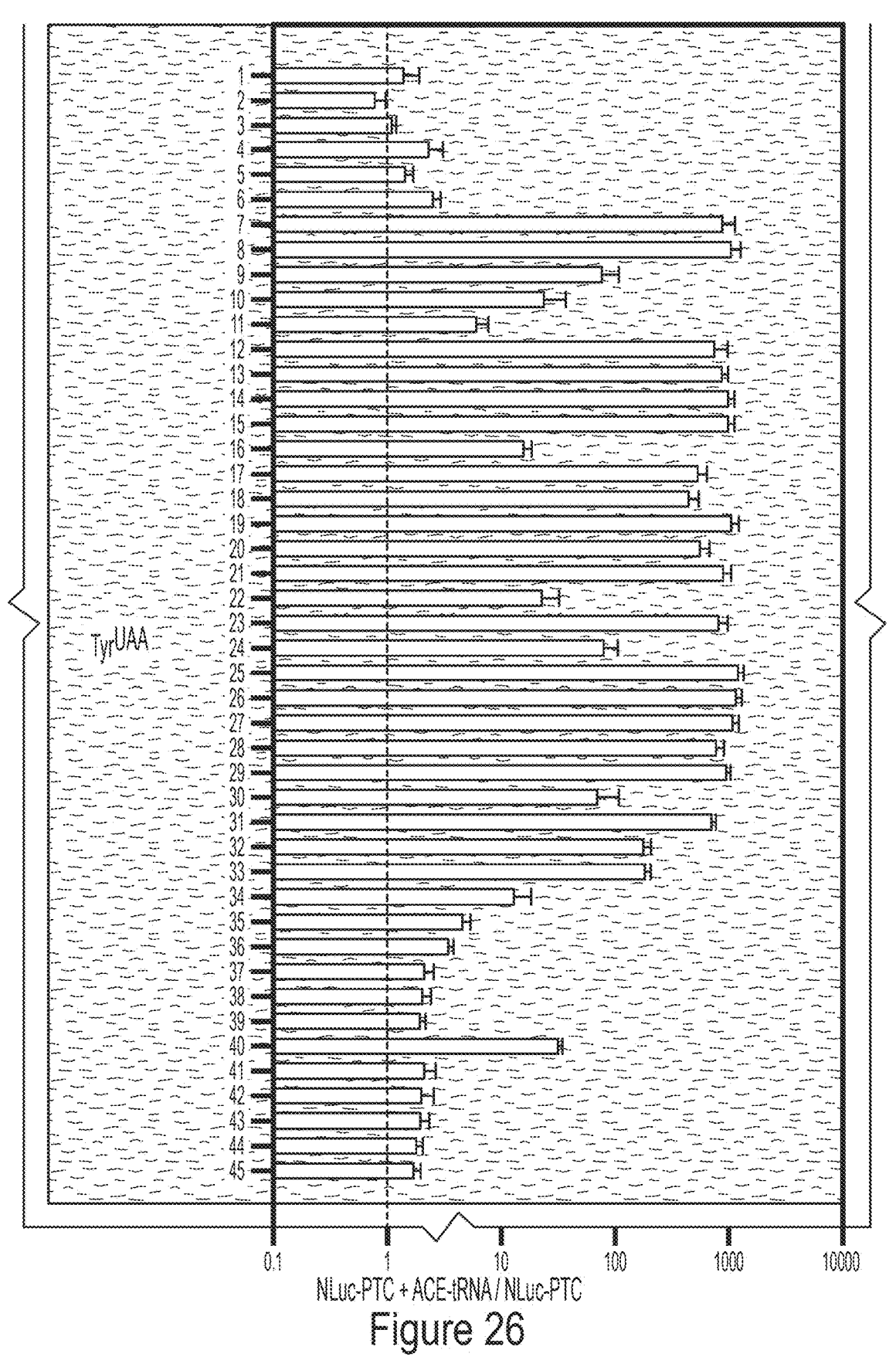
Figure 26:
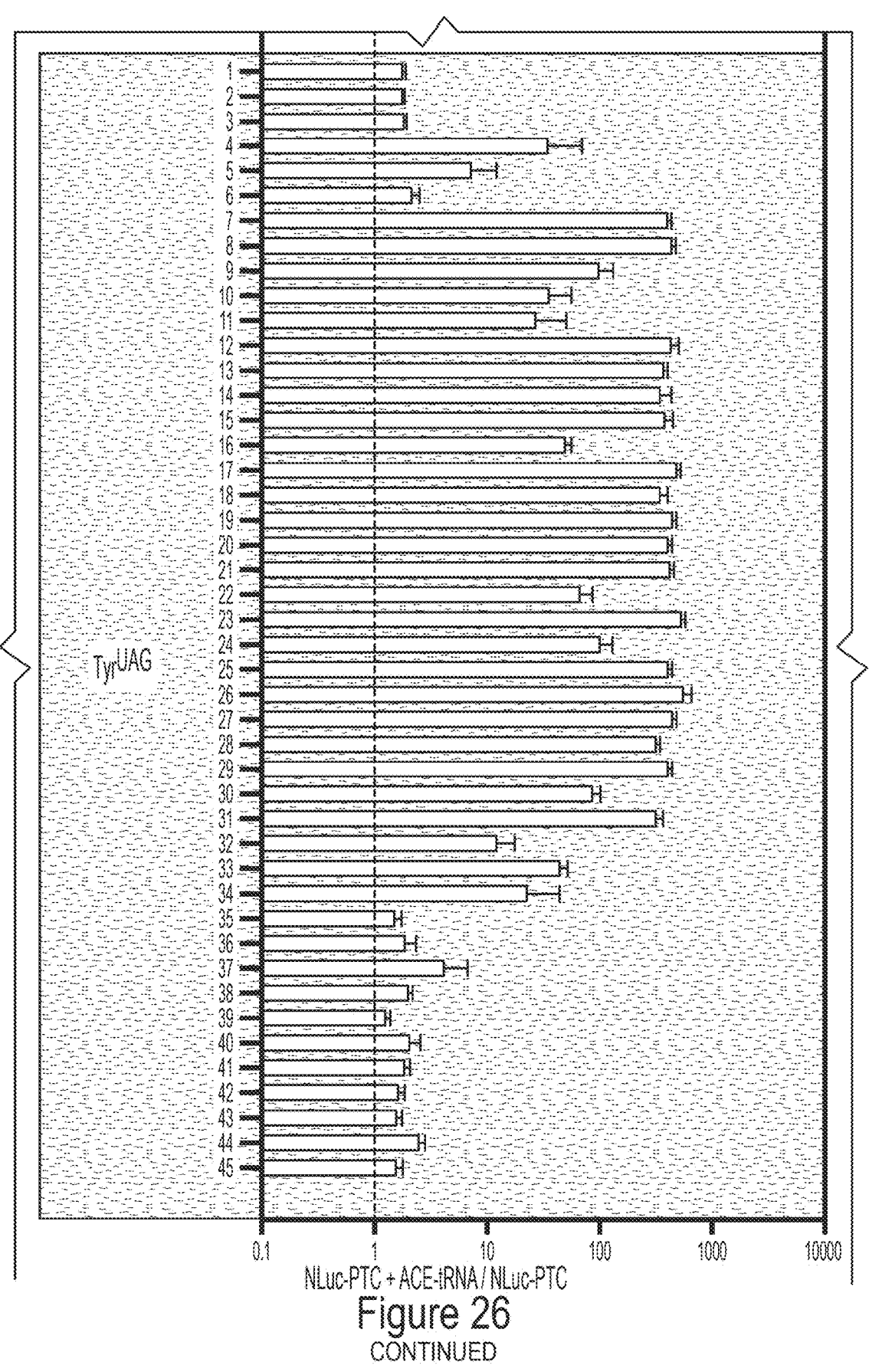
Figure 26:
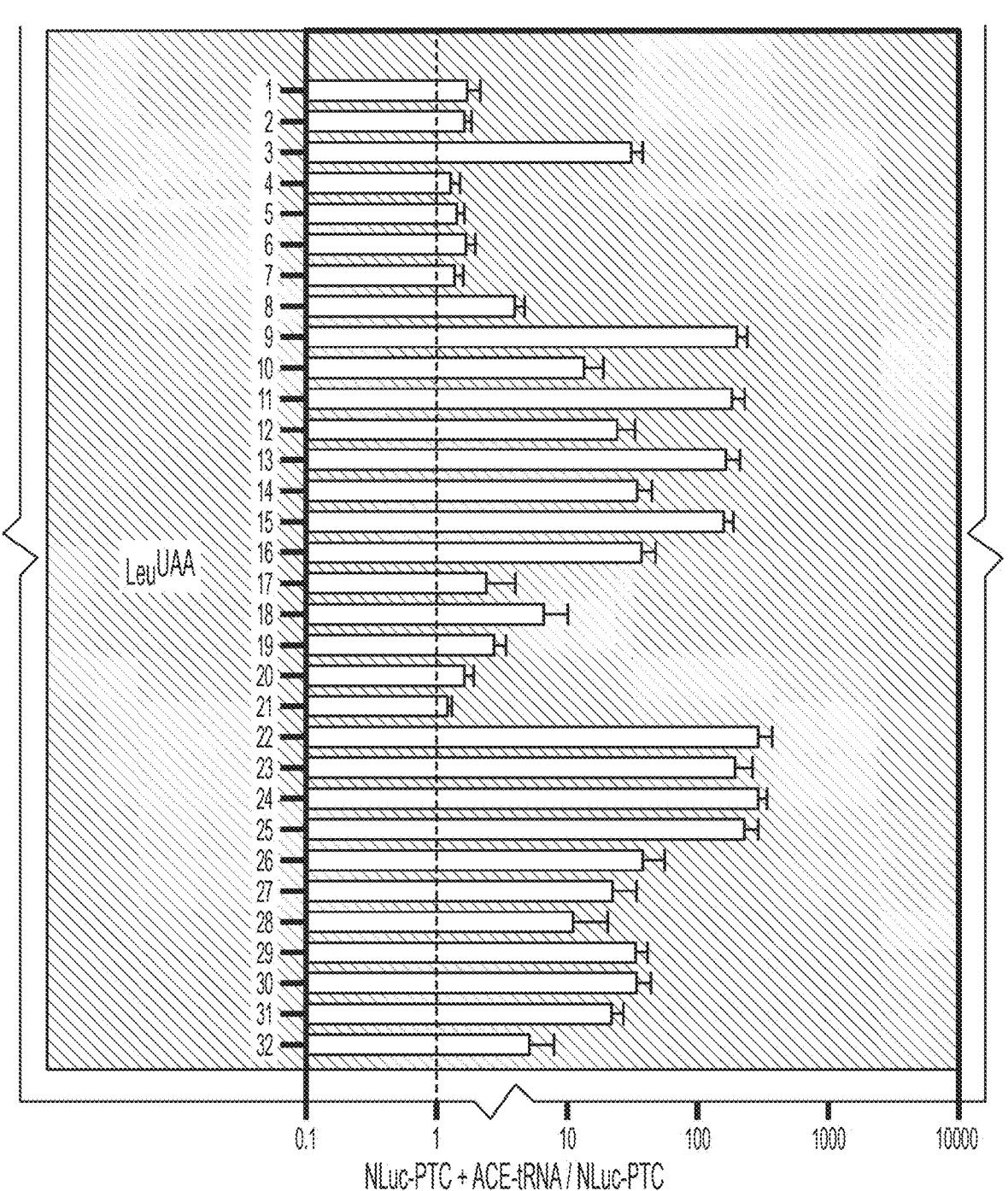
Figure 26:
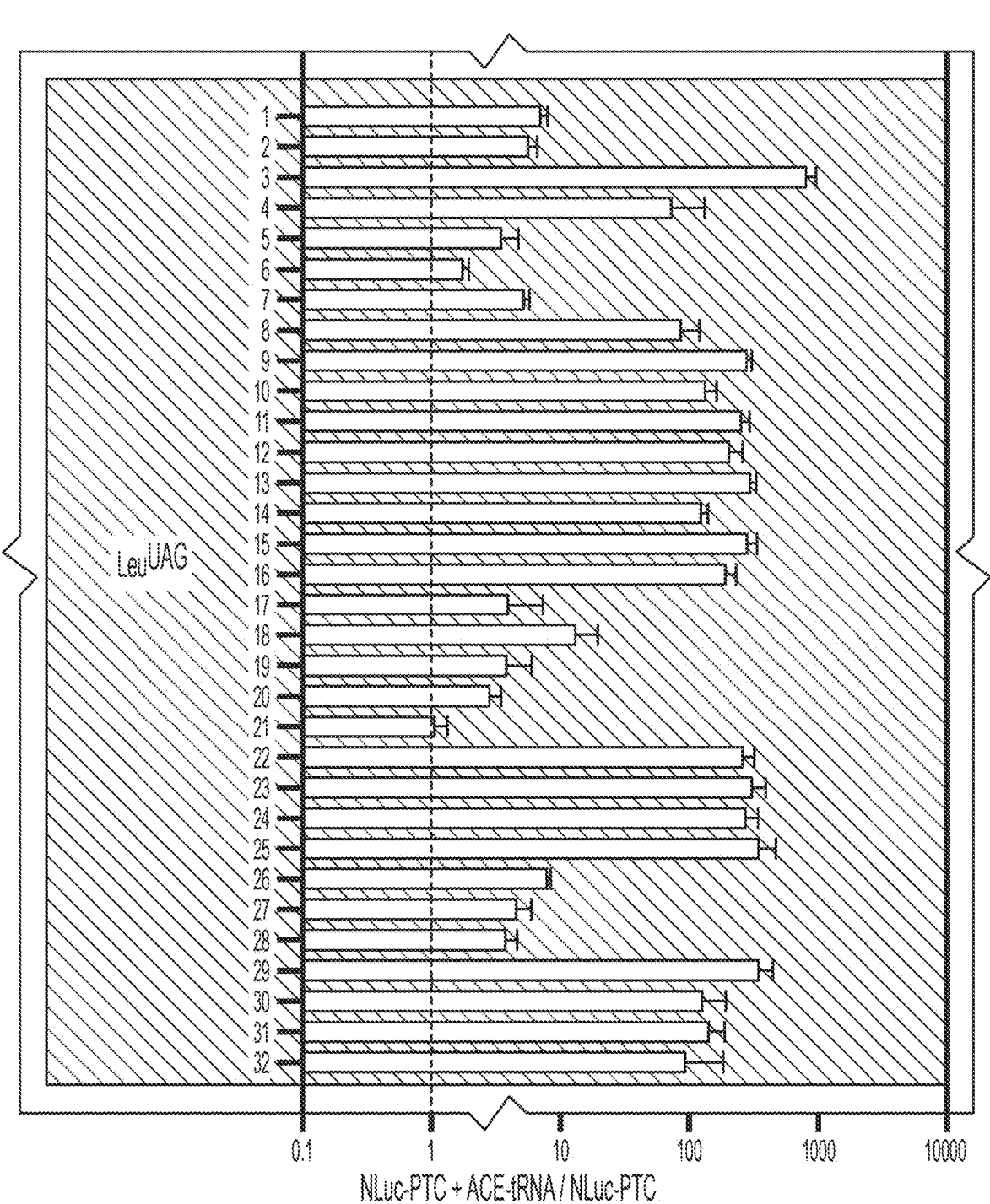
Figure 26:
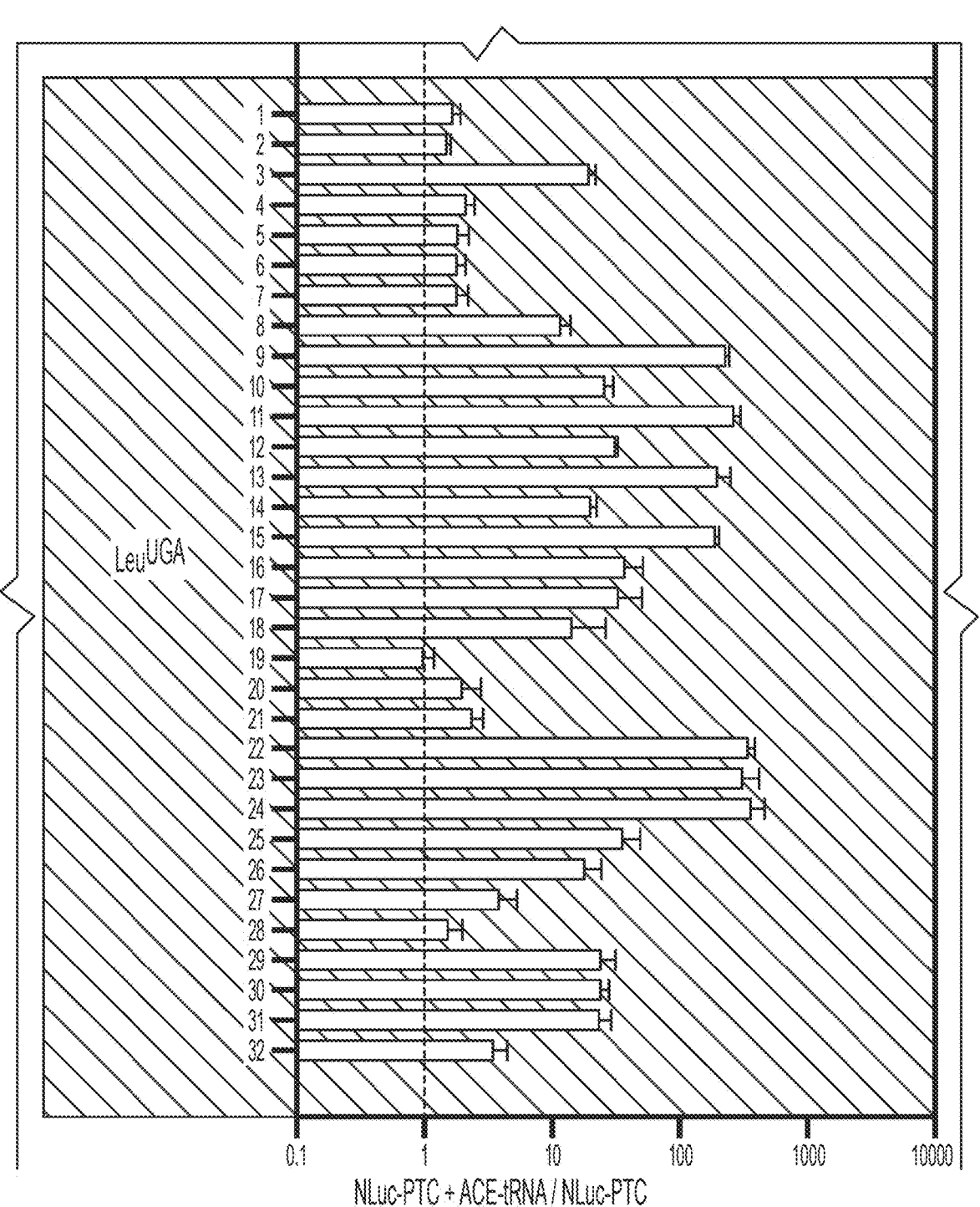
Figure 26:
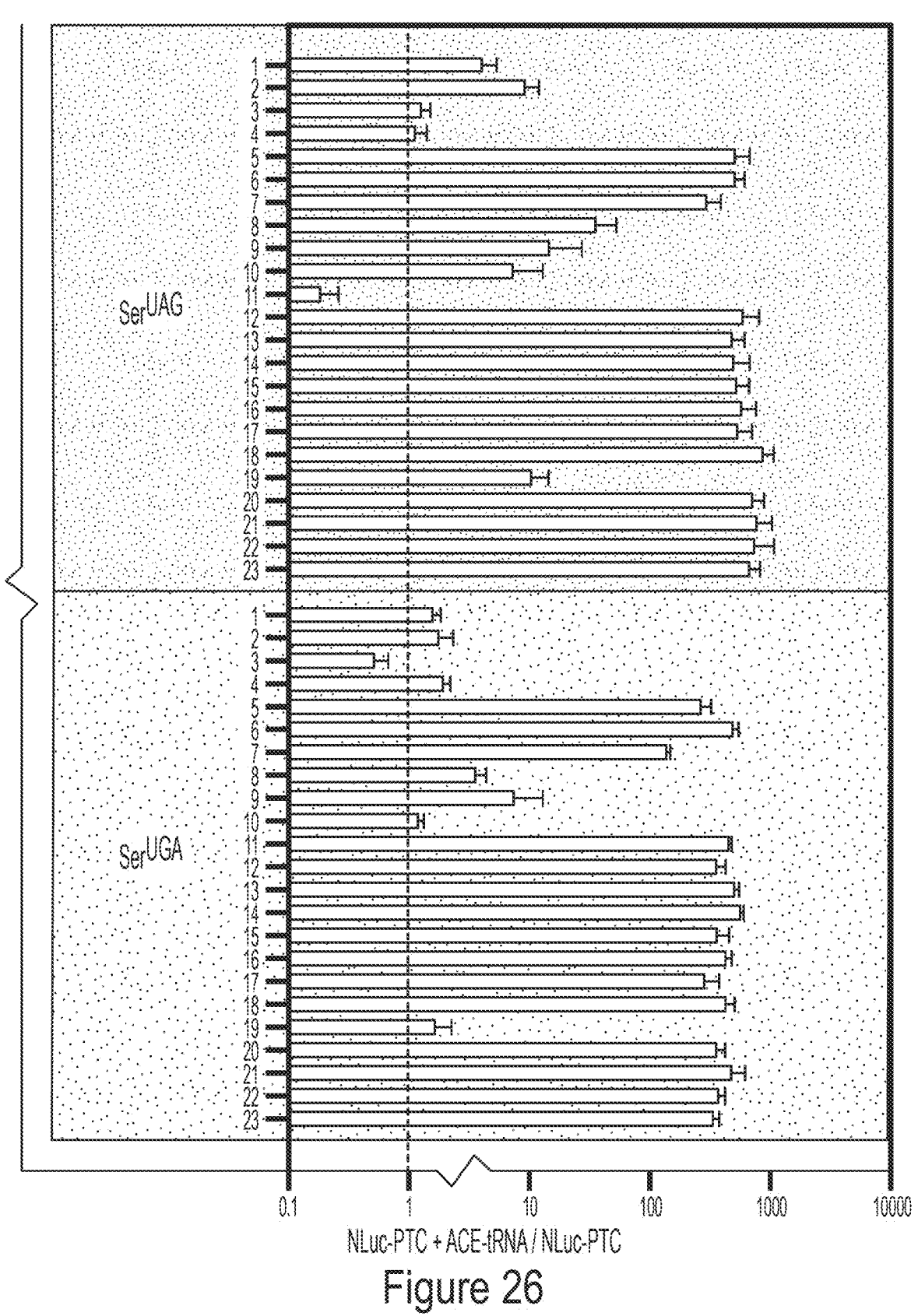
Figure 26:
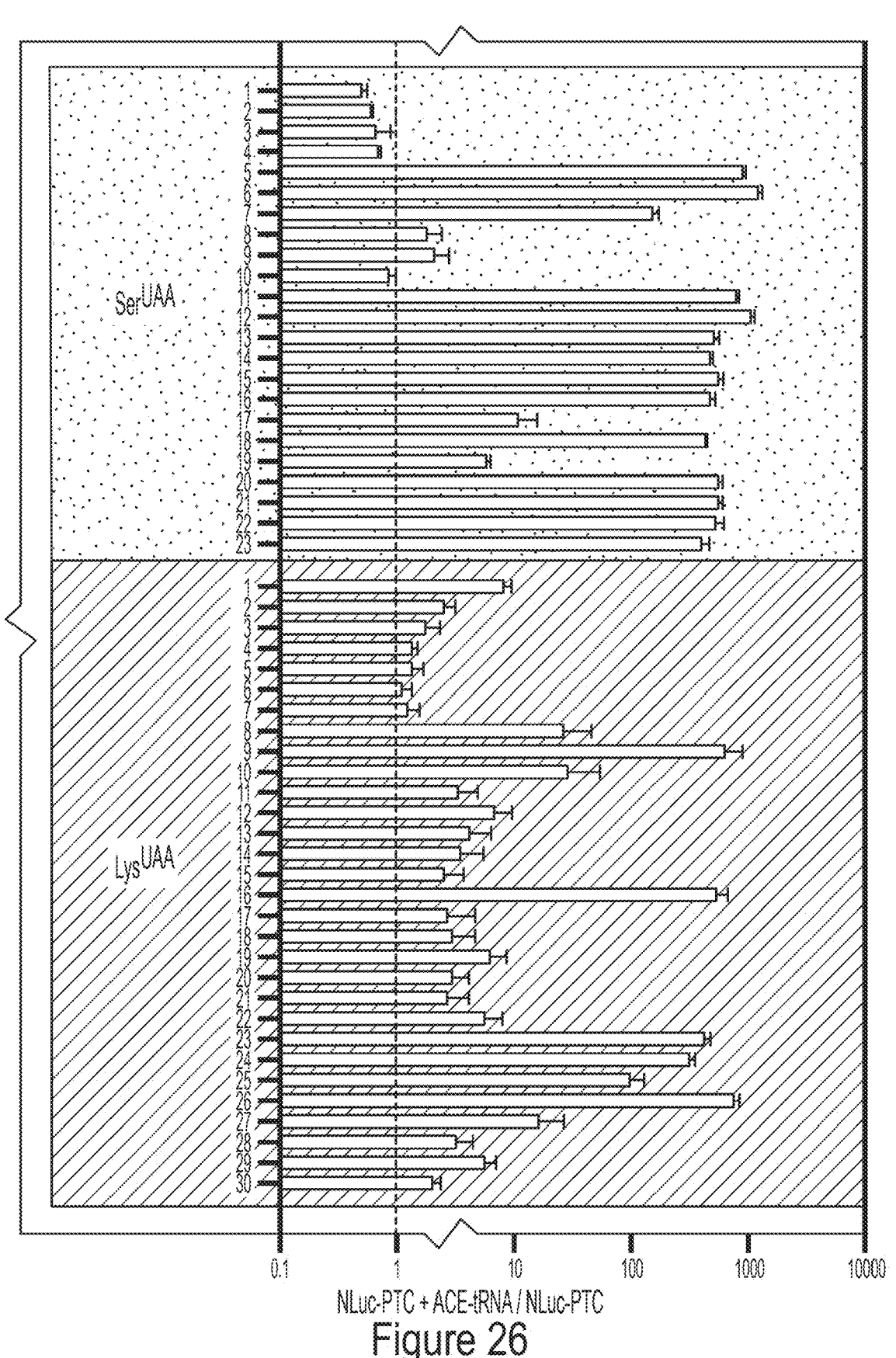
Figure 26:
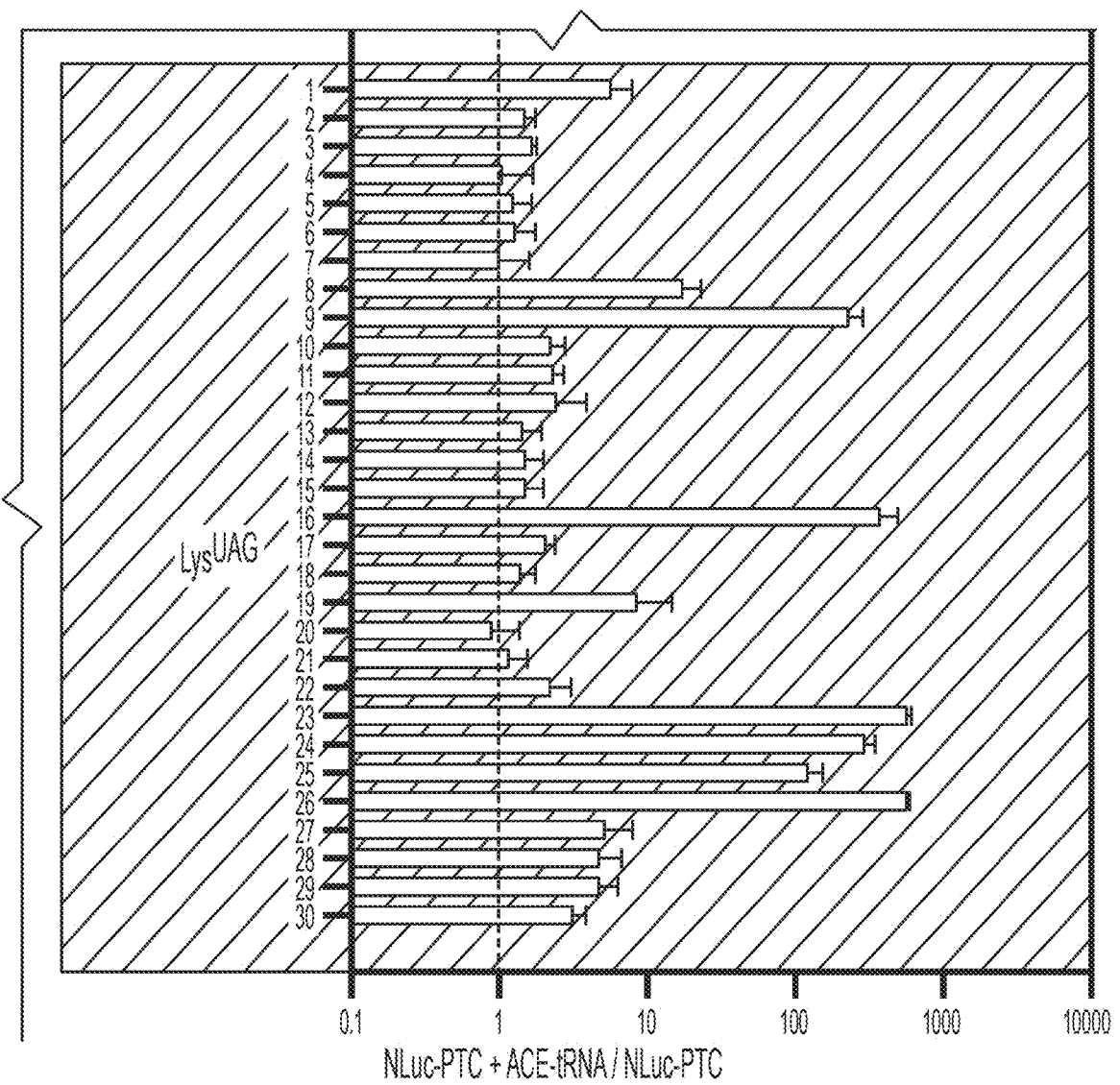

HTC of ACE-tRNA Library tRNA gene sequences were obtained from the tRNA database tRNAscan-SE (http://gtrnadb.ucsc.edu/index.html; PMID: 26673694). Sequences of all tRNA genes used in this study are numbered in FIG. 26 and Table 9. tRNA sequences were synthesized as complementary Ultramers from Integrated DNA Technologies (IDT, USA) in 96 well format at 200 pmol scale with their corresponding anticodons mutated appropriately (UAG, UGA or UAA). All tRNA sequences were synthesized with CGAC and GGAC overhangs (annotated 5'->3') on forward and reverse oligos, respectively. Ultramers were annealed by resuspending in annealing buffer (100 mM Potassium Acetate; 30 mM HEPES, pH 7.5) to 100 ng/μl, heated to 96° C. for 2 mains and cooled at 1° C./min in a thermocycler to 4° C. In 96 well PCR plates, each well contained 10 ng of HTC plasmid with appropriate PTC codon, 2 ng ACE-tRNA duplex, 1 mM ATP, 10 mM DTI, 400 Units T4 DNA Ligase, and 10 Units BbsI-HF, queued to 10 ul with ddH$_2$O. The 96 well plates were cycled as follows ([5 min@37° C., 5 min@20° C.]×30 cycles, 10 min @37° C., 10 min @ 80° C. and cooled to 4° C. in a thermocycler. In a deep welled 96 well plate 1 ul of the Golden Gate reaction was added to 10 ul of DH5α chemically competent cells (ThermoFisher, USA), heat-shocked @ 42° C. for 30 sec and resuspended in 100 ul of Super Optimal Broth (S.O.C., Thermofisher, USA). Transformations were outgrown at 37° C. for 1 hr. 250 rpm and then added to 2 ml of Luria-Bertani liquid media (LB) supplemented with 100 ug/ml Carbenicillin and grown in covered deep 48 well plates @ 37° C. for 20 hrs, 300 rpm. *E. coli* outgrowth was performed in deep well plates and clamps from Enzyscreen (http://www.enzyscreen.com). *E. coli* suspension cultures were spun down (10 min, 4,000 g at RT) and plasmid DNA was prepared and diluted to 125 ng/μl (IBI scientific, USA). All clones were sequence verified. Using this method, 100% cloning efficiency was achieved.

HTS of ACE-tRNA Library

The day before transfection, HEK293 cells (<40 passages) were plated at 1.4×10$^4$ cells/well in 96 well cell culture treated plates in Dulbecco's Modified Essential Medium (DMEM) supplemented with 10% FBS, 1% Pen/Step and 2 mM L-Glutamine (Thermofisher, USA). The all-in-one nonsense reporter with ACE-tRNA genes were transfected in triplicate/plate using Calfectin (Signagen, USA). 16 hrs post-transfection, the media was aspirated and 20 ul of PBS was added to each well. 15 ul of lytic Nano-Glo® Luciferase Assay Reagent was added to each well (1:50 reagent to buffer; Promega, USA). The plates were incubated for 2 min after rotational shaking and read using a SpectraMax i3 plate reader (Molecular Devices, USA; integration time, 200 ms; All wavelengths collected in endpoint mode). Luminescence was averaged across three wells for each experiment and all ACE-tRNAs were repeated >3 times in this fashion. Each plate also contained in triplicate wells transfected with the all-in-one nonsense reporter with no ACE-tRNA to server as control for transfection efficiency and baseline PTC readthrough. All values are reported as ratios of ACE-tRNA luminescence over baseline PTC readthrough luminescence ±SEM. One-way ANOVAs were performed with Tukey's post-hoc analysis across all ACE-tRNAs in a given amino acid family.

CFTR, HDH-his-Strep and 4×ACE-tRNA Expression Plasmids

For expression in mammalian cells, the cDNA for the coding region and 200 base-pair of the 3' untranslated region (UTR) of human CFTR was ligated into pcDNA3.1(+) (Promega, USA) using the KpnI and XbaI restriction enzymes. The G542tga and W1282tga mutations were introduced using QuickChange XL II (Stratagene, USA). For expression in *Xenopus laevis* oocytes, the cDNA for the coding region and 140 base-pair of the 5' and 244 base-pair 3' UTR of human CFTR was ligated into pGEM-HE (Promega, USA). Bothe the G542tga and W1282tga mutations were introduced using QuickChange XL II. The cDNA encoding the *E. coli* histidinol dehydrogenase was codon optimized for *Mus musculus* and synthesized (BioBasic Inc, Canada) with a c-terminal 8×His-Strep-tag ("8×His" disclosed as SEQ ID NO: 647) for protein purification from mammalian cells. The synthesized cDNA was ligated into pcDNA3.1(+) using EcoRI and XhoI restriction sites. The nonsense mutations tag, taa and tga were introduced using QuickChange XL II. To generate multiplexed ACE-tRNA expression plasmids, a novel parent Golden Gate pUC57 (amp) plasmid was generated by inserting a BbsI "multiple cloning site" (5'-GAATTCTTCCCGAGACGTTC-CAAGTCTTCATGAAGACTACAGGCGTCTCCCAG-GAAG CT-3' (SEQ ID NO: 653); directional BbsI recognition sequences are italicized and unique four base-pair overhangs for ligation are bolded) between the EcoRI and HindIII restriction sites. pUC57(amp) was chosen as a parent plasmid because it is relatively small in size and lacks backbone BbsI restriction sites and T7 and T3 promoter sequence. A feature included in the HTS plasmid is T7 and T3 promoter sequence flanking the ACE-tRNA cassette, giving universal primer binding sequences with comparable melting temperatures (T$_m$), ideal for per amplification. Using the NEB Golden Gate Assembly Tool (https://gold-engate.neb.com/editor) per primers were generated that annealed to the T7 and T3 flanking sequence and created unique four base-pair overhangs following cleavage of distal BbsI recognition sequence. The end result was the generation of four ACE-tRNA per products using universal per primers that could be "daisy-chained" through complementary four base-pair overhangs and ligated into the puc57 Golden Gate plasmid using a one-pot Golden Gate reaction. All clones were sequence verified.

Cell Culture, Protein Expression and Western Blot

HEK293T cells (ATCC, USA) were grown in standard grown media containing (% in v/v) 10% FBS (HiClone, USA), 1% Pen Strep, 1% L-Glut in high glucose DMEM (Gibco, USA) at 37° C., 5% CO2. cDNA was transfected at 75% confluency using Calfectin according to standard protocols (SignaGen Laboratories, USA). Following 36 hrs the cells were scraped and pelleted at 7,000 g for 8 min at 4° C.

in PBS supplemented with 0.5 μg/ml pepstatin, 2.5 μg/ml aprotinin, 2.5 μg/ml leupeptin, 0.1 mM PMSF, 0.75 mM benzamidine. For CFTR expressing cells, the cell pellet was vigorously doused in 100 mM sucrose, 150 mM NaCl, 1 mM DTT, 0.5 μg/ml pepstatin, 2.5 μg/ml aprotinin, 2.5 μg/ml leupeptin, 0.1 mM PMSF, 0.75 mM benzamidine, 50 mM Tris-HCL ph 7.4 and centrifuged at 100,000 g to separate total membranes from the soluble cytosolic proteins. Pellets were solubilized in a buffer containing 1% triton, 250 mM NaCl, 50 mM tris-HCl pH 7.4, and 0.5 μg/ml pepstatin, 2.5 μg/ml aprotinin, 2.5 μg/ml leupeptin, 0.1 mM PMSF, 0.75 mM benzamidine. Equal cell-lysate was loaded on a 3-15% separating gradient SDS-page with 4% stacking gel in the presence of 1% 2-mercaptoethanol, separated at 55 V O/N and transferred to 0.45 μM LF PVDF (Bio-Rad, USA). PVDF was immunoblotted using anti-CFTR antibody M3A7(1:1000; Millipore, USA) in 2% non-fat milk and imaged on LI-COR Odyssey Imaging System (LI-COR, USA). For HDH-His-Strep expressing cells, the cell pellet was vigorously dounce homogenized in 100 mM sucrose, 1 mM DTT, 1 mM EDTA, 20 mM tris-HCl pH 8.0, 0.5 μg/ml pepstatin, 2.5 μg/ml aprotinin, 2.5 μg/ml leupeptin, 0.1 mM PMSF and 0.75 mM benzamidine. The lysate was centrifuged at 100,000 g for 30 min at 4° C. The supernatant (soluble cellular protein) was separated on 4-12% Bis-Tris SDS-page acrylamide gels (ThermoFisher, USA) in the presence of 1% 2-mercaptoethanol, transferred to 0.22 μM LF PVDF (Bio-Rad, USA) and immunoblotted using anti-Strep antibody (1:5000; iba, Germany) in 2% non-fat milk and imaged on LI-COR Odyssey Imaging System (LI-COR, USA).

Mass Spectrometry

Fragmentation data on purified HDH-His-Strep protein were obtained at the University of Iowa Proteomics Facility. Briefly, HDH-His-Strep protein from the soluble fraction of the high-speed spin was passed through StrepTrap HP columns (GE Healthcare, Sweden) and washed with 5 column volumes of 100 mM sucrose, 1 mM DTT, 1 mM EDTA, 20 mM tris-HCl pH 8.0, 0.5 μg/ml pepstatin, 2.5 μg/ml aprotinin, 2.5 μg/ml leupeptin, 0.1 mM PMSF and 0.75 mM benzamidine. The protein was eluted in wash buffer supplemented with 10 mM d-desthbiotin and concentrated in 30 kDA cutoff Amicon-Ultra filtration columns (Millipore, USA). The concentrated protein was loaded on NuPage 4-12% Bis-Tris precast gels (Invitrogen, USA) and separated at 150V for 1.5 hrs. The gel was stained using a Pierce mass spec compatible silver stain kit (ThermoFisher Scientific, USA).

In-gel Trypsin Digestion. Briefly, the targeted protein bands from SDS-PAGE gel were manually excised, cut into 1 mm 3 pieces, and washed in 100 mM ammonium bicarbonate:acetonitrile (1:1, v/v) and 25 mM ammonium bicarbonate/acetonitrile (1:1, v/v), respectively to achieve complete destaining. The gel pieces were further treated with ACN, and dried via speed vac. After drying, gel pieces were reduced in 50 IA of 10 mM DTT at 56° C. for 60 min and then alkylated by 55 mM IAM for 30 min at room temperature. The gel pieces were washed with 25 mM ammonium bicarbonate:acetonitrile (1:1, v/v) twice to removed excess DTT and IAM. After drying, the gel pieces were placed on ice in 50 μL of trypsin solution at 10 ng/μL in 25 mM ammonium bicarbonate and incubated on ice for 60 min. Then, digestion was performed at 37° C. for 16 h. Peptide extraction was performed twice for 0.5 h with 100 μl 50% acetonitrile/0.2% formic acid. The combined extracts were concentrated in a Speed Vac to ~15 μl.

LC-MS/MS. The mass spectrometry data were collected using an Orbitrap Fusion Lumos mass spectrometer (Thermo Fisher Scientific, San Jose, CA) coupled to an Eksigent Ekspert™ nanoLC 425 System (Sciex). A Trap-Elute Jumper Chip (P/N:800-00389) and a coupled to a ⅟16" 10 port Valco directed loading performed by the gradient 1 pump and final elution (by the gradient 2 pump). The column assembly was designed as two tandem 75 μmx15 cm columns (ChromXP C18-CL, 3 μm 120A, Eksigent part of AB SCIEX) mounted in the Ekspert™ cHiPLC system. For each injection, an estimated 0.5 μg of total digest was loaded. Peptides were separated in-line with the mass spectrometer using a 120 min gradient composed of linear and static segments wherein Buffer A is 0.1% formic acid and B is 95% ACN, 0.1% Formic acid. The gradient begins first holds at 4% for 3 min then makes the following transitions (% B, min): (26, 48), (35, 58), (35, 64), (50, 72), (50, 78), (94, 84), (94, 96), (4, 100), (4, 120).

Tandem mass spectrometry on the LUMOS Orbitrap. Scan sequences began with a full survey (m/z 350-1500) acquired on an Orbitrap Fusion Lumos mass spectrometer (Thermo) at a resolution of 60,000 in the off axis Orbitrap segment (MS1). Every 3 seconds of the gradient MS1 scans were acquired during the 120 min gradient described above. The most abundant precursors were selected among 2-8 charge state ions at a 2.0 E5 threshold. Ions were dynamically excluded for 30 seconds if they were targeted twice in the prior 30 sec. Selected ions were isolated by a multi-segment quadrupole with a mass window on m/z 2, then sequentially subjected to both CID and HCD activation conditions in the IT and the ioin routing multipole respectively. The AGC target for CID was 4.0 E04, 35% collision energy, an activation Q of 0.25 and a 100 milliseconds maximum fill time. Targeted precursors were also fragmented by high energy collision-induced dissociation (HCD) at 40% collision energy, and an activation Q of 0.25. HCD fragment ions were analyzed using the Orbitrap (AGC 1.2 E05, maximum injection time 110 ms, and resolution set to 30,000 at 400 Th). Both MS2 channels were recorded as centroid and the MS1 survey scans were recorded in profile mode.

Proteomic Searches. Initial spectral searches were performed with Proteome Discoverer version 2.1.1.21 (ThermoFisher Scientific, USA) using Sequest HT. Spectra were also searched with Byonic search engine (Protein Metrics) ver. 2.8.2. Search databases were composed of the Uniprot KB for species 9606 (Human) downloaded Oct. 24, 2016 containing 92645 sequences and Uniprot KB for taxonomy 562 (*E. coli*) downloaded on Nov. 8, 2016 containing 10079 sequences. For Byonic searches, these two data bases were directly concatenated. In either search an equal number of decoy entries were created and searched simultaneously by reversing the original entries in the Target databases.

In vitro cRNA transcription. G5-42X$_{UGA}$, W1282X$_{UGA}$, and WT CFTR pGEMHE (Mense et al., 2006; PMID: 1703051) plasmids were linearized by 10x excess of NheI-HF restriction enzyme (site positioned 3' of coding region) (New England BioLabs, USA) for 3 hrs at 37° C. and purified using standard cDNA precipitation methods. All cRNAs were transcribed using the mMessage mMachine T7 Kit (ThermoFisher Scientific, USA). Purification of the cRNA from the transcription reaction was conducted on columns from the RNeasy Mini Kit (Qiagen, Germany). Concentration was determined by absorbance measurements at 260 nm and quality was confirmed on a 1% agarose gel (RNase-free). All cRNA was queued to 1 μg/ml before use and all results were generated from ≥2:2 cRNA preparations.

In vitro tRNA transcription. Trpchr17.trna39 and. Glychr19.trna2, the top performing Trp and Gly ACE-tRNAs, were transcribed in vitro using Cell Script 17-Scribe Standard RNA IVT Kit (CELLSCRIPT, USA). Equimolar concentration of T7 oligo (5'-taatacgactcactata-3') (SEQ ID NO: 656) was annealed to ACE-tRNA PAGE-purified Ultramers (20 ug; Integrated DNA Technologies, Coralville, IA) coding for the ACE-tRNA and preceded by a T7 promoter (italics), Importantly, the three terminal nucleotides containing CCA were included (bold).

```
Trpchr17.trna39 (3'->5'):
                                    (SEQ ID NO: 654)
TGGTGACCCCGACGTGATTTGAACACGCAACCTTCTGATCTGAAGTCA

GACGCGCTACCGTTGCGCCACGAGGCCTATAGTGAGTCGTATTA

Glychr19.trna2 (3'->5'):
                                    (SEQ ID NO: 655)
TGGTGCGTTGGCCGGGAATCGAACCCGGGTCAATGCTTTGAAGGAGCT

ATGCTAACCATATACCACCAACGCTATAGTGAGTCGTATTA
```

The total reaction volume was adjusted to 100 µl and the kit reagents were added in the following amounts: 10 µl of 1.0×T7-Scribe transcription buffer, 7.5 ul of each nucleotide (100 mM stocks), 10 µl of 100 mM Dithiothreitol, 2.5 µl ScriptGuard RNase Inhibitor, 10 µl T7-Scribe enzyme solution. After the reaction was incubated for 4-5 hr at 37° C., the DNA template was digested with 5 µl DNase (1 U/µl) provided with the kit for 30-60 min. The ACE-tRNA was extracted from the reaction with acidic phenol chloroform (5:1, pH 4.5) and precipitated with ethanol. The precipitates ACE-tRNA was pelleted, washed, dried and resuspended in 100 µl DEPC-treated water and further purified with Chroma Spin-30 columns (Clontech, USA). The procedure yielded roughly 100 µl of ~5 µg/µl ACE-tRNA. ACE-tRNAs were re-pelleted in ug aliquots, washed, lyophilized and stored at −80° C. until use. All results were generated from ≥2 ACE-tRNA preparations.

Ribosome Footprint Profiling Library preparation. HEK293 cells transiently transfected with ACE-tRNAs and control plasmid (puc57GG) were grown in standard grown media in the absence of Pen-Strep for 48 h. Libraries were prepared as described[55], with a few modifications. Briefly, cells were rapidly cooled by addition of ice-cold PBS, lysed in lysis buffer (20 mM Tris-HCl/pH7.4, 150 mM NaCl, 5 mM MgCl$_2$, 1 mM DTT, 1% (v/v) Triton X-100, and 25 U ml$^{-1}$ Turbo DNase I) for 10 min on ice, and triturated with ten times through a 26-G needle. After clearance by centrifugation at 16,000 g for 10 min at 4° C., the lysates were digested with 100 U RNase I (Ambion, USA) per A$_{260}$ lysate at room temperature for 45 min with gentle agitation prior to adding 200 U RiboLock RNase Inhibitor (Thermo Scientific). Ribosome protected mRNA fragments were then isolated by loading lysates onto a 1 M sucrose cushion prepared in modified polysome buffer (20 mM Tris-HCl/pH7.4, 150 mM NaCl, 8.5 mM MgCl$_2$, 0.5 mM DTT, 20 U ml$^{-1}$ RiboLock RNase Inhibitor) and centrifugated at 70,000 rpm at 4° C. for 2 h using a Beckmen TLA-110 rotor. Ribosome pellets containing mRNA footprints were extracted using TRIzol and separated on a denaturing 12% polyacrylamide gel containing 8 M urea. RNA fragments with sizes ranging from 26 to 34 nt were manually excised from the gel stained with SYBR Gold (Invitrogen) and isolated to generate the ribosome-protected fragment library. Contaminating rRNA fragments depleted using a Ribo-Zero kit (Illumina). 3' Oligonucleotide adaptor ligation, reverse transcription, circularization, and secondary rRNA depletion using biotinylated rRNA depletion oligos (Table 9) were performed as described[55]. Libraries were barcoded using indexing primers for each sample during PCR amplification. Barcoded libraries were then pooled with 3% PhiX (Illumina) and sequenced in an Illumina NextSeq 500 as per manufacturer protocol to typically generate 18-27 million reads per sample.

Ribosome Footprint Data analysis. Data files for each barcoded sample (minus adaptor sequence at 3' end) were first mapped to four rRNA sequences (RNA5S1; NR_023363, RNA5-8SN5; NR_003285, RNA18SN5; NR_003286, and RNA28SN5; NR_003287) using HISAT 2.0.3[56] to eliminate rRNA contaminant reads. The remaining reads were aligned to the sense stands of the longest transcript variant of each human gene (UCSC RefSeq GRCh38). Transcripts with 3'UTR length of at least 75 nt (18,101 sequences) were used for subsequence analysis. A maximum of two mismatches at the 5' end of reads was allowed. All multi-mapped reads were discarded. Fragment reads with lengths between 26 to 34 nt were defined as ribosome footprints and used for analysis. The 5' end nucleotide from each footprint was annotated and mapped on each transcript. Position of the ribosome A-site occupying the 16th-18th nucleotides of each footprint[57, 58] was used to infer the position of the ribosome on each transcript. RPKM (footprint Reads Per Kilobase of transcript per total Million-mapped reads) on each individual transcript (18,101 sequences) was calculated. Only transcripts with a minimum threshold of 5 RPKM in the coding sequence and 0.5 RPKM in 3'UTR region in two replicate libraries (254 transcripts in G418 and 495-748 transcripts in ACE-tRNAs) were included for analysis in FIG. 24A. For transcriptome-wide metagene plots in FIG. 2B, footprint counts for each nucleotide within the region from −35 to +65 nt relative to the first nucleotide of stop codon were normalized per total million-mapped reads. All transcripts (18,101 sequences) were used for mapping, and more than 5,200 transcripts were mapped to at least 1 footprint in the region of interest. Next, we examined the in vivo bioactivity of ACE-tRNAs Glychr19.trna2 and Trpchr17.trna39 to rescue PTC. The sequencing data was analyzed using Galaxy platform[59]. Graphs were generated using Prism 7 (GraphPad Software).

Generation of stable NLuc reporter cell lines. The cDNAs encoding pNLuc with tag, taa and tga stop codons at amino acid position 160 were inserted into AgeI and NotI restriction sites within the multiple cloning site of the retroviral vector pQCXIP (Clontech, USA) using Gibson Assembly (New England Biolabs, USA). PhoenixGP cells (PMID: 7690960) were cotransfected with pNLuc-STOP-pQCXIP and cmv-VSV-G (VSV-G envelope pseudotyping) plasmids using Calfectin (SignaGen Laboratories, USA) and placed in a 33° C. CO2-controlled (5%) cell incubator for 48 hr. The culture media (20 mls) containing retroviral particles was chilled to 4° C. and spun at 10,000 g to remove cell debris and filtered through a 0.45 um MCE-membrane syringe filter (Millipore, USA) onto two 10 cm dishes seeded with low-passage HEK293 cells at 30% confluency. Cell culture dishes were sealed with Parafilm and spun for 90 minutes at 3,500 g at 24° C. and placed in a 37° C. CO2 controlled (5%) cell culture incubator. Cells were selected 24 hr later with puromycin (1 ug/ml) until the control dish (no infection) showed complete cell death. Cells were monodispersed into 96-well plates using FACS and clonal populations were subsequently. Puromycin was not used to maintain selected clones during experimentation and standard DMEM media (DMEM—Dulbecco's Modified Eagle Medium-high glucose with L-glutamine supplemented with 10% FBS, 1% Pen/Step and 2 mM L-Glutamine; ThermoFisher, USA) was used in all studies. 2

RNA transfection. FIEK293 cells stably expressing pNLuc-UGA were plated at $1.4 \times 10^4$ cells/well in 96 well cell culture treated plates in Dulbecco's Modified Essential Medium (DMEM) supplemented with 10% FBS, 1% Pen/ Step and 2 mM L-Glutamine (Thermofisher, USA). 16-24 hr later the cells were transfected with ACE-tRNAs using lipofectamine 2000 (ThermoFisher Scientific, USA). Briefly, 3 µg of ACE-tRNA were suspended in 1500 of OptiMEM and 12 µl of Lipofectamine 2000 was mixed with 150 ul of OptiMEM. The volumes were combined, thoroughly mixed and incubated for 10 mins at RT. 75 ul of the transfection complex was added to each well. PTC suppression by ACE-tRNA transcripts was quantified as described above.

Expression in *Xenopus laevis* oocytes. *Xenopus laevis* oocytes (stage V and VI) were purchased from Ecocyte (Austin, TX). Prior to injection, each ACE-tRNA pellet was resuspended in 2 µl of ddH$_2$O and debris was pelleted at 21,000×g, 4° C. for 25 min. To determine dose response of ACE-tRNAs on CFTR channel rescue, serial dilutions were generated of ACE-tRNA aliquots (200, 100, 50, 25, 12.5, 6.25, 3.125 and 1.562 ng/oocyte) balanced in volume with ddH$_2$O. In all experiments 25 ng of CFTR cRNA was injected per oocyte and injection volumes were 50 nl. ddH$_2$O was used in no ACE-tRNA background control experiments. After injection, oocytes were kept in OR-3 (50% Leibovitz's medium, 250 mg/l gentamycin, 1 mM L-glutamine, 10 mM HEPES (pH 7.6)) at 18° C. for 36 hr.

Two-electrode voltage clamp (TENT) recordings. CFTR Cl$^-$ currents were recorded in ND96 bath solution that contained (in mM): 96 NaCl, 2 KCl, 1 MgCl$_2$, and 5 HEPES (pH 7.5) in the presence of a maximal CFTR activation cocktail, forskolin (10 µM; adenylate cyclase activator) and 3-isobutyl-1-methylxanthine (1 mM; phosphodiesterase inhibitor). Glass microelectrodes backfilled with 3 M KCl had resistances of 0.5-2 MΩ. Data were filtered at 1 kHz and digitized at 10 kHz using a Digidata 1322A controlled by the pClamp 9.2 software (Molecular Devices, USA). CFTR currents were elicited using 5 mV voltage steps from −60 to +35 mV using an OC-725C voltage clamp amplifier (Warner Instruments, USA). Oocytes where the CFTR Cl$^-$ current reversed positive of −20 mV were discarded. Clampfit 9.2 software was used for current analysis. All values are presented as mean±SEM.

Animals and in vivo imaging. Nu/J mice were purchased from Jackson labs. Animal experiments were approved by the Institutional Animal Care and Use Committee at the Wistar Institute (protocol number: 112762). Mice were treated by injecting 10-20 ug of DNA resuspended in 30 ul of water into the tibialis anterior muscle followed by electroporation. 10 ug pNano-TGA+10 ug Arg ACE-tRNA (right tibialis anterior) or 10 ug pNano-TGA+10 ug empty pUC57 (left tibialis anterior) were injected into 3 mice. As controls 3 other mice were injected with 10 ug pNano-WT (right tibialis anterior; positive control) or water (left tibialis anterior; negative control). The DNA was formulated with 333 IU/ml of hyaluronidase (Sigma). One minute after DNA injection, electroporation with CELLECTRA 3P device (Inovio Pharmaceuticals) was performed. Nanoluciferase activity was imaged in mice by injecting 100 ul of furimazine (40× dilution of Nano-Glo substrate) intraperitoneally and imaged mice on an IVIS Spectrum (Perkin Elmer) 5 minutes after injection. Imaging was with open filter and images were acquired at 40 seconds. The images were analyzed using Living Image Software (Perkin Elmer).

TABLE 9

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| | tRNAscan-SE ID | Sequence | SEQ ID NO |
|---|---|---|---|
| 1 | TrpTGAchr17.trna39 | GGCCTCGTGGCGCAACGGTAGCGCGTCTGACT*tca*GA TCAGAAGGt TGCGTGTTCAAATCACGTCGGGGTCA | 56 |
| 2 | TrpTGAchr17.trna10 | GACCTCGTGGCGCAATGGTAGCGCGTCTGACT*tca*GA TCAGAAGGt TGCGTGTTCAAGTCACGTCGGGGTCA | 57 |
| 3 | TrpTGAchr6.trna171 | GACCTCGTGGCGCAACGGTAGCGCGTCTGACT*tca*GA TCAGAAGGt TGCGTGTTCAAATCACGTCGGGGTCA | 58 |
| 4 | TrpTGAchr12.trna6 | GACCTCGTGGCGCAACGGTAGCGCGTCTGACT*tca*GA TCAGAAGGc TGCGTGTTCGAATCACGTCGGGGTCA | 59 |
| 5 | TrpTGAchr7.trna3 | GACCTCGTGGCGCAACGGCAGCGCGTCTGACT*tca*GA TCAGAAGGt TGCGTGTTCAAATCACGTCGGGGTCA | 60 |
| 6 | TrpTGAchr7.trna31 | GGCCTCATGGTGCAACAGTAGTGTGTCTGACT*tca*GA TCAGAAGGt TGTATGTTCAAATCACGTAGGGGTCA | 61 |
| 1 | TrpTAGchr17.trna39 | GGCCTCGTGGCGCAACGGTAGCGCGTCTGACT*cta*GA TCAGAAGGt TGCGTGTTCAAATCACGTCGGGGTCA | 62 |
| 2 | TrpTAGchr17.trna10 | GACCTCGTGGCGCAATGGTAGCGCGTCTGACT*cta*GA TCAGAAGGt TGCGTGTTCAAGTCACGTCGGGGTCA | 63 |
| 3 | TrpTAGchr6.trna171 | GACCTCGTGGCGCAACGGTAGCGCGTCTGACT*cta*GAT CAGAAGGt TGCGTGTTCAAATCACGTCGGGGTCA | 64 |
| 4 | TrpTAGchr12.trna6 | GACCTCGTGGCGCAACGGTAGCGCGTCTGACT*cta*GA TCAGAAGGc TGCGTGTTCGAATCACGTCGGGGTCA | 65 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 5 | TrpTAGchr7.trna3 | GACCTCGTGGCGCAACGGCAGCGCGTCTGACT*cta*GA TCAGAAGGtTGCGTGTTCAAATCACGTCGGGGTCA | 66 |
| 6 | TrpTAGchr7.trna31 | GGCCTCATGGTGCAACAGTAGTGTGTCTGACT*cta*GA TCAGAAGGtTGTATGTTCAAATCACGTAGGGGTCA | 67 |
| 1 | GlyTGAchr1.trna122 | GCATTGGTGGTTCAGTGGTAGAATTCTCGCCT*tca*AC GCGGGAGaCCCGGGTTCAATTCCCGGCCAATGCA | 68 |
| 2 | GlyTGAchr2.trna25 | GCGCCGCTGGTGTAGTGGTATCATGCAAGATT*tca*aA TTCTTGCGaCCCGGGTTCGATTCCCGGGCGGCGCA | 69 |
| 3 | GlyTGAchr17.trna11 | GCATTGGTGGTTCAATGGTAGAATTCTCGCCT*tca*AC GCAGGAGaCCCAGGTTCGATTCCTGGCCAATGCA | 70 |
| 4 | GlyTGAchr1.trna120 | GCGTTGGTGGTTTAGTGGTAGAATTCTCGCCT*tca*AT GCGGGAGaCCCGGGTTCAATTCCCGGCCACTGCA | 71 |
| 5 | GlyTGAchr1.trna2 | GCCTTGGTGGTGCAGTGGTAGAATTCTCGCCT*tca*AC GTGGGAGaCCCGGGTTCAATTCCCGGCCAATGCA | 72 |
| 6 | GlyTGAchr1.trna83 | GGTGGTTCAGTGGTAGAATTCTCGCCT*tca*ACGCGGG AGaCCCGGGTTTAATTCCCGGTCA | 73 |
| 7 | GlyTGAchr2.trna1 | GTGGTCTAGTGGTTAGGATTCAGCGCT*tca*ACCGCCG CAGCCCGGGTTCGATTCCCGGtCA | 74 |
| 8 | GlyTGAchr1.random. trna2 | GCGTCAGTGGTTTAGTGGTGGAATTCCTGCCT*tca*AT GCACGAGATCCGTGTTCAACTCCTGGTTGGTGCA | 75 |
| 9 | GlyTGAchr1.trna102 | GCGTCAGTGgTTTTAGTGGTGGAATTCCTGCCT*tca*A TGCACGAGATCCGTGTTCAACTCCTGGTTGGTGCA | 76 |
| 10 | GlyTGAchr1.trna16 | GCGTTGGCAGTTCAGTGGTAGAATTCTCGCCT*tca*AC CCGGGAGaCCTGGATTCCATTTCCGGCAAATGCA | 77 |
| 11 | GlyTGAchr1.trna34 | GCATGGGTGGTTCAGTGGTAGAATTCTCGCCT*tca*AC GCGGGAGGCCCGGGTTCGATTCCCGGCCCATGCA | 78 |
| 12 | GlyTGAchr1.trna61 | GCATTGGTGGTTCAGTGGTAGAATTCTCGCCT*tca*AC GCGGGAGGCCCGGGTTCGATTCCCGGCCAATGCA | 79 |
| 13 | GlyTGAchr16.trna25 | GCATTGGTGGTTCAGTGGTAGAATTCTCGCCT*tca*AC GCGGGAGGCCCGGGTTTGATTCCCGGCCAGTGCA | 80 |
| 14 | GlyTGAchr1.trna42 | GCATAGGTGGTTCAGTGGTAGAATTCTTGCCT*tca*AC GCAGGAGGCCCAGGTTTGATTCCTGGCCCATGCA | 81 |
| 15 | GlyTGAchr16.trna19 | GCATTGGTGGTTCAGTGGTAGAATTCTCGCCT*tca*AT GCGGGCGGCCGGGCTTCGATTCCTgGCCAATGCA | 82 |
| 16 | GlyTGAchr6.trna80 | GCATGGGTGATTCAGTGGTAGAATTTTCACCT*tca*AT GCAGGAGGTCCAGGTTCATTTCCTGGCCTATGCA | 83 |
| 17 | GlyTGAchr19.trna2 | GCGTTGGTGGTATAGTGGTtAGCATAGCTGCCT*tca*A AGCAGTTGaCCCGGGTTCGATTCCCGGCCAACGCA | 84 |
| 18 | GlyTGAchr1.trna107 | GCGTTGGTGGTATAGTGGTgAGCATAGCTGCCT*tca*A AGCAGTTGaCCCGGGTTCGATTCCCGGCCAACGCA | 85 |
| 19 | GlyTGAchr17.trna9 | GCGTTGGTGGTATAGTGGTaAGCATAGCTGCCT*tca*A AGCAGTTGaCCCGGGTTCGATTCCCGGCCAACGCA | 86 |
| 20 | GlyTGAchr1.trna75 | GCGTTGGTGGTATAGTGGTgAGCATAGTTGCCT*tca*A AGCAGTTGaCCCGGGCTCGATTCCCGCCCAACGCA | 87 |
| 21 | GlyTGAchr1.trna75-mod | GCGTTGGTGGTATAGTGGTgAGCATAGTTGCCT*tca*A AGCAGTTGaCCCGGGCTCGATTCCCGgCCAACGCA | 88 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 1 | ArgTGAchr6.trna6 | GGGCCAGTGGCGCAATGGAtAACGCGTCTGACTtcaG ATCAGAAGAtTCCAGGTTCGACTCCTGGCTGGCTCG | 89 |
| 2 | ArgTGAchr3.trna8 | GGGCCAGTGGCGCAATGGAtAACGCGTCTGACTtcaG ATCAGAAGAtTCTAGGTTCGACTCCTGGCTGGCTCG | 90 |
| 3 | ArgTGAchr6.trna115 | GGCCGCGTGGCCTAATGGAtAAGGCGTCTGATTtcaG ATCAGAAGAtTGAGGGTTCGAGTCCCTTCGTGGTCG | 91 |
| 4 | ArgTGAchr17.trna21 | GACCCAGTGGCCTAATGGAtAAGGCATCAGCCTtcaG AGCTGGGGAtTGTGGGTTCGAGTCCCATCTGGGTCG | 92 |
| 5 | ArgTGAchr17.trna16 | GCCCCAGTGGCCTAATGGAtAAGGCACTGGCCTtcaA AGCCAGGGAtTGTGGGTTCGAGTCCCACCTGGGGTA | 93 |
| 6 | ArgTGAchr17.trna19 | GCCCCAGTGGCCTAATGGAtAAGGCACTGGCCTtcaA AGCCAGGGAtTGTGGGTTCGAGTCCCACCTGGGGTG | 94 |
| 7 | ArgTGAchr16.trna3 | GCCCCGGTGGCCTAATGGAtAAGGCATTGGCCTtcaA AGCCAGGGAtTGTGGGTTCGAGTCCCACCCGGGGTA | 95 |
| 8 | ArgTGAchr7.trna5 | GCCCCAGTGGCCTAATGGAtAAGGCATTGGCCTtcaA AGCCAGGGAtTGTGGGTTCGAGTCCCATCTGGGGTG | 96 |
| 9 | ArgTGAchr16.trna13 | GCCCCAGTGGCCTGATGGAtAAGGTACTGGCCTtcaA AGCCAGGGAtTGTGGGTTCGAGTTCCACCTGGGGTA | 97 |
| 10 | ArgTGAchr15.trna4 | GGCCGCGTGGCCTAATGGAtAAGGCGTCTGACTtcaG ATCAGAAGAtTGCAGGTTCGAGTCCTGCCGCGGTCG | 98 |
| 11 | ArgTGAchr6.trna4 | GACCACGTGGCCTAATGGAtAAGGCGTCTGACTtcaG ATCAGAAGAtTGAGGGTTCGAATCCCTCCGTGGTTA | 99 |
| 12 | ArgTGAchr17.trna17 | GACCGCGTGGCCTAATGGAtAAGGCGTCTGACTtcaG ATCAGAAGAtTGAGGGTTCGAGTCCCTTCGTGGTCG | 100 |
| 13 | ArgTGAchr6.trna3 | GACCACGTGGCCTAATGGAtAAGGCGTCTGACTtcaG ATCAGAAGAtTGAGGGTTCGAATCCCTTCGTGGTTA | 101 |
| 14 | ArgTGAchr6.trna125 | GACCACGTGGCCTAATGGAtAAGGCGTCTGACTtcaG ATCAGAAGAtTGAGGGTTCGAATCCCTTCGTGGTTG | 102 |
| 15 | ArgTGAchr9.trna5 | GGCCGTGTGGCCTAATGGAtAAGGCGTCTGACTtcaG ATCAAAAGAtTGCAGGTTTGAGTTCTGCCACGGTCG | 103 |
| 16 | ArgTGAchr1.trna10 | GGCTCCGTGGCGCAATGGAtAGCGCATTGGACTtcaA gaggctgaaggcATTCAAAGGtTCCGGGTTCGAGTCC CGGCGGAGTCG | 104 |
| 17 | ArgTGAchr1.trna10/ nointron | GGCTCCGTGGCGCAATGGAtAGCGCATTGGACTtcaA ATTCAAAGGtTCCGGGTTCGAGTCCCGGCGGAGTCG | 105 |
| 18 | ArgTGAchr17.trna3 | GGCTCTGTGGCGCAATGGAtAGCGCATTGGACTtcaA gtgacgaatagagcaATTCAAAGGtTGTGGGTTCGAA TCCCACCAGAGTCG | 106 |
| 19 | ArgTGAchr17.trna3/ nointron | GGCTCTGTGGCGCAATGGAtAGCGCATTGGACTtcaA ATTCAAAGGtTGTGGGTTCGAATCCCACCAGAGTCG | 107 |
| 20 | ArgTGAchr9.trna6 | GGCTCTGTGGCGCAATGGAtAGCGCATTGGACTtcaA gctgagcctagtgtggtcATTCAAAGGtTGTGGGTTC GAGTCCCACCAGAGTCG | 108 |
| 21 | ArgTGAchr9.trna6/ nointron | GGCTCTGTGGCGCAATGGAtAGCGCATTGGACTtcaA ATTCAAAGGtTGTGGGTTCGAGTCCCACCAGAGTCG | 109 |
| 22 | ArgTGAchr11.trna3 | GGCTCTGTGGCGCAATGGAtAGCGCATTGGACTtcaA gatagttagagaaATTCAAAGGtTGTGGGTTCGAGTC CCACCAGAGTCG | 110 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 23 | ArgTGAchr1.trna79 | GTCTCTGTGGCGCAATGGA*cg*AGCGCGCTGGACT*tca*<br>AATCCAGAGG*t*TCCGGGTTCGAGTCCCGGCAGAGATG | 111 |
| 24 | ArgTGAchr6.trna52 | GGCTCTGTGGCGCAATGGA*t*AGCGCATTGGACT*tca*A<br>gcctaaatcaagagATTCAAAGG*t*TGCGGGTTCGAGT<br>CCCTCCAGAGTCG | 112 |
| 25 | ArgTGAchr6.trna52/<br>nointron | GGCTCTGTGGCGCAATGGA*t*AGCGCATTGGACT*tca*A<br>ATTCAAAGG*t*TGCGGGTTCGAGTCCCTCCAGAGTCG | 113 |
| 26 | ArgTGAchr5.trna4 | GGCAGCATAGCAGAGTGGT*t*CAGGTTACAGGT*tca*AG<br>ATGTAAACTGAGTTCAAATCCCAGTTCTGCCA | 114 |
| 1 | GlnTAGnmt-tRNA-Gln<br>chr10.trna6 | TGGTGTAATAGGTAGCACAGAGAATT*cta*GATTCTCA<br>GGGGTAGGTTCAATTCCTAT | 115 |
| 2 | GlnTAGnmt-tRNA-Gln<br>chrX.trna1 | TAGGACATGGTGTGATAGGTAGCATGGAGAATT*cta*G<br>ATTCTCAGGGGTAGGTTCAATTCCTACAGTTCTAG | 116 |
| 3 | GlnTAGnmt-tRNA-Gln<br>chr7.trna32 | TAGGACGTGGTGTGATAGGTAGCATGGGGAATT*cta*G<br>ATTCTCAGGGGTGGGTTCAATTCCTATAGTTCTAG | 117 |
| 4 | GlnTAGnmt-tRNA-Gln<br>chr7.trna7 | TAGGACGTGGTGTAGTAGGTAGCATGGAGAATG*cta*A<br>ATTCTCAGGGGTAGGTTCAATTCCTATAGTTCTAG | 118 |
| 5 | GlnTAGnmt-tRNA-Gln<br>chr2.trna24 | TAGGACATGGTGTAATAGGTAGAATGGAGAATT*cta*A<br>ATTCTCAGGGGTAGGTTCAATTCCTATAGTTCTAG | 119 |
| 6 | GlnTAGnmt-tRNA-Gln<br>chr3.trna7 | TAGGATGTGGTGTATTAGGTAGCACAGAGAATT*cta*G<br>ATTCTCAGGGGTAGGTTCGATTCCTATAATTCTAC | 120 |
| 7 | GlnTAGnmt-tRNA-Gln<br>chr16.trna15 | TAGGACTTGGTGTAATGGGTAGCACAGAGAATT*cta*G<br>ATTCTCAGGGGTGGGTTCAATTCCTTTCGTCCTAG | 121 |
| 8 | GlnTAGnmt-tRNA-Gln<br>chr12.trna15 | TCTAGGA*t*gTGGTGTGATAGGTAGCATGGAGAATT*ct*<br>*a*GATTCTCAGGGGTAGGTTCAATTCCTATa*TT*CTAGA<br>A | 122 |
| 9 | GlnTAGnmt-tRNA-Gln<br>chr2.trna21 | TAGGACGTGGTGTGATAGGTAGCATGGAGAATT*cta*G<br>ATTCTCAGGGATGGGTTCAATTCCTATAGTCCTAG | 123 |
| 10 | GlnTAGnmt-tRNA-Gln<br>chr2.trna9 | TAGGACGTGGTGTGATAGGTAGCACGGAGAATT*cta*G<br>ATTCTCAGGGATGGGTTCAATTCCTGTAGTTCTAG | 124 |
| 11 | GlnTAGchr6.trna1 | GGTTCCATGGTGTAATGGT*t*AGCACTCTGGACT*cta*A<br>ATCCAGCGa*t*TCCGAGTTCAAATCTCGGTGGAACCT | 125 |
| 12 | GlnTAGchr1.trna104 | GGTTCCATGGTGTAATGGT*g*ACCACTTTGGACT*cta*A<br>ATACAGTGATCAGAGTTCAAGTCTCACTGGAACCT | 126 |
| 13 | GlnTAGchr1.trna28 | GGTTCCATGGTGTAATGGT*g*AGGGCTTTGGACT*cta*A<br>CTACAGT*g*a*t*CAGAGTTCAAGTCTCAGTGGGACCT | 127 |
| 14 | GlnTAGchr12.trna3 | GGTTCCATGGTGTAATGGT*a*AGCACCCTGGACT*cta*A<br>ATCCAGCA*a*CCAGAGTTCCAGTCTCAGCG*t*GGACCT | 128 |
| 15 | GlnTAGchr5.trna23 | GGTAGTGTAGTCTACTGGTTAAACGCTTGG*g*CT*cta*A<br>CATTAA*c*G*t*CCTGGGTTCAAATCCCAGCTTTGTCA | 129 |
| 16 | GlnTAGchr6.trna147 | GGTTCCATGGTGTAATGGT*t*AGCACTCTGGACT*cta*A<br>ATCCAGCGa*t*CCGAGTTCAAGTCTCGGTGGAACCT | 130 |
| 17 | GlnTAGchr1.trna17 | GGTTCCATGGTGTAATGGT*g*AGCACTCTGGACT*cta*A<br>ATCCAGCGa*t*CCGAGTTCGAGTCTCGGTGGAACCT | 131 |
| 18 | GlnTAGchr1.trna101 | GGTTCCATGGTGTAATGGT*a*AGCACTCTGGACT*cta*A<br>ATCCAGCGa*t*CCGAGTTCGAGTCTCGGTGGAACCT | 132 |
| 19 | GlnTAGchr6.trna42 | GGTTCCATGGTGTAATGGT*t*AGCACTCTGGACT*cta*A<br>ATCCGGTAa*t*CCGAGTTCAAATCTCGGTGGAACCT | 133 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 20 | GlnTAGchr6.trna132 | GGCCCCATGGTGTAATGGTcAGCACTCTGGACT*cta*A ATCCAGCGaTCCGAGTTCAAATCTCGGTGGGACCC | 134 |
| 21 | GlnTAGchr1.trna23 | GGTTCCATGGTGTAATGGTaAGCACTCTGGACT*cta*A ATCCAGCCATCTGAGTTCGAGTCTCTGTGGAACCT | 135 |
| 22 | GlnTAGchr1.trna111 | GGTTCCATGGTGTAATGGTgAGCACTTTGGACT*cta*A ATACAGTGATCAGAGTTCAAGTCTCACTGGGACCT | 136 |
| 23 | GlnTAGchr1.trna24 | GGTTCCATGgGTTAATGGTgAGCACCCTGGACT*cta*A ATCAAGCGaTCCGAGTTCAAATCTCGGTGGTACCT | 137 |
| 24 | GlnTAGchr19.trna4 | GTTTCCATGGTGTAATGGTgAGCACTCTGGACT*cta*A ATCCAGAAATACATTCAAAGAATTAAGAACA | 138 |
| 25 | GlnTAGchr17.trna14 | GGTCCCATGGTGTAATGGTtAGCACTCTGGACT*cta*A ATCCAGCGaTCCGAGTTCAAATCTCGGTGGGACCT | 139 |
| 26 | GlnTAGchr6.trna63 | GGTCCCATGGTGTAATGGTtAGCACTCTGGACT*cta*A ATCCAGCAaTCCGAGTTCGAATCTCGGTGGGACCT | 140 |
| 27 | GlnTAGchr6.trna175 | GGCCCCATGGTGTAATGGTtAGCACTCTGGACT*cta*A ATCCAGCGaTCCGAGTTCAAATCTCGGTGGGACCT | 141 |
| 28 | GlnTAGchr6.trna82 | GGTCCCATGGTGTAATGGTtAGCACTCTGGGCT*cta*A ATCCAGCAaTCCGAGTTCGAATCTTGGTGGGACCT | 142 |
| 29 | GlnTAGchr2.trna26 | GGCTGTGTACCTCAGTGGGcAAGGGTATGGACT*cta*A AGCCAGACTaTTTGGGTTCAAATCCCAGCTTGGCCT | 143 |
| 30 | GlnTAGchr4.trna4 | GACCATGTGGCCTAAGGGAaAAGACATCTCACT*cta*G GTCAGAAGAtTGAGGGTTCAAGTCCTTTCATGGTCA | 144 |
| 31 | GlnTAGchr8.trna10 | GGTACAGTGTTAAAGGGGagaAAAATTGCTGACT*cta* AATaCAGTAGaCCTAGGTTTGAATCCTGGCTTTACCA | 145 |
| 1 | GlnTAAnmt-tRNA-Gln chr10.trna6 | TGGTGTAATAGGTAGCACAGAGAATT*tta*GATTCTCA GGGGTAGGTTCAATTCCTAT | 146 |
| 2 | GlnTAAnmt-tRNA-Gln chrX.trna1 | TAGGACATGGTGTGATAGGTAGCATGGAGAATT*tta*G ATTCTCAGGGGTAGGTTCAATTCCTACAGTTCTAG | 147 |
| 3 | GlnTAAnmt-tRNA-Gln chr7.trna32 | TAGGACGTGGTGTGATAGGTAGCATGGGGAATT*tta*G ATTCTCAGGGGTGGGTTCAATTCCTATAGTTCTAG | 148 |
| 4 | GlnTAAnmt-tRNA-Gln chr7.trna7 | TAGGACGTGGTGTAGTAGGTAGCATGGAGAATG*tta*A ATTCTCAGGGGTAGGTTCAATTCCTATAGTTCTAG | 149 |
| 5 | GlnTAAnmt-tRNA-Gln chr2.trna24 | TAGGACATGGTGTAATAGGTAGAATGGAGAATT*tta*A ATTCTCAGGGGTAGGTTCAATTCCTATAGTTCTAG | 150 |
| 6 | GlnTAAnmt-tRNA-Gln chr3.trna7 | TAGGATGTGGTGTATTAGGTAGCACAGAGAATT*tta*G ATTCTCAGGGGTAGGTTCGATTCCTATAATTCTAC | 151 |
| 7 | GlnTAAnmt-tRNA-Gln chr16.trna15 | TAGGACTTGGTGTAATGGGTAGCACAGAGAATT*tta*G ATTCTCAGGGGTGGGTTCAATTCCTTTCGTCCTAG | 152 |
| 8 | GlnTAAnmt-tRNA-Gln chr12.trna15 | TCTAGGAt*g*TGGTGTGATAGGTAGCATGGAGAATT*tt a*GATTCTCAGGGGTAGGTTCAATTCCTATa*TTCTAGA A | 153 |
| 9 | GlnTAAnmt-tRNA-Gln chr2.trna21 | TAGGACGTGGTGTGATAGGTAGCATGGAGAATT*tta*G ATTCTCAGGGATGGGTTCAATTCCTATAGTCCTAG | 154 |
| 10 | GlnTAAnmt-tRNA-Gln chr2.trna9 | TAGGACGTGGTGTGATAGGTAGCACGGAGAATT*tta*G ATTCTCAGGGATGGGTTCAATTCCTGTAGTTCTAG | 155 |
| 11 | GlnTAAchr6.trna1 | GGTTCCATGGTGTAATGGTtAGCACTCTGGACT*tta*A ATCCAGCGaTCCGAGTTCAAATCTCGGTGGAACCT | 156 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 12 | GlnTAAchr1.trna104 | GGTTCCATGGTGTAATGGTgACCACTTTGGACT*tta*A ATACAGTGATCAGAGTTCAAGTCTCACTGGAACCT | 157 |
| 13 | GlnTAAchr1.trna28 | GGTTCCATGGTGTAATGGTgAGGGCTTTGGACT*tta*A CTACAGTGaTCAGAGTTCAAGTCTCAGTGGGACCT | 158 |
| 14 | GlnTAAchr12.trna3 | GGTTCCATGGTGTAATGGTaAGCACCCTGGACT*tta*A ATCCAGCAaCCAGAGTTCCAGTCTCAGCGtGGACCT | 159 |
| 15 | GlnTAAchr5.trna23 | GGTAGTGTAGTCTACTGGTTAAACGCTTGGgCT*tta*A CATTAAcGtCCTGGGTTCAAATCCCAGCTTTGTCA | 160 |
| 16 | GlnTAAchr6.trna147 | GGTTCCATGGTGTAATGGTtAGCACTCTGGACT*tta*A ATCCAGCGaTCCGAGTTCAAGTCTCGGTGGAACCT | 161 |
| 17 | GlnTAAchr1.trna17 | GGTTCCATGGTGTAATGGTgAGCACTCTGGACT*tta*A ATCCAGCGaTCCGAGTTCGAGTCTCGGTGGAACCT | 162 |
| 18 | GlnTAAchr1.trna101 | GGTTCCATGGTGTAATGGTaAGCACTCTGGACT*tta*A ATCCAGCGaTCCGAGTTCGAGTCTCGGTGGAACCT | 163 |
| 19 | GlnTAAchr6.trna42 | GGTTCCATGGTGTAATGGTtAGCACTCTGGACT*tta*A ATCCGGTAaTCCGAGTTCAAATCTCGGTGGAACCT | 164 |
| 20 | GlnTAAchr6.trna132 | GGCCCCATGGTGTAATGGTcAGCACTCTGGACT*tta*A ATCCAGCGaTCCGAGTTCAAATCTCGGTGGGACCC | 165 |
| 21 | GlnTAAchr1.trna23 | GGTTCCATGGTGTAATGGTaAGCACTCTGGACT*tta*A ATCCAGCCATCTGAGTTCGAGTCTCTGTGGAACCT | 166 |
| 22 | GlnTAAchr1.trna111 | GGTTCCATGGTGTAATGGTgAGCACTTTGGACT*tta*A ATACAGTGATCAGAGTTCAAGTCTCACTGGGACCT | 167 |
| 23 | GlnTAAchr1.trna24 | GGTTCCATGgGTTAATGGTgAGCACCCTGGACT*tta*A ATCAAGCGaTCCGAGTTCAAATCTCGGTGGTACCT | 168 |
| 24 | GlnTAAchr19.trna4 | GTTTCCATGGTGTAATGGTgAGCACTCTGGACT*tta*A ATCCAGAAATACATTCAAAGAATTAAGAACA | 169 |
| 25 | GlnTAAchr17.trna14 | GGTCCCATGGTGTAATGGTtAGCACTCTGGACT*tta*A ATCCAGCGaTCCGAGTTCAAATCTCGGTGGGACCT | 170 |
| 26 | GlnTAAchr6.trna63 | GGTCCCATGGTGTAATGGTtAGCACTCTGGACT*tta*A ATCCAGCAaTCCGAGTTCGAATCTCGGTGGGACCT | 171 |
| 27 | GlnTAAchr6.trna175 | GGCCCCATGGTGTAATGGTtAGCACTCTGGACT*tta*A ATCCAGCGaTCCGAGTTCAAATCTCGGTGGGACCT | 172 |
| 28 | GlnTAAchr6.trna82 | GGTCCCATGGTGTAATGGTtAGCACTCTGGGCT*tta*A ATCCAGCAaTCCGAGTTCGAATCTTGGTGGGACCT | 173 |
| 29 | GlnTAAchr2.trna26 | GGCTGTGTACCTCAGTGGGcAAGGGTATGGACT*tta*A AGCCAGACTaTTTGGGTTCAAATCCCAGCTTGGCCT | 174 |
| 30 | GlnTAAchr4.trna4 | GACCATGTGGCCTAAGGGAaAAGACATCTCACT*tta*G GTCAGAAGAtTGAGGGTTCAAGTCCTTTCATGGTCA | 175 |
| 31 | GlnTAAchr8.trna10 | GGTACAGTGTTAAAGGGGagaAAAATTGCTGACT*tta* AATaCAGTAGaCCTAGGTTTGAATCCTGGCTTTACCA | 176 |
| 1 | GluTAAchr1.trna106 | TCCCTGGTGGTCTAGTGGTtAGGATTCGGCGCT*tta*A CCGCCGCGGCCCGGGTTCGATTCCCGGTCAGGGAA | 177 |
| 2 | GluTAAchr1.trna55 | TCCCTGGTGGTCTAGTGGTtAGGATTCGGCGCT*tta*A CCGCCGCGGCCCGGGTTCGATTCCCGGTCAGGAAA | 178 |
| 3 | GluTAAchr13.trna3 | CCCCTGGTGGTCTAGTGCTtAGGATTCGGTGCT*tta*A CCGCTGCTGCCTGCGTTCGATTCCCGGTCAGGGAA | 179 |
| 4 | GluTAAchr8.trna1 | TCCTTGATGTCTAGTGGTtAGGATTTGGTGCT*tta*AC TGCAGCAGCCTGGGTTCATTTCTCAGTCAGGGAA | 180 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 5 | GluTAAchr2.trna18 | TCCCATATGGTCTAGCGGT*t*AGGATTCCTGGTT*tta*A CCCAGGTGGCCCGGGTTCGACTCCCGGTATGGGAA | 181 |
| 6 | GluTAAchr1.trna92 | TCCGTGGTGGTCTAGTGGC*t*AGGATTCGGCGCT*tta*A CCGCCTGCAGCTCGAGTTCGATTCCTGGTCAGGGAA | 182 |
| 7 | GluTAAchr14.trna15 | CCCTGTGGTCTAGTGGC*t*AAGACTTTGTGCT*tta*ATT GCTGCA*t*CCTAGGTTCAATTCCCAGTCAGGGA | 183 |
| 8 | GluTAAchr13.trna2 | TCCCACATGGTCTAGCGGT*t*AGGATTCCTGGTT*tta*A CCCAGGCGGCCCGGGTTCGACTCCCGGTGTGGGAA | 184 |
| 9 | GluTAAchr1.trna5 | TCCCTGGTGGTCTAGTGGC*t*AGGATTCGGCGCT*tta*A CCGCCGCGGCCCGGGTTCGATTCCCGGCCAGGGAA | 185 |
| 10 | GluTAAchr1.trna123 | TCCCTGGTGGTCTAGTGGC*t*AGGATTCGGCGCT*tta*A CCGCCGCGGCCCGGGTTCGATTCCCGGTCAGGGAA | 186 |
| 11 | GluTAAchr1.trna45 | GCGTTGGTGGTGTAGTGGT*g*AGCACAGCTGCCT*tta*A AGCAGTTA*a*CGCGGGTTCGATTCCCGGGTAACGAA | 187 |
| 12 | GluTAAchr1.trna99 | TCCTTGGTGGTCTAGTGGC*t*AGGATTCGGTGCT*tta*A CCTGTGCGGCCCGGGTTCAATTCCCGATGAAGGAA | 188 |
| 13 | GluTAAchr1.trna95 | TGTCTGGTGGTCAAGTGGC*t*AGGATTTGGCGCT*tta*A CTGCCGCGGCCCGCGTTCGATTCCCGGTCAGGGAA | 189 |
| 14 | GluTAAchr1.trna86 | TCCCTGGTGGTCTAGTGGC*t*AGGATTCGGCGCT*tta*A CCGCCTGCAGCTCGAGTTCGATTCCTGGTCAGGGAA | 190 |
| 15 | GluTAAchr2.trna16 | GCAATGGTGGTTCAGTGGTAGAATTCTCGCCT*tta*AC ACAGGAGa*C*CCGGGTTCAATTCCTGACCCATGTA | 191 |
| 1 | GluTAGchr1.trna106 | TCCCTGGTGGTCTAGTGGT*t*AGGATTCGGCGCT*cta*A CCGCCGCGGCCCGGGTTCGATTCCCGGTCAGGGAA | 192 |
| 2 | GluTAGchr1.trna55 | TCCCTGGTGGTCTAGTGGT*t*AGGATTCGGCGCT*cta*A CCGCCGCGGCCCGGGTTCGATTCCCGGTCAGGAAA | 193 |
| 3 | GluTAGchr13.trna3 | CCCCTGGTGGTCTAGTGCT*t*AGGATTCGGTGCT*cta*A CCGCTGCTGCCTGCGTTCGATTCCCGGTCAGGGAA | 194 |
| 4 | GluTAGchr8.trna1 | TCCTTGATGTCTAGTGGT*t*AGGATTTGGTGCT*cta*AC TGCAGCAGCCTGGGTTCATTTCTCAGTCAGGGAA | 195 |
| 5 | GluTAGchr2.trna18 | TCCCATATGGTCTAGCGGT*t*AGGATTCCTGGTT*cta*A CCCAGGTGGCCCGGGTTCGACTCCCGGTATGGGAA | 196 |
| 6 | GluTAGchr1.trna92 | TCCGTGGTGGTCTAGTGGC*t*AGGATTCGGCGCT*cta*A CCGCCTGCAGCTCGAGTTCGATTCCTGGTCAGGGAA | 197 |
| 7 | GluTAGchr14.trna15 | CCCTGTGGTCTAGTGGC*t*AAGACTTTGTGCT*cta*ATT GCTGCA*t*CCTAGGTTCAATTCCCAGTCAGGGA | 198 |
| 8 | GluTAGchr13.trna2 | TCCCACATGGTCTAGCGGT*t*AGGATTCCTGGTT*cta*A CCCAGGCGGCCCGGGTTCGACTCCCGGTGTGGGAA | 199 |
| 9 | GluTAGchr1.trna5 | TCCCTGGTGGTCTAGTGGC*t*AGGATTCGGCGCT*cta*A CCGCCGCGGCCCGGGTTCGATTCCCGGCCAGGGAA | 200 |
| 10 | GluTAGchr1.trna123 | TCCCTGGTGGTCTAGTGGC*t*AGGATTCGGCGCT*cta*A CCGCCGCGGCCCGGGTTCGATTCCCGGTCAGGGAA | 201 |
| 11 | GluTAGchr1.trna45 | GCGTTGGTGGTGTAGTGGT*g*AGCACAGCTGCCT*cta*A AGCAGTTA*a*CGCGGGTTCGATTCCCGGGTAACGAA | 202 |
| 12 | GluTAGchr1.trna99 | TCCTTGGTGGTCTAGTGGC*t*AGGATTCGGTGCT*cta*A CCTGTGCGGCCCGGGTTCAATTCCCGATGAAGGAA | 203 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 13 | GluTAGchr1.trna95 | TGTCTGGTGGTCAAGTGGC*t*AGGATTTGGCGCT*cta*A CTGCCGCGGCCCGCGTTCGATTCCCGGTCAGGGAA | 204 |
| 14 | GluTAGchr1.trna86 | TCCCTGGTGGTCTAGTGGC*t*AGGATTCGGCGCT*cta*A CCGCCTGCAGCTCGAGTTCGATTCCTGGTCAGGGAA | 205 |
| 15 | GluTAGchr2.trna16 | GCAATGGTGGTTCAGTGGTAGAATTCTCGCCT*ctact* a*ACACAGGAGa*CCCGGGTTCAATTCCTGACCCATGTA | 206 |
| 1 | TyrTAA chr2.trna13 | CCTTCAATAGTTCAGCTGGTAGAGCAGAGGACT*tta*G *ctacttcctcagtaggagac*GTCCTTAGG*t*TGCTGGT TCGATTCCAGCTTGAAGGA | 207 |
| 2 | TyrTAAchr2.trna13/ nointron | CCTTCAATAGTTCAGCTGGTAGAGCAGAGGACT*tta*G GTCCTTAGG*t*TGCTGGTTCGATTCCAGCTTGAAGGA | 208 |
| 3 | TyrTAAchr1.trna11 | GGTAAAATGGCTGAGTAAGCTTTAGACT*ttaa*AATCT AAAGAGAGATTGAGCTCTCTTTTTACCA | 209 |
| 4 | TyrTAAchr1.trna52 | GGTAAAATGACTGAGTAAGCATTAGACT*tta*AATCTA AAGaCAGAGGTCAAGACCTCTTTTTACCA | 210 |
| 5 | TyrTAAchr11.trna9 | GGTAAAATGGCTGAGTAAGCATTAGACT*tta*AATCTA AAGaCAGAGGTCAAGGCCTCTTTTTACCA | 211 |
| 6 | TyrTAAchr9.trna2 | GGTAAAATGGCTGAGTAAGCATTAGACT*tta*AATCTA AAGaCAGAGGTCAAGGCCTTTTTACCA | 212 |
| 7 | TyrTAAchr6.trna14 | CCTTCGATAGCTCAGTTGGTAGAGCGGAGGACT*tta*G *ttggctgtgtccttagac*ATCCTTAGG*t*CGCTGGTTC GAATCCGGCTCGAAGGA | 213 |
| 8 | TyrTAAchr6.trna14/ nointron | CCTTCGATAGCTCAGTTGGTAGAGCGGAGGACT*tta*G ATCCTTAGG*t*CGCTGGTTCGAATCCGGCTCGAAGGA | 214 |
| 9 | TyrTAA chr7.trna12 | GGGGGTATAGCTCAGGGC*t*AGAGCT*t*TTTGACT*tta*G AGCAAGAGG*t*CCCTGGTTCAAATCCAGGTTCTCCCT | 215 |
| 10 | TyrTAAchr7.trna28 | TATAGCTCAGTGGTAGAGCATTTAACT*tta*GATCAAG AGG*t*CCCTGGATCAACTCTGGGTG | 216 |
| 11 | TyrTAAchr15.trna6 | GTCAGTGTTGCACAACGGT*ta*AGTGAAGAGGCT*tta*A ACCCAGACTGGATGGGTTCAATTCCCATCTCTGCCG | 217 |
| 12 | TyrTAAchr2.trna2 | CCTTCGATAGCTCAGTTGGTAGAGCGGAGGACT*tta*G *tggatagggcgtggca*ATCCTTAGG*t*CGCTGGTTCGA TTCCGGCTCGAAGGA | 218 |
| 13 | TyrTAAchr2.trna2/ nointron | CCTTCGATAGCTCAGTTGGTAGAGCGGAGGACT*tta*G ATCCTTAGG*t*CGCTGGTTCGATTCCGGCTCGAAGGA | 219 |
| 14 | TyrTAAchr6.trna16 | CCTTCGATAGCTCAGTTGGTAGAGCGGAGGACT*tta*G *gctcattaagcaaggt*ATCCTTAGG*t*CGCTGGTTCGA ATCCGGCTCGGAGGA | 220 |
| 15 | TyrTAAchr6.trna16/ nointron | CCTTCGATAGCTCAGTTGGTAGAGCGGAGGACT*tta*G ATCCTTAGG*t*CGCTGGTTCGAATCCGGCTCGGAGGA | 221 |
| 16 | TyrTAAchr14.trna19 | CCTTCGATAGCTCAGCTGGTAGAGCGGAGGACT*tta*G *attgtatagacatttgcggac*ATCCTTAGG*t*CGCTGG TTCGATTCCAGCTCGAAGGA | 222 |
| 17 | TyrTAAchr14.trna19/ nointron | CCTTCGATAGCTCAGCTGGTAGAGCGGAGGACT*tta*G ATCCTTAGG*t*CGCTGGTTCGATTCCAGCTCGAAGGA | 223 |
| 18 | TyrTAAchr8.trna2 | CCTTCGATAGCTCAGCTGGTAGAGCGGAGGACT*tta*G *ctacttcctcagcaggagac*ATCCTTAGG*t*CGCTGGT TCGATTCCGGCTCGAAGGA | 224 |
| 19 | TyrTAAchr8.trna2/ nointron | CCTTCGATAGCTCAGCTGGTAGAGCGGAGGACT*tta*G ATCCTTAGG*t*CGCTGGTTCGATTCCGGCTCGAAGGA | 225 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 20 | TyrTAAchr8.trna3 | CCTTCGATAGCTCAGCTGGTAGAGCGGAGGACT*ttaG* gcgcgcgcccgtggccATCCTTAGGtCGCTGGTTCGA TTCCGGCTCGAAGGA | 226 |
| 21 | TyrTAAchr8.trna3/ nointron | CCTTCGATAGCTCAGCTGGTAGAGCGGAGGACT*ttaG* ATCCTTAGGtCGCTGGTTCGATTCCGGCTCGAAGGA | 227 |
| 22 | TyrTAAchr14.trna20 | CCTTCGATAGCTCAGCTGGTAGAGCGGAGGACT*ttaa* GcctgtagaaacatttgtggacATCCTTAGGtCGCTG GTTCGATTCCGGCTCGAAGGA | 228 |
| 23 | TyrTAAchr14.trna20/ nointron | CCTTCGATAGCTCAGCTGGTAGAGCGGAGGACT*ttaG* ATCCTTAGGtCGCTGGTTCGATTCCGGCTCGAAGGA | 229 |
| 24 | TyrTAAchr14.trna17 | CCTTCGATAGCTCAGCTGGTAGAGCGGAGGACT*ttaG* attgtacagacatttgcggacATCCTTAGGtCGCTGG TTCGATTCCGGCTCGAAGGA | 230 |
| 25 | TyrTAAchr14.trna17/ nointron | CCTTCGATAGCTCAGCTGGTAGAGCGGAGGACT*ttaG* ATCCTTAGGtCGCTGGTTCGATTCCGGCTCGAAGGA | 231 |
| 26 | TyrTAAchr14.trna5 | CCTTCGATAGCTCAGCTGGTAGAGCGGAGGACT*ttaG* tacttaatgtgtggtcATCCTTAGGtCGCTGGTTCGA TTCCGGCTCGAAGGA | 232 |
| 27 | TyrTAAchr14.trna5/ nointron | CCTTCGATAGCTCAGCTGGTAGAGCGGAGGACT*ttaG* ATCCTTAGGtCGCTGGTTCGATTCCGGCTCGAAGGA | 233 |
| 28 | TyrTAAchr6.trna17 | CCTTCGATAGCTCAGCTGGTAGAGCGGAGGACT*ttaG* gggtttgaatgtggtcATCCTTAGGtCGCTGGTTCGA ATCCGGCTCGGAGGA | 234 |
| 29 | TyrTAAchr6.trna17/ nointron | CCTTCGATAGCTCAGCTGGTAGAGCGGAGGACT*ttaG* ATCCTTAGGtCGCTGGTTCGAATCCGGCTCGGAGGA | 235 |
| 30 | TyrTAAchr14.trna18 | CCTTCGATAGCTCAGCTGGTAGAGCGGAGGACT*ttaG* actgcggaaacgtttgtggacATCCTTAGGtCGCTGG TTCAATTCCGGCTCGAAGGA | 236 |
| 31 | TyrTAAchr14.trna18/ nointron | CCTTCGATAGCTCAGCTGGTAGAGCGGAGGACT*ttaG* ATCCTTAGGtCGCTGGTTCAATTCCGGCTCGAAGGA | 237 |
| 32 | TyrTAAchr6.trna15 | CTTTCGATAGCTCAGTTGGTAGAGCGGAGGACT*ttaG* gttcattaaactaaggcATCCTTAGGtCGCTGGTTCG AATCCGGCTCGAAGGA | 238 |
| 33 | TyrTAAchr6.trna15/ nointron | CTTTCGATAGCTCAGTTGGTAGAGCGGAGGACT*ttaG* ATCCTTAGGtCGCTGGTTCGAATCCGGCTCGAAGGA | 239 |
| 34 | TyrTAAchr8.trna11 | TCTTCAATAGCTCAGCTGGTAGAGCGGAGGACT*ttaa* GgtgcacgcccgtggccATTCTTAGGTGCTGGTTTGA TTCCGACTTGGAGAG | 240 |
| 35 | TyrTAAchr8.trna11/ nointron | TCTTCAATAGCTCAGCTGGTAGAGCGGAGGACT*ttaG* ATTCTTAGGTGCTGGTTTGATTCCGACTTGGAGAG | 241 |
| 36 | TyrTAAchr1.trna127 | GGTAAAATGGCTGAGTGAAGCATTGGACT*ttaA*ATCT AAGaCAGGGGTTAAGCCTCTTTTTACCA | 242 |
| 37 | TyrTAAchr10.trna3 | GGTAAAATGGCTGAGCAAGCATTGGACT*tta*AATCTA AAGaCAGATGTTGAGCCATCTTTTTAGCA | 243 |
| 38 | TyrTAAchr14.trna8 | GGTAAAATGGCTGAGTGAAGCATTGGACT*tta*AATCT AAAGaCAGGGGCTAAGCCTCTTTTTACCA | 244 |
| 39 | TyrTAAchr2.trna12 | GGTAAAATGGCTGAGCAAGCATTAGACT*tta*AATCTA AAGaCAGAGGTTAAGGCCTCTTTTTACCA | 245 |
| 40 | TyrTAAchr7.trna1 | GGTAAAATGGCTGAGTAAGCATTAGACT*tta*AATCTA AAGaCAGAGGTCAAGGCCTCTTTTTCCT | 246 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 41 | TyrTAAchr7.trna2 | GGTAAAATGGCTGAGCAAGCATTAGACT*tta*AATCTG AAA*a*CAGAGGTCAAAG*g*TCTCTTTTTACCA | 247 |
| 42 | TyrTAAchr7.trna6 | GGTAAAATGGCTGAGTAAGCATTAGACT*tta*AATCTA AAG*a*CAGAGGTCAAGGCCTCTTTTTACCA | 248 |
| 43 | TyrTAAchr8.trna7 | GGTAAAATGACTGAATAAGCCTTAGACT*tta*AATCTG AAG*a*CAGAGGTCAAGGCCTCTTTTTACCA | 249 |
| 44 | TyrTAAchr9.trna10 | GGTAAAATGGCTGAGTAAGCATTGGACT*tta*AATCTA AAG*a*CAGAGGTCAAGACCTCTTTTTACCA | 250 |
| 45 | TyrTAAchr9.trna4 | GGTAAAATGGCTGAGTAAAGCATTAGACT*tta*AATCT AAGG*a*CAGAGGCTAAACCTCTTTTTACCA | 251 |
| 1 | TyrTAGchr2.trna13 | CCTTCAATAGTTCAGCTGGTAGAGCAGAGGACT*cta*G ctacttcctcagtaggagacGTCCTTAGG*t*TGCTGGT TCGATTCCAGCTTGAAGGA | 252 |
| 2 | TyrTAGchr2.trna13/ nointron | CCTTCAATAGTTCAGCTGGTAGAGCAGAGGACT*cta*G GTCCTTAGG*t*TGCTGGTTCGATTCCAGCTTGAAGGA | 253 |
| 3 | TyrTAGchr1.trna11 | GGTAAAATGGCTGAGTAAGCTTTAGACT*cta*aAATCT AAAGAGAGATTGAGCTCTCTTTTTACCA | 254 |
| 4 | TyrTAGchr1.trna52 | GGTAAAATGACTGAGTAAGCATTAGACT*cta*AATCTA AAG*a*CAGAGGTCAAGACCTCTTTTTACCA | 255 |
| 5 | TyrTAGchr11.trna9 | GGTAAAATGGCTGAGTAAGCATTAGACT*cta*AATCTA AAG*a*CAGAGGTCAAGGCCTCTTTTTACCA | 256 |
| 6 | TyrTAGchr9.trna2 | GGTAAAATGGCTGAGTAAGCATTAGACT*cta*AATCTA AAG*a*CAGAGGTCAAGGCCTTTTTACCA | 257 |
| 7 | TyrTAGchr6.trna14 | CCTTCGATAGCTCAGTTGGTAGAGCGGAGGACT*cta*G ttggctgtgtccttagacATCCTTAGG*t*CGCTGGTTC GAATCCGGCTCGAAGGA | 258 |
| 8 | TyrTAGchr6.trna14/ nointron | CCTTCGATAGCTCAGTTGGTAGAGCGGAGGACT*cta*G ATCCTTAGG*t*CGCTGGTTCGAATCCGGCTCGAAGGA | 259 |
| 9 | TyrTAGchr7.trna12 | GGGGGTATAGCTCAGGGCt*a*GAGCT*t*TTTGACT*cta*a GAGCAAGAGG*t*CCCTGGTTCAAATCCAGGTTCTCCCT | 260 |
| 10 | TyrTAGchr7.trna28 | TATAGCTCAGTGGTAGAGCATTTAACT*cta*GATCAAG AGG*t*CCCTGGATCAACTCTGGGTG | 261 |
| 11 | TyrTAGchr15.trna6 | GTCAGTGTTGCACAACGGT*ta*AGTGAAGAGGCT*cta*A ACCCAGACTGGATGGGTTCAATTCCCATCTCTGCCG | 262 |
| 12 | TyrTAGchr2.trna2 | CCTTCGATAGCTCAGTTGGTAGAGCGGAGGACT*cta*G tggatagggcgtggcaATCCTTAGG*t*CGCTGGTTCGA TTCCGGCTCGAAGGA | 263 |
| 13 | TyrTAGchr2.trna2/ nointron | CCTTCGATAGCTCAGTTGGTAGAGCGGAGGACT*cta*G ATCCTTAGG*t*CGCTGGTTCGATTCCGGCTCGAAGGA | 264 |
| 14 | TyrTAGchr6.trna16 | CCTTCGATAGCTCAGTTGGTAGAGCGGAGGACT*cta*G gctcattaagcaaggtATCCTTAGG*t*CGCTGGTTCGA ATCCGGCTCGGAGGA | 265 |
| 15 | TyrTAGchr6.trna16/ nointron | CCTTCGATAGCTCAGTTGGTAGAGCGGAGGACT*cta*G ATCCTTAGG*t*CGCTGGTTCGAATCCGGCTCGGAGGA | 266 |
| 16 | TyrTAGchr14.trna19 | CCTTCGATAGCTCAGCTGGTAGAGCGGAGGACT*cta*G attgtatagacatttgcggacATCCTTAGG*t*CGCTGG TTCGATTCCAGCTCGAAGGA | 267 |
| 17 | TyrTAGchr14.trna19/ nointron | CCTTCGATAGCTCAGCTGGTAGAGCGGAGGACT*cta*G ATCCTTAGG*t*CGCTGGTTCGATTCCAGCTCGAAGGA | 268 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 18 | TyrTAGchr8.trna2 | CCTTCGATAGCTCAGCTGGTAGAGCGGAGGACT*ctaG* ctacttcctcagcaggagacATCCTTAGGtCGCTGGT TCGATTCCGGCTCGAAGGA | 269 |
| 19 | TyrTAGchr8.trna2/ nointron | CCTTCGATAGCTCAGCTGGTAGAGCGGAGGACT*ctaG* ATCCTTAGGtCGCTGGTTCGATTCCGGCTCGAAGGA | 270 |
| 20 | TyrTAGchr8.trna3 | CCTTCGATAGCTCAGCTGGTAGAGCGGAGGACT*ctaG* gcgcgcgcccgtggccATCCTTAGGtCGCTGGTTCGA TTCCGGCTCGAAGGA | 271 |
| 21 | TyrTAGchr8.trna3/ nointron | CCTTCGATAGCTCAGCTGGTAGAGCGGAGGACT*ctaG* ATCCTTAGGtCGCTGGTTCGATTCCGGCTCGAAGGA | 272 |
| 22 | TyrTAGchr14.trna20 | CCTTCGATAGCTCAGCTGGTAGAGCGGAGGACT*ctaG* cctgtagaaacatttgtggacATCCTTAGGtCGCTGG TTCGATTCCGGCTCGAAGGA | 273 |
| 23 | TyrTAGchr14.trna20/ nointron | CCTTCGATAGCTCAGCTGGTAGAGCGGAGGACT*ctaG* ATCCTTAGGtCGCTGGTTCGATTCCGGCTCGAAGGA | 274 |
| 24 | TyrTAGchr14.trna17 | CCTTCGATAGCTCAGCTGGTAGAGCGGAGGACT*ctaG* attgtacagacatttgcggacATCCTTAGGtCGCTGG TTCGATTCCGGCTCGAAGGA | 275 |
| 25 | TyrTAGchr14.trna17/ nointron | CCTTCGATAGCTCAGCTGGTAGAGCGGAGGACT*ctaG* ATCCTTAGGtCGCTGGTTCGATTCCGGCTCGAAGGA | 276 |
| 26 | TyrTAGchr14.trna5 | CCTTCGATAGCTCAGCTGGTAGAGCGGAGGACT*ctaG* tacttaatgtgtggtcATCCTTAGGtCGCTGGTTCGA TTCCGGCTCGAAGGA | 277 |
| 27 | TyrTAGchr14.trna5/ nointron | CCTTCGATAGCTCAGCTGGTAGAGCGGAGGACT*ctaG* ATCCTTAGGtCGCTGGTTCGATTCCGGCTCGAAGGA | 278 |
| 28 | TyrTAGchr6.trna17 | CCTTCGATAGCTCAGCTGGTAGAGCGGAGGACT*ctaG* gggtttgaatgtggtcATCCTTAGGtCGCTGGTTCGA ATCCGGCTCGGAGGA | 279 |
| 29 | TyrTAGchr6.trna17/ nointron | CCTTCGATAGCTCAGCTGGTAGAGCGGAGGACT*ctaG* ATCCTTAGGtCGCTGGTTCGAATCCGGCTCGGAGGA | 280 |
| 30 | TyrTAGchr14.trna18 | CCTTCGATAGCTCAGCTGGTAGAGCGGAGGACT*ctaG* actgcggaaacgtttgtggacATCCTTAGGtCGCTGG TTCAATTCCGGCTCGAAGGA | 281 |
| 31 | TyrTAGchr14.trna18/ nointron | CCTTCGATAGCTCAGCTGGTAGAGCGGAGGACT*ctaG* ATCCTTAGGtCGCTGGTTCAATTCCGGCTCGAAGGA | 282 |
| 32 | TyrTAGchr6.trna15 | CTTTCGATAGCTCAGTTGGTAGAGCGGAGGACT*ctaG* gttcattaaactaaggcATCCTTAGGtCGCTGGTTCG AATCCGGCTCGAAGGA | 283 |
| 33 | TyrTAGchr6.trna15/ nointron | CTTTCGATAGCTCAGTTGGTAGAGCGGAGGACT*ctaG* ATCCTTAGGtCGCTGGTTCGAATCCGGCTCGAAGGA | 284 |
| 34 | TyrTAGchr8.trna11 | TCTTCAATAGCTCAGCTGGTAGAGCGGAGGACT*ctaG* gtgcacgcccgtggccATTCTTAGGTGCTGGTTTGAT TCCGACTTGGAGAG | 285 |
| 35 | TyrTAGchr8.trna11/ nointron | TCTTCAATAGCTCAGCTGGTAGAGCGGAGGACT*ctaG* ATTCTTAGGTGCTGGTTTGATTCCGACTTGGAGAG | 286 |
| 36 | TyrTAGchr1.trna127 | GGTAAAATGGCTGAGTGAAGCATTGGACT*cta*AATCT AAAGaCAGGGGTTAAGCCTCTTTTTACCA | 287 |
| 37 | TyrTAGchr10.trna3 | GGTAAAATGGCTGAGCAAGCATTGGACT*cta*AATCTA AAGaCAGATGTTGAGCCATCTTTTTAGCA | 288 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| | tRNAscan-SE ID | Sequence | SEQ ID NO |
|---|---|---|---|
| 38 | TyrTAGchr14.trna8 | GGTAAAATGGCTGAGTGAAGCATTGGACT*cta*AATCT AAAGaCAGGGGCTAAGCCTCTTTTTACCA | 289 |
| 39 | TyrTAGchr2.trna12 | GGTAAAATGGCTGAGCAAGCATTAGACT*cta*AATCTA AAGaCAGAGGTTAAGGCCTCTTTTTACCA | 290 |
| 40 | TyrTAGchr7.trna1 | GGTAAAATGGCTGAGTAAGCATTAGACT*cta*AATCTA AAGaCAGAGGTCAAGGCCTCTTTTTTCCT | 291 |
| 41 | TyrTAGchr7.trna2 | GGTAAAATGGCTGAGCAAGCATTAGACT*cta*AATCTG AAAaCAGAGGTCAAAGgTCTCTTTTTACCA | 292 |
| 42 | TyrTAGchr7.trna6 | GGTAAAATGGCTGAGTAAGCATTAGACT*cta*AATCTA AAGaCAGAGGTCAAGGCCTCTTTTTACCA | 293 |
| 43 | TyrTAGchr8.trna7 | GGTAAAATGACTGAATAAGCCTTAGACT*cta*AATCTG AAGaCAGAGGTCAAGGCCTCTTTTTACCA | 294 |
| 44 | TyrTAGchr9.trna10 | GGTAAAATGGCTGAGTAAGCATTGGACT*cta*AATCTA AAGaCAGAGGTCAAGACCTCTTTTTACCA | 295 |
| 45 | TyrTAGchr9.trna4 | GGTAAAATGGCTGAGTAAAGCATTAGACT*cta*AATCT AAGGaCAGAGGCTAAACCTCTTTTTACCA | 296 |
| 1 | LeuTAAchr4.trna2 | GTTAAGATGGCAGAGCCtGGTa*tta*AACTTA AAATTTTATAAtCAGAGGTTCAACTCCTCTTCTTAAC A | 297 |
| 2 | LeuTAAnmtchrX.trna2 | GTTAAGATGGCAGAGCCcGGCa*tta*GACTTA AAACTTTATAAtCAGAGGTTCAACTCCTCTCATTAAC A | 298 |
| 3 | LeuTAAchr6.trna77 | GGTAGCGTGGCCGAGCGGTct*tta*AAGGCGCTGGATT*tta* GCTCCAGTCTCTTCGGGGGCGTGGGTTCAAATCCCAC CGCTGCCA | 299 |
| 4 | LeuTAAchr6.trna127 | GGTAGCGTGGCCGAGTGGTct*tta*AAGACGCTGGATT*tta* GCTCCAGTCTCTTCGGGGGCGTGGGTTTGAATCCCAC CGCTGCCA | 300 |
| 5 | LeuTAAchr2.trna4 | GGGCCAGTGGCTCAATGGAt*tta*AATGCGTCTGACT*tta*A ATCAGAAGAtTCCAGCCTTGACTCCTGGCTGGCTCA | 301 |
| 6 | LeuTAAchr20.trna1 | GGTAGGGTGGCCGAGCGGTct*tta*AAGGCACTGTATT*tta* ACTCCAGTCTCTTCAGAGGCATGGGTTTGAATCCCAC TGCTGCCA | 302 |
| 7 | LeuTAAchr5.trna20 | GCCGAGCGGTct*tta*AAGGCTCCGGATT*tta*GCGCCGGTG TCTTCGGAGgCATGGGTTCGAATTCCAC | 303 |
| 8 | LeuTAAchr6.trna100 | GTCAGGATGGCCGAGTGGTct*tta*AAGGCGCCAGACT*tta* GctaagcttcctccgcggtggggaTTCTGGTCTCCAA TGGAGGCGTGGGTTCGAATCCCACTTCTGACA | 304 |
| 9 | LeuTAAchr6.trna100/ nointron | GTCAGGATGGCCGAGTGGTct*tta*AAGGCGCCAGACT*tta* GTTCTGGTCTCCAATGGAGGCGTGGGTTCGAATCCCA CTTCTGACA | 305 |
| 10 | LeuTAAchr6.trna73 | GTCAGGATGGCCGAGTGGTct*tta*AAGGCGCCAGACT*tta* GcttggcttcctcgtgttgaggaTTCTGGTCTCCAAT GGAGGCGTGGGTTCGAATCCCACTTCTGACA | 306 |
| 11 | LeuTAAchr6.trna73/ nointron | GTCAGGATGGCCGAGTGGTct*tta*AAGGCGCCAGACT*tta* GTTCTGGTCTCCAATGGAGGCGTGGGTTCGAATCCCA CTTCTGACA | 307 |
| 12 | LeuTAAchr6.trna141 | GTCAGGATGGCCGAGTGGTct*tta*AAGGCGCCAGACT*tta* GcttactgcttcctgtgttcgggtcTTCTGGTCTCCG TATGGAGGCGTGGGTTCGAATCCCACTTCTGACA | 308 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 13 | LeuTAAchr6.trna141/ nointron | GTCAGGATGGCCGAGTGGT*ct*AAGGCGCCAGACT*tta* GTTCTGGTCTCCGTATGGAGGCGTGGGTTCGAATCCC ACTTCTGACA | 309 |
| 14 | LeuTAAchr6.trna142 | GTCAGGATGGCCGAGTGGT*ct*AAGGCGCCAGACT*tta* G*ttgctacttcccaggtttggggc*TTCTGGTCTCCGC ATGGAGGCGTGGGTTCGAATCCCACTTCTGACA | 310 |
| 15 | LeuTAAchr6.trna142/ nointron | GTCAGGATGGCCGAGTGGT*ct*AAGGCGCCAGACT*tta* GTTCTGGTCTCCGCATGGAGGCGTGGGTTCGAATCCC ACTTCTGACA | 311 |
| 16 | LeuTAAchr1.trna54 | GTCAGGATGGCCGAGTGGT*ct*AAGGCGCCAGACT*tta* G*gtaagcaccttgcctgcgggct*TTCTGGTCTCCGGA TGGAGGCGTGGGTTCGAATCCCACTTCTGACA | 312 |
| 17 | LeuTAAchr1.trna54/ nointron | GTCAGGATGGCCGAGTGGT*ct*AAGGCGCCAGACT*tta* G*t*TTCTGGTCTCCGGATGGAGGCGTGGGTTCGAATCC CACTTCTGACA | 313 |
| 18 | LeuTAAchr11.trna1 | GCCTCCTTAGTGCAGTAGGTAGCGCATCAGTCT*tta*A ATCTGAATG*gt*CCTGAGTTCAAGCCTCAGAGGGGGCA | 314 |
| 19 | LeuTAAchr1.trna59 | GTCAGGATGGCCGAGCAGT*ctt*AAGGCGCTGCGTT*tt a*ATCGCACCCTCCGCTGGAGGCGTGGGTTCGAATCCC ACTTTTGACA | 315 |
| 20 | LeuTAAchr9.trna3 | GGTTCCATGGTGTAATGGT*g*AGCACTCTGGACT*tta*A ATCCAGAAG*t*AGT*g*CTGGAACAA | 316 |
| 21 | LeuTAAchr9.trna7 | GTCAGGGTGGCTGAGCAGT*ct*GAGGGGCTGCGTT*tta* GTCGCAGTCTGCCCTGGAGGCGTGGGTTCGAATCCCA CTCCTGAAA | 317 |
| 22 | LeuTAAchr6.trna81 | ACCAGGATGGCCGAGTGGT*t*AAGGCGTTGGACT*tta*G ATCCAATGGACATATGTCCGCGTGGGTTCGAACCCCA CTCCTGGTA | 318 |
| 23 | LeuTAAchr6.trna135 | ACCGGGATGGCCGAGTGGT*t*AAGGCGTTGGACT*tta*G ATCCAATGGGCTGGTGCCCGCGTGGGTTCGAACCCCA CTCTCGGTA | 319 |
| 24 | LeuTAAchr11.trna4 | ACCAGAATGGCCGAGTGGT*t*AAGGCGTTGGACT*tta*G ATCCAATGGATTCATATCCGCGTGGGTTCGAACCCCA CTTCTGGTA | 320 |
| 25 | LeuTAAchr6.trna156 | ACCGGGATGGCTGAGTGGT*t*AAGGCGTTGGACT*tta*G ATCCAATGGACAGGTGTCCGCGTGGGTTCGAGCCCCA CTCCCGGTA | 321 |
| 26 | LeuTAAchr6.trna79 | ACTCATTTGGCTGAGTGGT*t*AAGGCATTGGACT*tta*G ATCCAATGGAGTAGTGGCTGTGTGGGTTTAAACCCCA CTACTGGTA | 322 |
| 27 | LeuTAAchr1.trna9 | GAGAAAGT*c*ATCGTAGTTACGAAGTTGGCT*tta*ACCC AGTTT*t*GGGAGGTTCAATTCCTTCCTTTCTCT | 323 |
| 28 | LeuTAAchr11.trna12 | ACCAGGATGGCCAAGTAGTT*a*AAGGCACTGGACT*tta* GAGCCAATGGACATATGTCTGTGTGGGTTTGAACCCC ACTCCTGGTG | 324 |
| 29 | LeuTAAchr17.trna42 | GGTAGCGTGGCCGAGCGGT*ct*AAGGCGCTGGATT*tta* GCTCCAGTCTCTTCGGAGGCGTGGGTTCGAATCCCAC CGCTGCCA | 325 |
| 30 | LeuTAAchr14.trna2 | GGTAGTGTGGCCGAGCGGT*ct*AAGGCGCTGGATT*tta* GCTCCAGTCTCTTCGGGGGCGTGGGTTCGAATCCCAC CACTGCCA | 326 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 31 | LeuTAAchr16.trna27 | GGTAGCGTGGCCGAGTGGT*ct*AAGGCGCTGGATT*tta* GCTCCAGTCATTTCGATG*g*CGTGGGTTCGAATCCCAC CGCTGCCA | 327 |
| 32 | LeuTAAchr14.trna16 | GGTAGTGTGGTTGAATGGT*ct*AAGGCACTGAATT*tta* GCTCCAGTCTCTTTGGGG*a*CGTGGGTTTAAATCCCAC TGCTGCAA | 328 |
| 1 | LeuTAGchr4.trna2 | GTTAAGATGGCAGAGCC*t*GGT*a*ATTGCA*cta*AACTTA AAATTTTATAA*t*CAGAGGTTCAACTCCTCTTCTTAAC A | 329 |
| 2 | LeuTAGnmtchrX.trna2 | GTTAAGATGGCAGAGCC*c*GG*Ca*ATTGCA*cta*GACTTA AAACTTTATAA*t*CAGAGGTTCAACTCCTCTCATTAAC A | 330 |
| 3 | LeuTAGchr6.trna77 | GGTAGCGTGGCCGAGCGGT*ct*AAGGCGCTGGATT*cta* GCTCCAGTCTCTTCGGGGGCGTGGGTTCAAATCCCAC CGCTGCCA | 331 |
| 4 | LeuTAGchr6.trna127 | GGTAGCGTGGCCGAGTGGT*ct*AAGACGCTGGATT*cta* GCTCCAGTCTCTTCGGGGGCGTGGGTTTGAATCCCAC CGCTGCCA | 332 |
| 5 | LeuTAGchr2.trna4 | GGGCCAGTGGCTCAATGGA*t*AATGCGTCTGACT*cta*A ATCAGAAGA*t*TCCAGCCTTGACTCCTGGCTGGCTCA | 333 |
| 6 | LeuTAGchr20.trna1 | GGTAGGGTGGCCGAGCGGT*ct*AAGGCACTGTATT*cta* ACTCCAGTCTCTTCAGAGGCATGGGTTTGAATCCCAC TGCTGCCA | 334 |
| 7 | LeuTAGchr5.trna20 | GCCGAGCGGT*ct*AAGGCTCCGGATT*cta*GCGCCGGTG TCTTCGGAG*g*CATGGGTTCGAATTCCAC | 335 |
| 8 | LeuTAGchr6.trna100 | GTCAGGATGGCCGAGTGGT*ct*AAGGCGCCAGACT*cta* G*ctaagcttcctccgcggtggggga*TTCTGGTCTCCAA TGGAGGCGTGGGTTCGAATCCCACTTCTGACA | 336 |
| 9 | LeuTAGchr6.trna100/ nointron | GTCAGGATGGCCGAGTGGT*ct*AAGGCGCCAGACT*cta* GTTCTGGTCTCCAATGGAGGCGTGGGTTCGAATCCCA CTTCTGACA | 337 |
| 10 | LeuTAGchr6.trna73 | GTCAGGATGGCCGAGTGGT*ct*AAGGCGCCAGACT*cta* G*cttggcttcctcgtgttgagga*TTCTGGTCTCCAAT GGAGGCGTGGGTTCGAATCCCACTTCTGACA | 338 |
| 11 | LeuTAGchr6.trna73/ nointron | GTCAGGATGGCCGAGTGGT*ct*AAGGCGCCAGACT*cta* GTTCTGGTCTCCAATGGAGGCGTGGGTTCGAATCCCA CTTCTGACA | 339 |
| 12 | LeuTAGchr6.trna141 | GTCAGGATGGCCGAGTGGT*ct*AAGGCGCCAGACT*cta* G*cttactgcttcctgtgttcgggtc*TTCTGGTCTCCG TATGGAGGCGTGGGTTCGAATCCCACTTCTGACA | 340 |
| 13 | LeuTAGchr6.trna141/ nointron | GTCAGGATGGCCGAGTGGT*ct*AAGGCGCCAGACT*cta* GTTCTGGTCTCCGTATGGAGGCGTGGGTTCGAATCCC ACTTCTGACA | 341 |
| 14 | LeuTAGchr6.trna142 | GTCAGGATGGCCGAGTGGT*ct*AAGGCGCCAGACT*cta* G*ttgctacttcccaggtttggggc*TTCTGGTCTCCGC ATGGAGGCGTGGGTTCGAATCCCACTTCTGACA | 342 |
| 15 | LeuTAGchr6.trna142/ nointron | GTCAGGATGGCCGAGTGGT*ct*AAGGCGCCAGACT*cta* GTTCTGGTCTCCGCATGGAGGCGTGGGTTCGAATCCC ACTTCTGACA | 343 |
| 16 | LeuTAGchr1.trna54 | GTCAGGATGGCCGAGTGGT*ct*AAGGCGCCAGACT*cta* G*gtaagcaccttgcctgcgggct*TTCTGGTCTCCGGA TGGAGGCGTGGGTTCGAATCCCACTTCTGACA | 344 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| | tRNAscan-SE ID | Sequence | SEQ ID NO |
|---|---|---|---|
| 17 | LeuTAGchr1.trna54/ nointron | GTCAGGATGGCCGAGTGGTct AAGGCGCCAGACT*cta* GtTTCTGGTCTCCGGATGGAGGCGTGGGTTCGAATCC CACTTCTGACA | 345 |
| 18 | LeuTAGchr11.trna1 | GCCTCCTTAGTGCAGTAGGTAGCGCATCAGTCT*cta*A ATCTGAATGgtCCTGAGTTCAAGCCTCAGAGGGGGCA | 346 |
| 19 | LeuTAGchr1.trna59 | GTCAGGATGGCCGAGCAGTct tAAGGCGCTGCGTT*ct a*ATCGCACCCTCCGCTGGAGGCGTGGGTTCGAATCCC ACTTTTGACA | 347 |
| 20 | LeuTAGchr9.trna3 | GGTTCCATGGTGTAATGGTgAGCACTCTGGACT*cta*A ATCCAGAAGtAGTgCTGGAACAA | 348 |
| 21 | LeuTAGchr9.trna7 | GTCAGGGTGGCTGAGCAGTct GAGGGGCTGCGTT*cta* GTCGCAGTCTGCCCTGGAGGCGTGGGTTCGAATCCCA CTCCTGAAA | 349 |
| 22 | LeuTAGchr6.trna81 | ACCAGGATGGCCGAGTGGTt AAGGCGTTGGACT*cta*G ATCCAATGGACATATGTCCGCGTGGGTTCGAACCCCA CTCCTGGTA | 350 |
| 23 | LeuTAGchr6.trna135 | ACCGGGATGGCCGAGTGGTt AAGGCGTTGGACT*cta*G ATCCAATGGGCTGGTGCCCGCGTGGGTTCGAACCCCA CTCTCGGTA | 351 |
| 24 | LeuTAGchr11.trna4 | ACCAGAATGGCCGAGTGGTt AAGGCGTTGGACT*cta*G ATCCAATGGATTCATATCCGCGTGGGTTCGAACCCCA CTTCTGGTA | 352 |
| 25 | LeuTAGchr6.trna156 | ACCGGGATGGCTGAGTGGTt AAGGCGTTGGACT*cta*G ATCCAATGGACAGGTGTCCGCGTGGGTTCGAGCCCCA CTCCCGGTA | 353 |
| 26 | LeuTAGchr6.trna79 | ACTCATTTGGCTGAGTGGTt AAGGCATTGGACT*ctaa* GATCCAATGGAGTAGTGGCTGTGTGGGTTTAAACCCC ACTACTGGTA | 354 |
| 27 | LeuTAGchr1.trna9 | GAGAAAGTcATCGTAGTTACGAAGTTGGCT*cta*ACCC AGTTTt GGGAGGTTCAATTCCTTCCTTTCTCT | 355 |
| 28 | LeuTAGchr11.trna12 | ACCAGGATGGCCAAGTAGTTaAAGGCACTGGACT*cta* GAGCCAATGGACATATGTCTGTGTGGGTTTGAACCCC ACTCCTGGTG | 356 |
| 29 | LeuTAGchr17.trna42 | GGTAGCGTGGCCGAGCGGTct AAGGCGCTGGATT*cta* GCTCCAGTCTCTTCGGAGGCGTGGGTTCGAATCCCAC CGCTGCCA | 357 |
| 30 | LeuTAGchr14.trna2 | GGTAGTGTGGCCGAGCGGTct AAGGCGCTGGATT*cta* GCTCCAGTCTCTTCGGGGGCGTGGGTTCGAATCCCAC CACTGCCA | 358 |
| 31 | LeuTAGchr16.trna27 | GGTAGCGTGGCCGAGTGGTct AAGGCGCTGGATT*cta* GCTCCAGTCATTTCGATGgCGTGGGTTCGAATCCCAC CGCTGCCA | 359 |
| 32 | LeuTAGchr14.trna16 | GGTAGTGTGGTTGAATGGTct AAGGCACTGAATT*cta* GCTCCAGTCTCTTTGGGGaCGTGGGTTTAAATCCCAC TGCTGCAA | 360 |
| 1 | LeuTGAchr4.trna2 | GTTAAGATGGCAGAGCCtGGTaATTGCA*tca*AACTTA AAATTTTATAAtCAGAGGTTCAACTCCTCTTCTTAAC A | 523 |
| 2 | LeuTGAnmtchrX.trna2 | GTTAAGATGGCAGAGCCcGGCaATTGCA*tca*GACTTA AAACTTTATAAtCAGAGGTTCAACTCCTCTCATTAAC A | 524 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

|   | tRNAscan-SE ID | Sequence | SEQ ID NO |
|---|---|---|---|
| 3 | LeuTGAchr6.trna77 | GGTAGCGTGGCCGAGCGGT*ct*AAGGCGCTGGATT*tca*GCTCCAGTCTCTTCGGGGGCGTGGGTTCAAATCCCACCGCTGCCA | 525 |
| 4 | LeuTGAchr6.trna127 | GGTAGCGTGGCCGAGTGGT*ct*AAGACGCTGGATT*tca*GCTCCAGTCTCTTCGGGGGCGTGGGTTTGAATCCCACCGCTGCCA | 526 |
| 5 | LeuTGAchr2.trna4 | GGGCCAGTGGCTCAATGGA*t*AATGCGTCTGACT*tca*AATCAGAAGA*t*TCCAGCCTTGACTCCTGGCTGGCTCA | 527 |
| 6 | LeuTGAchr20.trna1 | GGTAGGGTGGCCGAGCGGT*ct*AAGGCACTGTATT*tca*ACTCCAGTCTCTTCAGAGGCATGGGTTTGAATCCCACTGCTGCCA | 528 |
| 7 | LeuTGAchr5.trna20 | GCCGAGCGGT*ct*AAGGCTCCGGATT*tca*GCGCCGGTGTCTTCGGAG*g*CATGGGTTCGAATTCCAC | 529 |
| 8 | LeuTGAchr6.trna100 | GTCAGGATGGCCGAGTGGT*ct*AAGGCGCCAGACT*tca*Gct*aagcttcctccgcggtggggaTTCTGGTCTCCAATGGAGGCGTGGGTTCGAATCCCACTTCTGACA | 530 531 |
| 9 | LeuTGAchr6.trna100/nointron | GTCAGGATGGCCGAGTGGT*ct*AAGGCGCCAGACT*tca*GTTCTGGTCTCCAATGGAGGCGTGGGTTCGAATCCCACTTCTGACA | 532 |
| 10 | LeuTGAchr6.trna73 | GTCAGGATGGCCGAGTGGT*ct*AAGGCGCCAGACT*tca*Gct*tggcttcctcgtgttgaggaTTCTGGTCTCCAATGGAGGCGTGGGTTCGAATCCCACTTCTGACA | 533 |
| 11 | LeuTGAchr6.trna73/nointron | GTCAGGATGGCCGAGTGGT*ct*AAGGCGCCAGACT*tca*GTTCTGGTCTCCAATGGAGGCGTGGGTTCGAATCCCACTTCTGACA | 534 |
| 12 | LeuTGAchr6.trna141 | GTCAGGATGGCCGAGTGGT*ct*AAGGCGCCAGACT*tca*Gct*tactgcttcctgtgttcgggtcTTCTGGTCTCCGTATGGAGGCGTGGGTTCGAATCCCACTTCTGACA | 535 |
| 13 | LeuTGAchr6.trna141/nointron | GTCAGGATGGCCGAGTGGT*ct*AAGGCGCCAGACT*tca*GTTCTGGTCTCCGTATGGAGGCGTGGGTTCGAATCCCACTTCTGACA | 536 |
| 14 | LeuTGAchr6.trna142 | GTCAGGATGGCCGAGTGGT*ct*AAGGCGCCAGACT*tca*Gttgctacttcccaggtttggggc*TTCTGGTCTCCGCATGGAGGCGTGGGTTCGAATCCCACTTCTGACA | 537 |
| 15 | LeuTGAchr6.trna142/nointron | GTCAGGATGGCCGAGTGGT*ct*AAGGCGCCAGACT*tca*GTTCTGGTCTCCGCATGGAGGCGTGGGTTCGAATCCCACTTCTGACA | 538 |
| 16 | LeuTGAchr1.trna54 | GTCAGGATGGCCGAGTGGT*ct*AAGGCGCCAGACT*tca*Ggtaagcaccttgcctgcgggct*TTCTGGTCTCCGGATGGAGGCGTGGGTTCGAATCCCACTTCTGACA | 539 |
| 17 | LeuTGAchr1.trna54/nointron | GTCAGGATGGCCGAGTGGT*ct*AAGGCGCCAGACT*tca*G*t*TTCTGGTCTCCGGATGGAGGCGTGGGTTCGAATCCCACTTCTGACA | 540 |
| 18 | LeuTGAchr11.trna1 | GCCTCCTTAGTGCAGTAGGTAGCGCATCAGTCT*tca*AATCTGAATG*gt*CCTGAGTTCAAGCCTCAGAGGGGGCA | 541 |
| 19 | LeuTGAchr1.trna59 | GTCAGGATGGCCGAGCAGT*ct*tAAGGCGCTGCGTT*tc*aATCGCACCCTCCGCTGGAGGCGTGGGTTCGAATCCCACTTTTGACA | 542 |
| 20 | LeuTGAchr9.trna3 | GGTTCCATGGTGTAATGGT*g*AGCACTCTGGACT*tca*AATCCAGAAG*t*AGT*g*CTGGAACAA | 543 |
| 21 | LeuTGAchr9.trna7 | GTCAGGGTGGCTGAGCAGT*ct*GAGGGGCTGCGTT*tca*GTCGCAGTCTGCCCTGGAGGCGTGGGTTCGAATCCCACTCCTGAAA | 544 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 22 | LeuTGAchr6.trna81 | ACCAGGATGGCCGAGTGGTtAAGGCGTTGGACT*tca*GATC CAATGGACATATGTCCGCGTGGGTTCGAACCCCACTCCTG GTA | 545 |
| 23 | LeuTGAchr6.trna135 | ACCGGGATGGCCGAGTGGTtAAGGCGTTGGACT*tca*GATC CAATGGGCTGGTGCCCGCGTGGGTTCGAACCCCACTCTCG GTA | 546 547 |
| 24 | LeuTGAchr11.trna4 | ACCAGAATGGCCGAGTGGTtAAGGCGTTGGACT*tca*GATC CAATGGATTCATATCCGCGTGGGTTCGAACCCCACTTCTG GTA | 548 |
| 25 | LeuTGAchr6.trna156 | ACCGGGATGGCTGAGTGGTtAAGGCGTTGGACT*tca*GATC CAATGGACAGGTGTCCGCGTGGGTTCGAGCCCCACTCCCG GTA | 549 |
| 26 | LeuTGAchr6.trna79 | ACTCATTTGGCTGAGTGGTtAAGGCATTGGACT*tca*GATC CAATGGAGTAGTGGCTGTGTGGGTTTAAACCCCACTACTG GTA | 550 |
| 27 | LeuTGAchr1.trna9 | GAGAAAGT*c*ATCGTAGTTACGAAGTTGGCT*tca*ACCCAGT TT*t*GGGAGGTTCAATTCCTTCCTTTCTCT | 551 |
| 28 | LeuTGAchr11.trna12 | ACCAGGATGGCCAAGTAGTTa*AAGGCACTGGACT*tca*GAG CCAATGGACATATGTCTGTGTGGGTTTGAACCCCACTCCT GGTG | 552 |
| 29 | LeuTGAchr17.trna42 | GGTAGCGTGGCCGAGCGGTct*AAGGCGCTGGATT*tca*GCT CCAGTCTCTTCGGAGGCGTGGGTTCGAATCCCACCGCTGC CA | 553 |
| 30 | LeuTGAchr14.trna2 | GGTAGTGTGGCCGAGCGGTct*AAGGCGCTGGATT*tca*GCT CCAGTCTCTTCGGGGGCGTGGGTTCGAATCCCACCACTGC CA | 554 |
| 31 | LeuTGAchr16.trna27 | GGTAGCGTGGCCGAGTGGTct*AAGGCGCTGGATT*tca*GCT CCAGTCATTTCGATG*g*CGTGGGTTCGAATCCCACCGCTGC CA | 555 |
| 32 | LeuTGAchr14.trna16 | GGTAGTGTGGTTGAATGGTct*AAGGCACTGAATT*tca*GCT CCAGTCTCTTTGGGG*a*CGTGGGTTTAAATCCCACTGCTGC AA | 556 |
| 1 | SerTAGnmtchr2.trna19 | GAGAAGGT*c*ACAGAGGT*t*ATGGGATTGGCT*cta*AACC AGTCTG*t*GGGGGGGTTCGATTCCCTCCTTTTTCA | 361 |
| 2 | SerTAGnmtchr2.trna7 | GAGAAGGT*c*ATAGAGGT*t*ATGGGATTGGCT*cta*AACC AGTCTCTGGGGGGGTTCGATTCCCTCCTTTTTCA | 362 |
| 3 | SerTAGnmtchr17.trna31 | GAAAAAGTCATAGGGGTTATGAGGCTGGCT*cta*AACC AGCCT*t*AGGAGGTTCAATTCCTTCCTTTTTTG | 363 |
| 4 | SerTAGchr6.trna41 | GGCCGGTTAGCTCAGTTGGTtAGAGCGTGCTGCT*cta* AATGCCAGGG*t*CGAGGTTTCGATCCCCGTACGGGCCT | 364 |
| 5 | SerTAGchr6.trna148 | GTAGTCGTGGCCGAGTGGT*t*AAGGCGATGGACT*cta*A ATCCATTGGGGTTTCCCCGCGCAGGTTCGAATCCTGC CGACTACG | 365 |
| 6 | SerTAGchr6.trna50 | GTAGTCGTGGCCGAGTGGT*t*AAGGCGATGGACT*cta*A ATCCATTGGGGTTTCCCCACGCAGGTTCGAATCCTGC CGACTACG | 366 |
| 7 | SerTAGchr6.trna146 | GTAGTCGTGGCCGAGTGGT*t*AAGGTGATGGACT*ctaa* AACCCATTGGGGTCTCCCCGCGCAGGTTCGAATCCTG CCGACTACG | 367 |
| 8 | SerTAGchr7.trna15 | GGGTGTATGGCTCAGGGGTAGAGAATTTGACT*ct*a*GA TCAAGAGGt*CCCTGGTTCAAATCCAGGTGCCCCCT | 368 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 9 | SerTAGchr11.trna10 | AGTTGTAGCTGAGTGGTtAAGGCAACGAGCT*cta*AAT TCGTTGGTTTCTCTCTg TGCAGGTTTGAATCCTGCTA ATTA | 369 |
| 10 | SerTAGchr11.trna8 | CAAGAAATTCATAGAGGTTATGGGATTGGCT*cta*AAC CAGTTTcAGGAGGTTCGATTCCTTCCTTTTTGG | 370 |
| 11 | SerTAGchr17.trna41 | GCTGTGATGGCCGAGTGGTtAAGGCGTTGGACT*cta*A ATCCAATGGGGTCTCCCCGCGCAGGTTCGAATCCTGC TCACAGCG | 371 |
| 12 | SerTAGchr6.trna34 | GCTGTGATGGCCGAGTGGTtAAGGCGTTGGACT*cta*A ATCCAATGGGGTCTCCCCGCGCAGGTTCAAATCCTGC TCACAGCG | 372 |
| 13 | SerTAGchr6.trna138 | GCTGTGATGGCCGAGTGGTtAAGGTGTTGGACT*cta*A ATCCAATGGGGGTTCCCCGCGCAGGTTCAAATCCTGC TCACAGCG | 373 |
| 14 | SerTAGchr12.trna2 | GTCACGGTGGCCGAGTGGTtAAGGCGTTGGACT*cta*A ATCCAATGGGGTTTCCCCGCACAGGTTCGAATCCTGT TCGTGACG | 374 |
| 15 | SerTAGchr6.trna30 | GACGAGGTGGCCGAGTGGTtAAGGCGATGGACT*cta*A ATCCATTGTGCTCTGCACGCGTGGGTTCGAATCCCAC CCTCGTCG | 375 |
| 16 | SerTAGchr6.trna43 | GACGAGGTGGCCGAGTGGTtAAGGCGATGGACT*cta*A ATCCATTGTGCTCTGCACGCGTGGGTTCGAATCCCAC CTTCGTCG | 376 |
| 17 | SerTAGchr11.trna6 | GGCCGGTTAGCTCAGTTGGTtAGAGCGTGCT*cta*ACT AATGCCAGGGtCGAGGTTTCGATCCCCGTACGGGCCT | 377 |
| 18 | SerTAGchr6.trna61 | GACGAGGTGGCCGAGTGGTtAAGGCGATGGACT*cta*A ATCCATTGTGCTCTGCACACGTGGGTTCGAATCCCAT CCTCGTCG | 378 |
| 19 | SerTAGchr6.trna176 | GAGGCCTGGCCGAGTGGTtAAGGCGATGGACT*cta*AA TCCATTGTGCTCTGCACGCGTGGGTTCGAATCCCATC CTCG | 379 |
| 20 | SerTAGchr10.trna2 | GCAGCGATGGCCGAGTGGTtAAGGCGTTGGACT*cta*A ATCCAATGGGGTCTCCCCGCGCAGGTTCGAACCCTGC TCGCTGCG | 380 |
| 21 | SerTAGchr6.trna51 | GTAGTCGTGGCCGAGTGGTtAAGGCGATGGACT*cta*A ATCCATTGGGGTTTCCCCGCGCAGGTTCGAATCCTGC CGACTACG | 381 |
| 22 | SerTAGchr6.trna173 | GTAGTCGTGGCCGAGTGGTtAAGGCGATGGACT*cta*A ATCCATTGGGGTCTCCCCGCGCAGGTTCGAATCCTGC CGACTACG | 382 |
| 23 | SerTAGchr6.trna149 | GTAGTCGTGGCCGAGTGGTtAAGGCGATGGACT*cta*A ATCCATTGGGGTTTCCCCGCGCAGGTTCGAATCCTGT CGGCTACG | 383 |
| 1 | SerTGAnmtchr2.trna19 | GAGAAGGTcACAGAGGTtATGGGATTGGCT*tca*AACC AGTCTGtGGGGGGGTTCGATTCCCTCCTTTTTCA | 384 |
| 2 | SerTGAnmt-chr2.trna7 | GAGAAGGTcATAGAGGTtATGGGATTGGCT*tca*AACC AGTCTCTGGGGGGTTCGATTCCCTCCTTTTTCA | 385 |
| 3 | SerTGAnmtchr17.trna31 | GAAAAAGTCATAGGGGTTATGAGGCTGGCT*tca*AACC AGCCTtAGGAGGTTCAATTCCTTCCTTTTTTG | 386 |
| 4 | SerTGAchr6.trna41 | GGCCGGTTAGCTCAGTTGGTtAGAGCGTGCTGCT*tca* AATGCCAGGGtCGAGGTTTCGATCCCCGTACGGGCCT | 387 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 5 | SerTGAchr6.trna148 | GTAGTCGTGGCCGAGTGGTtAAGGCGATGGACT*tca*A ATCCATTGGGGTTTCCCCGCGCAGGTTCGAATCCTGC CGACTACG | 388 |
| 6 | SerTGAchr6.trna50 | GTAGTCGTGGCCGAGTGGTtAAGGCGATGGACT*tca*A ATCCATTGGGGTTTCCCCACGCAGGTTCGAATCCTGC CGACTACG | 389 |
| 7 | SerTGAchr6.trna146 | GTAGTCGTGGCCGAGTGGTtAAGGTGATGGACT*tca*A ACCCATTGGGGTCTCCCCGCGCAGGTTCGAATCCTGC CGACTACG | 390 |
| 8 | SerTGAchr7.trna15 | GGGTGTATGGCTCAGGGGTAGAGAATTTGACT*tca*GA TCAAGAGGt CCCTGGTTCAAATCCAGGTGCCCCCT | 391 |
| 9 | SerTGAchr11.trna10 | AGTTGTAGCTGAGTGGTtAAGGCAACGAGCT*tca*AAT TCGTTGGTTTCTCTCTg TGCAGGTTTGAATCCTGCTA ATTA | 392 |
| 10 | SerTGAchr11.trna8 | CAAGAAATTCATAGAGGTTATGGGATTGGCT*tca*AAC CAGTTT*c*AGGAGGTTCGATTCCTTCCTTTTTGG | 393 |
| 11 | SerTGAchr17.trna41 | GCTGTGATGGCCGAGTGGTtAAGGCGTTGGACT*tca*A ATCCAATGGGGTCTCCCCGCGCAGGTTCGAATCCTGC TCACAGCG | 394 |
| 12 | SerTGAchr6.trna34 | GCTGTGATGGCCGAGTGGTtAAGGCGTTGGACT*tca*A ATCCAATGGGGTCTCCCCGCGCAGGTTCAAATCCTGC TCACAGCG | 395 |
| 13 | SerTGAchr6.trna138 | GCTGTGATGGCCGAGTGGTtAAGGTGTTGGACT*tca*A ATCCAATGGGGGTTCCCCGCGCAGGTTCAAATCCTGC TCACAGCG | 396 |
| 14 | SerTGAchr12.trna2 | GTCACGGTGGCCGAGTGGTtAAGGCGTTGGACT*tca*A ATCCAATGGGGTTTCCCCGCACAGGTTCGAATCCTGT TCGTGACG | 397 |
| 15 | SerTGAchr6.trna30 | GACGAGGTGGCCGAGTGGTtAAGGCGATGGACT*tca*A ATCCATTGTGCTCTGCACGCGTGGGTTCGAATCCCAC CCTCGTCG | 398 |
| 16 | SerTGAchr6.trna43 | GACGAGGTGGCCGAGTGGTtAAGGCGATGGACT*tca*A ATCCATTGTGCTCTGCACGCGTGGGTTCGAATCCCAC CTTCGTCG | 399 |
| 17 | SerTGAchr11.trna6 | GGCCGGTTAGCTCAGTTGGTtAGAGCGTGCT*tca*ACT AATGCCAGGGt CGAGGTTTCGATCCCCGTACGGGCCT | 400 |
| 18 | SerTGAchr6.trna61 | GACGAGGTGGCCGAGTGGTtAAGGCGATGGACT*tca*A ATCCATTGTGCTCTGCACACGTGGGTTCGAATCCCAT CCTCGTCG | 401 |
| 19 | SerTGAchr6.trna176 | GAGGCCTGGCCGAGTGGTtAAGGCGATGGACT*tca*AA TCCATTGTGCTCTGCACGCGTGGGTTCGAATCCCATC CTCG | 402 |
| 20 | SerTGAchr10.trna2 | GCAGCGATGGCCGAGTGGTtAAGGCGTTGGACT*tca*A ATCCAATGGGGTCTCCCCGCGCAGGTTCGAACCCTGC TCGCTGCG | 403 |
| 21 | SerTGAchr6.trna51 | GTAGTCGTGGCCGAGTGGTtAAGGCGATGGACT*tca*A ATCCATTGGGGTTTCCCCGCGCAGGTTCGAATCCTGC CGACTACG | 404 |
| 22 | SerTGAchr6.trna173 | GTAGTCGTGGCCGAGTGGTtAAGGCGATGGACT*tca*A ATCCATTGGGGTCTCCCCGCGCAGGTTCGAATCCTGC CGACTACG | 405 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 23 | SerTGAchr6.trna149 | GTAGTCGTGGCCGAGTGGTt*AAGGCGATGGACTtcaA*ATCCATTGGGGTTTCCCCGCGCAGGTTCGAATCCTGTCGGCTACG | 406 |
| 1 | SerTAAnmtchr2.trna19 | GAGAAGGTc*ACAGAGGTtATGGGATTGGCTttaAACC*AGTCTGtGGGGGGGTTCGATTCCCTCCTTTTTCA | 557 |
| 2 | SerTAAnmtchr2.trna7 | GAGAAGGTc*ATAGAGGTtATGGGATTGGCTttaAACC*AGTCTCTGGGGGGTTCGATTCCCTCCTTTTTCA | 558 |
| 3 | SerTAAnmtchr17.trna31 | GAAAAAGTCATAGGGGTTATGAGGCTGGCT*ttaAACC*AGCCTtAGGAGGTTCAATTCCTTCCTTTTTTG | 559 |
| 4 | SerTAAchr6.trna41 | GGCCGGTTAGCTCAGTTGGTtAGAGCGTGCTGCT*tta*AATGCCAGGGtCGAGGTTTCGATCCCCGTACGGGCCT | 560 |
| 5 | SerTAAchr6.trna148 | GTAGTCGTGGCCGAGTGGTtAAGGCGATGGACT*ttaA*ATCCATTGGGGTTTCCCCGCGCAGGTTCGAATCCTGCCGACTACG | 561 |
| 6 | SerTAAchr6.trna50 | GTAGTCGTGGCCGAGTGGTtAAGGCGATGGACT*ttaA*ATCCATTGGGGTTTCCCCACGCAGGTTCGAATCCTGCCGACTACG | 562 |
| 7 | SerTAAchr6.trna146 | GTAGTCGTGGCCGAGTGGTtAAGGTGATGGACT*ttaA*ACCCATTGGGGTCTCCCCGCGCAGGTTCGAATCCTGCCGACTACG | 563 |
| 8 | SerTAAchr7.trna15 | GGGTGTATGGCTCAGGGGTAGAGAATTTGACT*ttaGA*TCAAGAGGtCCCTGGTTCAAATCCAGGTGCCCCCT | 564 |
| 9 | SerTAAchr11.trna10 | AGTTGTAGCTGAGTGGTtAAGGCAACGAGCT*ttaAAT*TCGTTGGTTTCTCTCTgTGCAGGTTTGAATCCTGCTAATTA | 565 |
| 10 | SerTAAchr11.trna8 | CAAGAAATTCATAGAGGTTATGGGATTGGCT*ttaAAC*CAGTTTcAGGAGGTTCGATTCCTTCCTTTTTGG | 566 |
| 11 | SerTAAchr17.trna41 | GCTGTGATGGCCGAGTGGTtAAGGCGTTGGACT*ttaA*ATCCAATGGGGTCTCCCCGCGCAGGTTCGAATCCTGCTCACAGCG | 567 |
| 12 | SerTAAchr6.trna34 | GCTGTGATGGCCGAGTGGTtAAGGCGTTGGACT*ttaA*ATCCAATGGGGTCTCCCCGCGCAGGTTCAAATCCTGCTCACAGCG | 568 |
| 13 | SerTAAchr6.trna138 | GCTGTGATGGCCGAGTGGTtAAGGTGTTGGACT*ttaA*ATCCAATGGGGGTTCCCCGCGCAGGTTCAAATCCTGCTCACAGCG | 569 |
| 14 | SerTAAchr12.trna2 | GTCACGGTGGCCGAGTGGTtAAGGCGTTGGACT*ttaA*ATCCAATGGGGTTTCCCCGCACAGGTTCGAATCCTGTTCGTGACG | 570 |
| 15 | SerTAAchr6.trna30 | GACGAGGTGGCCGAGTGGTtAAGGCGATGGACT*ttaA*ATCCATTGTGCTCTGCACGCGTGGGTTCGAATCCCACCCTCGTCG | 571 |
| 16 | SerTAAchr6.trna43 | GACGAGGTGGCCGAGTGGTtAAGGCGATGGACT*ttaA*ATCCATTGTGCTCTGCACGCGTGGGTTCGAATCCCACCTTCGTCG | 572 |
| 17 | SerTAAchr11.trna6 | GGCCGGTTAGCTCAGTTGGTtAGAGCGTGCT*ttaACT*AATGCCAGGGtCGAGGTTTCGATCCCCGTACGGGCCT | 573 |
| 18 | SerTAAchr6.trna61 | GACGAGGTGGCCGAGTGGTtAAGGcGATGGACT*ttaA*ATCCATTGTGCTCTGCACACGTGGGTTCGAATCCCATCCTCGTCG | 574 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 19 | SerTAAchr6.trna176 | GAGGCCTGGCCGAGTGGTtAAGGCGATGGACT*tta*AA TCCATTGTGCTCTGCACGCGTGGGTTCGAATCCCATC CTCG | 575 |
| 20 | SerTAAchr10.trna2 | GCAGCGATGGCCGAGTGGTtAAGGCGTTGGACT*tta*A ATCCAATGGGGTCTCCCCGCGCAGGTTCGAACCCTGC TCGCTGCG | 576 |
| 21 | SerTAAchr6.trna51 | GTAGTCGTGGCCGAGTGGTtAAGGCGATGGACT*tta*A ATCCATTGGGGTTTCCCCGCGCAGGTTCGAATCCTGC CGACTACG | 577 |
| 22 | SerTAAchr6.trna173 | GTAGTCGTGGCCGAGTGGTtAAGGCGATGGACT*tta*A ATCCATTGGGGTCTCCCCGCGCAGGTTCGAATCCTGC CGACTACG | 578 |
| 23 | SerTAAchr6.trna149 | GTAGTCGTGGCCGAGTGGTtAAGGCGATGGACT*tta*A ATCCATTGGGGTTTCCCCGCGCAGGTTCGAATCCTGT CGGCTACG | 579 |
| 1 | LysTAAchr19.trna6 | GCCCAGCTAGCTCAGTCGGTAGAGCATAAGACT*tta*A ATCTCAGGG*t*TGTGGATTCGTGCCCCATGCTGGGTG | 407 |
| 2 | LysTAAchr19.trna7 | CTGCAGCTAGCTCAGTCGGTAGAGCATGAGACT*tta*A ATCTCAGGG*t*CATGGGTTCGTGCCCCATGTTGGG | 408 |
| 3 | LysTAAchr1.trna8 | CCAGCATGTCTCAGTCGGTATAGTGTGAGACT*tta*AA TCTCAGGG*t*CGTGGGTTCAAGCCCCACATTGGG | 409 |
| 4 | LysTAAchr1.trna47 | GTCTAGCTAGATCAGTTGGTAGAGCATAAGACT*tta*A ATCTCAGGG*t*CATGGGTTTGAGCCCTACGTTGGGCG | 410 |
| 5 | LysTAAchr16.trna14 | GCCCAGCTAGCTCAGCCGGTAGAGCACAAGACT*tta*A ATCTCAGGG*t*CGTGGGTTTGAGCCCTGTGTTGAGCA | 411 |
| 6 | LysTAAchr11.trna2 | CCGAATAGCTTAGTTGAT*g*AAGCGTGAGACT*tta*AAT CTCAGGG*t*AGTGGGTTCAAGCCCCACATTGGA | 412 |
| 7 | LysTAAchr15.trna7 | GCCTGGCTACCTCAGTTGGTAGAGCATGGGACT*tta*A ATCCCAGAG*tc*AGTGGGTTCAAGCCTCACATTGAGTG | 413 |
| 8 | LysTAAchr16.trna31 | GCCCGGCTAGCTCAGTCGGTAGAGCATGAGACC*tta*A ATCTCAGGG*t*CGTGGGTTCGAGCCCCACGTTGGGCG | 414 |
| 9 | LysTAAchr16.trna11 | GCCCGGCTAGCTCAGTCGGTAGAGCATGGGACT*tta*A ATCTCAGGG*t*CGTGGGTTCGAGCCCCACGTTGGGCG | 415 |
| 10 | LysTAAchr16.trna30 | GCCCGGCTAGCTCAGTCGATAGAGCATGAGACT*tta*A ATCTCAGGG*t*CGTGGGTTCGAGCCGCACGTTGGGCG | 416 |
| 11 | LysTAAchr1.trna117 | GCCCAGCTAGCTCAGTCGGTAGAGCATGAGACT*tta*A ATCTCAGGG*t*CATGGGTTTGAGCCCCACGTTTGGTG | 417 |
| 12 | LysTAAchr16.trna6 | GCCTGGCTAGCTCAGTCGGCAAAGCATGAGACT*tta*A ATCTCAGGG*t*CGTGGGCTCGAGCTCCATGTTGGGCG | 418 |
| 13 | LysTAAchr5.trna25 | GCCCGACTACCTCAGTCGGT*g*GAGCATGGGACT*tta*C ATCCCAGGG*t*TGTGGGTTCGAGCCCCACATTGGGCA | 419 |
| 14 | LysTAAchr16.trna1 | CCCCGGCTGGCTCAGTCAGTAGATCATGAGACT*tta*A ATCTCAGGG*t*CGTGGGTTCACGCCCCACACTGGGCG | 420 |
| 15 | LysTAAchr7.trna30 | GCGCTAGTCAGTAGAGCATGAGACT*tta*AATCTCAGG G*t*CGTGGGTTCGAGCCCCACATCGGGCG | 421 |
| 16 | LysTAAchr16.trna23 | GCCTGGATAGCTCAGTTGGTAGAGCATCAGACT*tta*A ATCTGAGGG*t*CCAGGGTTCAAGTCCCTGTTCAGGCA | 422 |
| 17 | LysTAAchr19.trna10 | GCCAGGATAGTTCAGGTGGTAGAGCATCAGACT*ttaa* AACCTGAGGG*t*TCAGGGTTCAAGTCTCTGTTTGGGCG | 423 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 18 | LysTAAchr12.trna1 | ACCCAGATAGCTCAGTCAGTAGAGCATCAGACT*tta*A ATCTGAGGGtCCAAGGTTCATGTCCCTTTTTGGGTG | 424 |
| 19 | LysTAAchr19.trna8 | ACCTGGGTAGCTTAGTTGGTAGAGCATTGGACT*tta*A ATTTGAGGGcCCAGGTTTCAAGTCCCTGTTTGGGTG | 425 |
| 20 | LysTAAchr6.trna119 | GCCTGGGTAGCTCAGTCGGTAGAGCTaTCAGACT*tta* AGCCTGAGGAtTCAGGGTTCAATCCCTTGCTGGGGCG | 426 |
| 21 | LysTAAchr14.trna13 | GATAGCTCAGTTGATAGAGCATCAGACT*tta*AATCTG AGGGtCCAGGGTTCATGTCCCTGTT | 427 |
| 22 | LysTAAchr2.trna15 | GTTGGGGTAACTCAGTTGGTAGAGTAGCAGACT*tta*C ATCTGAGGGtCCAGGGTTTAAGTCCATGTCCAGGCA | 428 |
| 23 | LysTAAchr11.trna11 | GCCTGGATAGCTCAGTTGGTAGAGCATCAGACT*tta*A ATCTGAGGGtCCAGGGTTCAAGTCCCTGTTCAGGCG | 429 |
| 24 | LysTAAchr6.trna144 | GCCTGGATAGCTCAGTCGGTAGAGCATCAGACTttaA ATCTGAGGGtCCAGGGTTCAAGTCCCTGTTCAGGCG | 430 |
| 25 | LysTAAchr11.trna5 | GCCCGGATAGCTCAGTCGGTAGAGCATCAGACT*tta*A ATCTGAGGGtCCGGGGTTCAAGTCCCTGTTCGGGCG | 431 |
| 26 | LysTAAchr6.trna150 | GCCTGGGTAGCTCAGTCGGTAGAGCATCAGACT*tta*A ATCTGAGGGtCCAGGGTTCAAGTCCCTGTCCAGGCG | 432 |
| 27 | LysTAAchr6.trna70 | GCCTGGATAGCTCAGTTGGTAGAACATCAGACT*tta*A ATCTGACGGtGCAGGGTTCAAGTCCCTGTTCAGGCG | 433 |
| 28 | LysTAAchr1.trna50 | GCCCGGAGAGCTCAGTGGGTAGAGCATCAGACT*tta*A ATCTGAGGGtCCAGGGTTCAAGTCCTCGTTCGGGCA | 434 |
| 29 | LysTAAchr6.trna53 | ACCTGGGTAGCTCAGTAGGTAGAACATCAGACTttaA ATCTGAGGGtCTAGGGTTCAAGTCCCTGTCCAGGCG | 435 |
| 30 | LysTAAchr3.trna2 | GCCTGGATAGCTCCTTCGGTAGAGCATCATcagACT*t ta*AATGTGAGGGtCCAGGGTTCAAGTTCCTGTTTGGG CG | 436 |
| 1 | LysTAGchr19.trna6 | GCCCAGCTAGCTCAGTCGGTAGAGCATAAGACT*cta*A ATCTCAGGGtTGTGGATTCGTGCCCCATGCTGGGTG | 437 |
| 2 | LysTAGchr19.trna7 | CTGCAGCTAGCTCAGTCGGTAGAGCATGAGACT*cta*A ATCTCAGGGtCATGGGTTCGTGCCCCATGTTGGG | 438 |
| 3 | LysTAGchr1.trna8 | CCAGCATGTCTCAGTCGGTATAGTGTGAGACT*cta*AA TCTCAGGGtCGTGGGTTCAAGCCCCACATTGGG | 439 |
| 4 | LysTAGchr1.trna47 | GTCTAGCTAGATCAGTTGGTAGAGCATAAGACT*cta*A ATCTCAGGGtCATGGGTTTGAGCCCTACGTTGGGCG | 440 |
| 5 | LysTAGchr16.trna14 | GCCCAGCTAGCTCAGCCGGTAGAGCACAAGACT*cta*A ATCTCAGGGtCGTGGGTTTGAGCCCTGTGTTGAGCA | 441 |
| 6 | LysTAGchr11.trna2 | CCGAATAGCTTAGTTGATgAAGCGTGAGACT*cta*AAT CTCAGGGtAGTGGGTTCAAGCCCCACATTGGA | 442 |
| 7 | LysTAGchr15.trna7 | GCCTGGCTACCTCAGTTGGTAGAGCATGGGACT*cta*A ATCCCAGAGtcAGTGGGTTCAAGCCTCACATTGAGTG | 443 |
| 8 | LysTAGchr16.trna31 | GCCCGGCTAGCTCAGTCGGTAGAGCATGAGACC*cta*A ATCTCAGGGtCGTGGGTTCGAGCCCCACGTTGGGCG | 444 |
| 9 | LysTAGchr16.trna11 | GCCCGGCTAGCTCAGTCGGTAGAGCATGGGACT*cta*A ATCTCAGGGtCGTGGGTTCGAGCCCCACGTTGGGCG | 445 |
| 10 | LysTAGchr16.trna30 | GCCCGGCTAGCTCAGTCGATAGAGCATGAGACT*cta*A ATCTCAGGGtCGTGGGTTCGAGCCGCACGTTGGGCG | 446 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 11 | LysTAGchr1.trna117 | GCCCAGCTAGCTCAGTCGGTAGAGCATGAGACT*cta*A ATCTCAGGG*t*CATGGGTTTGAGCCCCACGTTTGGTG | 447 |
| 12 | LysTAGchr16.trna6 | GCCTGGCTAGCTCAGTCGGCAAAGCATGAGACT*cta*A ATCTCAGGG*t*CGTGGGCTCGAGCTCCATGTTGGGCG | 448 |
| 13 | LysTAGchr5.trna25 | GCCCGACTACCTCAGTCGGT*g*GAGCATGGGACT*cta*C ATCCCAGGG*t*TGTGGGTTCGAGCCCCACATTGGGCA | 449 |
| 14 | LysTAGchr16.trna1 | CCCCGGCTGGCTCAGTCAGTAGATCATGAGACT*cta*A ATCTCAGGG*t*CGTGGGTTCACGCCCCACACTGGGCG | 450 |
| 15 | LysTAGchr7.trna30 | GCGCTAGTCAGTAGAGCATGAGACT*cta*AATCTCAGG G*t*CGTGGGTTCGAGCCCCACATCGGGCG | 451 |
| 16 | LysTAGchr16.trna23 | GCCTGGATAGCTCAGTTGGTAGAGCATCAGACT*cta*A ATCTGAGGG*t*CCAGGGTTCAAGTCCCTGTTCAGGCA | 452 |
| 17 | LysTAGchr19.trna10 | GCCAGGATAGTTCAGGTGGTAGAGCATCAGACT*cta*A ACCTGAGGG*t*TCAGGGTTCAAGTCTCTGTTTGGGCG | 453 |
| 18 | LysTAGchr12.trna1 | ACCCAGATAGCTCAGTCAGTAGAGCATCAGACT*cta*A ATCTGAGGG*t*CCAAGGTTCATGTCCCTTTTTGGGTG | 454 |
| 19 | LysTAGchr19.trna8 | ACCTGGGTAGCTTAGTTGGTAGAGCATTGGACT*cta*A ATTTGAGGG*c*CCAGGTTTCAAGTCCCTGTTTGGGTG | 455 |
| 20 | LysTAGchr6.trna119 | GCCTGGGTAGCTCAGTCGGTAGAGCTaTCAGACT*cta* aAGCCTGAGGA*t*TCAGGGTTCAATCCCTTGCTGGGGC G | 456 |
| 21 | LysTAGchr14.trna13 | GATAGCTCAGTTGATAGAGCATCAGACT*cta*AATCTG AGGG*t*CCAGGGTTCATGTCCCTGTT | 457 |
| 22 | LysTAGchr2.trna15 | GTTGGGGTAACTCAGTTGGTAGAGTAGCAGACT*cta*C ATCTGAGGG*t*CCAGGGTTTAAGTCCATGTCCAGGCA | 458 |
| 23 | LysTAGchr11.trna11 | GCCTGGATAGCTCAGTTGGTAGAGCATCAGACT*cta*A ATCTGAGGG*t*CCAGGGTTCAAGTCCCTGTTCAGGCG | 459 |
| 24 | LysTAGchr6.trna144 | GCCTGGATAGCTCAGTCGGTAGAGCATCAGACT*cta*A ATCTGAGGG*t*CCAGGGTTCAAGTCCCTGTTCAGGCG | 460 |
| 25 | LysTAGchr11.trna5 | GCCCGGATAGCTCAGTCGGTAGAGCATCAGACT*cta*A ATCTGAGGG*t*CCGGGGTTCAAGTCCCTGTTCGGGCG | 461 |
| 26 | LysTAGchr6.trna150 | GCCTGGGTAGCTCAGTCGGTAGAGCATCAGACT*cta*A ATCTGAGGG*t*CCAGGGTTCAAGTCCCTGTTCCAGGCG | 462 |
| 27 | LysTAGchr6.trna70 | GCCTGGATAGCTCAGTTGGTAGAACATCAGACT*cta*A ATCTGACGG*t*GCAGGGTTCAAGTCCCTGTTCAGGCG | 463 |
| 28 | LysTAGchr1.trna50 | GCCCGGAGAGCTCAGTGGGTAGAGCATCAGACT*cta*A ATCTGAGGG*t*CCAGGGTTCAAGTCCTCGTTCGGGCA | 464 |
| 29 | LysTAGchr6.trna53 | ACCTGGGTAGCTCAGTAGGTAGAACATCAGACT*cta*A ATCTGAGGG*t*CTAGGGTTCAAGTCCCTGTTCCAGGCG | 465 |
| 30 | LysTAGchr3.trna2 | GCCTGGATAGCTCCTTCGGTAGAGCATCAT*cag*ACT*c ta*AATGTGAGGG*t*CCAGGGTTCAAGTTCCTGTTTGGG CG | 466 |
| 1 | CysTGAUndchr17.trna20 | GGCAGAATGGTGCAGCGGT*tc*AGCACCCAGG*t*CTT*tc a*G*c*CAGCTGTTGCCTGGGCTCAAATCCCAGCTCTGCC A | 467 |
| 2 | CysTGAchr5.trna30 | GGCTGTATAGCTCAGTGGTAGAGCATTTGACT*tca*G*a atcctatactcaggggaaggagaactgggggtttctc agtgggtcaaaggacttgtagtggtaaatcaaaagca actctataagctatgtaacaaa*CTTTAAAGTCATA*t*G TAG*c*TGGGTTCAAATCCTGTTTCTGCCA | 468 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 3 | CysTGAchr5.trna3/ nointron | GGCTGTATAGCTCAGTGGTAGAGCATTTGACT*tca*GC TTTAAAGTCATAt*GTAGc*TGGGTTCAAATCCTGTTTC TGCCA | 469 |
| 4 | CysTGAchr7.trna8 | GGGGGCATAGCTCAGTGGTAGAGCATTTGACT*tca*GA TCAAGAGG*t*CCCTGGTTCAAATCCAGGTGCCCCCT | 470 |
| 5 | CysTGAchr7.trna26 | GGGGGTATAGCTCAGGGGTAGAGCATTTGACT*tca*GA TCAAGAGG*t*CCCTGGTTCAAATCCAGGTGCCCCCC | 471 |
| 6 | CysTGAchr7.trna24 | GGGGGTATAGCTTAGCGGTAGAGCATTTGACT*tca*GA TCAAGAGG*t*CCCCGGTTCAAATCCGGGTGCCCCCT | 472 |
| 7 | CysTGAchr7.trna20 | GGGGGTATAGCTTAGGGGTAGAGCATTTGACT*tca*GA TCAAAAGG*t*CCCTGGTTCAAATCCAGGTGCCCCTT | 473 |
| 8 | CysTGAchr7.trna29 | GGGGGTATAGCTCAGGGGTAGAGCATTTGACT*tca*GA TCAAGAGG*t*CCCCAGTTCAAATCTGGGTGCCCCCT | 474 |
| 9 | CysTGAchr17.trna28 | GGGGGTATAGCTCAGGGGTAGAGCATTTGACT*tca*GA TCAAGAAG*t*CCCCGGTTCAAATCCGGGTGCCCCCT | 475 |
| 10 | CysTGAchr7.trna13 | GGGGGTATAGCTCAGGGGTAGAGCATTTGACT*tca*GA TCAAGAGG*t*CTCTGGTTCAAATCCAGGTGCCCCCT | 476 |
| 11 | CysTGAchr7.trna10 | GGGGGTATAGCTCAGGGGTAGAGCACTTGACT*tca*GA TCAAGAAG*t*CCTTGGTTCAAATCCAGGTGCCCCCT | 477 |
| 12 | CysTGAchr7.trna19 | GGGGATATAGCTCAGGGGTAGAGCATTTGACT*tca*GA TCAAGAGG*t*CCCCGGTTCAAATCCGGGTGCCCCCC | 478 |
| 13 | CysTGAchr7.trna27 | GGGGGTATAGTTCAGGGGTAGAGCATTTGACT*tca*GA TCAAGAGG*t*CCCTGGTTCAAATCCAGGTGCCCCCT | 479 |
| 14 | CysTGAchr7.trna21 | GGGGGTATAGCTCAGGGGTAGAGCATTTGACT*tca*AA TCAAGAGG*t*CCCTGATTCAAATCCAGGTGCCCCCT | 480 |
| 15 | CysTGAchr7.trna14 | GGGCGTATAGCTCAGGGGTAGAGCATTTGACT*tca*GA TCAAGAGG*t*CCCCAGTTCAAATCTGGGTGCCCCCT | 481 |
| 16 | CysTGAchr7.trna17 | GGGGGTATAGCTCACAGGTAGAGCATTTGACT*tca*GA TCAAGAGG*t*CCCCGGTTCAAATCTGGGTGCCCCCT | 482 |
| 17 | CysTGAchr7.trna11 | GGGCGTATAGCTCAGGGGTAGAGCATTTGACT*tca*GA TCAAGAGG*t*CCCCAGTTCAAATCTGGGTGCCCA | 483 |
| 18 | CysTGAchr7.trna22 | GGGGGTATAGCTCACAGGTAGAGCATTTGACT*tca*GA TCAAGAGG*t*CCCCGGTTCAAATCCGGTTACTCCCT | 484 |
| 19 | CysTGAchr17.trna29 | GGGGGTAGGGCTCAGGGAt*AGAGCATTTGACT*tca*GA TCAAGAGG*t*CCCCGGTTCGAATCTAGGTGCCCCCT | 485 |
| 20 | CysTGAchr3.trna9 | GGTATATCTCAGGGGGc*AGAGCATTTGACT*tca*GATC AAGAGG*t*CCCCGGTTGAAATCCGGGTGCT | 486 |
| 21 | CysTGAchr7.trna23 | GGGGGTATAGCTCAGGGGTAGAGCACTTGACT*tca*GA TCAAGAGG*t*CCCTGGTTCAAATCCAGGTGCCCCCT | 487 |
| 22 | CysTGAchr17.trna27 | GGGGGTATAGCTCAGTGGTAGAGCATTTGACT*tca*GA TCAAGAGG*t*CCCTGGTTCAAATCCGGGTGCCCCCT | 488 |
| 23 | CysTGAchr15.trna3 | GGGGGTATAGCTCAGTGGGTAGAGCATTTGACT*tca*G ATCAAGAGG*t*CCCCGGTTCAAATCCGGGTGCCCCCT | 489 |
| 24 | CysTGAchr3.trna6 | GGGGGTGTAGCTCAGTGGTAGAGCATTTGACT*tca*GA TCAAGAGG*t*CCCTGGTTCAAATCCAGGTGCCCCCT | 490 |
| 25 | CysTGAchr14.trna9 | GGGGGTATAGCTCAGGGGTAGAGCATTTGACT*tca*GA TCAAGAGG*t*CCCCGGTTCAAATCCGGGTGCCCCCT | 491 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 26 | CysTGAchr3.trna5 | GGGGGTATAGCTCAGGGGTAGAGCATTTGACT*tca*GA TCAAGAGG*t*CCCTGGTTCAAATCCAGGTGCCCCCT | 492 |
| | *Mus_musculus*chr11. trna817-Trp | GACCTCGTGGCGCAATGGTAGCGCGTCTGACT*tca*GA TCAGAAGG*t*TGCGTGTTCAAATCACGTCGGGGTCA | 493 |
| | *Mus_musculus*chr10. trna567 | GACCTCGTGGCACAATGGTAGCACGTCTGACT*tca*GA TCAGAAGG*t*TGCGTGTTCAAATCACGTCGGGGTCA | 494 |
| | *Saccharomyces_ cerevisiae*chrVII. trna33 | GAAGCGGTGGCTCAATGGTAGAGCTTTCGACT*tca*At taaatcttggaaattccacggaataagattgcaATCG AAGGG*t*TGCAGGTTCAATTCCTGTCCGTTTCA | 495 |
| | *Saccharomyces_ cerevisiae*chrVII. trna33 | GAAGCGGTGGCTCAATGGTAGAGCTTTCGACT*tca*AA TCGAAGGG*t*TGCAGGTTCAATTCCTGTCCGTTTCA | 496 |
| | *Pan_troglodytes*chr7. trna28 | GGCCTCATGGTGCAACAGTAGTGTGTCTGACT*tca*GA TCAGAAGG*t*TGTATGTTCAAATCACATAGGGGTCA | 497 |
| | *Oryctolagus_ cuniculus*chrUn0422. trna1 | GACCTCGTGGTGAAATGGTAGCATGTTTGACT*tca*AA TCAGGAGG*t*TGTGTGTTCAAGTCACATCAGGGTCA | 498 |
| | *Oryctolagus_ cuniculus_chrUn0563. trna1 | GACCTTGTGGCGCAATGGTAGCATGTTTGACT*tca*AA TCAGGAGG*t*TGTGTGTTCAAGTCACATCAGGGTCA | 499 |
| | *Oryctolagus_ cuniculus_chrUn0062. trna12 | GACCTCGTGGCGCAACGGTAGCGCGTCTGACT*tca*GA TCAGAAGG*t*CTGCGTGTTCGAATCACGCCGGGGTCA | 500 |
| | *Rattus_norvegicus_ chr13*.trna4571 | GACCTTGTGGCTCAATGGTAGCGCATCTGACT*tca*GA TCAGGAGG*t*TGCACGTTCAAATCATGCCGGGGTCA | 501 |
| | *Rattus_norvegicus_ chr17*.trna3948 | GACCTTGTGGCGCAACGGTAGCGCGTCTGACT*tca*GA TCAGAAGG*t*TGCGTGTTCAAATCACGTCGGGGTCA | 502 |
| | *Xenopus_tropicalis_ tRNA-Trp-CCA-10-1* | GACCTCGTGGCGCAACGGTAGCGCGTCTGACT*tca*GA TCAGAAGG*t*TGCGTATTCAAATCACGTCGGGGTCA | 503 |
| | *Xenopus_tropicalis_ tRNA-Trp-CCA-11-1* | GACCTCGTGGCGCAACGGCAGCGCGTCTGACT*tca*CA TTAGAAGG*t*TGCGTGTTCAAATCACGTCGGGGTCA | 504 |
| | *Xenopus_tropicalis_ tRNA-Trp-CCA-12-1* | GACCTCATGGCGCAACGGTAGCGCGTCTGACT*tca*GA TCAGAAGG*t*TGCGTGTTCAAATCACATCGGGGTCA | 505 |
| | *Xenopus_tropicalis_ tRNA-Trp-CCA-13-1* | GACCTCGTGGTGCAACGGTAGCGCGTATGATT*tca*GA TCAGAAGG*t*TGCGTGTTCAAATCACGTCGGGGTCA | 506 |
| | *Xenopus_tropicalis_ tRNA-Trp-CCA-3-1* | GACCTCGTAGCGCAACGGTAGCGCGTCTGACT*tca*GA TCAGAAGG*t*TGCGTGTTCAAATCACGTCGGGGTCA | 507 |
| | *Xenopus_tropicalis_ tRNA-Trp-CCA-5-1* | AGGGGTATAGCTCAATTGGCAGAGCGTCGGTCT*tca*A AACCGAAGG*t*TGTAGGTTCGATTCCTACTGCCCCTGC CA | 508 |
| | *Xenopus_tropicalis_ tRNA-Trp-CCA-6-1* | GACCTCATGGCGCAACGGTAGCGCGTCTGACT*tca*GA TCAGAAGG*t*TGCGTGTTCAAATCACGTCGGGGTCA | 509 |
| | *Xenopus_tropicalis_ tRNA-Trp-CCA-7-1* | GACCTCGTGGCGCAACGGTAGCGCGTCTAACT*tca*GA TCAGAAGG*t*TGCGTGTTCAAATCACGTCGGGGTCA | 510 |
| | *Xenopus_tropicalis_ tRNA-Trp-CCA-8-1* | ACGGGAGTAGCTCAGTTGGTAGAGCACCGGTCT*tca*A AACCGGGTG*t*CGGGAGTTCGAGCCTCTCCTCCCGTG | 511 |
| | *Xenopus_tropicalis_ tRNA-Trp-CCA-9-1* | GACCTCGTGGCGCAACGGTAGCGCGTCTGACT*tca*GA TCAGAAGG*t*TGCATGTTCAAATCACGTCGGGGTCA | 512 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| tRNAscan-SE ID | Sequence | SEQ ID NO |
|---|---|---|
| Drosophila_ melanogaster_ tRNA-Trp-CCA-2-1 | GACTCCGTGGCGCAACGGTAGCGCGTCCGACTtcaGA TCGGAAGGtTGCGTGTTCAAATCACGTCGGGGTCA | 513 |
| Drosophila_ melanogaster_ tRNA-Trp-CCA-1-1 | GACTCCGTGGCGCAACGGTAGCGCGTCTGACTtcaGA TCAGAAGGtTGCGTGTTCAAATCACGTCGGGGTCA | 514 |
| TrpWT-chr17.trna39 | GGCCTCGTGGCGCAACGGTAGCGCGTCTGACTccaGA TCAGAAGGtTGCGTGTTCAAATCACGTCGGGGTCA | 515 |
| HirshWT | GGCCTCGTGGCGCAACGGTAGCaCGTCTGACTccaGA TCAGAAGGtTGCGTGTTCAAATCACGTCGGGGTCA | 516 |
| HirshACE-tRNA | CGGCCTCGTGGCGCAACGGTAGCaCGTCTGACTtcaG ATCAGAAGGtTGCGTGTTCAAATCACGTCGGGGTCA | 517 |
| G9CWT | GGCCTCGTcGCGCAACGGTAGCGCGTCTGACTccaGA TCAGAAGGtTGCGTGTTCAAATCACGTCGGGGTCA | 518 |
| G9CACE-tRNA | GGCCTCGTcGCGCAACGGTAGCGCGTCTGACTtcaGA TCAGAAGGtTGCGTGTTCAAATCACGTCGGGGTCA | 519 |
| G9C + HirshWT | GGCCTCGTcGCGCAACGGTAGCaCGTCTGACTccaGA TCAGAAGGtTGCGTGTTCAAATCACGTCGGGGTCA | 520 |
| G9C + HirshACE-tRNA | GGCCTCGTcGCGCAACGGTAGCaCGTCTGACTtcaGA TCAGAAGGtTGCGTGTTCAAATCACGTCGGGGTCA | 521 |

Example 5 References

1. Maquat, L. E., Kinniburgh, A. J., Rachmilewitz, E. A. & Ross, J. Unstable beta-globin mRNA in mRNA-deficient beta o thalassemia. Cell 27, 543-553 (1981).

2. Popp, M. W. & Maquat, L. E. Organizing principles of mammalian nonsense-mediated mRNA decay. Annu Rev Genet 47, 139-165 (2013).

3. Chang, Y. F., Imam, J. S. & Wilkinson, M. F. The nonsense-mediated decay RNA surveillance pathway. Annu Rev Biochem 76, 51-74 (2007).

4. Cheng, S. H. et al. Defective intracellular transport and processing of CFTR is the molecular basis of most cystic fibrosis. Cell 63, 827-834 (1990).

5. Lefebvre, S. et al. Identification and characterization of a spinal muscular atrophy-determining gene. Cell 80, 155-165 (1995).

6. Das, A. K. et al. Molecular genetics of palmitoyl-protein thioesterase deficiency in the U.S. J Clin Invest 102, 361-370 (1998).

7. Chang, J. C. & Kan, Y. W. beta 0 thalassemia, a nonsense mutation in man. Proc Natl Acad Sci USA 76, 2886-2889 (1979).

8. Kalatzis, V. et al. Identification of 14 novel CTNS mutations and characterization of seven splice site mutations associated with cystinosis. Hum Mutat 20, 439-446 (2002).

9. Pan, Y., Metzenberg, A., Das, S., Jing, B. & Gitschier, J. Mutations in the V2 vasopressin receptor gene are associated with X-linked nephrogenic diabetes insipidus. Nat Genet 2, 103-106 (1992).

10. Ballabio, A. & Gieselmann, V. Lysosomal disorders: from storage to cellular damage. Biochim Biophys Acta 1793, 684-696 (2009).

11. Reiners, J., Nagel-Wolfrum, K., Jurgens, K., Marker, T. & Wolfrum, U. Molecular basis of human Usher syndrome: deciphering the meshes of the Usher protein network provides insights into the pathomechanisms of the Usher disease. Exp Eye Res 83, 97-119 (2006).

12. Gilad, S. et al. Ataxia-telangiectasia: founder effect among north African Jews. Hum Mol Genet 5, 2033-2037 (1996).

13. Krawczak, M. et al. Human gene mutation database-a biomedical information and research resource. Hum Mutat 15, 45-51 (2000).

14. Howard, M., Frizzell, R. A. & Bedwell, D. M. Aminoglycoside antibiotics restore CFTR function by overcoming premature stop mutations. Nat Med 2, 467-469 (1996).

15. Arakawa, M. et al. Negamycin restores dystrophin expression in skeletal and cardiac muscles of mdx mice. J Biochem 134, 751-758 (2003).

16. Welch, E. M. et al. PTC124 targets genetic disorders caused by nonsense mutations. Nature 447, 87-91 (2007).

17. Singh, A., Ursic, D. & Davies, J. Phenotypic suppression and misreading Saccharomyces cerevisiae. Nature 277, 146-148 (1979).

18. Palmer, E., Wilhelm, J. M. & Sherman, F. Phenotypic suppression of nonsense mutants in yeast by aminoglycoside antibiotics. Nature 277, 148-150 (1979).

19. Burke, J. F. & Mogg, A. E. Suppression of a nonsense mutation in mammalian cells in vivo by the aminoglycoside antibiotics G-418 and paromomycin. Nucleic Acids Res 13, 6265-6272 (1985).

20. Du, M. et al. PTC124 is an orally bioavailable compound that promotes suppression of the human CFTR-G542X nonsense allele in a CF mouse model. *Proc Natl Acad* Sci USA 105, 2064-2069 (2008).

21. Roy, B. et al. Ataluren stimulates ribosomal selection of near-cognate tRNAs to promote nonsense suppression. *Proc Natl Acad Sci USA* 113, 12508-12513 (2016).

22. Kotecha, B. & Richardson, G. P. Ototoxicity in vitro: effects of neomycin, gentamicin, dihydrostreptomycin, amikacin, spectinomycin, neamine, spermine and poly-L-lysine. *Hear Res* 73, 173-184 (1994).

23. Dai, W. J. et al. CRISPR-Cas9 for in vivo Gene Therapy: Promise and Hurdles. *Mol Ther Nucleic Acids* 5, e349 (2016).

24. Peng, R., Lin, G. & Li, J. Potential pitfalls of CRISPR/Cas9-mediated genome editing. *FEBS J* 283, 1218-1231 (2016).

25. Temple, G. F., Dozy, A. M., Roy, K. L. & Kan, Y. W. Construction of a functional human suppressor tRNA gene: an approach to gene therapy for beta-thalassaemia. *Nature* 296, 537-540 (1982).

26. Panchal, R. G., Wang, S., McDermott, J. & Link, C. J., Jr. Partial functional correction of xeroderma pigmentosum group A cells by suppressor tRNA. *Hum Gene Ther* 10, 2209-2219 (1999).

27. Buvoli, M., Buvoli, A. & Leinwand, L. A. Suppression of nonsense mutations in cell culture and mice by multimerized suppressor tRNA genes. *Mol Cell Biol* 20, 3116-3124 (2000).

28. Lowe, T. M. & Chan, P. P. tRNAscan-SE On-line: integrating search and context for analysis of transfer RNA genes. *Nucleic Acids Res* 44, W54-57 (2016).

29. Lowe, T. M. & Eddy, S. R. tRNAscan-SE: a program for improved detection of transfer RNA genes in genomic sequence. *Nucleic Acids Res* 25, 955-964 (1997).

30. Lee, J. H., Skowron, P. M., Rutkowska, S. M., Hong, S. S. & Kim, S. C. Sequential amplification of cloned DNA as tandem multimers using class-IIS restriction enzymes. *Genetic analysis: biomolecular engineering* 13, 139-145 (1996).

31. Wang, H. et al. Improved seamless mutagenesis by recombineering using ccdB for counterselection. *Nucleic Acids Res* 42, e37 (2014).

32. Dixon, A. S. et al. NanoLuc Complementation Reporter Optimized for Accurate Measurement of Protein Interactions in Cells. *ACS chemical biology* 11, 400-408 (2016).

33. Pang, Y. L., Poruri, K. & Martinis, S. A. tRNA synthetase: tRNA aminoacylation and beyond. *Wiley Interdiscip Rev RNA* 5, 461-480 (2014).

34. Hirsh, D. Tryptophan transfer RNA as the UGA suppressor. *J Mol Biol* 58, 439-458 (1971).

35. Smith, D. & Yarus, M. Transfer RNA structure and coding specificity. I. Evidence that a D-arm mutation reduces tRNA dissociation from the ribosome. *J Mol Biol* 206, 489-501 (1989).

36. Smith, D. & Yarus, M. Transfer RNA structure and coding specificity. II. A D-arm tertiary interaction that restricts coding range. *J Mol Biol* 206, 503-511 (1989).

37. Dalphin, M. E., Brown, C. M., Stockwell, P. A. & Tate, W. P. The translational signal database, TransTerm, is now a relational database. *Nucleic Acids Res* 26, 335-337 (1998).

38. Brown, C. M., Dalphin, M. E., Stockwell, P. A. & Tate, W. P. The translational termination signal database. *Nucleic Acids Res* 21, 3119-3123 (1993).

39. Major, L. L., Edgar, T. D., Yee Yip, P., Isaksson, L. A. & Tate, W. P. Tandem termination signals: myth or reality? *FEBS Lett* 514, 84-89 (2002).

40. Wheeler, T. M. et al. Reversal of RNA dominance by displacement of protein sequestered on triplet repeat RNA. *Science* 325, 336-339 (2009).

41. Wheeler, T. M., Lueck, J. D., Swanson, M. S., Dirksen, R. T. & Thornton, C. A. Correction of ClC-1 splicing eliminates chloride channelopathy and myotonia in mouse models of myotonic dystrophy. *J Clin Invest* 117, 3952-3957 (2007).

42. Muthumani, K. et al. Novel prostate cancer immunotherapy with a DNA-encoded anti-prostate-specific membrane antigen monoclonal antibody. Cancer *Immunol Immunother* 66, 1577-1588 (2017).

43. Bladen, C. L. et al. The TREAT-NMD DMD Global Database: analysis of more than 7,000 Duchenne muscular dystrophy mutations. *Hum Mutat* 36, 395-402 (2015).

44. Brown, C. M., Stockwell, P. A., Trotman, C. N. & Tate, W. P. Sequence analysis suggests that tetra-nucleotides signal the termination of protein synthesis in eukaryotes. *Nucleic Acids Res* 18, 6339-6345 (1990).

45. Sachs, M. S. et al. Toeprint analysis of the positioning of translation apparatus components at initiation and termination codons of fungal mRNAs. *Methods* 26, 105-114 (2002).

46. Amrani, N. et al. A faux 3'-UTR promotes aberrant termination and triggers nonsense-mediated mRNA decay. *Nature* 432, 112-118 (2004).

47. Bengtson, M. H. & Joazeiro, C. A. Role of a ribosome-associated E3 ubiquitin ligase in protein quality control. *Nature* 467, 470-473 (2010).

48. Crowder, J. J. et al. Rkr1/Ltn1 Ubiquitin Ligase-mediated Degradation of Translationally Stalled Endoplasmic Reticulum Proteins. *J Biol Chem* 290, 18454-18466 (2015).

49. Rowe, S. M., Miller, S. & Sorscher, E. J. Cystic fibrosis. *The New England journal of medicine* 352, 1992-2001 (2005).

50. Manuvakhova, M., Keeling, K. & Bedwell, D. M. Aminoglycoside antibiotics mediate context-dependent suppression of termination codons in a mammalian translation system. *RNA* 6, 1044-1055 (2000).

51. Bonetti, B., Fu, L., Moon, J. & Bedwell, D. M. The efficiency of translation termination is determined by a synergistic interplay between upstream and downstream sequences in Saccharomyces cerevisiae. J Mot Blot 251, 334-345 (1995).

52. Xue, X. et al. Synthetic aminoglycosides efficiently suppress cystic fibrosis transmembrane conductance regulator nonsense mutations and are enhanced by ivacaftor. *American journal of respiratory cell and molecular biology* 50, 805-816 (2014).

53. Gogakos, T. et al. Characterizing Expression and Processing of Precursor and Mature Human tRNAs by Hydro-tRNAseq and PAR-CLIP. *Cell Rep* 20, 1463-1475 (2017).

54. Geslain, R. & Pan, T. Functional analysis of human tRNA isodecoders. *J Mol Biol* 396, 821-831 (2010).

55. Ingolia, N. T., Brar, G. A., Rouskin, S., McGeachy, A. M. & Weissman, J. S. The ribosome profiling strategy for monitoring translation in vivo by deep sequencing of ribosome-protected mRNA fragments. *Nat Protoc* 7, 1534-1550 (2012).

56. Kim, D., Langmead, B. & Salzberg, S. L. HISAT: a fast spliced aligner with low memory requirements. *Nat Methods* 12, 357-360 (2015).

57. Ingolia, N. T., Ghaemmaghami, S., Newman, J. R. & Weissman, J. S. Genome-wide analysis in vivo of translation with nucleotide resolution using ribosome profiling. *Science* 324, 218-223 (2009).

58. Guydosh, N. R. & Green, R. Dom34 rescues ribosomes in 3' untranslated regions. *Cell* 156, 950-962 (2014).

59. Afgan, E. et al. The Galaxy platform for accessible, reproducible and collaborative biomedical analyses: 2016 update. *Nucleic Acids Res* 44, W3-W10 (2016).

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

What is claimed is:

1. A modified transfer RNA (tRNA) comprising a T-arm, a D-arm, an anticodon-arm and an acceptor arm,
    wherein the anticodon-arm comprises a tri-nucleotide anticodon, wherein the anticodon is 5'-UUA-3' and recognizes TAA stop codons,
    wherein the acceptor arm is operably linked to a glutamine, and
    wherein the modified tRNA is encoded by a sequence comprising sequence as set forth in SEQ ID NO: 172.

2. A modified transfer RNA (tRNA) comprising a T-arm, a D-arm, an anticodon-arm and an acceptor arm,
    wherein the anticodon-arm comprises a tri-nucleotide anticodon, wherein the anticodon is 5'-UUA-3' and recognizes TAA stop codons,
    wherein the acceptor arm is operably linked to a glutamine, and
    wherein the modified tRNA is encoded by a sequence that comprises the sequence as set forth in SEQ ID NO: 156.

3. A modified transfer RNA (tRNA) comprising a T-arm, a D-arm, an anticodon-arm and an acceptor arm,
    wherein the anticodon-arm comprises a tri-nucleotide anticodon, wherein the anticodon is 5'-UUA-3' and recognizes TAA stop codons, wherein the acceptor arm is operably linked to a glutamine, and
    wherein the modified tRNA is encoded by a sequence that comprises the sequence as set forth in SEQ ID NO: 161.

4. A modified transfer RNA (tRNA) comprising a T-arm, a D-arm, an anticodon-arm and an acceptor arm,
    wherein the anticodon-arm comprises a tri-nucleotide anticodon, wherein the anticodon is 5'-UUA-3' and recognizes TAA stop codons,
    wherein the acceptor arm is operably linked to a glutamine, and
    wherein the modified tRNA is encoded by a sequence that comprises the sequence as set forth in SEQ ID NO: 165.

5. A modified transfer RNA (tRNA) comprising a T-arm, a D-arm, an anticodon-arm and an acceptor arm,
    wherein the anticodon-arm comprises a tri-nucleotide anticodon, wherein the anticodon is 5'-UUA-3' and recognizes TAA stop codons,
    wherein the acceptor arm is operably linked to a glutamine, and
    wherein the modified tRNA is encoded by a sequence that comprises the sequence as set forth in SEQ ID NO: 171.

* * * * *